(12) United States Patent
Alpert et al.

(10) Patent No.: US 12,011,459 B2
(45) Date of Patent: Jun. 18, 2024

(54) METHODS FOR MANUFACTURING T CELLS BY DIRECT SORTING AND COMPOSITIONS THEREOF

(71) Applicants: Immatics US, Inc., Houston, TX (US); Immatics Biotechnologies GmbH, Tübingen (DE)

(72) Inventors: Amir Alpert, Houston, TX (US); Dominik Maurer, Moessingen (DE); Anastasiya Smith, Houston, TX (US); Claudia Wagner, Tuebingen (DE); Ali Mohamed, Sugar Land, TX (US)

(73) Assignees: IMMATICS US, INC., Houston, TX (US); IMMATICS BIOTECHNOLOGIES GMBH, Tübingen (DE)

(*) Notice: Subject to any disclaimer, the term of this patent is extended or adjusted under 35 U.S.C. 154(b) by 452 days.

(21) Appl. No.: 16/893,246

(22) Filed: Jun. 4, 2020

(65) Prior Publication Data
US 2021/0002610 A1    Jan. 7, 2021

Related U.S. Application Data

(60) Provisional application No. 62/858,167, filed on Jun. 6, 2019.

(30) Foreign Application Priority Data

Oct. 30, 2019  (DE) .......................... 102019129341.3

(51) Int. Cl.
| | | |
|---|---|---|
| A61K 35/17 | (2015.01) | |
| A61K 31/437 | (2006.01) | |
| A61K 31/5383 | (2006.01) | |
| A61K 35/76 | (2015.01) | |
| C07K 14/47 | (2006.01) | |
| C07K 14/725 | (2006.01) | |
| C12N 5/0783 | (2010.01) | |
| G01N 15/14 | (2006.01) | |
| G01N 33/554 | (2006.01) | |
| G01N 15/10 | (2006.01) | |
| G01N 15/149 | (2024.01) | |

(52) U.S. Cl.
CPC ............ *A61K 35/17* (2013.01); *A61K 31/437* (2013.01); *A61K 31/5383* (2013.01); *A61K 35/76* (2013.01); *C07K 14/47* (2013.01); *C07K 14/7051* (2013.01); *C12N 5/0636* (2013.01); *G01N 15/1459* (2013.01); *G01N 33/554* (2013.01); *C12N 2501/2307* (2013.01); *C12N 2501/50* (2013.01); *C12N 2523/00* (2013.01); *G01N 2015/1006* (2013.01); *G01N 2015/1402* (2013.01); *G01N 15/149* (2024.01); *G01N 2333/705* (2013.01); *G01N 2333/7051* (2013.01); *G01N 2500/10* (2013.01)

(58) Field of Classification Search
CPC ....................................................... A61K 35/17
USPC ....................................................... 435/372.3
See application file for complete search history.

(56) References Cited

FOREIGN PATENT DOCUMENTS

| | | |
|---|---|---|
| JP | 2020005581 A | 1/2020 |
| WO | 97/04311 A2 | 2/1997 |
| WO | 2014/096803 A1 | 6/2014 |
| WO | 2016/090177 A1 | 6/2016 |

OTHER PUBLICATIONS

Sims et al (Expert Rev Vaccines, 2010, ((7): 765-774).*
Dileepan et al (PLSOS ONE, 2015, 10 pages).*
Lissina et al (Journal of Immunological Methods, 2009, 340: 11-24).*
Newell et al (Nature Methods, 2009, 6(7): 497-499).*
Zhu et al (Cytotherapy, 2018, 20: 394-406).*
Utharala et al (Anal Chem, 2018, 90: 5982-5988).*
Andersen et al (Nature Protocols, 201, 7(5): 891-902).*
Morgan et al (J Immunol, 2998, 160(2): 643-651).*
Whelan et al (J Immunol, 1999, 163: 4342-4348).*
Oelke et al (Clinical Cancer Research, 2000, 6: 1997-2005).*
Chapuis, Aude G., et al. "Transferred WT1-reactive CD8+ T cells can mediate antileukemic activity and persist in post-transplant patients." Science translational medicine, (2013), vol. 5, No. 174: 174ra27-174ra27.
Ho, William Y., et al. "In vitro methods for generating CD8+ T-cell clones for immunotherapy from the naive repertoire." Journal of immunological methods, (2006), vol. 310, No. 1-2: 40-52.
Farhood et al., "CD8+ cytotoxic T lymphocytes in cancer immunotherapy: A review," J Cell Physiol., (2019), vol. 234: 8509-8521.
Karapetyan et al., "TCR Fingerprinting and Off-Target Peptide Identification," Frontiers in Immunology, (2019), vol. 10, Article 2501 (14 pages).

(Continued)

*Primary Examiner* — Sean E Aeder
(74) *Attorney, Agent, or Firm* — MeBee, Moore & Vanik IP, LLC

(57) ABSTRACT

Described herein are methods for preparing T cells, including isolating CD8+ T cells from a blood sample obtained from a patient or a donor, culturing the isolated CD8+ T cells in the presence of at least one cytokine, contacting the cultured CD8+ T cells with a multimer containing a target peptide in a complex with an MHC molecule and with at least one binding agent that binds to a T cell surface molecule, in which the multimer is labelled with a first detectable agent and the binding agent is labelled with a second detectable agent, sorting the contacted CD8+ T cells to collect the sorted CD8+ T cells that are detected positive for the first and the second detectable agents, and expanding the collected CD8+ T cells.

14 Claims, 81 Drawing Sheets
Specification includes a Sequence Listing.

(56) References Cited

OTHER PUBLICATIONS

Uemura et al., "Systematic Analysis of the Combinatorial Nature of Epitopes Recognized by TCR Leads to Identification of Mimicry Epitopes for Glutamic Acid Decarboxylase 65-Specific TCRs," The Journal of Immunology, (2003), vol. 170, No. 2, 15: 947-960.

International Search Report issued in counterpart application No. PCT/US2020/036398, dated Oct. 15, 2020.

Dunbar et al., "Direct isolation, phenotyping and cloning of low-frequency antigen-specific cytotoxic T lymphocytes from peripheral blood", Current Biology, Current Science, GB, vol. 8, No. 7, (Mar. 16, 1998), pp. 413-416.

Guillaume Philippe et al: "Fluorescence-activated cell sorting and cloning of bona fide CD8(+) CTL with reversible MHC-pepticte and antibody Fab' conjugates", The Journal of Immunology, American Association of Immunologists, US, vol. 177, No. 6, 1 (Sep. 1, 2006) 3903-3912.

Bagher Farhood et al: "CD8+ cytotoxic T lymphocytes in cancer immunotherapy: A review", Journal of Cellular Physiology, vol. 234, No. 6, (Nov. 22, 2018) pp. 8509-8521. Abstract.

Cameron, Brian J., et al. "Identification of a Titin-derived HLA-A1-presented peptide as a cross-reactive target for engineered MAGE A3-directed T cells" Science translational medicine, vol. 5, No. 197, Aug. 2013.

De Vries, I.J.M., et al. "In situ detection of antigen-specific T cells in cryo-sections using MHC class I tetramers after dendritic cell vaccination of melanoma patients" Cancer Immunology, Immunotherapy, vol. 56, pp. 1667-1676, 2007.

International Search Report issued in counterpart application No. PCT/EP2020/065567, dated Aug. 10, 2020.

Johnson, Laura A., et al. "Gene therapy with human and mouse T-cell receptors mediates cancer regression and targets normal tissues expressing cognate antigen" Blood, vol. 114, No. 3, pp. 535-546, Jul. 2009.

Lee, Peter P., et al. "Characterization of circulating T cells specific for tumor-associated antigens in melanoma patients" Nature Medicine, vol. 5, pp. 677-685, Jun. 1999.

Linette, Gerald P., et al. "Cardiovascular toxicity and titin cross-reactivity of affinity-enhanced T cells in myeloma and melanoma" Blood, vol. 122, No. 6, pp. 863-871, Aug. 2013.

Massilamany, Chandirasegaran, et al. "Direct Staining with Major Histocompatibility Complex Class II Dextramers Permits Detection of Antigen-Specific, Autoreactive CD4 T Cells In Situ" PLOS ONE, vol. 9, Issue 1, Jan. 2014.

Miller, Stephen D., et al. "Persistent infection with Theiler's virus leads to CNS autoimmunity via epitope spreading" Nature Medicine, vol. 3, pp. 1133-1136, Oct. 1997.

Pittet, Mikael J., et al. "Ex vivo analysis of tumor antigen specific CD8+ T cell responses using MHC/peptide tetramers in cancer patients" International immunopharmacology, vol. 1, No. 7, pp. 1235-1247, Jul. 2001.

Valmori, Danila, et al. "An antigen-targeted approach to adoptive transfer therapy of cancer" Cancer research, vol. 59, No. 9, pp. 2167-2173, May 1999.

Van Den Berg, Joost H., et al. "Case report of a fatal serious adverse event upon administration of T cells transduced With a MART-1-specific T-cell receptor" Molecular Therapy, vol. 23, No. 9, pp. 1541-1550, Sep. 2015.

Schlums, Kimberly S., et al. "Cytokine Control of Memory T-Cell Development and Survival" Nature Reviews—Immunology, vol. 3, pp. 269-279, Apr. 2003.

Gerber S A et al: "Absolute quantification of proteins and phosphoproteins from cell lysates by tandem MS", Proceedings of the National Academy of Sciences, National Academy of Sciences, vol. 100, No. 12, pp. 6940-6945 (2003).

Matsuda Shun et al: "Absolute quantification of acetylation and phosphorylation of the histone variant H2AX upon ionizing radiation reveals distinct cellular responses in two cancer cell lines", Radiation and Environmental Biophysics, Springer Berlin Heidelberg, Berlin/Heidelberg, vol. 54, No. 4, pp. 403-411 (2015).

Matsuda Shun et al: "Absolute quantification of [gamma]H2AX using liquid chromatography-triple quadrupole tandem mass spectrometry", Analytical and Bioanalytical Chemistry, vol. 407, No. 18, pp. 5521-5527 (2015).

Apps Richard et al: "Relative Expression Levels of the HLA Class-I Proteins in Normal and HIV-Infected Cells", The Journal of Immunology, vol. 194, No. 8, pp. 3594-3600 (2015).

International Searching Authority Issued in Corresponding International Application PCT/E P2022/055412, dated Mar. 3, 2022.

* cited by examiner

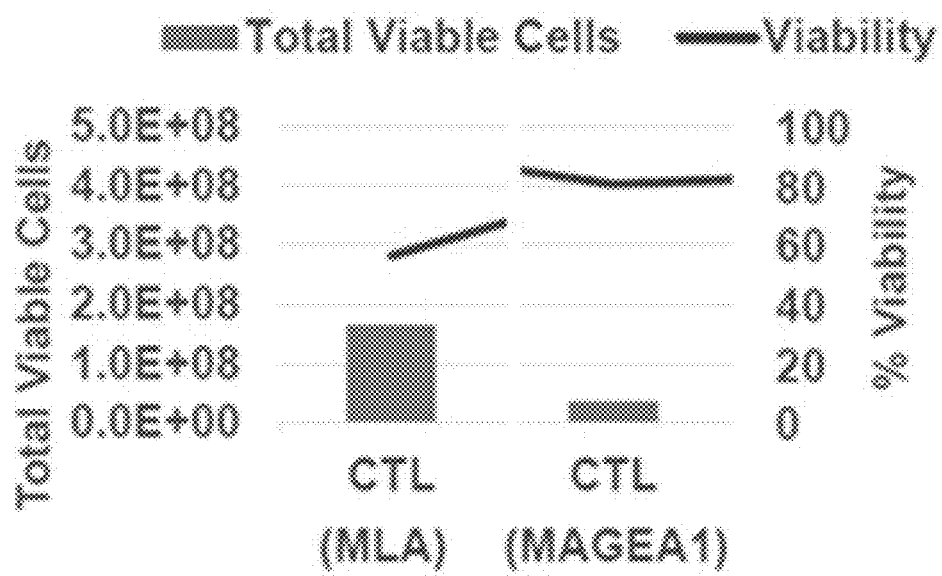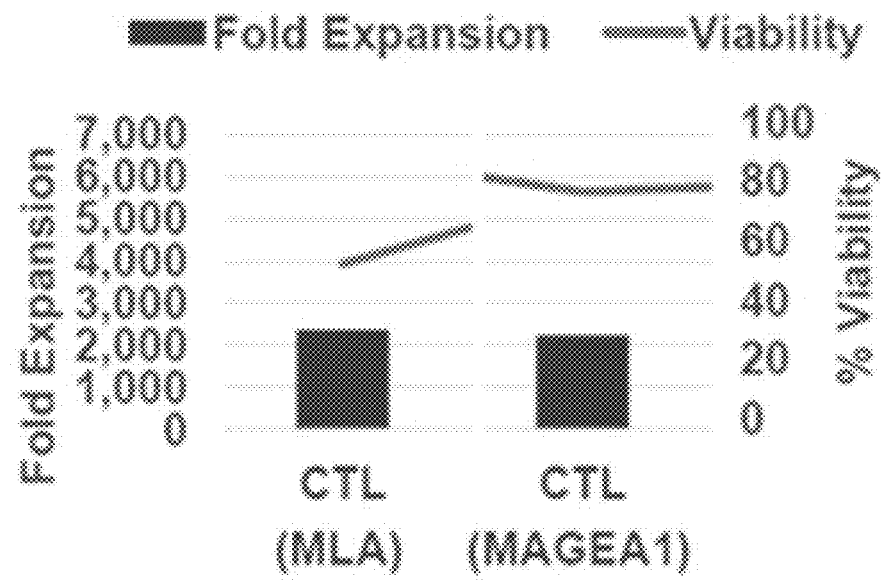
FIG. 15A

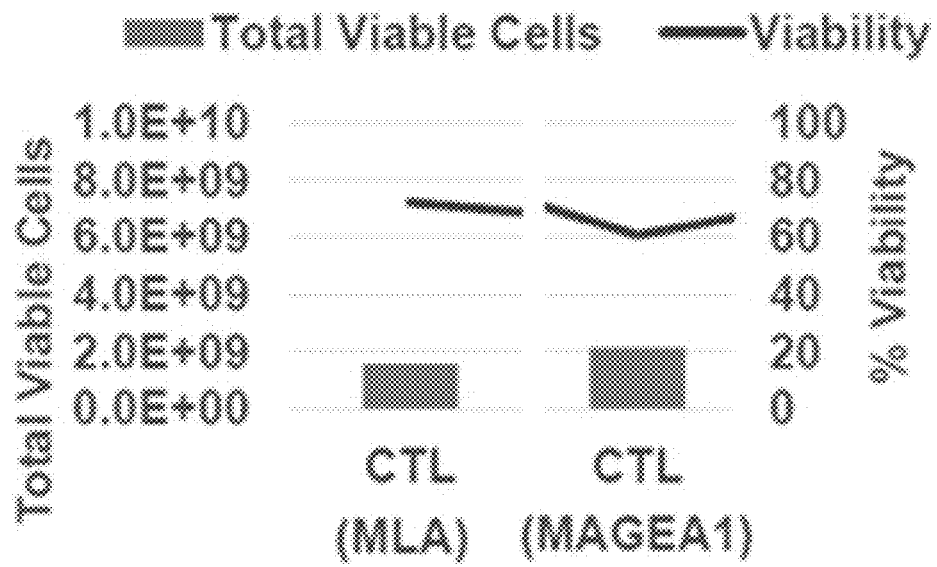
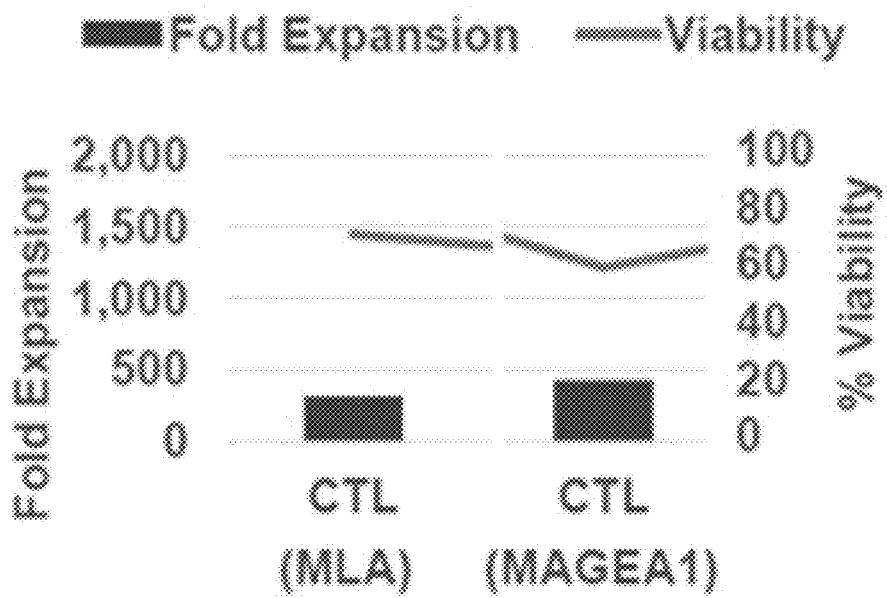
FIG. 15B

FIG. 18B
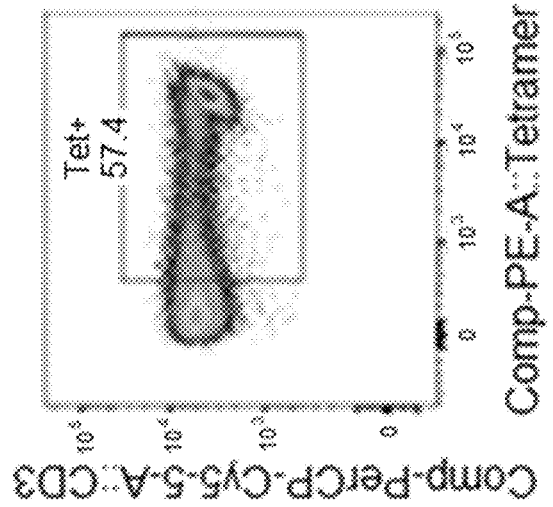
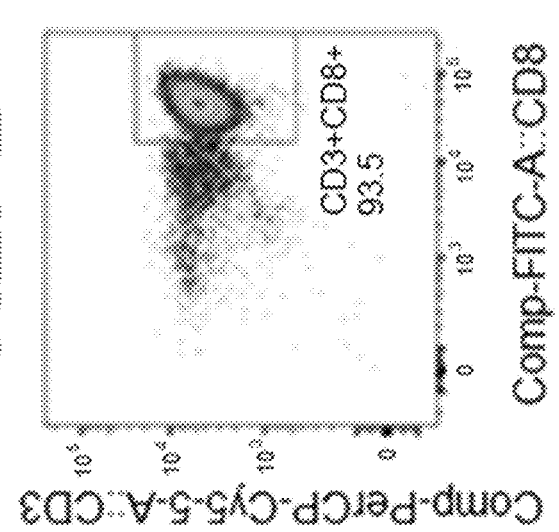
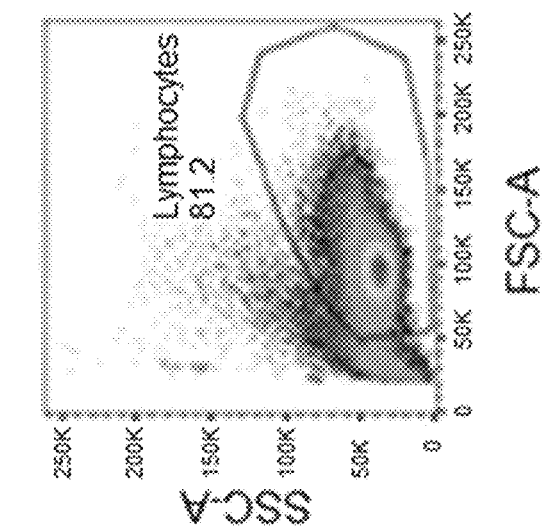

FIG. 19B
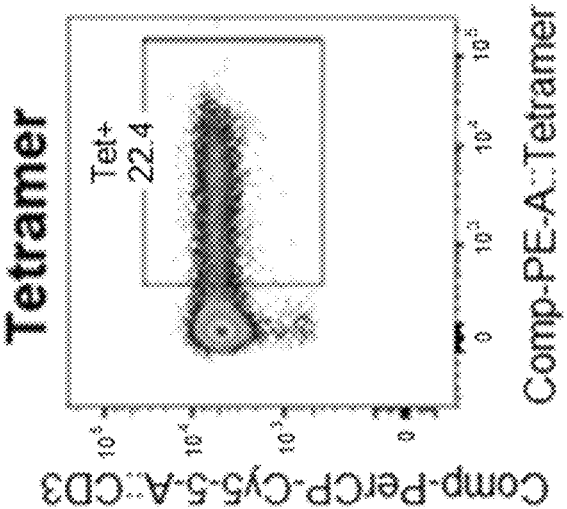
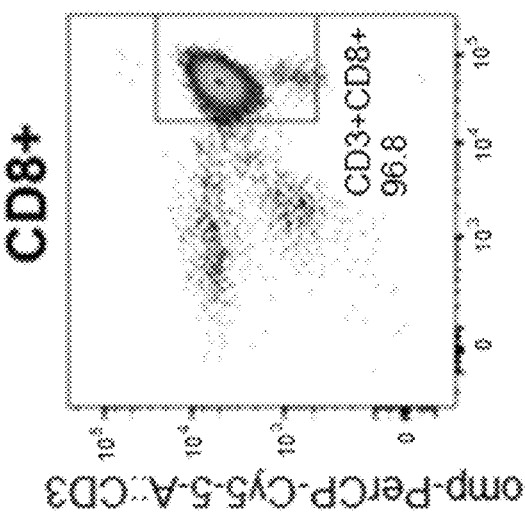
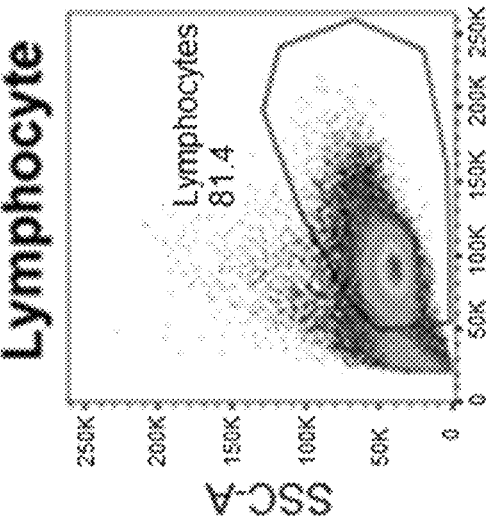

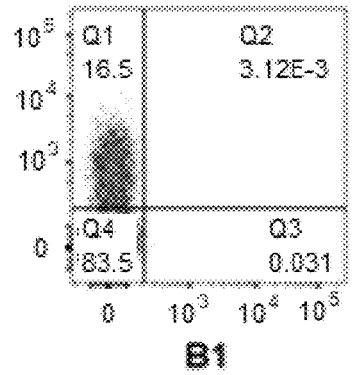
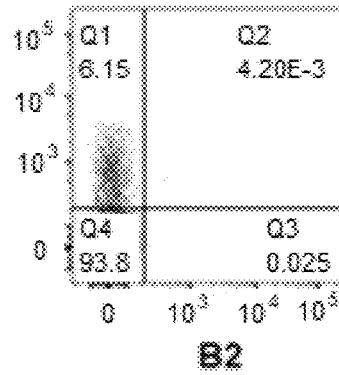
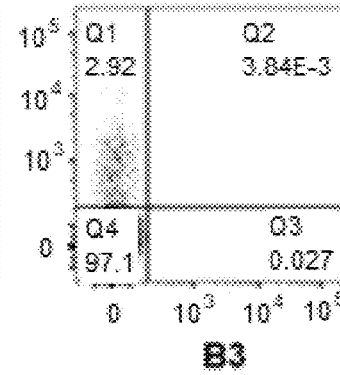
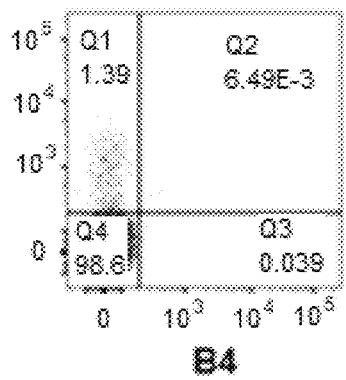
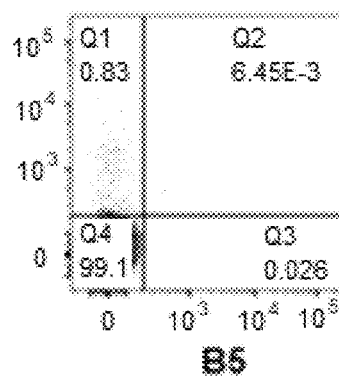
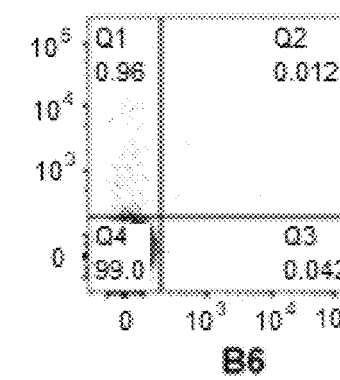
FIG. 24B

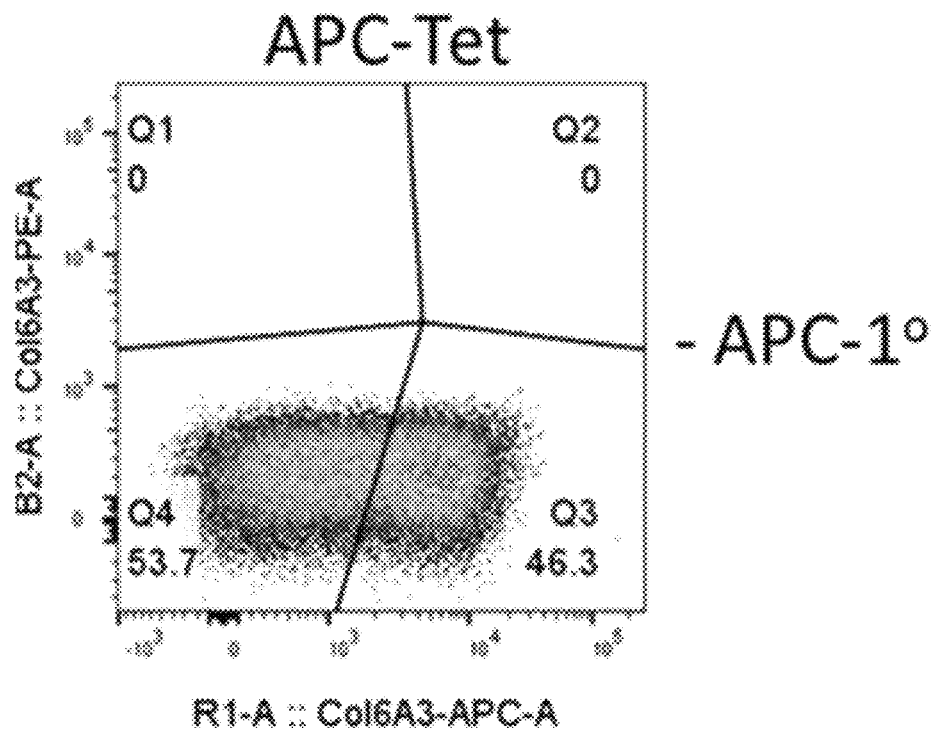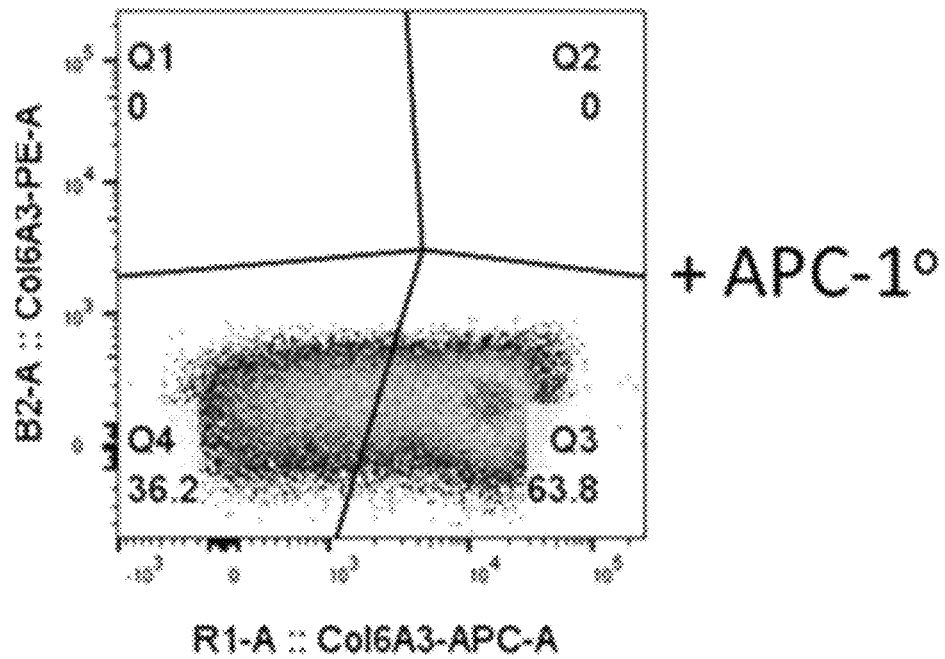
FIG. 25A

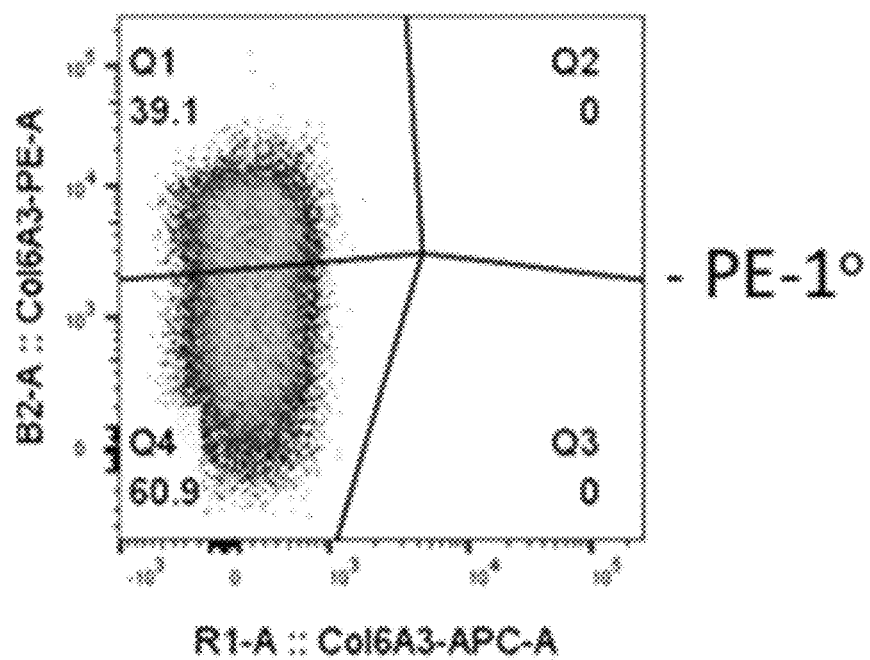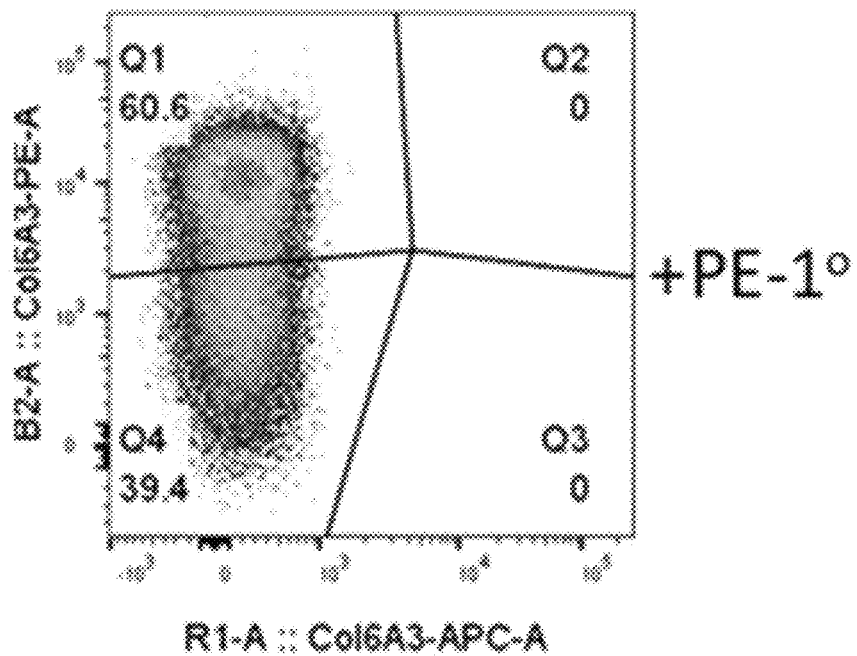
FIG. 25B

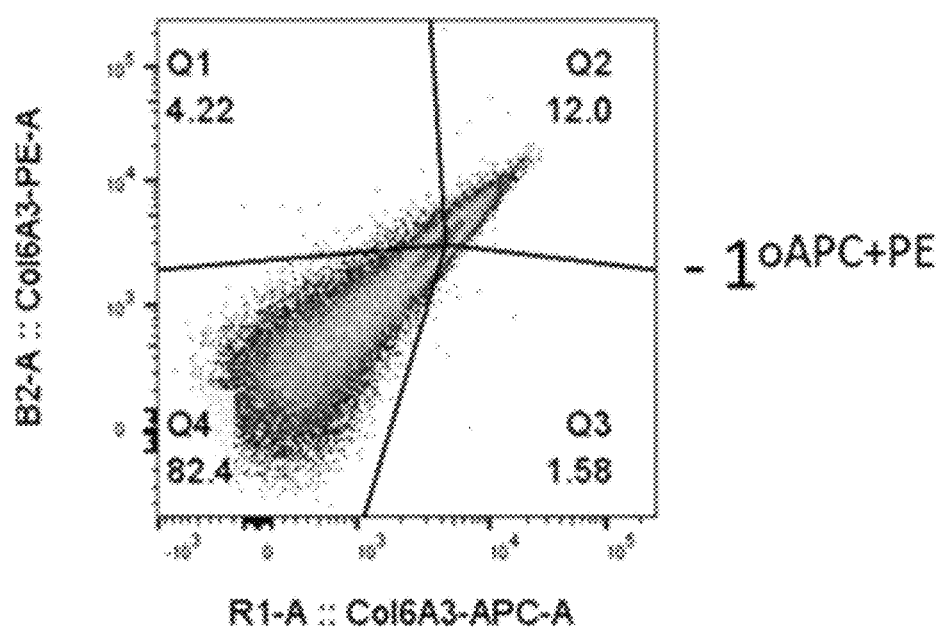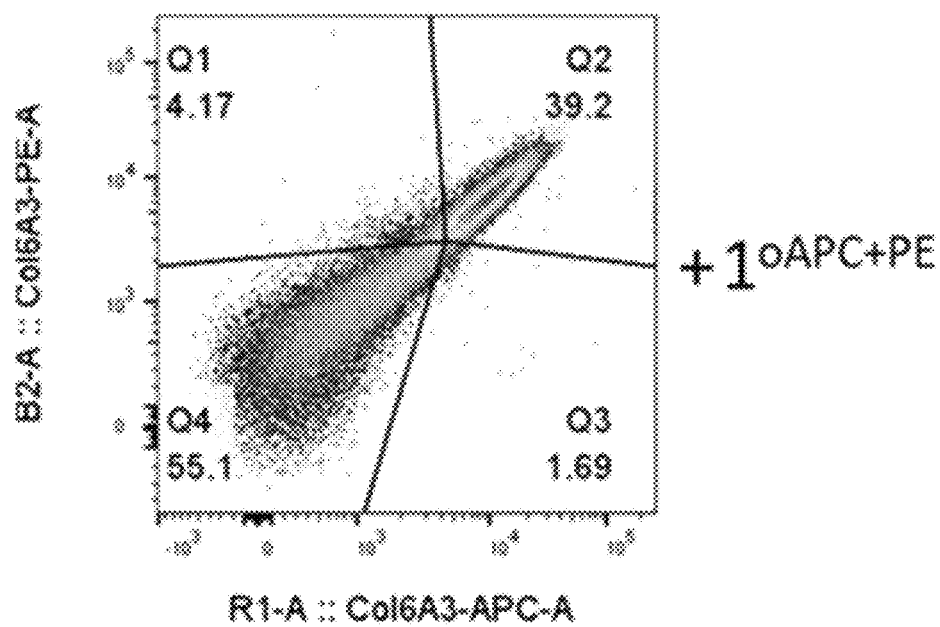
FIG. 25C

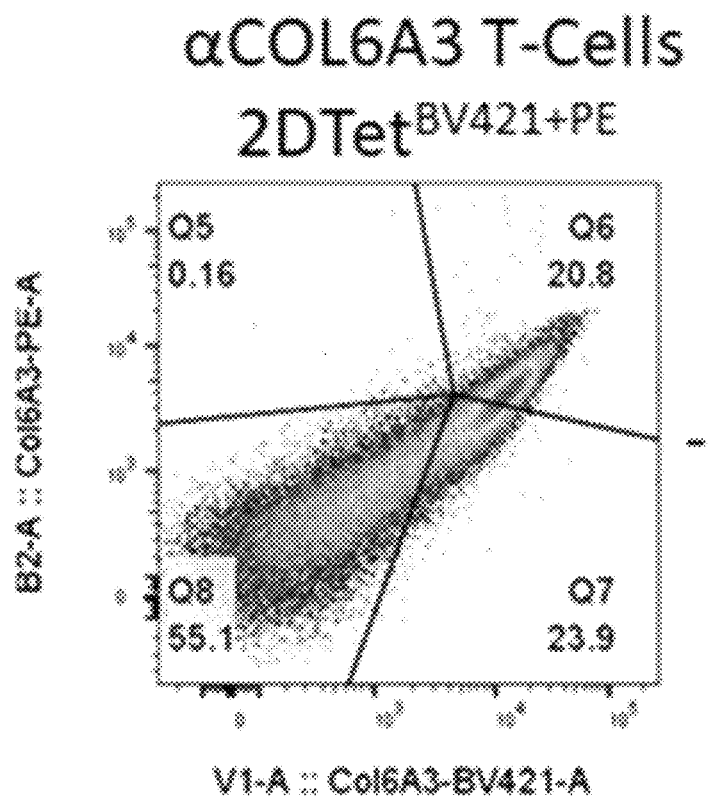
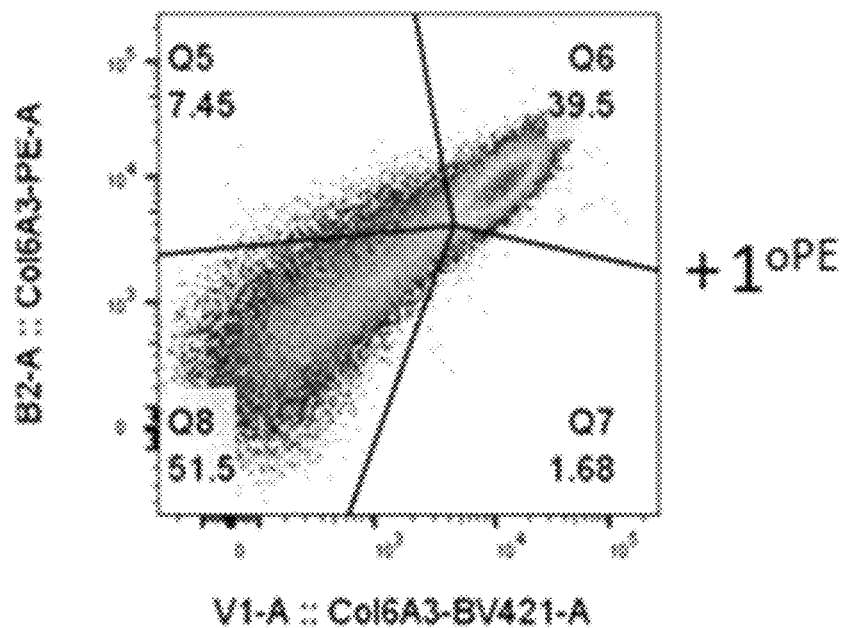
FIG. 25D

E1
αMLA T-Cells
2DTet$^{APC+PE}$ + 1$^{oAPC+PE}$
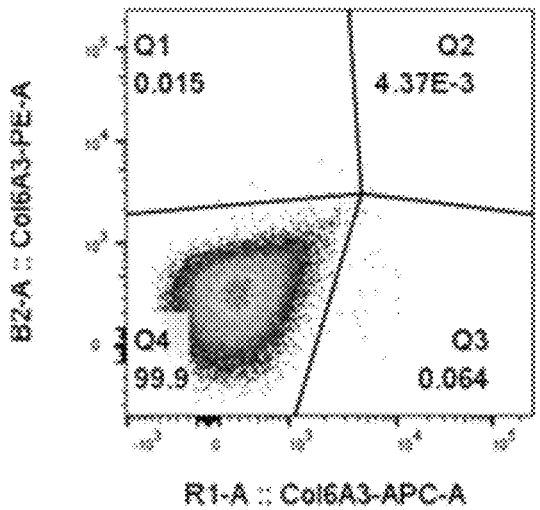
E2
αMLA T-Cells
2DTet$^{PE+BV421}$ + 1$^{PE}$
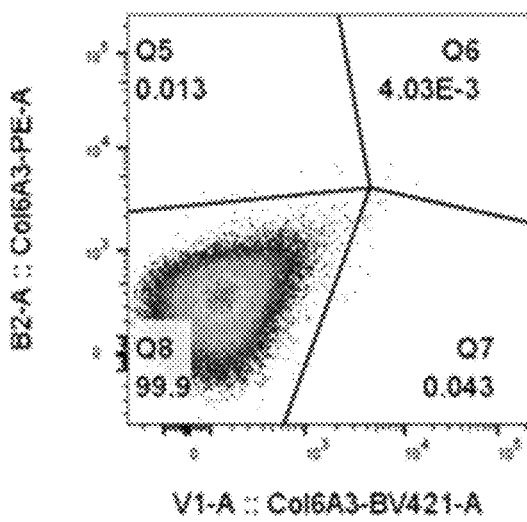
FIG. 25E

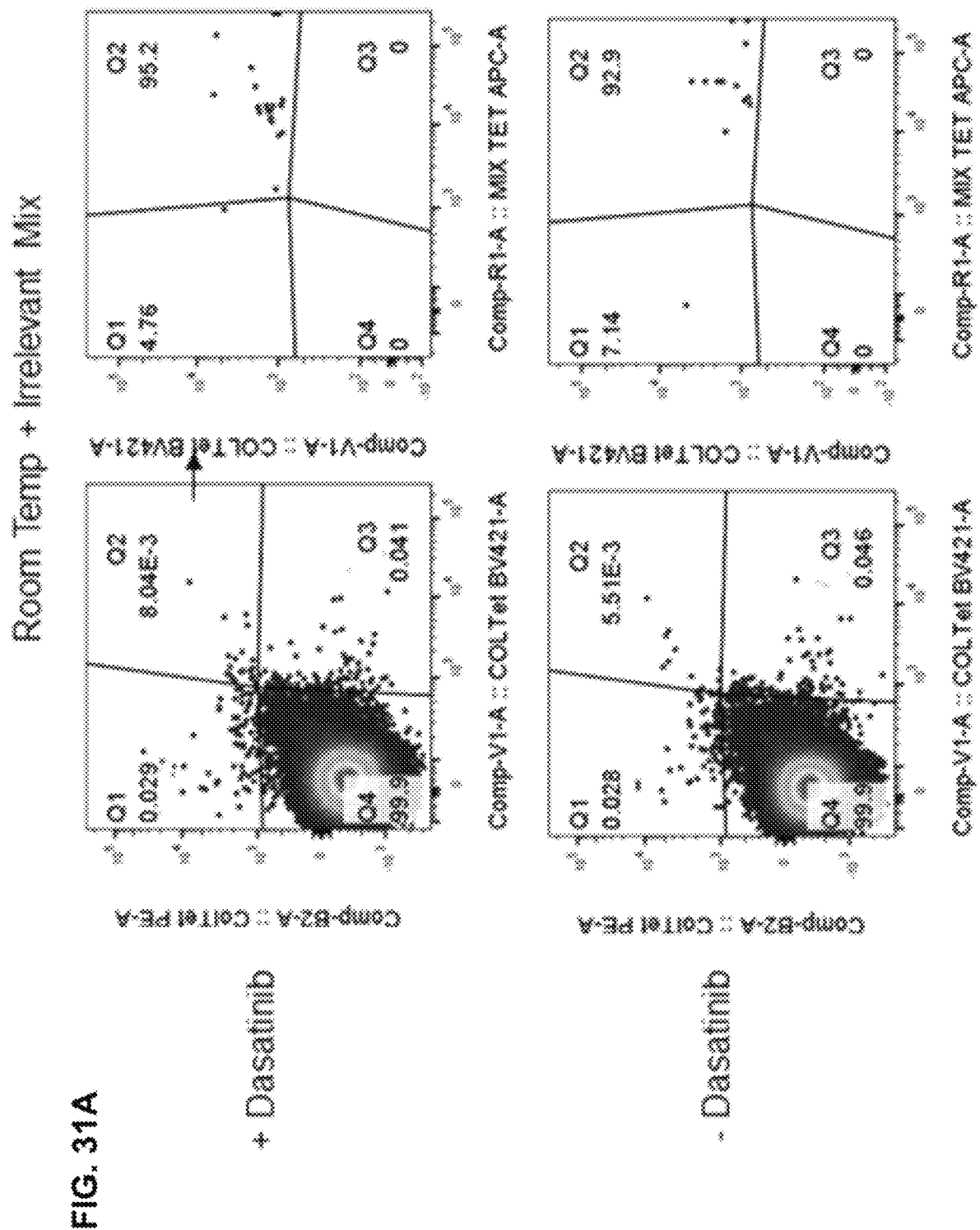

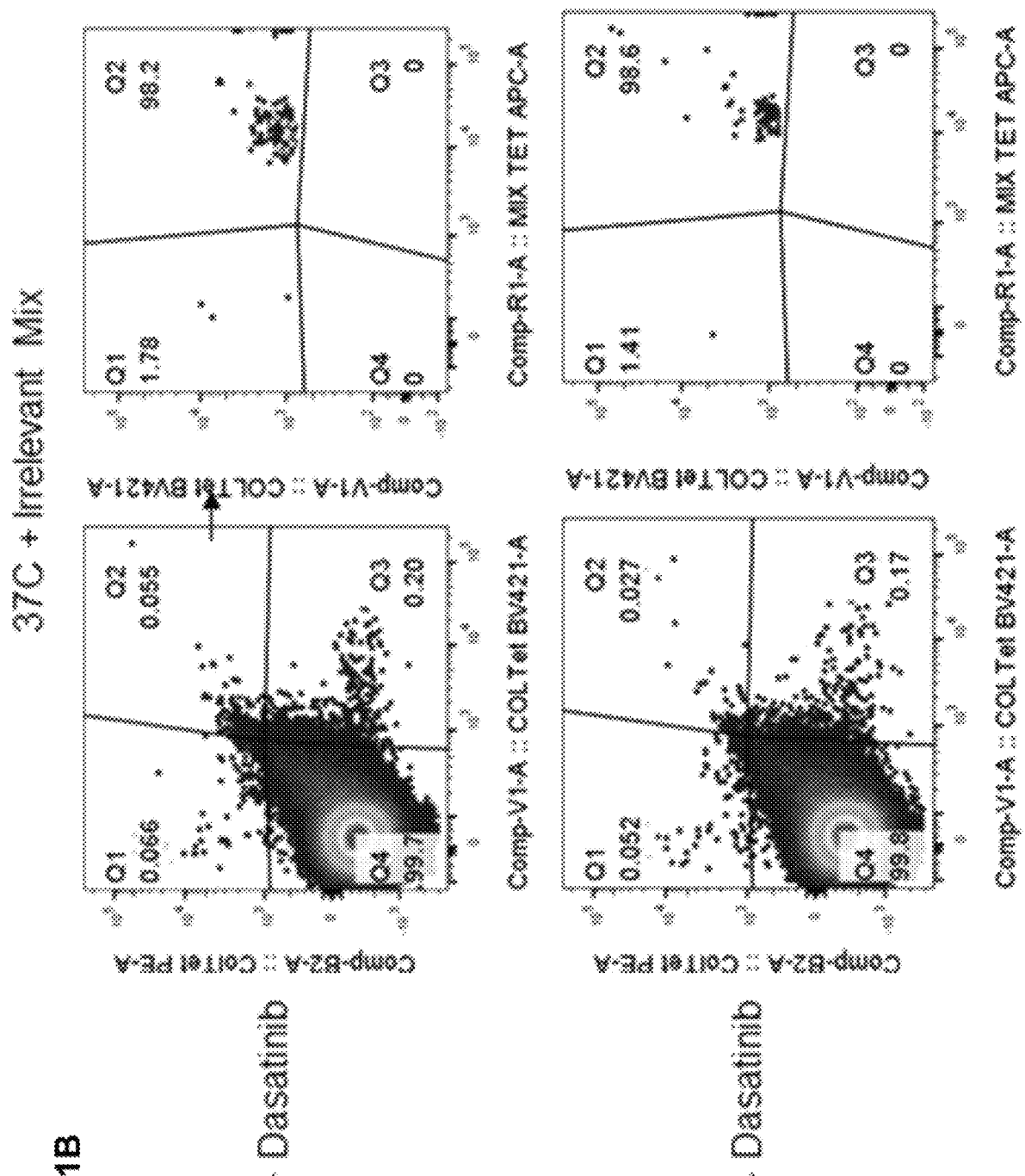

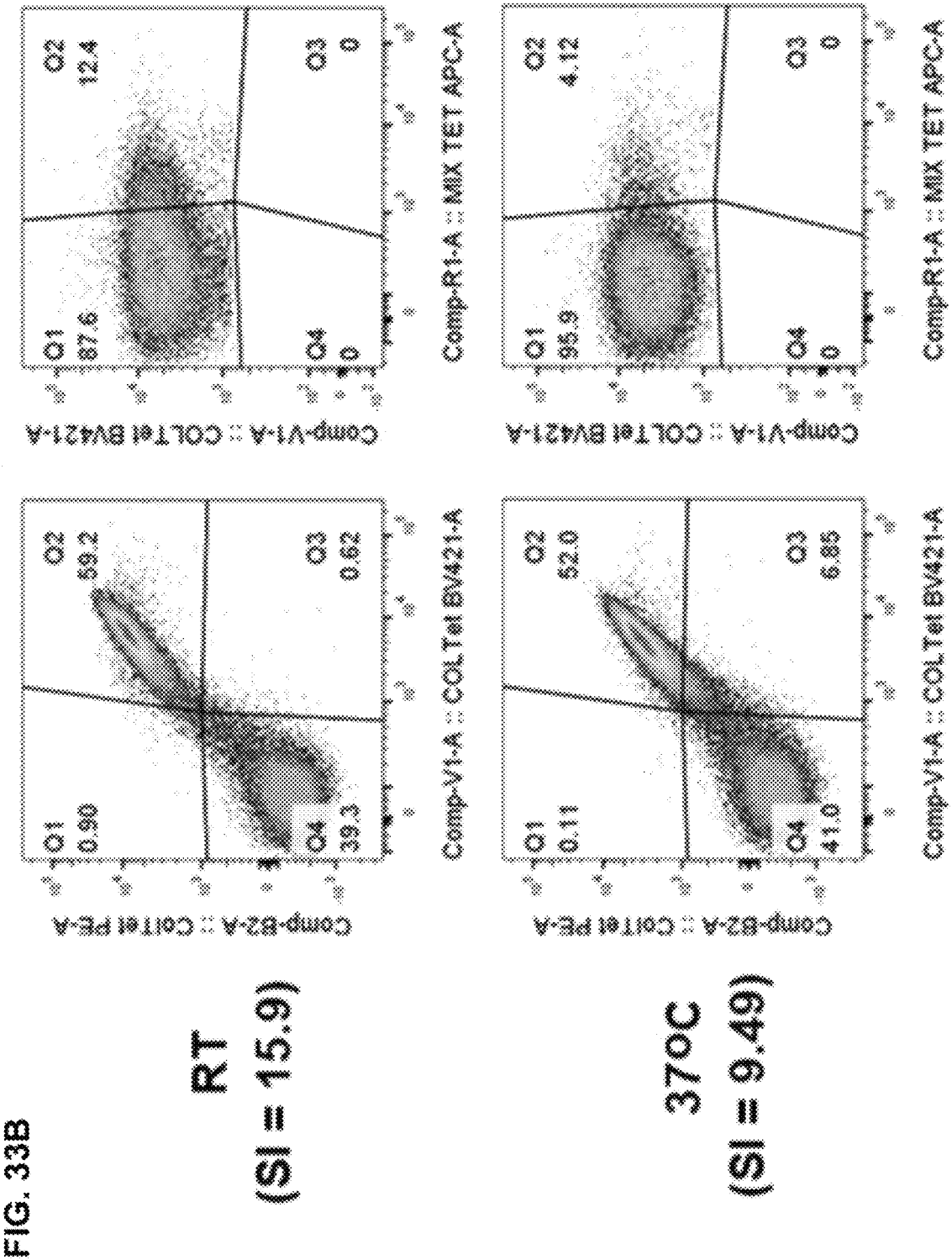

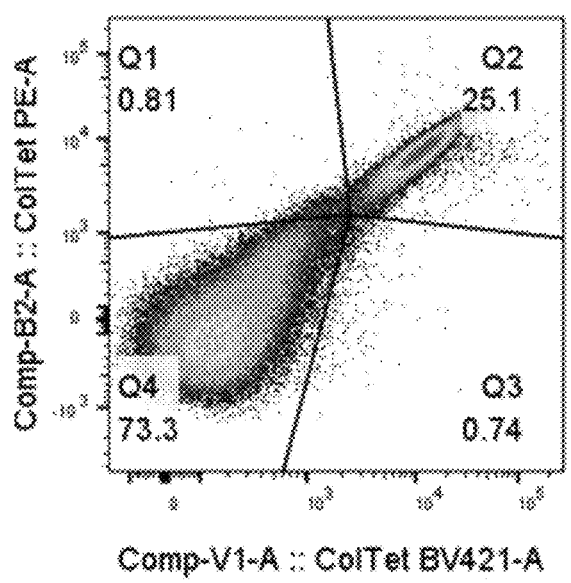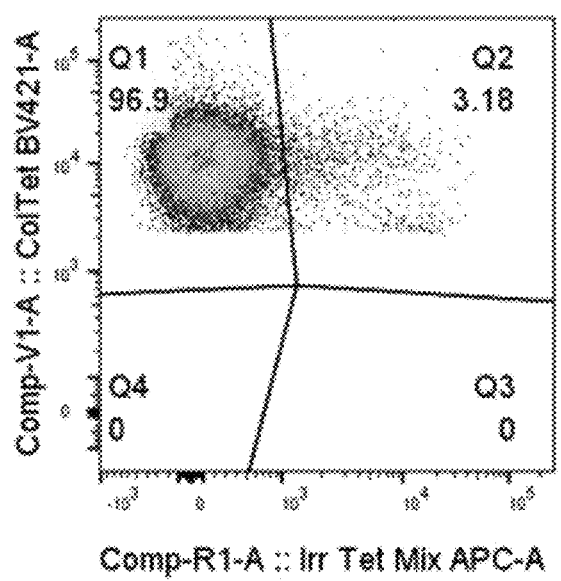
FIG. 34A

SEQUENCE LISTING

```
<160> NUMBER OF SEQ ID NOS: 161

<210> SEQ ID NO 1
<211> LENGTH: 10
<212> TYPE: PRT
<213> ORGANISM: Homo sapiens

<400> SEQUENCE: 1

Tyr Leu Tyr Asp Ser Glu Thr Lys Asn Ala
1               5                   10

<210> SEQ ID NO 2
<211> LENGTH: 9
<212> TYPE: PRT
<213> ORGANISM: Homo sapiens

<400> SEQUENCE: 2

His Leu Met Asp Gln Pro Leu Ser Val
1               5

<210> SEQ ID NO 3
<211> LENGTH: 9
<212> TYPE: PRT
<213> ORGANISM: Homo sapiens

<400> SEQUENCE: 3

Gly Leu Leu Lys Lys Ile Asn Ser Val
```

```
1               5

<210> SEQ ID NO 4
<211> LENGTH: 9
<212> TYPE: PRT
<213> ORGANISM: Homo sapiens

<400> SEQUENCE: 4

Phe Leu Val Asp Gly Ser Ser Ala Leu
1               5

<210> SEQ ID NO 5
<211> LENGTH: 10
<212> TYPE: PRT
<213> ORGANISM: Homo sapiens

<400> SEQUENCE: 5

Phe Leu Phe Asp Gly Ser Ala Asn Leu Val
1               5                   10

<210> SEQ ID NO 6
<211> LENGTH: 9
<212> TYPE: PRT
<213> ORGANISM: Homo sapiens

<400> SEQUENCE: 6

Phe Leu Tyr Lys Ile Ile Asp Glu Leu
1               5

<210> SEQ ID NO 7
<211> LENGTH: 11
<212> TYPE: PRT
<213> ORGANISM: Homo sapiens

<400> SEQUENCE: 7

Phe Ile Leu Asp Ser Ala Glu Thr Thr Thr Leu
1               5                   10

<210> SEQ ID NO 8
<211> LENGTH: 9
<212> TYPE: PRT
<213> ORGANISM: Homo sapiens

<400> SEQUENCE: 8

Ser Val Asp Val Ser Pro Pro Lys Val
1               5

<210> SEQ ID NO 9
<211> LENGTH: 8
<212> TYPE: PRT
<213> ORGANISM: Homo sapiens

<400> SEQUENCE: 9

Val Ala Asp Lys Ile His Ser Val
1               5

<210> SEQ ID NO 10
<211> LENGTH: 9
<212> TYPE: PRT
<213> ORGANISM: Homo sapiens

<400> SEQUENCE: 10

Ile Val Asp Asp Leu Thr Ile Asn Leu
1               5
```

<210> SEQ ID NO 11
<211> LENGTH: 9
<212> TYPE: PRT
<213> ORGANISM: Homo sapiens

<400> SEQUENCE: 11

Gly Leu Leu Glu Glu Leu Val Thr Val
1               5

<210> SEQ ID NO 12
<211> LENGTH: 10
<212> TYPE: PRT
<213> ORGANISM: Homo sapiens

<400> SEQUENCE: 12

Thr Leu Asp Gly Ala Ala Val Asn Gln Val
1               5                   10

<210> SEQ ID NO 13
<211> LENGTH: 10
<212> TYPE: PRT
<213> ORGANISM: Homo sapiens

<400> SEQUENCE: 13

Ser Val Leu Glu Lys Glu Ile Tyr Ser Ile
1               5                   10

<210> SEQ ID NO 14
<211> LENGTH: 9
<212> TYPE: PRT
<213> ORGANISM: Homo sapiens

<400> SEQUENCE: 14

Leu Leu Asp Pro Lys Thr Ile Phe Leu
1               5

<210> SEQ ID NO 15
<211> LENGTH: 9
<212> TYPE: PRT
<213> ORGANISM: Homo sapiens

<400> SEQUENCE: 15

Tyr Thr Phe Ser Gly Asp Val Gln Leu
1               5

<210> SEQ ID NO 16
<211> LENGTH: 9
<212> TYPE: PRT
<213> ORGANISM: Homo sapiens

<400> SEQUENCE: 16

Tyr Leu Met Asp Asp Phe Ser Ser Leu
1               5

<210> SEQ ID NO 17
<211> LENGTH: 9
<212> TYPE: PRT
<213> ORGANISM: Homo sapiens

<400> SEQUENCE: 17

Lys Val Trp Ser Asp Val Thr Pro Leu
1               5

<210> SEQ ID NO 18

```
<211> LENGTH: 11
<212> TYPE: PRT
<213> ORGANISM: Homo sapiens

<400> SEQUENCE: 18

Leu Leu Trp Gly His Pro Arg Val Ala Leu Ala
1               5                   10

<210> SEQ ID NO 19
<211> LENGTH: 11
<212> TYPE: PRT
<213> ORGANISM: Homo sapiens

<400> SEQUENCE: 19

Lys Ile Trp Glu Glu Leu Ser Val Leu Glu Val
1               5                   10

<210> SEQ ID NO 20
<211> LENGTH: 9
<212> TYPE: PRT
<213> ORGANISM: Homo sapiens

<400> SEQUENCE: 20

Leu Leu Ile Pro Phe Thr Ile Phe Met
1               5

<210> SEQ ID NO 21
<211> LENGTH: 9
<212> TYPE: PRT
<213> ORGANISM: Homo sapiens

<400> SEQUENCE: 21

Phe Leu Ile Glu Asn Leu Leu Ala Ala
1               5

<210> SEQ ID NO 22
<211> LENGTH: 11
<212> TYPE: PRT
<213> ORGANISM: Homo sapiens

<400> SEQUENCE: 22

Leu Leu Trp Gly His Pro Arg Val Ala Leu Ala
1               5                   10

<210> SEQ ID NO 23
<211> LENGTH: 9
<212> TYPE: PRT
<213> ORGANISM: Homo sapiens

<400> SEQUENCE: 23

Phe Leu Leu Glu Arg Glu Gln Leu Leu
1               5

<210> SEQ ID NO 24
<211> LENGTH: 9
<212> TYPE: PRT
<213> ORGANISM: Homo sapiens

<400> SEQUENCE: 24

Ser Leu Ala Glu Thr Ile Phe Ile Val
1               5

<210> SEQ ID NO 25
<211> LENGTH: 9
<212> TYPE: PRT
```

-continued

```
<213> ORGANISM: Homo sapiens

<400> SEQUENCE: 25

Thr Leu Leu Glu Gly Ile Ser Arg Ala
1               5

<210> SEQ ID NO 26
<211> LENGTH: 9
<212> TYPE: PRT
<213> ORGANISM: Homo sapiens

<400> SEQUENCE: 26

Ile Leu Gln Asp Gly Gln Phe Leu Val
1               5

<210> SEQ ID NO 27
<211> LENGTH: 10
<212> TYPE: PRT
<213> ORGANISM: Homo sapiens

<400> SEQUENCE: 27

Val Ile Phe Glu Gly Glu Pro Met Tyr Leu
1               5                   10

<210> SEQ ID NO 28
<211> LENGTH: 9
<212> TYPE: PRT
<213> ORGANISM: Homo sapiens

<400> SEQUENCE: 28

Ser Leu Phe Glu Ser Leu Glu Tyr Leu
1               5

<210> SEQ ID NO 29
<211> LENGTH: 9
<212> TYPE: PRT
<213> ORGANISM: Homo sapiens

<400> SEQUENCE: 29

Ser Leu Leu Asn Gln Pro Lys Ala Val
1               5

<210> SEQ ID NO 30
<211> LENGTH: 9
<212> TYPE: PRT
<213> ORGANISM: Homo sapiens

<400> SEQUENCE: 30

Gly Leu Ala Glu Phe Gln Glu Asn Val
1               5

<210> SEQ ID NO 31
<211> LENGTH: 9
<212> TYPE: PRT
<213> ORGANISM: Homo sapiens

<400> SEQUENCE: 31

Lys Leu Leu Ala Val Ile His Glu Leu
1               5

<210> SEQ ID NO 32
<211> LENGTH: 9
<212> TYPE: PRT
<213> ORGANISM: Homo sapiens
```

```
<400> SEQUENCE: 32

Thr Leu His Asp Gln Val His Leu Leu
1               5

<210> SEQ ID NO 33
<211> LENGTH: 11
<212> TYPE: PRT
<213> ORGANISM: Homo sapiens

<400> SEQUENCE: 33

Thr Leu Tyr Asn Pro Glu Arg Thr Ile Thr Val
1               5                   10

<210> SEQ ID NO 34
<211> LENGTH: 9
<212> TYPE: PRT
<213> ORGANISM: Homo sapiens

<400> SEQUENCE: 34

Lys Leu Gln Glu Lys Ile Gln Glu Leu
1               5

<210> SEQ ID NO 35
<211> LENGTH: 10
<212> TYPE: PRT
<213> ORGANISM: Homo sapiens

<400> SEQUENCE: 35

Ser Val Leu Glu Lys Glu Ile Tyr Ser Ile
1               5                   10

<210> SEQ ID NO 36
<211> LENGTH: 11
<212> TYPE: PRT
<213> ORGANISM: Homo sapiens

<400> SEQUENCE: 36

Arg Val Ile Asp Asp Ser Leu Val Val Gly Val
1               5                   10

<210> SEQ ID NO 37
<211> LENGTH: 9
<212> TYPE: PRT
<213> ORGANISM: Homo sapiens

<400> SEQUENCE: 37

Val Leu Phe Gly Glu Leu Pro Ala Leu
1               5

<210> SEQ ID NO 38
<211> LENGTH: 9
<212> TYPE: PRT
<213> ORGANISM: Homo sapiens

<400> SEQUENCE: 38

Gly Leu Val Asp Ile Met Val His Leu
1               5

<210> SEQ ID NO 39
<211> LENGTH: 9
<212> TYPE: PRT
<213> ORGANISM: Homo sapiens

<400> SEQUENCE: 39
```

```
Phe Leu Asn Ala Ile Glu Thr Ala Leu
1               5

<210> SEQ ID NO 40
<211> LENGTH: 9
<212> TYPE: PRT
<213> ORGANISM: Homo sapiens

<400> SEQUENCE: 40

Ala Leu Leu Gln Ala Leu Met Glu Leu
1               5

<210> SEQ ID NO 41
<211> LENGTH: 9
<212> TYPE: PRT
<213> ORGANISM: Homo sapiens

<400> SEQUENCE: 41

Ala Leu Ser Ser Ser Gln Ala Glu Val
1               5

<210> SEQ ID NO 42
<211> LENGTH: 11
<212> TYPE: PRT
<213> ORGANISM: Homo sapiens

<400> SEQUENCE: 42

Ser Leu Ile Thr Gly Gln Asp Leu Leu Ser Val
1               5                   10

<210> SEQ ID NO 43
<211> LENGTH: 9
<212> TYPE: PRT
<213> ORGANISM: Homo sapiens

<400> SEQUENCE: 43

Gln Leu Ile Glu Lys Asn Trp Leu Leu
1               5

<210> SEQ ID NO 44
<211> LENGTH: 9
<212> TYPE: PRT
<213> ORGANISM: Homo sapiens

<400> SEQUENCE: 44

Leu Leu Asp Pro Lys Thr Ile Phe Leu
1               5

<210> SEQ ID NO 45
<211> LENGTH: 9
<212> TYPE: PRT
<213> ORGANISM: Homo sapiens

<400> SEQUENCE: 45

Arg Leu His Asp Glu Asn Ile Leu Leu
1               5

<210> SEQ ID NO 46
<211> LENGTH: 9
<212> TYPE: PRT
<213> ORGANISM: Homo sapiens

<400> SEQUENCE: 46

Tyr Thr Phe Ser Gly Asp Val Gln Leu
1               5
```

<210> SEQ ID NO 47
<211> LENGTH: 9
<212> TYPE: PRT
<213> ORGANISM: Homo sapiens

<400> SEQUENCE: 47

Gly Leu Pro Ser Ala Thr Thr Thr Val
1               5

<210> SEQ ID NO 48
<211> LENGTH: 11
<212> TYPE: PRT
<213> ORGANISM: Homo sapiens

<400> SEQUENCE: 48

Gly Leu Leu Pro Ser Ala Glu Ser Ile Lys Leu
1               5                   10

<210> SEQ ID NO 49
<211> LENGTH: 9
<212> TYPE: PRT
<213> ORGANISM: Homo sapiens

<400> SEQUENCE: 49

Lys Thr Ala Ser Ile Asn Gln Asn Val
1               5

<210> SEQ ID NO 50
<211> LENGTH: 9
<212> TYPE: PRT
<213> ORGANISM: Homo sapiens

<400> SEQUENCE: 50

Ser Leu Leu Gln His Leu Ile Gly Leu
1               5

<210> SEQ ID NO 51
<211> LENGTH: 9
<212> TYPE: PRT
<213> ORGANISM: Homo sapiens

<400> SEQUENCE: 51

Tyr Leu Met Asp Asp Phe Ser Ser Leu
1               5

<210> SEQ ID NO 52
<211> LENGTH: 9
<212> TYPE: PRT
<213> ORGANISM: Homo sapiens

<400> SEQUENCE: 52

Leu Met Tyr Pro Tyr Ile Tyr His Val
1               5

<210> SEQ ID NO 53
<211> LENGTH: 9
<212> TYPE: PRT
<213> ORGANISM: Homo sapiens

<400> SEQUENCE: 53

Lys Val Trp Ser Asp Val Thr Pro Leu
1               5

```
<210> SEQ ID NO 54
<211> LENGTH: 11
<212> TYPE: PRT
<213> ORGANISM: Homo sapiens

<400> SEQUENCE: 54

Leu Leu Trp Gly His Pro Arg Val Ala Leu Ala
1               5                   10

<210> SEQ ID NO 55
<211> LENGTH: 9
<212> TYPE: PRT
<213> ORGANISM: Homo sapiens

<400> SEQUENCE: 55

Val Leu Asp Gly Lys Val Ala Val Val
1               5

<210> SEQ ID NO 56
<211> LENGTH: 9
<212> TYPE: PRT
<213> ORGANISM: Homo sapiens

<400> SEQUENCE: 56

Gly Leu Leu Gly Lys Val Thr Ser Val
1               5

<210> SEQ ID NO 57
<211> LENGTH: 9
<212> TYPE: PRT
<213> ORGANISM: Homo sapiens

<400> SEQUENCE: 57

Lys Met Ile Ser Ala Ile Pro Thr Leu
1               5

<210> SEQ ID NO 58
<211> LENGTH: 11
<212> TYPE: PRT
<213> ORGANISM: Homo sapiens

<400> SEQUENCE: 58

Gly Leu Leu Glu Thr Thr Gly Leu Leu Ala Thr
1               5                   10

<210> SEQ ID NO 59
<211> LENGTH: 9
<212> TYPE: PRT
<213> ORGANISM: Homo sapiens

<400> SEQUENCE: 59

Thr Leu Asn Thr Leu Asp Ile Asn Leu
1               5

<210> SEQ ID NO 60
<211> LENGTH: 9
<212> TYPE: PRT
<213> ORGANISM: Homo sapiens

<400> SEQUENCE: 60

Val Ile Ile Lys Gly Leu Glu Glu Ile
1               5

<210> SEQ ID NO 61
<211> LENGTH: 9
```

```
<212> TYPE: PRT
<213> ORGANISM: Homo sapiens

<400> SEQUENCE: 61

Tyr Leu Glu Asp Gly Phe Ala Tyr Val
1               5

<210> SEQ ID NO 62
<211> LENGTH: 11
<212> TYPE: PRT
<213> ORGANISM: Homo sapiens

<400> SEQUENCE: 62

Lys Ile Trp Glu Glu Leu Ser Val Leu Glu Val
1               5                   10

<210> SEQ ID NO 63
<211> LENGTH: 9
<212> TYPE: PRT
<213> ORGANISM: Homo sapiens

<400> SEQUENCE: 63

Leu Leu Ile Pro Phe Thr Ile Phe Met
1               5

<210> SEQ ID NO 64
<211> LENGTH: 10
<212> TYPE: PRT
<213> ORGANISM: Homo sapiens

<400> SEQUENCE: 64

Ile Ser Leu Asp Glu Val Ala Val Ser Leu
1               5                   10

<210> SEQ ID NO 65
<211> LENGTH: 10
<212> TYPE: PRT
<213> ORGANISM: Homo sapiens

<400> SEQUENCE: 65

Lys Ile Ser Asp Phe Gly Leu Ala Thr Val
1               5                   10

<210> SEQ ID NO 66
<211> LENGTH: 11
<212> TYPE: PRT
<213> ORGANISM: Homo sapiens

<400> SEQUENCE: 66

Lys Leu Ile Gly Asn Ile His Gly Asn Glu Val
1               5                   10

<210> SEQ ID NO 67
<211> LENGTH: 9
<212> TYPE: PRT
<213> ORGANISM: Homo sapiens

<400> SEQUENCE: 67

Ile Leu Leu Ser Val Leu His Gln Leu
1               5

<210> SEQ ID NO 68
<211> LENGTH: 9
<212> TYPE: PRT
<213> ORGANISM: Homo sapiens
```

```
<400> SEQUENCE: 68

Leu Asp Ser Glu Ala Leu Leu Thr Leu
1               5

<210> SEQ ID NO 69
<211> LENGTH: 13
<212> TYPE: PRT
<213> ORGANISM: Homo sapiens

<400> SEQUENCE: 69

Val Leu Gln Glu Asn Ser Ser Asp Tyr Gln Ser Asn Leu
1               5                   10

<210> SEQ ID NO 70
<211> LENGTH: 11
<212> TYPE: PRT
<213> ORGANISM: Homo sapiens

<400> SEQUENCE: 70

His Leu Leu Gly Glu Gly Ala Phe Ala Gln Val
1               5                   10

<210> SEQ ID NO 71
<211> LENGTH: 9
<212> TYPE: PRT
<213> ORGANISM: Homo sapiens

<400> SEQUENCE: 71

Ser Leu Val Glu Asn Ile His Val Leu
1               5

<210> SEQ ID NO 72
<211> LENGTH: 9
<212> TYPE: PRT
<213> ORGANISM: Homo sapiens

<400> SEQUENCE: 72

Tyr Thr Phe Ser Gly Asp Val Gln Leu
1               5

<210> SEQ ID NO 73
<211> LENGTH: 9
<212> TYPE: PRT
<213> ORGANISM: Homo sapiens

<400> SEQUENCE: 73

Ser Leu Ser Glu Lys Ser Pro Glu Val
1               5

<210> SEQ ID NO 74
<211> LENGTH: 10
<212> TYPE: PRT
<213> ORGANISM: Homo sapiens

<400> SEQUENCE: 74

Ala Met Phe Pro Asp Thr Ile Pro Arg Val
1               5                   10

<210> SEQ ID NO 75
<211> LENGTH: 9
<212> TYPE: PRT
<213> ORGANISM: Homo sapiens

<400> SEQUENCE: 75
```

Phe Leu Ile Glu Asn Leu Leu Ala Ala
1               5

<210> SEQ ID NO 76
<211> LENGTH: 9
<212> TYPE: PRT
<213> ORGANISM: Homo sapiens

<400> SEQUENCE: 76

Phe Thr Ala Glu Phe Leu Glu Lys Val
1               5

<210> SEQ ID NO 77
<211> LENGTH: 9
<212> TYPE: PRT
<213> ORGANISM: Homo sapiens

<400> SEQUENCE: 77

Ala Leu Tyr Gly Asn Val Gln Gln Val
1               5

<210> SEQ ID NO 78
<211> LENGTH: 9
<212> TYPE: PRT
<213> ORGANISM: Homo sapiens

<400> SEQUENCE: 78

Leu Phe Gln Ser Arg Ile Ala Gly Val
1               5

<210> SEQ ID NO 79
<211> LENGTH: 11
<212> TYPE: PRT
<213> ORGANISM: Homo sapiens

<400> SEQUENCE: 79

Ile Leu Ala Glu Glu Pro Ile Tyr Ile Arg Val
1               5                   10

<210> SEQ ID NO 80
<211> LENGTH: 9
<212> TYPE: PRT
<213> ORGANISM: Homo sapiens

<400> SEQUENCE: 80

Phe Leu Leu Glu Arg Glu Gln Leu Leu
1               5

<210> SEQ ID NO 81
<211> LENGTH: 10
<212> TYPE: PRT
<213> ORGANISM: Homo sapiens

<400> SEQUENCE: 81

Leu Leu Leu Pro Leu Glu Leu Ser Leu Ala
1               5                   10

<210> SEQ ID NO 82
<211> LENGTH: 9
<212> TYPE: PRT
<213> ORGANISM: Homo sapiens

<400> SEQUENCE: 82

Ser Leu Ala Glu Thr Ile Phe Ile Val

<210> SEQ ID NO 83
<211> LENGTH: 11
<212> TYPE: PRT
<213> ORGANISM: Homo sapiens

<400> SEQUENCE: 83

Ala Ile Leu Asn Val Asp Glu Lys Asn Gln Val
1               5                   10

<210> SEQ ID NO 84
<211> LENGTH: 9
<212> TYPE: PRT
<213> ORGANISM: Homo sapiens

<400> SEQUENCE: 84

Arg Leu Phe Glu Glu Val Leu Gly Val
1               5

<210> SEQ ID NO 85
<211> LENGTH: 9
<212> TYPE: PRT
<213> ORGANISM: Homo sapiens

<400> SEQUENCE: 85

Tyr Leu Asp Glu Val Ala Phe Met Leu
1               5

<210> SEQ ID NO 86
<211> LENGTH: 11
<212> TYPE: PRT
<213> ORGANISM: Homo sapiens

<400> SEQUENCE: 86

Lys Leu Ile Asp Glu Asp Glu Pro Leu Phe Leu
1               5                   10

<210> SEQ ID NO 87
<211> LENGTH: 9
<212> TYPE: PRT
<213> ORGANISM: Homo sapiens

<400> SEQUENCE: 87

Lys Leu Phe Glu Lys Ser Thr Gly Leu
1               5

<210> SEQ ID NO 88
<211> LENGTH: 11
<212> TYPE: PRT
<213> ORGANISM: Homo sapiens

<400> SEQUENCE: 88

Ser Leu Leu Glu Val Asn Glu Ala Ser Ser Val
1               5                   10

<210> SEQ ID NO 89
<211> LENGTH: 10
<212> TYPE: PRT
<213> ORGANISM: Homo sapiens

<400> SEQUENCE: 89

Gly Val Tyr Asp Gly Arg Glu His Thr Val
1               5                   10

<210> SEQ ID NO 90
<211> LENGTH: 10
<212> TYPE: PRT
<213> ORGANISM: Homo sapiens

<400> SEQUENCE: 90

Gly Leu Tyr Pro Val Thr Leu Val Gly Val
1               5                   10

<210> SEQ ID NO 91
<211> LENGTH: 9
<212> TYPE: PRT
<213> ORGANISM: Homo sapiens

<400> SEQUENCE: 91

Ala Leu Leu Ser Ser Val Ala Glu Ala
1               5

<210> SEQ ID NO 92
<211> LENGTH: 9
<212> TYPE: PRT
<213> ORGANISM: Homo sapiens

<400> SEQUENCE: 92

Thr Leu Leu Glu Gly Ile Ser Arg Ala
1               5

<210> SEQ ID NO 93
<211> LENGTH: 9
<212> TYPE: PRT
<213> ORGANISM: Homo sapiens

<400> SEQUENCE: 93

Ser Leu Ile Glu Glu Ser Glu Glu Leu
1               5

<210> SEQ ID NO 94
<211> LENGTH: 9
<212> TYPE: PRT
<213> ORGANISM: Homo sapiens

<400> SEQUENCE: 94

Ala Leu Tyr Val Gln Ala Pro Thr Val
1               5

<210> SEQ ID NO 95
<211> LENGTH: 10
<212> TYPE: PRT
<213> ORGANISM: Homo sapiens

<400> SEQUENCE: 95

Lys Leu Ile Tyr Lys Asp Leu Val Ser Val
1               5                   10

<210> SEQ ID NO 96
<211> LENGTH: 9
<212> TYPE: PRT
<213> ORGANISM: Homo sapiens

<400> SEQUENCE: 96

Ile Leu Gln Asp Gly Gln Phe Leu Val
1               5

<210> SEQ ID NO 97

```
<211> LENGTH: 9
<212> TYPE: PRT
<213> ORGANISM: Homo sapiens

<400> SEQUENCE: 97

Ser Leu Leu Asp Tyr Glu Val Ser Ile
1               5

<210> SEQ ID NO 98
<211> LENGTH: 9
<212> TYPE: PRT
<213> ORGANISM: Homo sapiens

<400> SEQUENCE: 98

Leu Leu Gly Asp Ser Ser Phe Phe Leu
1               5

<210> SEQ ID NO 99
<211> LENGTH: 10
<212> TYPE: PRT
<213> ORGANISM: Homo sapiens

<400> SEQUENCE: 99

Val Ile Phe Glu Gly Glu Pro Met Tyr Leu
1               5                   10

<210> SEQ ID NO 100
<211> LENGTH: 9
<212> TYPE: PRT
<213> ORGANISM: Homo sapiens

<400> SEQUENCE: 100

Ala Leu Ser Tyr Ile Leu Pro Tyr Leu
1               5

<210> SEQ ID NO 101
<211> LENGTH: 9
<212> TYPE: PRT
<213> ORGANISM: Homo sapiens

<400> SEQUENCE: 101

Phe Leu Phe Val Asp Pro Glu Leu Val
1               5

<210> SEQ ID NO 102
<211> LENGTH: 11
<212> TYPE: PRT
<213> ORGANISM: Homo sapiens

<400> SEQUENCE: 102

Ser Glu Trp Gly Ser Pro His Ala Ala Val Pro
1               5                   10

<210> SEQ ID NO 103
<211> LENGTH: 9
<212> TYPE: PRT
<213> ORGANISM: Homo sapiens

<400> SEQUENCE: 103

Ala Leu Ser Glu Leu Glu Arg Val Leu
1               5

<210> SEQ ID NO 104
<211> LENGTH: 9
<212> TYPE: PRT
```

<213> ORGANISM: Homo sapiens

<400> SEQUENCE: 104

Ser Leu Phe Glu Ser Leu Glu Tyr Leu
1               5

<210> SEQ ID NO 105
<211> LENGTH: 9
<212> TYPE: PRT
<213> ORGANISM: Homo sapiens

<400> SEQUENCE: 105

Lys Val Leu Glu Tyr Val Ile Lys Val
1               5

<210> SEQ ID NO 106
<211> LENGTH: 10
<212> TYPE: PRT
<213> ORGANISM: Homo sapiens

<400> SEQUENCE: 106

Val Leu Leu Asn Glu Ile Leu Glu Gln Val
1               5                   10

<210> SEQ ID NO 107
<211> LENGTH: 9
<212> TYPE: PRT
<213> ORGANISM: Homo sapiens

<400> SEQUENCE: 107

Ser Leu Leu Asn Gln Pro Lys Ala Val
1               5

<210> SEQ ID NO 108
<211> LENGTH: 9
<212> TYPE: PRT
<213> ORGANISM: Homo sapiens

<400> SEQUENCE: 108

Lys Met Ser Glu Leu Gln Thr Tyr Val
1               5

<210> SEQ ID NO 109
<211> LENGTH: 11
<212> TYPE: PRT
<213> ORGANISM: Homo sapiens

<400> SEQUENCE: 109

Ala Leu Leu Glu Gln Thr Gly Asp Met Ser Leu
1               5                   10

<210> SEQ ID NO 110
<211> LENGTH: 11
<212> TYPE: PRT
<213> ORGANISM: Homo sapiens

<400> SEQUENCE: 110

Val Ile Ile Lys Gly Leu Glu Glu Ile Thr Val
1               5                   10

<210> SEQ ID NO 111
<211> LENGTH: 9
<212> TYPE: PRT
<213> ORGANISM: Homo sapiens

<400> SEQUENCE: 111

Lys Gln Phe Glu Gly Thr Val Glu Ile
1               5

<210> SEQ ID NO 112
<211> LENGTH: 9
<212> TYPE: PRT
<213> ORGANISM: Homo sapiens

<400> SEQUENCE: 112

Lys Leu Gln Glu Glu Ile Pro Val Leu
1               5

<210> SEQ ID NO 113
<211> LENGTH: 9
<212> TYPE: PRT
<213> ORGANISM: Homo sapiens

<400> SEQUENCE: 113

Gly Leu Ala Glu Phe Gln Glu Asn Val
1               5

<210> SEQ ID NO 114
<211> LENGTH: 9
<212> TYPE: PRT
<213> ORGANISM: Homo sapiens

<400> SEQUENCE: 114

Asn Val Ala Glu Ile Val Ile His Ile
1               5

<210> SEQ ID NO 115
<211> LENGTH: 9
<212> TYPE: PRT
<213> ORGANISM: Homo sapiens

<400> SEQUENCE: 115

Ala Leu Ala Gly Ile Val Thr Asn Val
1               5

<210> SEQ ID NO 116
<211> LENGTH: 12
<212> TYPE: PRT
<213> ORGANISM: Homo sapiens

<400> SEQUENCE: 116

Asn Leu Leu Ile Asp Asp Lys Gly Thr Ile Lys Leu
1               5                   10

<210> SEQ ID NO 117
<211> LENGTH: 10
<212> TYPE: PRT
<213> ORGANISM: Homo sapiens

<400> SEQUENCE: 117

Val Leu Met Gln Asp Ser Arg Leu Tyr Leu
1               5                   10

<210> SEQ ID NO 118
<211> LENGTH: 9
<212> TYPE: PRT
<213> ORGANISM: Homo sapiens

<400> SEQUENCE: 118

```
<210> SEQ ID NO 119
<211> LENGTH: 9
<212> TYPE: PRT
<213> ORGANISM: Homo sapiens

<400> SEQUENCE: 119

Leu Leu Trp Gly Asn Leu Pro Glu Ile
1               5

<210> SEQ ID NO 120
<211> LENGTH: 9
<212> TYPE: PRT
<213> ORGANISM: Homo sapiens

<400> SEQUENCE: 120

Ser Leu Met Glu Lys Asn Gln Ser Leu
1               5

<210> SEQ ID NO 121
<211> LENGTH: 9
<212> TYPE: PRT
<213> ORGANISM: Homo sapiens

<400> SEQUENCE: 121

Lys Leu Leu Ala Val Ile His Glu Leu
1               5

<210> SEQ ID NO 122
<211> LENGTH: 10
<212> TYPE: PRT
<213> ORGANISM: Homo sapiens

<400> SEQUENCE: 122

Ala Leu Gly Asp Lys Phe Leu Leu Arg Val
1               5                   10

<210> SEQ ID NO 123
<211> LENGTH: 11
<212> TYPE: PRT
<213> ORGANISM: Homo sapiens

<400> SEQUENCE: 123

Phe Leu Met Lys Asn Ser Asp Leu Tyr Gly Ala
1               5                   10

<210> SEQ ID NO 124
<211> LENGTH: 10
<212> TYPE: PRT
<213> ORGANISM: Homo sapiens

<400> SEQUENCE: 124

Lys Leu Ile Asp His Gln Gly Leu Tyr Leu
1               5                   10

<210> SEQ ID NO 125
<211> LENGTH: 12
<212> TYPE: PRT
<213> ORGANISM: Homo sapiens

<400> SEQUENCE: 125

Gly Pro Gly Ile Phe Pro Pro Pro Pro Gln Pro
1               5                   10
```

(Preceding sequence, top of page:)

```
Lys Val Leu Glu His Val Val Arg Val
1               5
```

<210> SEQ ID NO 126
<211> LENGTH: 9
<212> TYPE: PRT
<213> ORGANISM: Homo sapiens

<400> SEQUENCE: 126

Ala Leu Asn Glu Ser Leu Val Glu Cys
1               5

<210> SEQ ID NO 127
<211> LENGTH: 9
<212> TYPE: PRT
<213> ORGANISM: Homo sapiens

<400> SEQUENCE: 127

Gly Leu Ala Ala Leu Ala Val His Leu
1               5

<210> SEQ ID NO 128
<211> LENGTH: 9
<212> TYPE: PRT
<213> ORGANISM: Homo sapiens

<400> SEQUENCE: 128

Leu Leu Leu Glu Ala Val Trp His Leu
1               5

<210> SEQ ID NO 129
<211> LENGTH: 9
<212> TYPE: PRT
<213> ORGANISM: Homo sapiens

<400> SEQUENCE: 129

Ser Ile Ile Glu Tyr Leu Pro Thr Leu
1               5

<210> SEQ ID NO 130
<211> LENGTH: 9
<212> TYPE: PRT
<213> ORGANISM: Homo sapiens

<400> SEQUENCE: 130

Thr Leu His Asp Gln Val His Leu Leu
1               5

<210> SEQ ID NO 131
<211> LENGTH: 9
<212> TYPE: PRT
<213> ORGANISM: Homo sapiens

<400> SEQUENCE: 131

Ser Leu Leu Met Trp Ile Thr Gln Cys
1               5

<210> SEQ ID NO 132
<211> LENGTH: 11
<212> TYPE: PRT
<213> ORGANISM: Homo sapiens

<400> SEQUENCE: 132

Phe Leu Leu Asp Lys Pro Gln Asp Leu Ser Ile
1               5                   10

```
<210> SEQ ID NO 133
<211> LENGTH: 10
<212> TYPE: PRT
<213> ORGANISM: Homo sapiens

<400> SEQUENCE: 133

Tyr Leu Leu Asp Met Pro Leu Trp Tyr Leu
1               5                   10

<210> SEQ ID NO 134
<211> LENGTH: 9
<212> TYPE: PRT
<213> ORGANISM: Homo sapiens

<400> SEQUENCE: 134

Gly Leu Leu Asp Cys Pro Ile Phe Leu
1               5

<210> SEQ ID NO 135
<211> LENGTH: 9
<212> TYPE: PRT
<213> ORGANISM: Homo sapiens

<400> SEQUENCE: 135

Val Leu Ile Glu Tyr Asn Phe Ser Ile
1               5

<210> SEQ ID NO 136
<211> LENGTH: 11
<212> TYPE: PRT
<213> ORGANISM: Homo sapiens

<400> SEQUENCE: 136

Thr Leu Tyr Asn Pro Glu Arg Thr Ile Thr Val
1               5                   10

<210> SEQ ID NO 137
<211> LENGTH: 9
<212> TYPE: PRT
<213> ORGANISM: Homo sapiens

<400> SEQUENCE: 137

Ala Val Pro Pro Pro Pro Ser Ser Val
1               5

<210> SEQ ID NO 138
<211> LENGTH: 9
<212> TYPE: PRT
<213> ORGANISM: Homo sapiens

<400> SEQUENCE: 138

Lys Leu Gln Glu Glu Leu Asn Lys Val
1               5

<210> SEQ ID NO 139
<211> LENGTH: 11
<212> TYPE: PRT
<213> ORGANISM: Homo sapiens

<400> SEQUENCE: 139

Lys Leu Met Asp Pro Gly Ser Leu Pro Pro Leu
1               5                   10

<210> SEQ ID NO 140
<211> LENGTH: 9
```

<212> TYPE: PRT
<213> ORGANISM: Homo sapiens

<400> SEQUENCE: 140

Ala Leu Ile Val Ser Leu Pro Tyr Leu
1               5

<210> SEQ ID NO 141
<211> LENGTH: 9
<212> TYPE: PRT
<213> ORGANISM: Homo sapiens

<400> SEQUENCE: 141

Phe Leu Leu Asp Gly Ser Ala Asn Val
1               5

<210> SEQ ID NO 142
<211> LENGTH: 10
<212> TYPE: PRT
<213> ORGANISM: Homo sapiens

<400> SEQUENCE: 142

Ala Leu Asp Pro Ser Gly Asn Gln Leu Ile
1               5                   10

<210> SEQ ID NO 143
<211> LENGTH: 9
<212> TYPE: PRT
<213> ORGANISM: Homo sapiens

<400> SEQUENCE: 143

Ile Leu Ile Lys His Leu Val Lys Val
1               5

<210> SEQ ID NO 144
<211> LENGTH: 9
<212> TYPE: PRT
<213> ORGANISM: Homo sapiens

<400> SEQUENCE: 144

Val Leu Leu Asp Thr Ile Leu Gln Leu
1               5

<210> SEQ ID NO 145
<211> LENGTH: 9
<212> TYPE: PRT
<213> ORGANISM: Homo sapiens

<400> SEQUENCE: 145

His Leu Ile Ala Glu Ile His Thr Ala
1               5

<210> SEQ ID NO 146
<211> LENGTH: 9
<212> TYPE: PRT
<213> ORGANISM: Homo sapiens

<400> SEQUENCE: 146

Ser Met Asn Gly Gly Val Phe Ala Val
1               5

<210> SEQ ID NO 147
<211> LENGTH: 9
<212> TYPE: PRT
<213> ORGANISM: Homo sapiens

<400> SEQUENCE: 147

Met Leu Ala Glu Lys Leu Leu Gln Ala
1               5

<210> SEQ ID NO 148
<211> LENGTH: 9
<212> TYPE: PRT
<213> ORGANISM: Homo sapiens

<400> SEQUENCE: 148

Tyr Met Leu Asp Ile Phe His Glu Val
1               5

<210> SEQ ID NO 149
<211> LENGTH: 11
<212> TYPE: PRT
<213> ORGANISM: Homo sapiens

<400> SEQUENCE: 149

Ala Leu Trp Leu Pro Thr Asp Ser Ala Thr Val
1               5                   10

<210> SEQ ID NO 150
<211> LENGTH: 9
<212> TYPE: PRT
<213> ORGANISM: Homo sapiens

<400> SEQUENCE: 150

Gly Leu Ala Ser Arg Ile Leu Asp Ala
1               5

<210> SEQ ID NO 151
<211> LENGTH: 9
<212> TYPE: PRT
<213> ORGANISM: Homo sapiens

<400> SEQUENCE: 151

Ala Leu Ser Val Leu Arg Leu Ala Leu
1               5

<210> SEQ ID NO 152
<211> LENGTH: 9
<212> TYPE: PRT
<213> ORGANISM: Homo sapiens

<400> SEQUENCE: 152

Ser Tyr Val Lys Val Leu His His Leu
1               5

<210> SEQ ID NO 153
<211> LENGTH: 9
<212> TYPE: PRT
<213> ORGANISM: Homo sapiens

<400> SEQUENCE: 153

Val Tyr Leu Pro Lys Ile Pro Ser Trp
1               5

<210> SEQ ID NO 154
<211> LENGTH: 9
<212> TYPE: PRT
<213> ORGANISM: Homo sapiens

<400> SEQUENCE: 154

Asn Tyr Glu Asp His Phe Pro Leu Leu
1               5

<210> SEQ ID NO 155
<211> LENGTH: 9
<212> TYPE: PRT
<213> ORGANISM: Homo sapiens

<400> SEQUENCE: 155

Val Tyr Ile Ala Glu Leu Glu Lys Ile
1               5

<210> SEQ ID NO 156
<211> LENGTH: 12
<212> TYPE: PRT
<213> ORGANISM: Homo sapiens

<400> SEQUENCE: 156

Val His Phe Glu Asp Thr Gly Lys Thr Leu Leu Phe
1               5                   10

<210> SEQ ID NO 157
<211> LENGTH: 9
<212> TYPE: PRT
<213> ORGANISM: Homo sapiens

<400> SEQUENCE: 157

Val Leu Ser Pro Phe Ile Leu Thr Leu
1               5

<210> SEQ ID NO 158
<211> LENGTH: 9
<212> TYPE: PRT
<213> ORGANISM: Homo sapiens

<400> SEQUENCE: 158

His Leu Leu Glu Gly Ser Val Gly Val
1               5

<210> SEQ ID NO 159
<211> LENGTH: 9
<212> TYPE: PRT
<213> ORGANISM: Homo sapiens

<400> SEQUENCE: 159

Ala Leu Arg Glu Glu Glu Glu Gly Val
1               5

<210> SEQ ID NO 160
<211> LENGTH: 10
<212> TYPE: PRT
<213> ORGANISM: Homo sapiens

<400> SEQUENCE: 160

Lys Glu Ala Asp Pro Thr Gly His Ser Tyr
1               5                   10

<210> SEQ ID NO 161
<211> LENGTH: 9
<212> TYPE: PRT
<213> ORGANISM: Homo sapiens

```
<400> SEQUENCE: 161

Thr Leu Asp Glu Lys Val Ala Glu Leu
1               5
```

METHODS FOR MANUFACTURING T CELLS BY DIRECT SORTING AND COMPOSITIONS THEREOF

CROSS-REFERENCE TO RELATED APPLICATIONS

This U.S. Patent Application claims the benefit of U.S. Provisional Patent Application No. 62/858,167, filed Jun. 6, 2019, and German Patent Application No. DE 102019129341.3, filed Oct. 30, 2019, the contents of each of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "3000011-012001_SEQLIST_ST25.txt", created on Jun. 4, 2020, and having a size of 25,152 bytes and is filed concurrently with the specification. The sequence listing contained in this ASCII formatted document is part of the specification and is herein incorporated by reference in its entirety.

FIELD

The present disclosure generally relates to methods of manufacturing T cells for adoptive immunotherapy. The disclosure further provides for methods of using T cells, and T cell populations thereof.

BACKGROUND

Adoptive T cell therapy (ACT) creates a productive immune response in hosts. T cells may be harvested from a patient's blood or tumor, then stimulated to grow and expand in an in vitro culture system. After sufficient in vitro expansion, these cells may be reinfused into hosts, where they will ideally mediate tumor destruction. Thus, this process is applicable to the vast majority of cancer patients that do not seem to possess a productive anti-cancer response prior to intervention.

In vitro methods employing various forms of antigen and stimulator cells as antigen-presenting cells (APC) have been shown to be effective at expanding ex vivo memory T cells, e.g., viral-specific, that have been primed in the host by previous in vivo exposure to the antigen.

Ho et al. (*J Immunol Methods* 2006; 31040-52) teach that tumor-specific CD8+ T cell clones may be generated in vitro from repeated antigen-specific stimulation of patient-derived (autologous) or donor-derived (allogeneic) T cells by monocyte-derived dendritic cells (DC) and that successful expansion of the Wilms tumor antigen 1 (WT1) peptide-specific CD8+ T cells appear to be more dependent upon cell culture conditions. Ho et al., however, does not teach generation of tumor-specific CD8+ T cell clones by expanding T cells that were not activated or stimulated prior to expansion.

Chapuis et al. (*Sci Transl Med* 2013; 5:174ra27) disclose the use of allogeneic CD8+ T cells with activity against WT1 in leukemia patients who relapsed after allogeneic hematopoietic stem cell transplantation. Clones may be generated by leukapheresis of human leukocyte antigen (HLA)-matched donor cells and repeated stimulation with peptide-pulsed, autologous APCs, e.g., dendritic cells, over several months. Adoptively transferred lymphocytes remained detectable in patient blood long-term, and transient responses were observed in 2/11 of these high relapse-risk patients, with stable disease observed in 3 others. Chapuis et al., however, does not teach generation of WT1-specific CD8+ T cell clones by expanding T cells that were not activated or stimulated prior to expansion.

There is a need for simple, efficient, and cost-effective methods of manufacturing T cells for ACT. A solution to this technical problem is provided herein.

BRIEF SUMMARY

In an aspect, the present disclosure relates to methods for preparing T cells, including isolating CD8+ T cells from a blood sample obtained from a patient or a donor, culturing the isolated CD8+ T cells in the presence of at least one cytokine, contacting the cultured CD8+ T cells with a multimer containing a target peptide in a complex with an MHC molecule and with at least one binding agent that binds to a T cell surface molecule, in which the multimer is labelled with a first detectable agent and the binding agent is labelled with a second detectable agent, in which the first detectable agent is detectably different from the second detectable agent, sorting the contacted CD8+ T cells to collect the sorted CD8+ T cells that are detected positive for the first and the second detectable agents, and expanding the collected CD8+ T cells.

In another aspect, the multimer may be HLA-complex, molecule, or peptide sequence containing a target peptide of interest in a monovalent or multivalent fashion.

In another aspect, the contacting may be performed in the presence of a multimer containing an irrelevant peptide in a complex with an MHC molecule.

In another aspect, the culturing the isolated CD8+ T cells may be in the absence of a T cell activation agent so that the isolated CD8+ T cells are not activated.

In another aspect, the contacting the cultured CD8+ T cells may be in the presence of the multimers and in the absence of the binding agents.

In another aspect, the at least one binding agent may be an antibody.

In another aspect, the binding agent may be a multimer, e.g., a dextramer.

In another aspect, the method may further include sorting the collected CD8+ T cells to obtain the collected CD8+ T cells that are detected positive for the first and the second detectable agents prior to the expanding.

In another aspect, the blood sample may be peripheral blood mononuclear cell (PBMC) or a product of leukapheresis.

In another aspect, the blood sample may be obtained from a patient.

In another aspect, the blood sample may be obtained from a donor.

In another aspect, the at least one cytokine may be selected from interleukin (IL)-1, IL-2, IL-6, IL-7, IL-10, IL-12, IL-15, IL-17, IL-21, and IL-23.

In another aspect, the multimer may be a tetramer.

In another aspect, the MHC molecule may be a class I MHC molecule.

In another aspect, the first and the second detectable agents each may include a fluorescent compound.

In another aspect, the T cell surface molecule may include a $T_{NAIVE}$ cell surface marker.

In another aspect, the $T_{NAIVE}$ cell surface marker may be selected from CD45, CD197, CD28, CD27, IL-7 receptor (IL-7Rα), CD57, CD95, CD127, and CD62L.

In another aspect, sorting may be performed by using any cell sorters, e.g., BD FACS® sorter.

In another aspect, the expanding may be performed in the presence of at least one cytokine.

In another aspect, the sorting, the collecting, and the expanding may be performed in a closed system.

In another aspect, the closed system may include Clini-MACS Prodigy™, WAVE (XURI™) Bioreactor, WAVE (XURI™) Bioreactor in combination with BioSafe Sepax™ II, G-Rex/GatheRex™ closed system, or G-Rex/GatheRex™ closed system in combination with BioSafe Sepax™ II.

In an aspect, the present disclosure relates to methods for preparing T cells, including isolating CD8+ T cells from a blood sample obtained from a patient or a donor, culturing the isolated CD8+ cells in the presence of at least one cytokine, contacting the cultured CD8+ T cells with a first multimer containing the peptide in a complex with an MHC molecule, a first binding agent that binds to a T cell surface molecule, a second multimer containing an irrelevant peptide, which is different from the peptide contained in the first multimer, in a complex with an MHC molecule, and a second binding agent that binds to the first multimer, in which the first multimer may be labelled with a first detectable agent and the first binding agent is labelled with a second detectable agent, in which the second multimer may be labelled with a third detectable agent, in which the first, the second, and the third detectable agents may be detectably different detectable agents, sorting the contacted CD8+ T cells to collect the sorted CD8+ T cells that are detected positive for the first and the second detectable agents and are detected negative for the third detectable agent, and expanding the collected CD8+ T cells.

In another aspect, the second binding agent binds to the first detectable agent.

In another aspect, the first detectable agent comprises at least two fluorochromes.

In another aspect, the contacting may be performed in the presence of an protein kinase inhibitor (PKI).

In another aspect, the PKI may be selected from afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, or vemurafenib.

In another aspect, the exclusion of a T cell activation agent may include exclusion of an antigen presenting cell.

In another aspect, the exclusion of a T cell activation agent may include exclusion of an anti-CD3 antibody and anti-CD28 antibody.

In an aspect, the present disclosure relates to compositions containing the peptide-specific T cells prepared by the method of the present disclosure.

In another aspect, the compositions may further contain an adjuvant.

In another aspect, the adjuvant may be selected from anti-CD40 antibody, imiquimod, resiquimod, GM-CSF, cyclophosphamide, interferon-alpha, interferon-beta, CpG oligonucleotides, poly-(I:C), RNA, sildenafil, particulate formulations with poly(lactide co-glycolide) (PLG), virosomes, IL-1, IL-2, IL-4, IL-6, IL-7, IL-12, IL-13, IL-15, IL-21, and IL-23.

In an aspect, the present disclosure relates to methods of treating a patient who has cancer, including administering to said patient the composition of the present disclosure, in which said cancer may be selected from hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer (BRCA), chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), and uterine cancer (UEC).

In another aspect, the contacting may be performed in the presence of a PKI at a concentration from about 1 nM to about 1000 nM, from about 1 nM to about 900 nM, from about 1 nM to about 800 nM, from about 1 nM to about 700 nM, from about 1 nM to about 600 nM, from about 1 nM to about 500 nM, from about 1 nM to about 400 nM, from about 1 nM to about 300 nM, from about 1 nM to about 200 nM, from about 1 nM to about 100 nM, from about 5 nM to about 100 nM, from about 10 nM to about 100 nM, from about 20 nM to about 100 nM, from about 30 nM to about 100 nM, from about 40 nM to about 100 nM, from about 50 nM to about 100 nM, from about 60 nM to about 100 nM, from about 70 nM to about 100 nM, from about 10 nM to about 250 nM, about 20 nM to about 200 nM, about 30 nm to about 150 nm, or about 50 n<to about 120 nM.

In another aspect, the present disclosure relates to methods for preparing T cells, including isolating CD8+ T cells from a blood sample obtained from a patient or a donor, culturing the isolated CD8+ T cells in the presence of at least one cytokine, contacting the cultured CD8+ T cells with a first multimer comprising a target peptide in a complex with an MHC molecule and a second multimer comprising an irrelevant peptide in a complex with an MHC molecule, in which the first multimer is labelled with a first detectable agent and the second multimer is labelled with a second detectable agent, in which the first detectable agent is detectably different from the second detectable agent, sorting the contacted CD8+ T cells to collect sorted CD8+ T cells that are detected positive for the first detectable agent and detected negative for the second detectable agents, and expanding the collected CD8+ T cells.

In an aspect, the present disclosure relates to methods for preparing T cells, including culturing CD8+ T cells in the presence of at least one cytokine, contacting the cultured CD8+ T cells with a multimer containing a target peptide in a complex with an MHC molecule and with at least one binding agent that binds to a T cell surface molecule, in which the multimer is labelled with a first detectable agent and the binding agent is labelled with a second detectable agent, in which the first detectable agent is detectably different from the second detectable agent, sorting the contacted CD8+ T cells to collect the sorted CD8+ T cells that are detected positive for the first and the second detectable agents, and expanding the collected CD8+ T cells.

In another aspect, the present disclosure relates to methods for preparing T cells, contacting a blood sample with a first multimer comprising a target peptide in a complex with an MHC molecule, wherein the first multimer is labelled with a first detectable agent, and a second multimer comprising an irrelevant peptide, which is different from the target peptide, in a complex with an MHC molecule, wherein the second multimer is labelled with a second detectable agent, in which the first and the second detectable agents are detectably different detectable agents, sorting the contacted cells to collect the sorted cells that are detected positive for the first detectable agent and are detected negative for the second detectable agent, and expanding the collected T cells.

In another aspect, the contacting may be performed in the presence of a first binding agent binding to the first detectable agent and/or a second binding agent binding to the second detectable agent.

In another aspect, the first binding agent and the second binding agent may be antibodies.

In another aspect, the contacting may be performed at about 4° C., room temperature, about 37° C., about 2° C. to about 8° C., about 18° C. to about 26° C., or about 32° C. to about 38° C.

In another aspect, the irrelevant peptide may be at least one selected from the group consisting of SEQ ID NO: 1-161.

In another aspect, the contacting may be performed in the presence of a third multimer containing a target peptide in a complex with an MHC molecule, in which the third multimer is labelled with a third detectable agent, in which the third detectable agent may be detectably different from the first and the second detectable agents, and in which the sorting comprises collecting the sorted CD8+ T cells that are detected positive for the first and the third detectable agents and detected negative for the second detectable agents.

In another aspect, the multimers may be filtered through a filter prior to use in the contacting.

In another aspect, the blood sample may contain cells at a concentration from about $0.1 \times 10^6$ cells/ml to about $1000 \times 10^6$ cells/ml, from about $1 \times 10^6$ cells/ml to about $900 \times 10^6$ cells/ml, from about $5 \times 10^6$ cells/ml to about $800 \times 10^6$ cells/ml, from about $10 \times 10^6$ cells/ml to about $700 \times 10^6$ cells/ml, from about $20 \times 10^6$ cells/ml to about $600 \times 10^6$ cells/ml, from about $25 \times 10^6$ cells/ml to about $500 \times 10^6$ cells/ml, from about $30 \times 10^6$ cells/ml to about $400 \times 10^6$ cells/ml, from about $35 \times 10^6$ cells/ml to about $300 \times 10^6$ cells/ml, from about $40 \times 10^6$ cells/ml to about $200 \times 10^6$ cells/ml, from about $45 \times 10^6$ cells/ml to about $150 \times 10^6$ cells/ml, from about $50 \times 10^6$ cells/ml to about $100 \times 10^6$ cells/ml, from about $55 \times 10^6$ cells/ml to about $100 \times 10^6$ cells/ml, from about $60 \times 10^6$ cells/ml to about $100 \times 10^6$ cells/ml, from about $65 \times 10^6$ cells/ml to about $100 \times 10^6$ cells/ml, from about $70 \times 10^6$ cells/ml to about $100 \times 10^6$ cells/ml, from about $75 \times 10^6$ cells/ml to about $100 \times 10^6$ cells/ml, from about $80 \times 10^6$ cells/ml to about $100 \times 10^6$ cells/ml, from about $85 \times 10^6$ cells/ml to about $100 \times 10^6$ cells/ml, from about $90 \times 10^6$ cells/ml to about $100 \times 10^6$ cells/ml, or from about $95 \times 10^6$ cells/ml to about $100 \times 10^6$ cells/ml.

BRIEF DESCRIPTION OF THE DRAWINGS

FIG. 15A shows, post REP1, cell count, viability, and fold expansion of MLA and MAGEA1 direct sorted T cells.

FIG. 15B shows, post REP2, cell count, viability, and fold expansion of MLA and MAGEA1 direct sorted T cells.

FIG. 18B shows the flow cytometry data of MLA post REP2 in FIGS. 16B and 17B.

FIG. 19B shows the flow cytometry data of Ag001-002 post REP2.

FIG. 24B shows the flow cytometry data using single staining tetramers in accordance with another embodiment of the present disclosure.

FIG. 25A shows the flow cytometry data using single staining tetramers and anti-fluorochrome antibody in accordance with one embodiment of the present disclosure.

FIG. 25B shows the flow cytometry data using single staining tetramers and anti-fluorochrome antibody in accordance with another embodiment of the present disclosure.

FIG. 25C shows the flow cytometry data using double staining tetramers and anti-fluorochrome antibodies in accordance with one embodiment of the present disclosure.

FIG. 25D shows the flow cytometry data using double staining tetramers and anti-fluorochrome antibody in accordance with another embodiment of the present disclosure.

FIG. 25E shows the flow cytometry data of control cells stained with double staining tetramers and anti-fluorochrome antibodies.

FIG. 31A shows the flow cytometry data obtained from staining conditions in accordance with some embodiments of the present disclosure.

FIG. 31B shows the flow cytometry data obtained from staining conditions in accordance with some embodiments of the present disclosure.

FIG. 33B shows the flow cytometry data obtained from staining conditions in accordance with some embodiments of the present disclosure.

FIG. 34A shows the flow cytometry data obtained from staining condition in accordance with one embodiment of the present disclosure.

DETAILED DESCRIPTION

Figure 1:
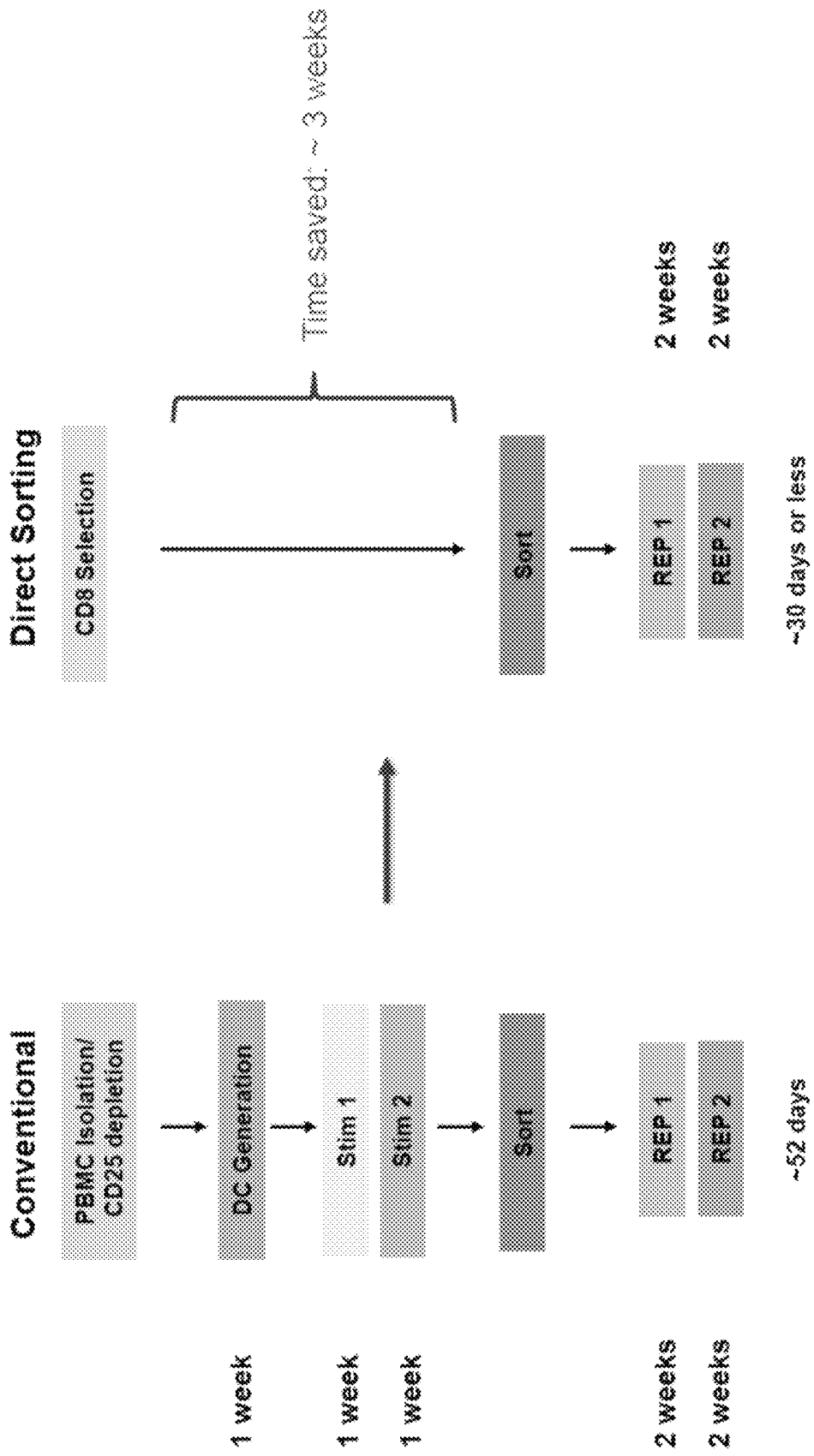
FIG. 1 shows a comparison between conventional T cell manufacturing process and direct sorting T cell manufacturing in accordance with one embodiment of the present disclosure.

Adoptive cellular therapy (ACT) is the transfer of cells into a patient and is a personalized, multi-targeted ACT approach in which T-cell products may be manufactured against relevant tumor target peptide antigens for patients whose tumors are positive against at least one target selected from a panel of tumor antigens associated with the particular tumor type and/or the individual patient's tumor profile. See, for example, Table 1 herein.

ACT for the treatment or prevention of disease may be performed by administering cells that have been selected, manipulated, or altered outside the body. As more cell-based therapeutic products progress into clinical trials and commercialization, developing bioprocesses compliant with current good manufacturing practices (CGMP) has been challenging. This may be because the final products are not traditional biological (secreted) molecules, such as monoclonal antibodies, but rather the cells themselves. As such, one focus has been on cell isolation, because of the importance of cell purity and the special considerations related to protocol compliance to CGMP regulations.

The general steps for conventional manufacturing of a cell-based product, e.g., T cells, may include harvesting, debulking, and isolation, ex vivo manipulation, e.g., activation, expansion, and/or genetic modification, and cryopreservation. A number of methods may be used for generating T cells in vitro. For example, autologous tumor-infiltrating lymphocytes can be used in the generation of cytotoxic T cells (CTL). Plebanski et al. (*Eur. J Immunol* 25 (1995):1783-1787), the contents of which are herein incorporated by reference in their entirety, made use of autologous peripheral blood lymphocytes (PBLs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (*J Immunol* 171 (2003): 4974-4978), the contents of which are herein incorporated by reference in their entirety, describe the in vitro priming of T cells by using artificial antigen presenting cells (aAPCs), which is also a suitable way for generating T cells against the peptide of choice. For example, aAPCs may be generated by the coupling of preformed MHC:peptide complexes to the surface of polystyrene particles (microbeads) by biotin:streptavidin biochemistry. This system may permit the exact control of the MHC density on aAPCs, which allows selective elicitation of high- or low-avidity antigen-specific T cell responses with high efficiency from blood samples. Apart from MHC:peptide complexes, aAPCs may carry other proteins with co-stimulatory activity like anti-CD28 antibodies coupled to their surface. Furthermore, such aAPC-based systems may include appropriate soluble factors, e.g., cytokines, like interleukin-12.

FIG. 1 (left flowchart) shows a conventional process for T cell manufacturing that may include PBMC isolation and CD25 depletion, followed by (1) dendritic cell (DC) generation for a week, (2) a first stimulation (Stim 1) of T cells by DC for a week, (3) re-stimulation (Stim 2) of Stim 1 T cells by DC for a week, (4) sorting the stimulated cells, (5) expanding the sorted cells by a first "rapid expansion protocol" (REP1) for 2 weeks, and (6) expanding the REP1-expanded T cells for 2 weeks (REP2).

The present disclosure provides for improved methods of generating T cell products. FIG. 1 (right flowchart) shows one embodiment of the direct process for T cell manufacturing that may include CD8+ T cell isolation, stimulating the isolated CD8+ T cells followed by (1) sorting the stimulated cells, (2) expanding the sorted cells by a first "rapid expansion protocol" (REP1) for 2 weeks, and (3) expanding the REP1-expanded T cells for 2 weeks (REP2). Alternatively, the sorted T cells may be expanded by stimulation of T-cells with agnostic antibodies, e.g., anti-CD3 antibody and anti-CD28 antibody, or artificial antigen presenting cells.

In one aspect, direct sorting processes described herein provide for viable T cell generation in significantly less time than conventional processes. For example, FIG. 1 shows the conventional process may take from about 50 days to about 55 days, e.g., about 52 days, to complete, whereas the direct sorting may take 30 days or less to complete, e.g., from about 7 days to about 14 days, from about 7 days to about 21 days, from about 7 days to about 28 days, from about 14 days to about 21 days, from about 14 days to about 28 days, or from about 21 days to about 28 days, about 30 days or less to complete, or about 16 days or less to complete, e.g., only one run of REP.

In another aspect, the direct sorting processes may include CD8+ T cell isolation. CD8+ T cells may be isolated from normal tissues, diseased tissues, e.g., tumors, whole blood, PBMCs, leukapheresis products, and/or tumor-infiltrating lymphocytes (TIL) obtained from patients to be treated, or from healthy donors.

In another aspect, the purity of CD8+ T cells may be at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another aspect, the direct sorting processes may be carried out using PBMCs as starting materials, e.g., without CD8+ cell isolation.

In another aspect, the isolated CD8+ T cells may be rested in tissue culture in the presence or absence of cytokines. As used herein, a resting T cell means a T cell that is not dividing or producing cytokines. Resting T cells are small (approximately 6-8 microns) in size compared to activated T cells (approximately 12-15 microns).

In an aspect, the isolated CD8+ T cells that have not been previously activated in vitro may be rested in the presence or in the absence of cytokines. Resting may be carried out within a period of from about 0.5 hours to about 120 hours, about 0.5 hours to about 108 hours, about 0.5 hours to about 96 hours, about 0.5 hours to about 84 hours, about 0.5 hours to about 72 hours, about 0.5 hours to about 60 hours, about 0.5 hours to about 48 hours, about 0.5 hours to about 36 hours, about 12 hours to about 96 hours, about 24 to 72 hours, about 12 to about 60 hours, about 0.5 hours to about 24 hours, about 0.5 hours to about 18 hours, about 0.5 hours to about 12 hours, about 0.5 hours to about 6 hours, about 1 hour to about 24 hours, about 1 hours to about 12 hours, about 2 to about 8 hours, about 3 hours to about 6 hours, or about 1 hours to about 5 hours.

In another aspect, resting may be in the absence of cytokines or in the presence of cytokines, e.g., IL-2, IL-7, IL-10, IL-12, IL-15, IL-21, or a combination thereof, such as IL-7 or IL-7+IL-15, for from about 0.5 hours to about 48 hours, about 0.5 hours to about 36 hours, about 0.5 hours to about 24 hours, about 0.5 hours to about 18 hours, about 0.5 hours to about 12 hours, about 0.5 hours to about 6 hours, about 1 hour to about 6 hours, about 2 hours to about 5 hours, about 3 hours to about 5 hours, about 4 hours to 6 hours, about 1 hour to about 24 hours, about 2 to about 24 hours, about 12 to about 48 hours, about 0.5 hours to about 120 hours, about 0.5 hours to about 108 hours, about 0.5 hours to about 96 hours, about 0.5 hours to about 84 hours, about 0.5 hours to about 72 hours, or about 0.5 hours to about 60 hours, about 4 to about 6 hours, about 12 hours to about 96 hours, about 24 to 72 hours, about 12 to about 60 hours, about 0.5 hours to about 24 hours, about 0.5 hours to about 18 hours, about 0.5 hours to about 12 hours, about 0.5 hours to about 6 hours, about 1 hour to about 24 hours, about 1 hours to about 12 hours, or about 2 to about 8 hours.

In an aspect, direct sorting processes does not include activating the isolated CD8+ T cells prior to sorting. For example, the isolated CD8+ T cells may not be activated via signal 1 by peptide-pulsed DC or peptide-specific aAPC; and/or signal 2 by agonists for CD3 (e.g., anti-CD3 antibody), CD28 (e.g., or anti-CD28 antibody), OX40 (CD134), ICOS (CD278), and/or 4-1BBL (CD137).

Cell Sorting

The present invention encompasses a more efficient way of isolating CD8+ T cells utilizing cell sorting technologies. Cell sorting based on surface markers may be carried out by one or more technologies including, but not limited to, fluorescence-activated cell sorting (FACS), magnetically activated cell sorting (MACS), panning, resetting, and the like, which typically employ antibodies or other reagents that specifically recognize and bind to the cell surface features of interest. Cell sorting based on intracellular markers may be carried out using FACS by fixing and permeabilizing cells, followed by staining, e.g., with a labelled antibody specific for the intracellular marker. Lymphocytes may be sorted into subsets of interest using FACS, e.g., using a commercially available instrument and manufacturer's protocols and kits, such as a BD Biosciences FACS Aria III or a BD Biosciences Influx (BD Biosciences, San Jose, Calif.). Sorting or isolating lymphocytes based on antigen-specificity of either T cell receptors or B cell receptors may be carried out using FACS, or FACS in combination with other technologies, such as MACS. Cell sorters, such as the FACS Aria (BD), use pressure pumps with complicated fluidic lines not meant to be disposable for every experiment. Users of these cell sorters may perform rigorous washing steps in between experiments to avoid cross contamination.

Cell sorting may also be performed using microchips. Cell sorting on microchips provides numerous advantages over conventional methods by reducing the size of the necessary equipment, eliminating potentially biohazardous aerosols, and simplifying the complex protocols commonly associated with cell sorting. Additionally, microchip devices may be well suited for parallelization, enabling complete lab-on-a-chip devices for cellular isolation, analysis, and experimental processing.

In one aspect, the isolated CD8+ T cells may be labelled with peptide/MHC multimer, e.g., tetramer, tagged with detectable agents, e.g., fluorophores, for subsequent sorting using multi-parameter sorting using microchip-based cell sorters, e.g., MACSQuant® Tyto® Cell Sorter (Miltenyi Biotec) and On-Chip Sort (On-chip Biotechnologies), which may use pressure or syringe pumps to have a consistent flow rate for sorting. Microchip-based cell sorters are generally easy to use benchtop sorters utilizing a fully closed and sterile cartridge system. As such, the chip sorting is very gentle on the cells, allowing for multiple sequential sorts without the loss of viability.

In an aspect, the direct sorting processes may produce peptide tetramer-positive T cells at post sorting prior to expansion containing at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of precursor $T_{NAIVE}$.

In an aspect, the direct sorting processes may produce a similar percentage of precursor $T_{NAIVE}$ cells as post purity sort prior to expansion to the final products generated by the conventional processes.

In one aspect, the sorted T cells obtained by direct sorting may be expanded using at least one round of "rapid expansion protocol" (REP). The term "rapid expansion protocol" (REP) used herein refers to clonal populations of T cells, e.g., TILs and CD8+ T cells, expanded in vitro using the REP protocol as previously described in Riddell et al. (*J. Immunol. Methods* 128, 189; the content of which is incorporated by reference in its entirety). For example, approximately $5 \times 10^4$ CD8+ T cells (or a single cell colony from a 96-well cloning plate) may be added to a T25 tissue culture flask containing 25 ml of cloning mix consisting of CTL medium with $5 \times 10^6$ irradiated TM-LCL, $25 \times 10^6$ irradiated allogeneic PBMC, 30 ng/ml OKT3 and 50 IU/ml IL-2. Cultures may be harvested and resuspended in an equal volume of fresh CTL medium supplemented with 50 IU/ml IL-2 after 4 days of culture. Cultures may be fed by replacing half of the volume of the media every 3-4 days with fresh CTL media and IL-2 to a final concentration of 50 IU/ml. Cells may be harvested for analysis by multimer staining or chromium release assay after day 12 of culture.

In an aspect, the sorted T cells may be expanded in the presence of cytokines, such as IL-2, IL-7, IL-12, IL-15, and/or IL-21.

In an aspect, the concentration of IL-2 may be from about 10 IU/ml to 1000 IU/ml, about 20 IU/ml to 900 IU/ml, about 30 IU/ml to 800 IU/ml, about 40 IU/ml to 700 IU/ml, about 50 IU/ml to 600 IU/ml, about 50 IU/ml to 550 IU/ml, about 50 IU/ml to 500 IU/ml, about 50 IU/ml to 450 IU/ml, about 50 IU/ml to 400 IU/ml, about 50 IU/ml to 350 IU/ml, about 50 IU/ml to 300 IU/ml, about 50 IU/ml to 250 IU/ml, about 50 IU/ml to 200 IU/ml, about 50 IU/ml to 150 IU/ml, or about 50 IU/ml to 100 IU/ml.

In another aspect, the concentration of IL-7 may be from about 1 ng/ml to 100 ng/ml, about 1 ng/ml to 90 ng/ml, about 1 ng/ml to 80 ng/ml, about 1 ng/ml to 70 ng/ml, about 1 ng/ml to 60 ng/ml, about 1 ng/ml to 50 ng/ml, about 1 ng/ml to 40 ng/ml, about 1 ng/ml to 30 ng/ml, about 1 ng/ml to 20 ng/ml, about 1 ng/ml to 15 ng/ml, about 1 ng/ml to 10 ng/ml, about 2 ng/ml to 10 ng/ml, about 4 ng/ml to 10 ng/ml, about 6 ng/ml to 10 ng/ml, or about 5 ng/ml to 10 ng/ml.

In another aspect, the concentration of IL-12 may be from about 1 ng/ml to 100 ng/ml, about 1 ng/ml to 90 ng/ml, about 1 ng/ml to 80 ng/ml, about 1 ng/ml to 70 ng/ml, about 1 ng/ml to 60 ng/ml, about 1 ng/ml to 50 ng/ml, about 1 ng/ml to 40 ng/ml, about 1 ng/ml to 30 ng/ml, about 1 ng/ml to 20 ng/ml, about 1 ng/ml to 15 ng/ml, about 1 ng/ml to 10 ng/ml, about 2 ng/ml to 10 ng/ml, about 4 ng/ml to 10 ng/ml, about 6 ng/ml to 10 ng/ml, or about 5 ng/ml to 10 ng/ml.

In an aspect, the concentration of IL-15 may be from about 5 ng/ml to 500 ng/ml, about 5 ng/ml to 400 ng/ml, about 5 ng/ml to 300 ng/ml, about 5 ng/ml to 200 ng/ml, about 5 ng/ml to 150 ng/ml, about 5 ng/ml to 100 ng/ml, about 10 ng/ml to 100 ng/ml, about 20 ng/ml to 100 ng/ml, about 30 ng/ml to 100 ng/ml, about 40 ng/ml to 100 ng/ml, about 50 ng/ml to 100 ng/ml, about 60 ng/ml to 100 ng/ml, about 70 ng/ml to 100 ng/ml, about 80 ng/ml to 100 ng/ml, about 90 ng/ml to 100 ng/ml, about 1 ng/ml to 50 ng/ml, about 5 ng/ml to 50 ng/ml, about 10 ng/ml to 50 ng/ml, or about 20 ng/ml to 50 ng/ml.

In an aspect, the concentration of IL-21 may be from about 5 ng/ml to 500 ng/ml, about 5 ng/ml to 400 ng/ml, about 5 ng/ml to 300 ng/ml, about 5 ng/ml to 200 ng/ml, about 5 ng/ml to 150 ng/ml, about 5 ng/ml to 100 ng/ml, about 10 ng/ml to 100 ng/ml, about 20 ng/ml to 100 ng/ml, about 30 ng/ml to 100 ng/ml, about 40 ng/ml to 100 ng/ml, about 50 ng/ml to 100 ng/ml, about 60 ng/ml to 100 ng/ml, about 70 ng/ml to 100 ng/ml, about 80 ng/ml to 100 ng/ml, about 90 ng/ml to 100 ng/ml, about 1 ng/ml to 50 ng/ml, about 5 ng/ml to 50 ng/ml, about 10 ng/ml to 50 ng/ml, or about 20 ng/ml to 50 ng/ml.

In an aspect, the direct sorting processes may produce T cells at post expansion containing at least 20%, at least 30%, at least 40%, at least 50%, at least 55%, at least 60%, at least 65%, at least 70%, at least 75%, at least 80%, at least 85%, at least 90%, or at least 95% of cell viability.

In an aspect, the direct sorting processes may produce T cells at post expansion achieving at least 50-fold, 100-fold, 150-fold, 200-fold, 500-fold, 1000-fold, 2000-fold, 3000-fold, 4000-fold, 5000-fold, 6000-fold, 7000-fold, 8000-fold, 9000-fold, or 10000-fold expansion.

Advantages of the present disclosure may include (1) microchip-based sorting having very gentle effect on the cells, allowing for multiple sequential sorts without the loss of viability, (2) high-speed cartridges capable of sorting at about 8 ml/hour (about twice the speed of the standard cartridge), (3) a series of sorts with cell concentrations ranging from $2 \times 10^7$ cells/ml to $4 \times 10^7$ cells/ml followed by a rapid sort for purity, yielding high purity antigen specific T cells against multiple targets, (4) rapid expansion of the sorted cells to high cell numbers in the presence of cytokines and feeder cells producing antigen specific T cells phenotypically similar to those generated using conventional stimulation with APCs, (5) the initial CD8+ T cell selection+ tetramer sort, minimizing expansion of contaminating CD4+ T cells maintaining purity of the product throughout the rapid expansion phase, (6) the shortened process of the present disclosure requiring nearly 50% less time to manufacture T cell products and not limited by the availability of APCs or to the number of tumor targets for which a product can be generated, (7) the process capable of being easily translated to a closed system for manufacturing under CGMP, using clinical grade automated CD8 selection, a fully closed sorting cartridge, followed by any choice of closed system expansion technology, and (8) a method for preparation of target-peptide selective T-cells providing T-cells highly specific to their desired target peptide with a decreased cross-reactivity against the peptides having similar (but not identical) sequences to the desired target peptide.

In conventional processes for isolating and selecting tumor-specific T cells, the isolated cells undergo T cell activation. The use of anti-CD3/CD28, for example, provides the activation signal for the T cell population. T cells may require at least two signals for activation. Signal one (signal-1) is antigen specific and is elicited by peptide/major histocompatibility complex (MHC) complexes presented by antigen-presenting cells (APC) and received through the T-cell receptor (TCR)/CD3 complex. Signal two (signal-2) (which is antigen non-specific) is also delivered by antigen presenting cells and one of the candidate molecules for its receptor is the T cell antigen CD28. It is thought that when both the TCR/CD3 and CD28 T cell receptors are occupied by appropriate ligands, T cells are stimulated to proliferate and produce IL-2 (a cytokine essential for T cell proliferation), whereas occupation of the T cell receptor alone favors T cell anergy or apoptosis. In vitro it has been shown that T cell growth and cytokine production can be stimulated by culturing T cells with anti-CD3 antibodies which have been immobilized to a solid phase (for example beads or tissue culture plates) and adding soluble CD28 antibodies. Further, it has been shown that co-immobilizing both CD3 and CD28 antibodies to the same solid phase or to different solid phases can also induce T cell proliferation.

TCR is a molecule found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. In immunology, the CD3 antigen (CD stands for cluster of differentiation) is a protein complex composed of four distinct chains (CD3-γ, CD3δ, and two times CD3ε) in mammals that associates with molecules known as the T-cell receptor (TCR) and the ζ-chain to generate an activation signal in T lymphocytes. The TCR, ζ-chain, and CD3 molecules together contain the TCR complex. The CD3-γ, CD3δ, and CD3ε chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCRα and TCRβ). The intracellular tails of the CD3 molecules contain a single conserved motif known as an immunoreceptor tyrosine-based activation motif (ITAM), which is essential for the signaling capacity of the TCR.

CD28 is one of the molecules expressed on T cells that provide co-stimulatory signals, which are required for T cell activation. CD28 is the receptor for B7.1 (CD80) and B7.2 (CD86). When activated by Toll-like receptor ligands, the B7.1 expression is upregulated in antigen presenting cells (APCs). The B7.2 expression on antigen presenting cells is constitutive. CD28 is the only B7 receptor constitutively expressed on naive T cells. Stimulation through CD28 in addition to the TCR can provide a potent co-stimulatory signal to T cells for the production of various interleukins (IL-2 and IL-6 in particular).

A number of other methods are used in the conventional process for generating T cells in vitro. For example, autologous tumor-infiltrating lymphocytes can be used in the generation of CTL. For example, autologous peripheral blood lymphocytes (PBLs) may be used in the preparation of T cells. Furthermore, the production of autologous T cells by pulsing dendritic cells (DC) with peptide or polypeptide, or via infection with recombinant virus, is possible. Also, B cells can be used in the production of autologous T cells. In addition, macrophages pulsed with peptide or polypeptide, or infected with recombinant virus, may be used in the preparation of autologous T cells. Further, the in vitro priming of T cells by using artificial antigen presenting cells (aAPCs) may also be a suitable way for generating T cells against the peptide of choice. For example, aAPCs may be generated by the coupling of preformed MHC:peptide complexes to the surface of polystyrene particles (microbeads) by biotin:streptavidin biochemistry. This system permits the exact control of the MHC density on aAPCs, which allows selective elicitation of high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines, like interleukin-12.

ACT for solid cancers using endogenous T cells, however, may be a lengthy and complex process requiring the use of antigen presenting cells (APCs). Stimulation of antigen specific T cells using APCs may be variable and cumbersome by adding processing steps, time, and cost to the manufacturing process. Therefore, embodiments of the present disclosure includes using a more direct approach, for example, the manufacturing time and process may be significantly shortened by starting with sorted low frequency antigen specific precursors from fresh leukapheresis products or fresh peripheral blood mononuclear cells (PBMCs), eliminating the need for T cell activation agents, such as APCs and/or anti-CD3 antibody and anti-CD28 antibody.

Peptide/MHC Complex

In an aspect of the invention, the direct sorting process comprises a step of contacting CD8+ T cells with a multimer comprising a target peptide in a complex with a major histocompatibility complex (MHC) molecule and with at least one antibody that binds to a T cell surface molecule. T-cell based immunotherapy targets peptide epitopes derived from tumor-associated antigens (TAA) or tumor-specific proteins, which are presented by molecules of the MHC. The antigens that are recognized by the tumor specific T lymphocytes, that is, the epitopes thereof, can be molecules derived from all protein classes, such as enzymes, receptors, transcription factors, etc., which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation. MHC class II molecules can be found predominantly on professional antigen presenting cells (APCs), and primarily present peptides of exogenous or transmembrane proteins that are taken up by APCs e.g., during endocytosis, and are subsequently processed.

Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. It is well known that the TCR, the peptide and the MHC are thereby present in a stoichiometric amount of 1:1:1.

CD4-positive helper T-cells play an important role in inducing and sustaining effective responses by CD8-positive cytotoxic T-cells. The identification of CD4-positive T-cell epitopes derived from tumor associated antigens (TAA) is of great importance for the development of pharmaceutical products for triggering anti-tumor immune responses. At the tumor site, T helper cells support a cytotoxic T-cell- (CTL-) friendly cytokine milieu and attract effector cells, e.g., CTLs, natural killer (NK) cells, macrophages, and granulocytes.

In the absence of inflammation, expression of MHC class II molecules is mainly restricted to cells of the immune system, especially professional antigen-presenting cells (APC), e.g., monocytes, monocyte-derived cells, macrophages, and dendritic cells. In cancer patients, cells of the tumor have been found to express MHC class II molecules. Elongated (longer) peptides of the description can function as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T-cells are sufficient for inhibiting manifestation of tumors via inhibition of angiogenesis by secretion of interferon-gamma (IFN-γ). There is evidence for CD4-positive T-cells as direct anti-tumor effectors.

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1, the contents of which are incorporated by reference in their entirety).

Since both types of response, CD8 and CD4 dependent, contribute jointly and synergistically to the anti-tumor effect, the identification and characterization of tumor-associated antigens recognized by either CD8+ T-cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way, each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T-cells bearing specific T-cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e., copy numbers of the respective peptide per cell).

Tumor-specific and tumor-associated antigens are often derived from proteins directly involved in transformation of a normal cell to a tumor cell due to their function, e.g., in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach. It is essential that epitopes are present in the amino acid sequence of the antigen, in order to ensure that such a peptide ("immunogenic peptide"), being derived from a tumor associated antigen, and leads to an in vitro or in vivo T-cell-response.

Therefore, TAAs are a starting point for the development of a T-cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T-cell with a corresponding TCR has to be present and the immunological tolerance for this particular epitope needs to be absent or minimal. In a very preferred embodiment of the description it is therefore important to select only those over- or selectively presented peptides against which a functional and/or a proliferating T-cell can be found. Such a functional T-cell is defined as a T-cell, which upon stimulation with a specific antigen can be clonally expanded and is able to execute effector functions ("effector T-cell" or $T_{EM}$).

In an aspect, tumor associated antigen (TAA) peptides that are capable of use with the methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, U.S. Publication 20170260249, U.S. Publication 20180051080, U.S. Publication No. 20180164315, U.S. Publication 20180291082, U.S. Publication 20180291083, U.S. Publication 20190255110, U.S. Pat. Nos. 9,717,774, 9,895,415, U.S. Publication 20190247433, U.S. Publication 20190292520, U.S. Publication 20200085930, U.S. Pat. Nos. 10,336,809, 10,131,703, 10,081,664, 10,081,664, 10,093,715, 10,583,573, and US20200085930, the contents of each of these publications and sequence listings described therein are herein incorporated by reference in their entireties.

In an aspect, T cells described herein selectively recognize cells which present a TAA peptide described in one of more the patents and publications described above.

In another aspect, TAA that are capable of use with the methods and embodiments described herein include at least one selected from SEQ ID NO: 1 to SEQ ID NO: 161. In an aspect, T cells selectively recognize cells which present a TAA peptide described in SEQ ID NO: 1-161 or any of the patents or applications described herein.

TABLE 1

List of TAAs

| SEQ ID NO: | Amino Acid Sequence |
|---|---|
| 1 | YLYDSETKNA |
| 2 | HLMDQPLSV |
| 3 | GLLKKINSV |
| 4 | FLVDGSSAL |
| 5 | FLFDGSANLV |
| 6 | FLYKIIDEL |
| 7 | FILDSAETTTL |
| 8 | SVDVSPPKV |
| 9 | VADKIHSV |
| 10 | IVDDLTINL |
| 11 | GLLEELVTV |
| 12 | TLDGAAVNQV |
| 13 | SVLEKEIYSI |
| 14 | LLDPKTIFL |
| 15 | YTFSGDVQL |
| 16 | YLMDDFSSL |
| 17 | KVWSDVTPL |
| 18 | LLWGHPRVALA |
| 19 | KIWEELSVLEV |
| 20 | LLIPFTIFM |
| 21 | FLIENLLAA |
| 22 | LLWGHPRVALA |
| 23 | FLLEREQLL |
| 24 | SLAETIFIV |
| 25 | TLLEGISRA |
| 26 | ILQDGQFLV |
| 27 | VIFEGEPMYL |
| 28 | SLFESLEYL |
| 29 | SLLNQPKAV |
| 30 | GLAEFQENV |
| 31 | KLLAVIHEL |
| 32 | TLHDQVHLL |
| 33 | TLYNPERTITV |
| 34 | KLQEKIQEL |
| 35 | SVLEKEIYSI |

TABLE 1-continued

List of TAAs

| SEQ ID NO: | Amino Acid Sequence |
|---|---|
| 36 | RVIDDSLVVGV |
| 37 | VLFGELPAL |
| 38 | GLVDIMVHL |
| 39 | FLNAIETAL |
| 40 | ALLQALMEL |
| 41 | ALSSSQAEV |
| 42 | SLITGQDLLSV |
| 43 | QLIEKNWLL |
| 44 | LLDPKTIFL |
| 45 | RLHDENILL |
| 46 | YTFSGDVQL |
| 47 | GLPSATTTV |
| 48 | GLLPSAESIKL |
| 49 | KTASINQNV |
| 50 | SLLQHLIGL |
| 51 | YLMDDFSSL |
| 52 | LMYPYIYHV |
| 53 | KVWSDVTPL |
| 54 | LLWGHPRVALA |
| 55 | VLDGKVAVV |
| 56 | GLLGKVTSV |
| 57 | KMISAIPTL |
| 58 | GLLETTGLLAT |
| 59 | TLNTLDINL |
| 60 | VIIKGLEEI |
| 61 | YLEDGFAYV |
| 62 | KIWEELSVLEV |
| 63 | LLIPFTIFM |
| 64 | ISLDEVAVSL |
| 65 | KISDFGLATV |
| 66 | KLIGNIHGNEV |
| 67 | ILLSVLHQL |
| 68 | LDSEALLTL |
| 69 | VLQENSSDYQSNL |
| 70 | HLLGEGAFAQV |
| 71 | SLVENIHVL |
| 72 | YTFSGDVQL |
| 73 | SLSEKSPEV |
| 74 | AMFPDTIPRV |
| 75 | FLIENLLAA |
| 76 | FTAEFLEKV |
| 77 | ALYGNVQQV |
| 78 | LFQSRIAGV |
| 79 | ILAEEPIYIRV |
| 80 | FLLEREQLL |
| 81 | LLLPLELSLA |
| 82 | SLAETIFIV |
| 83 | AILNVDEKNQV |
| 84 | RLFEEVLGV |
| 85 | YLDEVAFML |
| 86 | KLIDEDEPLFL |
| 87 | KLFEKSTGL |
| 88 | SLLEVNEASSV |
| 89 | GVYDGREHTV |
| 90 | GLYPVTLVGV |
| 91 | ALLSSVAEA |
| 92 | TLLEGISRA |
| 93 | SLIEESEEL |
| 94 | ALYVQAPTV |
| 95 | KLIYKDLVSV |
| 96 | ILQDGQFLV |
| 97 | SLLDYEVSI |
| 98 | LLGDSSFFL |
| 99 | VIFEGEPMYL |
| 100 | ALSYILPYL |
| 101 | FLFVDPELV |
| 102 | SEWGSPHAAVP |
| 103 | ALSELERVL |
| 104 | SLFESLEYL |
| 105 | KVLEYVIKV |
| 106 | VLLNEILEQV |
| 107 | SLLNQPKAV |
| 108 | KMSELQTYV |
| 109 | ALLEQTGDMSL |
| 110 | VIIKGLEEITV |

TABLE 1-continued

List of TAAs

| SEQ ID NO: | Amino Acid Sequence |
|---|---|
| 111 | KQFEGTVEI |
| 112 | KLQEEIPVL |
| 113 | GLAEFQENV |
| 114 | NVAEIVIHI |
| 115 | ALAGIVTNV |
| 116 | NLLIDDKGTIKL |
| 117 | VLMQDSRLYL |
| 118 | KVLEHVVRV |
| 119 | LLWGNLPEI |
| 120 | SLMEKNQSL |
| 121 | KLLAVIHEL |
| 122 | ALGDKFLLRV |
| 123 | FLMKNSDLYGA |
| 124 | KLIDHQGLYL |
| 125 | GPGIFPPPPPQP |
| 126 | ALNESLVEC |
| 127 | GLAALAVHL |
| 128 | LLLEAVWHL |
| 129 | SIIEYLPTL |
| 130 | TLHDQVHLL |
| 131 | SLLMWITQC |
| 132 | FLLDKPQDLSI |
| 133 | YLLDMPLWYL |
| 134 | GLLDCPIFL |
| 135 | VLIEYNFSI |
| 136 | TLYNPERTITV |
| 137 | AVPPPPSSV |
| 138 | KLQEELNKV |
| 139 | KLMDPGSLPPL |
| 140 | ALIVSLPYL |
| 141 | FLLDGSANV |
| 142 | ALDPSGNQLI |
| 143 | ILIKHLVKV |
| 144 | VLLDTILQL |
| 145 | HLIAEIHTA |
| 146 | SMNGGVFAV |
| 147 | MLAEKLLQA |
| 148 | YMLDIFHEV |
| 149 | ALWLPTDSATV |
| 150 | GLASRILDA |
| 151 | ALSVLRLAL |
| 152 | SYVKVLHHL |
| 153 | VYLPKIPSW |
| 154 | NYEDHFPLL |
| 155 | VYIAELEKI |
| 156 | VHFEDTGKTLLF |
| 157 | VLSPFILTL |
| 158 | HLLEGSVGV |
| 159 | ALREEEEGV |
| 160 | KEADPTGHSY |
| 161 | TLDEKVAEL |

Sources of T Cells

T cells may be harvested either from tumor (tumor-infiltrating lymphocytes, TILs), peripheral blood (peripheral blood lymphocytes, PBMCs), or leukapheresis products. TILs can be expanded non-specifically since they are preferentially tumor-specific prior to culture. In contrast, tumor specificity may be induced in PBMCs and leukapheresis products, either through antigen-specific expansion or genetic engineering.

Prior to expansion and genetic modification of T cells, a source of T cells may be obtained from a healthy or diseased subject. In an aspect, a subject may include human. In another aspect, a subject may include mouse, e.g., humanized mouse, rat, rabbit, dog, cat, and monkey. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments, any number of T cell lines available in the art may be used. In certain embodiments, T cells can be obtained from a unit of blood collected from a subject using any number of techniques known to the skilled artisan, such as Ficoll™ separation. In one preferred embodiment, cells from the circulating blood of an individual may be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells may be washed with phosphate buffered saline (PBS), or with a wash solution that lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{3+}$-free, $Mg^{2+}$-free PBS, PlasmaLyte A, or other saline solution with or without buffer. Alternatively, the undesirable components of the apheresis sample may be removed, and the cells directly resuspended in culture media.

In another embodiment, T cells may be isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45+, and CD45RO+ T cells, can be further isolated by positive or negative selection techniques. In a positive selection protocol, the desired cells are the target cells. For example, in one embodiment, T cells may be isolated by incubation with anti-CD3/anti-CD28 (i.e., 3×28)-conjugated beads, such as DYNABEADS® M-450 CD3/CD28 T, for positive selection of the desired T cells.

In a negative selection protocol, the desired T cells remain in the sample following the removal of the non-desired T cells, i.e., negatively selected cells. For example, enrichment of a T cell population by negative selection can be accomplished with a combination of antibodies directed to surface markers unique to the negatively selected cells. One method may be cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically may include antibodies to CD14, CD20, CD11 b, CD16, HLA-DR, and CD8. In certain embodiments, it may be desirable to enrich for or positively select for regulatory T cells, which typically may express CD4+, CD25+, CD62L1, GITR+, and FoxP3+. Alternatively, in certain embodiments, T regulatory cells may be depleted by anti-CD25 conjugated beads or other similar method of selection.

In another aspect, T cells may be obtained from tumor infiltrating lymphocytes (TIL). One ACT strategy involves the transplantation of autologous TIL expanded ex vivo from tumor fragments or single cell enzymatic digests of tumor metastases. T cell infiltrates in tumors are polyclonal in nature and collectively recognize multiple tumor antigens. See, for example, Rosenberg et al., N. Engl. J. Med. (1988) 319:1676-1680, which is herein incorporated by reference in its entirety.

In an exemplary TIL ACT protocol, tumors may be resected from patients and cut into small (for example, 3-5 $mm^2$) fragments under sterile conditions. The fragments may be placed into culture plates or flasks with growth medium and treated with high-dose IL-2. This initial TIL expansion-phase (also known as the "Pre-REP" phase) typically lasts about 3 to about 5 weeks, during which time about $5\times10^7$ or more TILs may be produced. The resulting TILs may be then further expanded (e.g., following a rapid expansion protocol (REP)) to produce TILs suitable for infusion into a subject. The pre-REP TILs can be cryopreserved for later expansion, or they may be expanded immediately. Pre-REP TILs can also be screened to identify cultures with high anti-tumor reactivity prior to expansion. A typical REP may involve activating TILs using a T-cell stimulating antibody, e.g., an anti-CD3 mAb, in the presence of irradiated PBMC feeder cells. The feeder cells can be obtained from the patient or from healthy donor subjects. IL-2 may be added to the REP culture at concentrations of about 6,000 U/mL to promote rapid TIL cell division. Expansion of TILs in this manner can take about 2 weeks or longer, and results in a pool of about 10-150 billion TILs. The expanded cells may be washed and pooled, and may be suitable for infusion into a patient. Patients may typically receive 1 or 2 infusions (separated by 1-2 weeks) of $10^9$–$10^{11}$ cells. Patients have been administered high-dose IL-2 therapy (e.g., $7.2\times10^5$ IU/kg every 8 hours for about 2 to about 3 days) to help support the TIL cells after infusion. See, for example, Rosenberg et al., Nat. Rev. Cancer (2008) 8:299-308, which is herein incorporated by reference in its entirety. Before infusion, a patient can optionally be lymphodepleted using cyclophosphamide (Cy) and fludaribine (Flu). See, for example, Dudley et al., Science (2003) 298:850-854, which is herein incorporated by reference in its entirety. In addition, to prevent the re-emergence of endogenous regulatory T cells (Tregs), total body irradiation (TBI) has been used with lymphodepletion, See, for example, Dudley et al., J. Clin. Oncol. (2008) 26(32):5233-5239, which is herein incorporated by reference in its entirety.

T Cell Phenotype

During T cell activation, the TCR interacts with antigens displayed on the MHC complex of an antigen presenting cell. Recognition of the antigen-MHC complex by the TCR leads to T cell stimulation, which in turn leads to differentiation of both T helper cells (CD4+) and cytotoxic T lymphocytes (CD8+) in memory and effector lymphocytes. These cells then can expand in a clonal manner to give an activated subpopulation within the whole T cell population capable of reacting to one particular antigen.

T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells ($T_E$) (antigen-experienced, cytotoxic). $T_M$ cells can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). In certain embodiments, a central memory T cell is CD4+, CD44Hi, and CD62LHi T cell or a CD8+, CD44Hi, and CD62LHi T cell. In still further embodiments, T cells include memory T stem cells ($T_{MSC}$), which have the following phenotype: CD44Lo CD45RAHi CD62LHi CD95Hi CD122Hi sca-1+, and are capable of generating $T_{CM}$ and $T_{EM}$ subsets while maintaining themselves. Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Helper T cells (TH) are CD4+ cells that influence the activity of other immune cells by releasing cytokines. CD4+ T cells can activate and suppress an adaptive immune response, and which action is induced will depend on presence of other cells and signals. T cells also include γδ T cells, MAIT T cells, and Tregs. T cells can be collected in accordance with known techniques, and the various subpopulations or combinations thereof can be enriched or depleted by known techniques, such as by affinity binding to antibodies, flow cytometry, or immuno-magnetic selection. For example, in certain embodiments, CD8+ or CD4+ T cells can be sorted into CD62LHi (naïve and central memory T cells) or CD62LLo T cells (effector memory and effector T cells).

CD8+ T cells or cytotoxic T lymphocytes (CTLs) are thought to be essential in killing tumor cells. These cells typically are able to induce apoptosis in cancer cells when the cancer cell displays some antigen on its surface that was previously displayed on the MHC complex by an antigen presenting cell. Normally, following action against target cells, CTLs may undergo apoptosis when the cellular threat is cleared, with a subset of lymphocytes remaining that will further differentiate into memory T cells to persist in case the body is exposed to the antigen again. The pool of memory lymphocytes may be highly heterogeneous. Two types of memory T-cells have been identified: effector memory T-cells (CD45RA-CCR7-, CD62L-) and central memory T-cells that are CD45RA negative cells characterized by the expression of CCR7 and CD62L, two molecules required for homing in T-cell areas of secondary lymphoid organs. Upon antigenic stimulation, central memory T-cells produce low levels of effector cytokines such as IL-4 and IFN-γ, but high levels of IL-2, which is able to sustain their rapid and consistent proliferation. Upon antigen encounter central memory T-cells undergo: 1) proliferation, resulting in an auto-regenerative process, aimed at increasing their pool, and 2) differentiation, resulting in the generation of effector memory T-cells, which are characterized by a low proliferative potential but are able to migrate to inflamed non-lymphoid tissues and mediate the effector phase of the immune response.

Isolation of CD8+ T Cells

For isolation of a desired population of cells by positive or negative selection, the concentration of cells and surface (e.g., particles, such as beads) can be varied. In certain embodiments, it may be desirable to significantly decrease the volume, in which beads and cells may be mixed together (i.e., increase the concentration of cells), to ensure maximum contact of cells and beads. For example, in one embodiment, a concentration of 2 billion cells/ml may be used. In one embodiment, a concentration of 1 billion cells/ml may be used. In a further embodiment, greater than 100 million cells/ml may be used. In a further embodiment, a concentration of cells of 10, 15, 20, 25, 30, 35, 40, 45, or 50 million cells/ml may be used. In yet another embodiment, a concentration of cells from 75, 80, 85, 90, 95, or 100 million cells/ml may be used. In further embodiments, concentrations of 125 or 150 million cells/ml can be used. Using high concentrations can result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells may allow more efficient selection of CD8+ T cells that normally have weaker CD28 expression. In a related embodiment, it may be desirable to use lower concentrations of cells. By significantly diluting the mixture of T cells and surface (e.g., by using particles such as beads), interactions between the particles and cells may be minimized. This may select for cells that express high amounts of desired antigens to be bound to the particles.

Embodiments of the present disclosure may include utilizing CD8+positive selected T cells isolated from fresh leukapheresis product or fresh PBMCs. In one embodiment, cell population may be enriched for CD8+ T cells. A T cell culture may be depleted of CD4+ cells and enriched for CD8+ cells using, for example, a CD8 microbead separation (e.g., using a Clini-MACSPplus CD8 microbead system (Miltenyi Biotec™). Enriching for CD8+ T cells may improve the outcome of ACT by removing CD4+ T regulatory cells.

Peptide/MHC Multimers

Peptide/MHC multimers, e.g., peptide/MHC tetramers (Tet), may be formed by a streptavidin (SA or Sa). Streptavidin is a tetrameric protein from the bacterium *Streptomyces avidinii*. SA has extraordinary affinity and four unique binding sites, arranged tetrahedrally for its natural ligand biotin (Kd$^{-10\text{-}15}$ mol/L). The molar binding capacity of Streptavidin for biotin is 4:1 biotin:SA. While SA does not have to specifically bind to the binding molecule (e.g. via biotin interaction). In one aspect, streptavidin, binding molecules (e.g. MHC molecules) can be biotinylated, to enable the tetrameric assembly with the protein-ligand pair SA. In some embodiments, binding molecules can also be coupled to SA via covalent linkages (such as amide coupling), and therefore not necessarily through the biotin-SA interaction. The skilled person will be able to identify the most appropriate binding based on the experimental design of choice. In several embodiments of the present disclosure, SA may be used to assemble peptide/MHC monomers into tetramers. For example, MHC chains may be biotinylated with the enzyme BirA and refolded with the antigenic peptide, e.g., TAA, of interest. Biotin is a small protein that forms a strong bond with streptavidin. Fluorophore tagged streptavidin may be added to the bioengineered MHC monomers, and the biotin-streptavidin interaction causes four MHC monomers to bind to the streptavidin and create a tetramer. When the peptide/MHC tetramers are mixed with a sample, e.g., CD8+ T cells, they will bind to CD8+ T cells expressing the appropriate antigen specific receptor, e.g., TAA-specific TCR, that binds the TAA/MHC complex. Any MHC tetramers that are not bound are washed out of the sample before it is analyzed with flow cytometry.

Fluorescence-Activated Cell Sorting (FACS) Analysis

FACS of live cells separates a population of cells into sub-populations based on fluorescent labeling. Sorting involves more complex mechanisms in the flow cytometer than a non-sorting analysis. Cells stained using fluorophore-tagged peptide/MHC tetramers and/or fluorophore-conjugated antibodies can be separated from one another depending on which fluorophore they have been stained with. For example, a cell expressing one cell marker may be detected using a fluorescein isothiocyanate (FITC)-conjugated antibody that recognizes the marker, and another cell type expressing a different marker could be detected using a phycoerythrin (PE)-conjugated antibody specific for that marker.

The data generated by FACS may be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols may exist for diagnostic and clinical purposes especially in relation to hematology. For example, singles gating may allow individual single cells to be distinguished from cell doublets or higher aggregates by their "time-of-flight" (denoted also as a "pulse-width") through the narrowly focused laser beam. Dump gating may be used to reduce cells that are not of interest in the analysis. The plots may be made on logarithmic scales. Because different fluorescent dyes' emission spectra overlap, signals at the detectors have to be compensated electronically as well as computationally. Data accumulated using the flow cytometer can be analyzed using software. Once the data is collected, there is no need to stay connected to the flow cytometer and analysis may be performed on a separate computer.

Methods of Treatment

In an aspect, adoptive cell transfer or therapy (ACT) may include a treatment method, in which cells are removed from a donor, cultured and/or manipulated in vitro, and administered to a patient for the treatment of a disease. In some embodiments, transferred cells may be autologous cells, meaning that the patient acts as his or her own donor. In some embodiments, transferred cells may be lymphocytes, e.g., T cells. In some embodiments, transferred cells may be genetically engineered prior to administration to a patient. For example, the transferred cells can be engineered to express a T cell receptor (TCR) having specificity for an antigen of interest. In one embodiment, transferred cells may be engineered to express a chimeric antigen receptor (CAR). In certain embodiments, transferred cells may be engineered (e.g., by transfection or conjugation) to express a molecule that enhances the anti-tumor activity of the cells, such as a cytokine (IL-2, IL-12), an anti-apoptotic molecule (BCL-2, BCL-X), or a chemokine (CXCR2, CCR4, CCR2B). In certain embodiments, transferred cells may be engineered to express both a CAR and a molecule that enhances anti-tumor activity or persistence of cells.

In an aspect, expanded engineered T cells described herein are useful for treating a disorder associated with abnormal apoptosis or a differentiative process (e.g., cellular proliferative disorders or cellular differentiative disorders, such as cancer). Non-limiting examples of cancers that may be amenable to treatment with the methods of the present invention are described below.

Examples of cellular proliferative and/or differentiative disorders may include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions of the present disclosure (e.g., minimally ex vivo expanded engineered T cells) can be administered to a patient who has cancer.

Administration of Autologous Cells

The autologous cells can be administered by any suitable route as known in the art. Preferably, the cells may be administered as an intra-arterial or intravenous infusion, which lasts about 30 to about 60 minutes. Other exemplary routes of administration may include intraperitoneal, intrathecal and intralymphatic.

Likewise, any suitable dose of autologous cells can be administered. For example, in one embodiment, from about $1.0 \times 10^8$ cells to about $1.0 \times 10^{12}$ cells may be administered. In one embodiment, from about $1.0 \times 10^{10}$ cells to about $13.7 \times 10^{10}$ T-cells may be administered, with an average of around $5.0 \times 10^{10}$ T-cells. Alternatively, in another embodiment, from about $1.2 \times 10^{10}$ to about $4.3 \times 10^{10}$ T-cells may be administered.

In one embodiment, the autologous cells used for ACT may be lymphocytes, e.g., T cells. In one embodiment, the T cells may be "young" T cells, e.g., between 19-35 days old, as described in, for example, U.S. Pat. No. 8,383,099, incorporated by reference herein in its entirety. Young T cells are believed to have longer telomeres than older T cells, and longer telomere length may be associated with improved clinical outcome following ACT in some instances.

Infusion of expanded Tet+ CD8+ T cells obtained by direct sort of the present disclosure to subjects receiving an ACT regimen may promote the persistence of the transferred cells, stimulate the persistence, proliferation and survival of transferred cells, and/or improve tumor regression.

Embodiments of the present disclosure may include expanding the sorted CD8+ T cells by stimulation with IL-2, or other cytokines that bind the common gamma-chain, e.g., IL-1, IL-7, IL-10, IL-12, IL-15, IL-17, IL-21, and IL-23. In one aspect, the sorted CD8+ T cells may be expanded by at least one round of "rapid expansion protocol" (REP), in which T cells may be expanded with, e.g., IL-2 or IL-15, OKT-3, and irradiated allogeneic peripheral blood mononuclear cells (PBMCs) as feeder cells, including accessory cells expressing Fc-γI receptor (FcγRI). The Fc-portion of immunoglobulin (Ig)G2a-subclass mouse antibodies, including the OKT-3 antibody, attach to FcγRI on human feeder cells. An anti-CD3 antibody bound to FcγRI induces a more optimal proliferation/differentiation signal to CD8+ T cell than anti-CD3/CD28 immobilized on a solid surface. This may reflect the dual benefit of anti-CD3-T-cell receptor (TCR) crosslinking and the costimulation provided by cell-cell interaction between T cells and FcγRI+ accessory cells. In another aspect, the sorted CD8+ T cells may be expanded in the presence of anti-CD3 and anti-CD28 antibodies immobilized on beads to simultaneously deliver signal-1 and costimulatory signal-2 to induce T-cell proliferation without provoking energy or early apoptosis.

Cell Culture Closed Systems

Direct sort of the present disclosure may be carried out in combination with any cell culture closed systems to manufacture T cell products. Cell culture closed systems may include commercially available systems, e.g., CliniMACS Prodigy™ (Miltenyi), WAVE (XURI™) Bioreactor (GE Biosciences) alone or in combination with BioSafe Sepax™ II, and G-Rex/GatheRex™ closed system (Wilson Wolf) alone or in combination with BioSafe Sepax™ II. G-Rex™-closed system is the expansion vessel and GatheRex™ is the pump for concentrating and harvesting.

Clinimacs Prodigy™ (Miltenyi)

CliniMACS Prodigy™ with TCT process software and the TS520 tubing set may allow closed-system processing for cell enrichment, transduction, washing and expansion. For example, MACS-CD4 and CD8-MicroBeads may be used for enrichment, TransACT beads, e.g., CD3/CD28 reagents, may be used for activation, lentiviral vectors expressing a recombinant TCR may be used for transduction, TexMACS medium-3%-HS-IL2 for culture and phosphate-buffered saline/ethylenediaminetetraacetic acid buffer for washing. This system may yield about $4\text{-}5 \times 10^9$ cells, contain automated protocols for manufacturing with chamber maximum ~300 mL fill volume, and perform selection and activation (TransACT beads), transduction, and expansion over a 10 to 14-day process.

WAVE (Xuri™) Bioreactor (GE Biosciences)

WAVE (Xuri™) Bioreactor allows T cells to be cultured in culture bags, e.g., Xuri Cellbags, with and/or without perfusion. Medium bag for feeding may be 5-liter Hyclone Labtainer. Waste bag may be Mbag (purchased from GE Healthcare). This system may yield about $15\text{-}30 \times 10^9$ cells, use unicorn software that allows for culture control and monitoring, contain a rocking tray that may hold from about 0.3-liter to about 25 liters, and perform a perfusion function to maintain culture volume while mediating gas exchange and introducing fresh media and cytokines to the cell culture.

WAVE (Xuri™) Bioreactor may include Xuri Bags for expansion, Saint Gobain's VueLife bags for thawing and resting, and VueLife AC bags for activation. WAVE (Xuri™) Bioreactor may be used in combination with other technologies, e.g., Sepax™ cell separation system (GE Biosciences) for culture washing and volume reduction steps. Sterile welder (Terumo BCT™) may be used for connecting sterile bags for solution transfer and heat sealer for sealing tubing.

Sepax™ cell separation system relies on a separation chamber that provides both separation through rotation of the syringe chamber (centrifugation) and component transfer through displacement of the syringe piston. An optical sensor measures the light absorbency of the separated components and manages the flow direction of each of them in the correct output container, for example, plasma, buffy coat, and red blood cells may be thus separated and collected from blood samples.

Definitions

The term "activation" refers to the state of a T cell that has been stimulated to induce detectable cellular proliferation. Activation can also be associated with induced cytokine production, and detectable effector functions. The term "activated T cells" refers to, among other things, T cells that are proliferating. Signals generated through the TCR alone are insufficient for full activation of the T cell and one or more secondary or costimulatory signals are also required. Thus, T cell activation includes a primary stimulation signal through the TCR/CD3 complex and one or more secondary costimulatory signals. Costimulation can be evidenced by proliferation and/or cytokine production by T cells that have received a primary activation signal, such as stimulation through the CD3/TCR complex or through CD2. For example, an anti-CD3 antibody, an anti-CD2 antibody, or a protein kinase C activator in conjunction with a calcium ionophore may be used to activate a population of T cells.

Activation can be detected by any phenotypic of gene expression signature that is differentially expressed relative to the resting state. Such changes may be induced by the culturing with any known mitogens or biosimilars, which induce T-cell growth, effector function, and/or change in cell cycle state.

To induce proliferation, an activated population of T cells may be contacted with a second agent, which stimulates an accessory molecule on the surface of the T cells. For example, a population of CD4+ T cells can be stimulated to proliferate with an anti-CD28 antibody directed to the CD28 molecule on the surface of the T cells. Alternatively, CD4+ T cells can be stimulated with a natural ligand for CD28, such as B7-1 and B7-2. The natural ligand can be soluble, on a cell membrane, or coupled to a solid phase surface. Proliferation of a population of CD8+ T cells may be accomplished by use of a monoclonal antibody ES5.2D8, which binds to CD9, an accessory molecule having a molecular weight of about 27 kD present on activated T cells. Alternatively, proliferation of an activated population of T cells can be induced by stimulation of one or more intracellular signals, which result from ligation of an accessory molecule, such as CD28.

The agent providing the primary activation signal and the agent providing the costimulatory agent can be added either in soluble form or coupled to a solid phase surface. In a preferred embodiment, the two agents may be coupled to the same solid phase surface. The culturing of T-cells in such an environment leads to the indiscriminate activation of all T-cells which express the cognate receptors.

Following activation and stimulation of an accessory molecule on the surface of the T cells, the progress of proliferation of the T cells in response to continuing exposure to the ligand or other agent, which acts intracellularly to simulate a pathway mediated by the accessory molecule, may be monitored. When the rate of T cell proliferation decreases, T cells may be reactivated and re-stimulated, such as with additional anti-CD3 antibody and a co-stimulatory ligand, to induce further proliferation. In one embodiment, the rate of T cell proliferation may be monitored by examining cell size. Alternatively, T cell proliferation may be monitored by assaying for expression of cell surface molecules in response to exposure to the ligand or other agent, such as CD28 or CD27. The monitoring and re-stimulation of T cells can be repeated for sustained proliferation to produce a population of T cells increased in number from about 100- to about 100,000-fold over the original T cell population.

In an aspect, activation described herein may be carried out within a period of from about 1 hour to about 120 hours, about 1 hour to about 108 hours, about 1 hour to about 96 hours, about 1 hour to about 84 hours, about 1 hour to about 72 hours, about 1 hour to about 60 hours, about 1 hour to about 48 hours, about 1 hour to about 36 hours, about 1 hour to about 24 hours, about 2 hours to about 24 hours, about 4 hours to about 24 hours, about 6 hours to about 24 hours, about 8 hours to about 24 hours, about 10 hours to about 24 hours, about 12 hours to about 24 hours, about 12 hours to about 72 hours, about 24 hours to about 72 hours, about 6 hours to about 48 hours, about 24 hours to about 48 hours, about 6 hours to about 72 hours, or about 1 hours to about 12 hours.

The method of the present disclosure can be used to expand selected T cell populations for use in treating an infectious disease or cancer. The resulting T cell population can be genetically transduced and used for immunotherapy or can be used for in vitro analysis of infectious agents. Following expansion of the T cell population to sufficient numbers, the expanded T cells may be restored to the individual. The method of the present disclosure may also provide a renewable source of T cells. Thus, T cells from an individual can be expanded ex vivo, a portion of the expanded population can be re-administered to the individual and another portion can be frozen in aliquots for long term preservation, and subsequent expansion and administration to the individual. Similarly, a population of tumor-infiltrating lymphocytes can be obtained from an individual afflicted with cancer and the T cells stimulated to proliferate to sufficient numbers and restored to the individual.

In an aspect, the expanding may be performed for from about 1 day to 2 days, from about 1 day to 3 days, from about 1 day to about 4 days, from about 1 day to about 5 days, from about 1 day to 6 days, from about 1 day to 7 days, from about 1 day to 8 days, from about 1 day to 9 days, from about 1 day to 10 days, from about 2 days to 3 days, from about 2 days to 4 days, from about 2 days to 5 days, from about 2 days to 6 days, from about 2 days to 7 days, from about 2 days to 8 days, from about 2 days to 9 days, from about 2 days to 10 days, from about 3 days to 4 days, from about 3 days to 5 days, from about 3 days to 6 days, from about 3 days to 7 days, from about 3 days to 8 days, from about 3 days to 9 days, from about 3 days to 10 days, from about 4 days to 5 days, from about 4 days to 6 days, from about 4 days to 7 days, from about 4 days to 8 days, from about 4 days to 9 days, from about 4 days to 10 days, from about 5 days to 6 days, from about 5 days to 7 days, from about 5 days to 8 days, from about 5 days to 9 days, or from about 5 days to 10 days.

The term "rapid expansion" means an increase in the number of antigen-specific T cells of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. For example, a rapid expansion protocol (REP), as previously described (Dudley et al. *J. Immunother.* 26:332-42 (2003) and Riddell et al. *J. Immunol. Methods* 128:189-201 (1990), the contents of which are incorporated by reference in their entireties, may be used by culturing the antigen-specific T cells with irradiated (e.g., 40 Gy) allogeneic peripheral blood mononuclear "feeder" cells in complete medium (CM) with anti-CD3 antibody (e.g., 30 ng/mL) and IL-2 (e.g., 6000 IU/mL).

The term "T-cell receptor (TCR)" as used herein refers to a protein receptor on T cells that is composed of a heterodimer of an alpha ($\alpha$) and beta ($\beta$) chain, although in some cells the TCR consists of gamma and delta ($\gamma/\delta$) chains. In embodiments of the disclosure, the TCR may be modified on any cell having a TCR, including a helper T cell, a cytotoxic T cell, a memory T cell, regulatory T cell, natural killer T cell, and gamma delta T cell, for example.

The terms "T cell" or "T lymphocyte" may include thymocytes, naïve T lymphocytes, immature T lymphocytes, mature T lymphocytes, resting T lymphocytes, or activated T lymphocytes. Illustrative populations of T cells suitable for use in particular embodiments include, but are not limited to, helper T cells (HTL; CD4+ T cell), a cytotoxic T cell (CTL; CD8+ T cell), CD4+CD8+ T cell, CD4-CD8- T cell, or any other subset of T cells. Other illustrative populations of T cells suitable for use in particular embodiments include, but are not limited to, T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

In an aspect, an "irrelevant peptide" is a peptide that is not the target peptide and whose use in a sorting process facilitates exclusion of non-target specific T cells, Irrelevant peptide may be defined as a peptide that is not of interest such that the irrelevant peptide/MHC complexes do not lead to the desired T-cell response. For example, an irrelevant peptide may refer to a peptide having less than 50%, 60%, 70%, 80%, 90%, 95%, 96%, 97%, 98%, 99%, or 100% sequence identity to the target peptide such that an irrelevant peptide/MHC complex does not bind to the same T cells as does a target peptide/MHC complex. In a further example, an irrelevant peptide may refer to a peptide having less than 30%, less than 40%, less than 50%, such as less than 30% sequence identity to the target peptide such that an irrelevant peptide/MHC complex does not bind to the same T cells as does a target peptide/MHC complex. The amino acid sequence of an irrelevant peptide comprises typically 8-16 amino acids in length. The irrelevant peptide may be encoded by a housekeeping gene. As such, the selection of TCR-target peptide complexes while excluding potential irrelevant peptide, in which the irrelevant peptide/MHC complexes do not lead to the desired T-cell response. A target-similar peptide comprises typically 8-16 amino acids in length, preferably 8-11 amino acids in length and has a similarity to the amino acid sequence of the target peptide of at least 50%, at least 60%, at least 70%, at least 80% or at least 90%. Typically, the target similar peptide differs by five amino acids or less, four amino acids or less, three amino acids or less or one amino acid substitution with regard to the amino acid sequence of the target peptide. Furthermore, preferred target-peptide/MHC binding T cells do not bind to a target-similar peptide/MHC complex and primarily or only bind to a target peptide/MHC complex. This is due to the fact that T cells that bind both, to the target peptide/MHC complex and the target-similar peptide/MHC complex will show an undesired T-cell response, i.e. may lead to adverse reactions, such as "on target/off tumor" side effects, cross reactivity with target similar peptides on healthy tissues etc. (Lowdell et al., Cytotherapy, 2018; 00: 1-17).

A peripheral blood mononuclear cell (PBMC) refers to any blood cell with a round nucleus (i.e., a lymphocyte, a monocyte, or a macrophage). These blood cells are a critical component in the immune system to fight infection and adapt to intruders. The lymphocyte population consists of CD4+ and CD8+ T cells, B cells and Natural Killer (NK) cells, CD14+monocytes, and basophils/neutrophils/eosinophils/dendritic cells. These cells are often separated from whole blood or from leukopacks using FICOLL™, a hydrophilic polysaccharide that separates layers of blood, with monocytes and lymphocytes forming a buffy coat under a layer of plasma. In one embodiment, "PBMCs" refers to a population of cells containing at least T cells, and optionally NK cells, and antigen presenting cells.

Cell sorting technique used herein can be accomplished by using the method or equipment commonly used in the art, without any limitation in the disclosure. Any technologies, methods and equipment to sort cells may be used in the disclosure, as long as the surface markers are used to sort cells in these technologies, methods and equipment. For example, a magnetic sorting technique or a flow cytometry can be used. The experimental processes of the cell sorting technique such as a magnetic separation technique or a flow cytometry can be found in various scientific literatures, or may be performed according to instructions or recommended protocols provided by the manufacturer of the equipment or instrument. A person skilled in the art would have the ability to obtain these specific experimental processes or protocols.

The term "direct sort" used herein refers to any sorting activity that does not rely on clonal culturing (i.e. culturing by which the starting cells are separated into multiple sub-cultures) of T-cells before sorting. For example, directly sorting T cells, e.g., isolated CD8+ T cells from non-clonally cultured T cells may be sorted by using fluorophore-tagged peptide/MHC multimer, e.g., tetramer, and other fluorophore-tagged antibodies binding to T cell surface molecules including CD45, CD197, CD28, CD27, IL-7 receptor (IL-7R$\alpha$), CD57, CD95, CD127, and CD62L. T cells thus obtained by direct sorting may contain primarily low frequency antigen specific precursor T cells.

As used herein, the terms "cancer" (or "cancerous"), "hyperproliferative," and "neoplastic" may be used to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells may occur in disease states characterized by malignant tumor growth. Examples of non-pathologic hyperproliferative cells may include proliferation of cells associated with wound repair.

The term "cancer" or "neoplasm" may be used to refer to malignancies of the various organ systems, including those affecting the lung, breast, thyroid, lymph glands and lymphoid tissue, gastrointestinal organs, and the genitourinary tract, as well as to adenocarcinomas, which may be generally considered to include malignancies, such as most colon cancers, renal cell carcinoma, prostate cancer and/or testicular tumors, non-small cell carcinoma of the lung, cancer of the small intestine and cancer of the esophagus. With respect to the methods of the invention, the cancer can be any cancer, including any of acute lymphocytic cancer, acute myeloid leukemia, alveolar rhabdomyo sarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colon cancer, and hepatobiliary cancer.

The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term may also include carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders may include hematopoietic neoplastic disorders. As used herein, the term "hematopoietic neoplastic disorders" may include diseases involving hyperplastic/neoplastic cells of hematopoietic origin, e.g., arising from myeloid, lymphoid or erythroid lineages, or precursor cells thereof. Preferably, the diseases may arise from poorly differentiated acute leukemias (e.g., erythroblastic leukemia and acute megakaryoblastic leukemia). Additional exemplary myeloid disorders may include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas may include but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for expanded engineered T cells sufficient to reduce tumor growth and size, or a therapeutically effective amount, may vary not only on the particular compositions selected, but also with the route of administration, the nature of the condition being treated, and the age and condition of the patient, and will ultimately be at the discretion of the patient's physician or pharmacist. The length of time during which minimally expanded engineered T cells used in the instant methods may be given varies on an individual basis. It will be appreciated by those skilled in the art that reference herein to treatment extends to prophylaxis as well as the treatment of the noted cancers and symptoms.

EXAMPLES

Example 1

Comparison Between Direct Sorting Process and Conventional Process

FIG. 1 shows it may take about 52 days to prepare T cell products using the conventional process starting with PBMC isolation, followed by one week of dendritic cell (DC) generation, two rounds of stimulations (Stim1 and Stim2) at one week per round, sorting, and two rounds of rapid expansion protocol (REP), i.e., REP1 and REP2, at two weeks per round. In contrast, it may take about 30 days or less using direct sorting starting with CD8+ T cell isolation, followed by sorting and two rounds of expansions (REP1 and REP2) at two weeks per round. Thus, direct sorting may save about 3 weeks of time to complete T cell manufacturing as compared with conventional process.

Example 2

Direct Sort with Improved Gating Strategy

MLA Direct Sort

CD8+ T Cell Selection

Figure 2B:
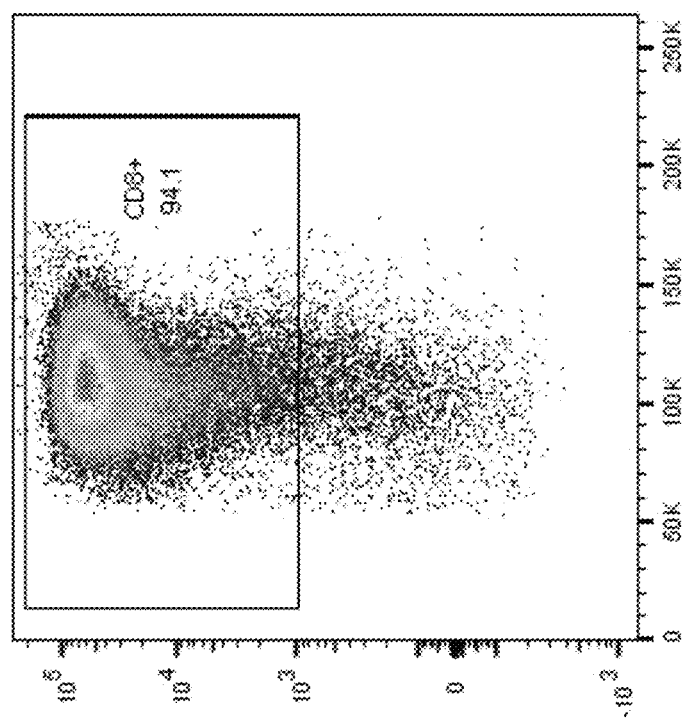
FIGS. 2A-2D show CD8+ cell isolation for MLA peptide sort.
Figure 2A:
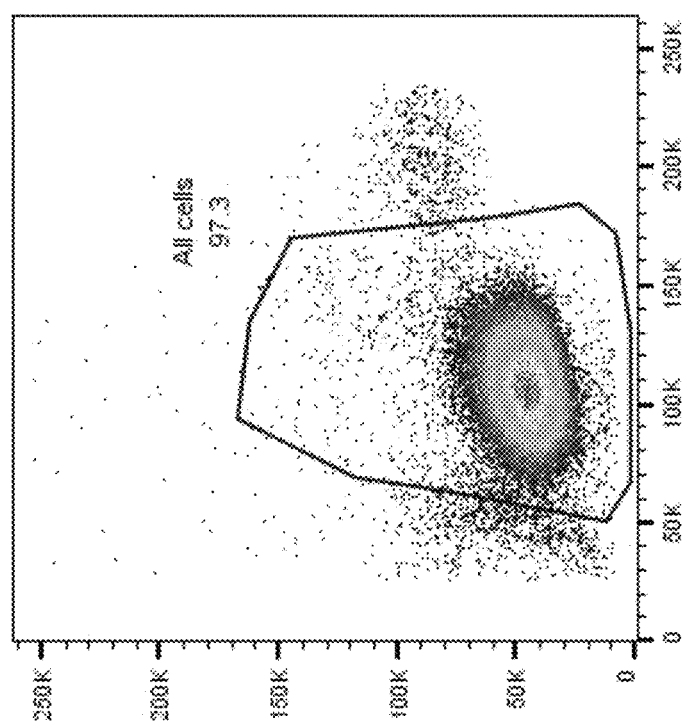
Figure 2D:
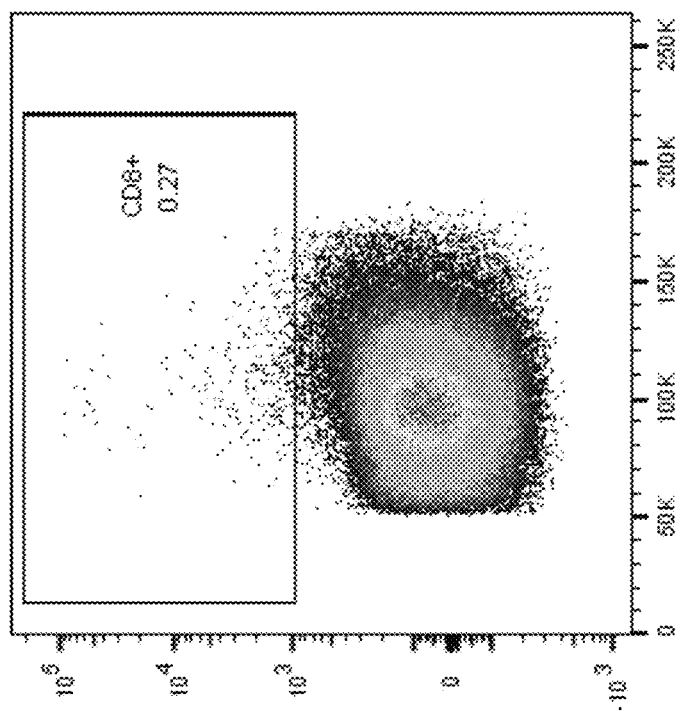
Figure 2C:
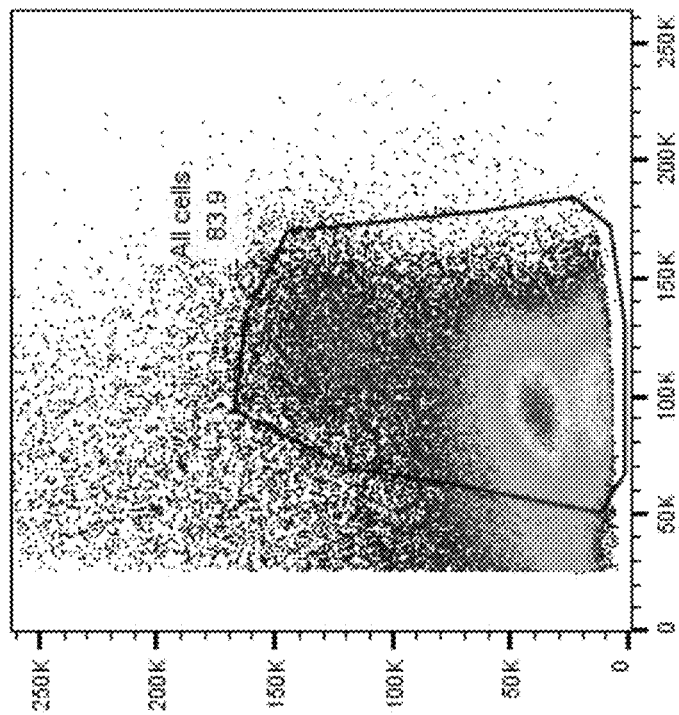

CD8+ T cells were isolated from fresh Leuko Paks obtained from Donor 2 (Stem Express®). FIGS. 2A-2D show the purity of CD8+ T cells used for MLA direct sorting from Donor 2. FIG. 2A shows 97.3% of lymphocytes present in the isolated CD8+ T cells. FIG. 2B shows 94.1% ($8.5 \times 10^8$ cells) of the lymphocytes were positive for CD8, i.e., purity is about 94%. In the CD8-negative fractions, FIG. 2C shows 83.9% of lymphocytes. FIG. 2D shows 0.27% of lymphocytes were positive for CD8.

Sort #1

Figure 3:
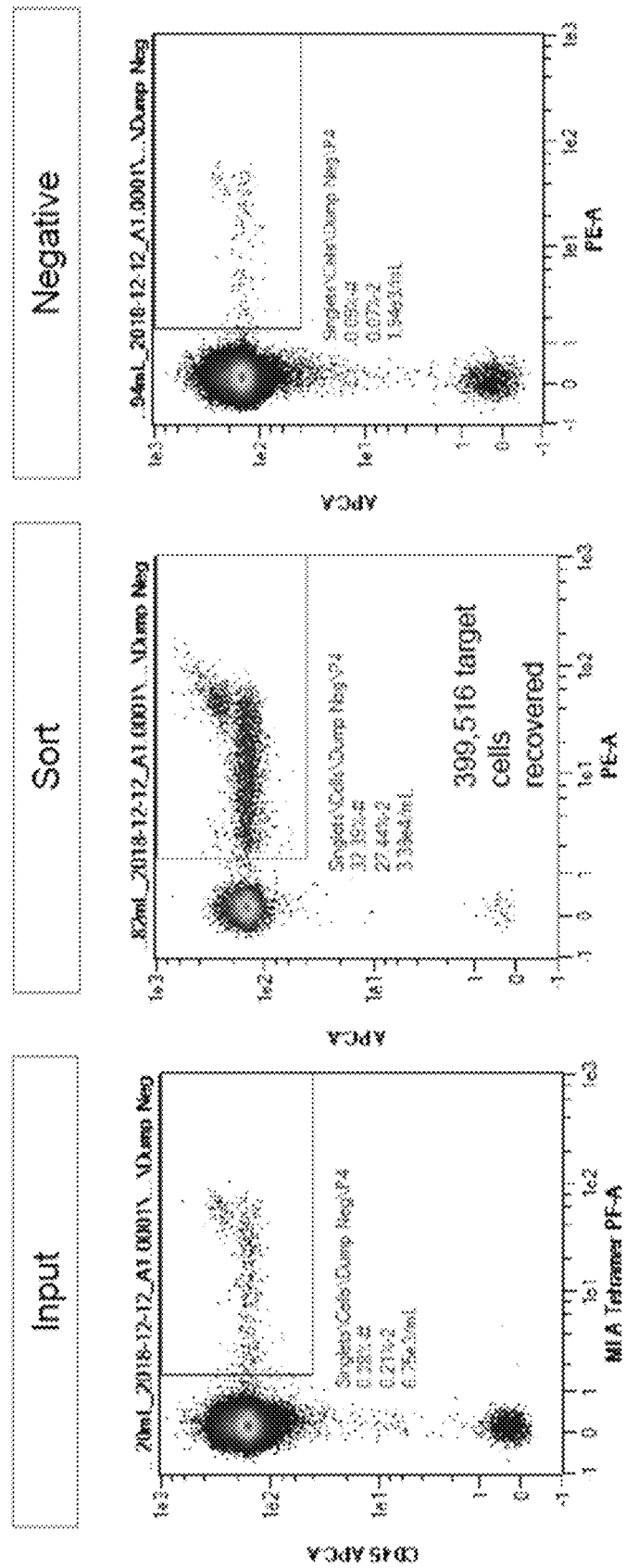
FIG. 3 shows a first MLA sorting

The isolated CD8+ T cells were cultured in the presence of IL-7 overnight, followed by direct sort. In the "dump negative," i.e., CD8+ T cells, which are detected negative for irrelevant peptide-Tet, CD56, CD19, and CD14, were sorted to remove MLA Tet-negative or CD45-negative CD8+ T cells. FIG. 3 shows, after sort #1, 399,516 MLA Tet-positive and CD45-positive CD8+ T cells were recovered (middle panel) as compared with the input (left panel) and the negative control (right panel).

TABLE 2

Sort #1 results

| Purity | Depletion Yield | Sort Efficiency | SA Δ Purity | SA Δ Sort Efficiency |
|---|---|---|---|---|
| 27.4% | 66.7% | 66.6% | 49.1% | 21.0% |

Theoretical purity is 25.6%
Input concentration = 31.8 × $10^6$ cells/ml and 0.21% targets
SA Δ = Self Aware Prediction – Actual Result from Quant
Self Aware Predictions are expected to be accurate due to high background cell concentration and trigger strategy.

Sort #2

Figure 4:
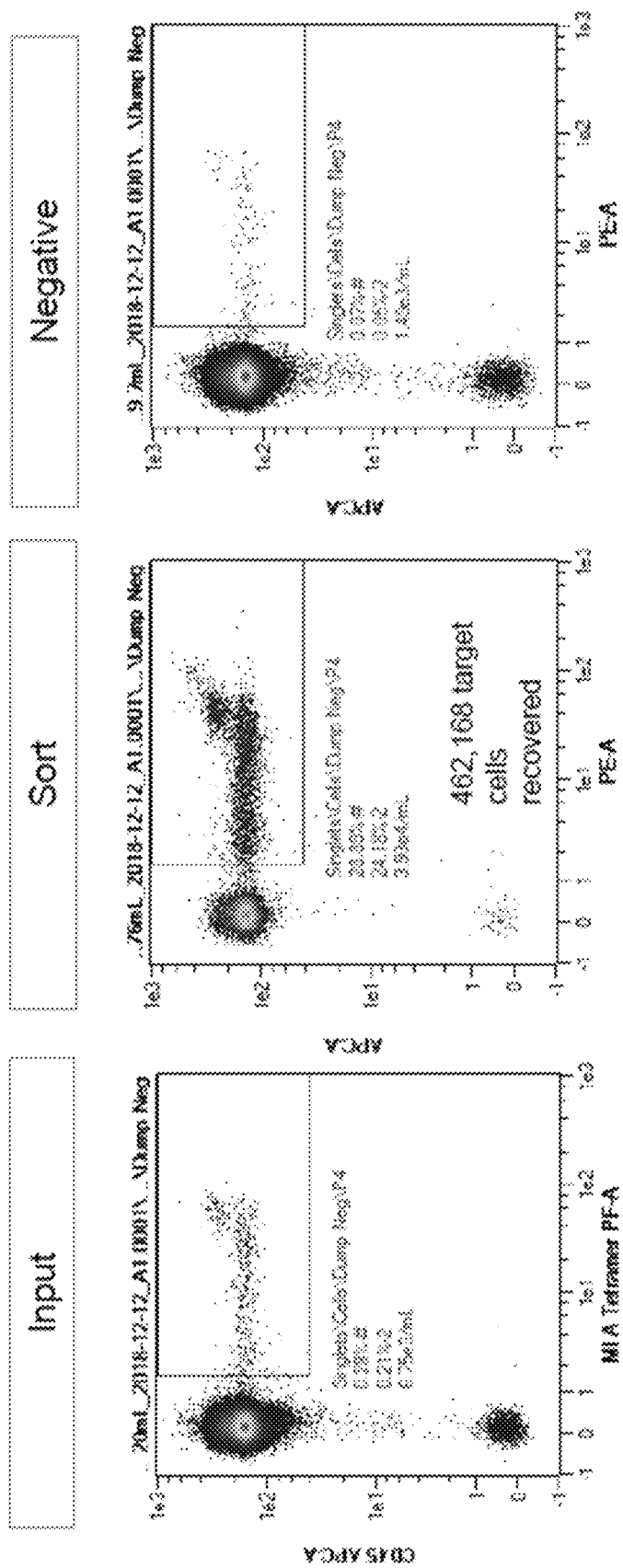
FIG. 4 shows a second MLA sorting

Similar to Sort #1, the isolated CD8+ T cells were cultured in the presence of IL-7 overnight, followed by direct sort. In the "dump negative," i.e., CD8+ T cells, which are detected negative for irrelevant peptide-Tet, CD56, CD19, and CD14, were debulked to remove MLA Tet-negative or CD45-negative CD8+ T cells. FIG. 4 shows, after debulk sort, 462,168 MLA Tet-positive and CD45-positive CD8+ T cells were recovered (middle panel) as compared with the input (left panel) and the negative control (right panel).

TABLE 3

Sort #2 Results

| Purity | Depletion Yield | Sort Efficiency | SA Δ Purity | SA Δ Sort Efficiency |
|---|---|---|---|---|
| 24.2% | 76.2% | 76.2% | 49.5% | 9.2% |

Theoretical purity is 23.7%
Input concentration = about 30 × $10^6$ cells/ml and 0.21% targets Sort #3

Figure 5:
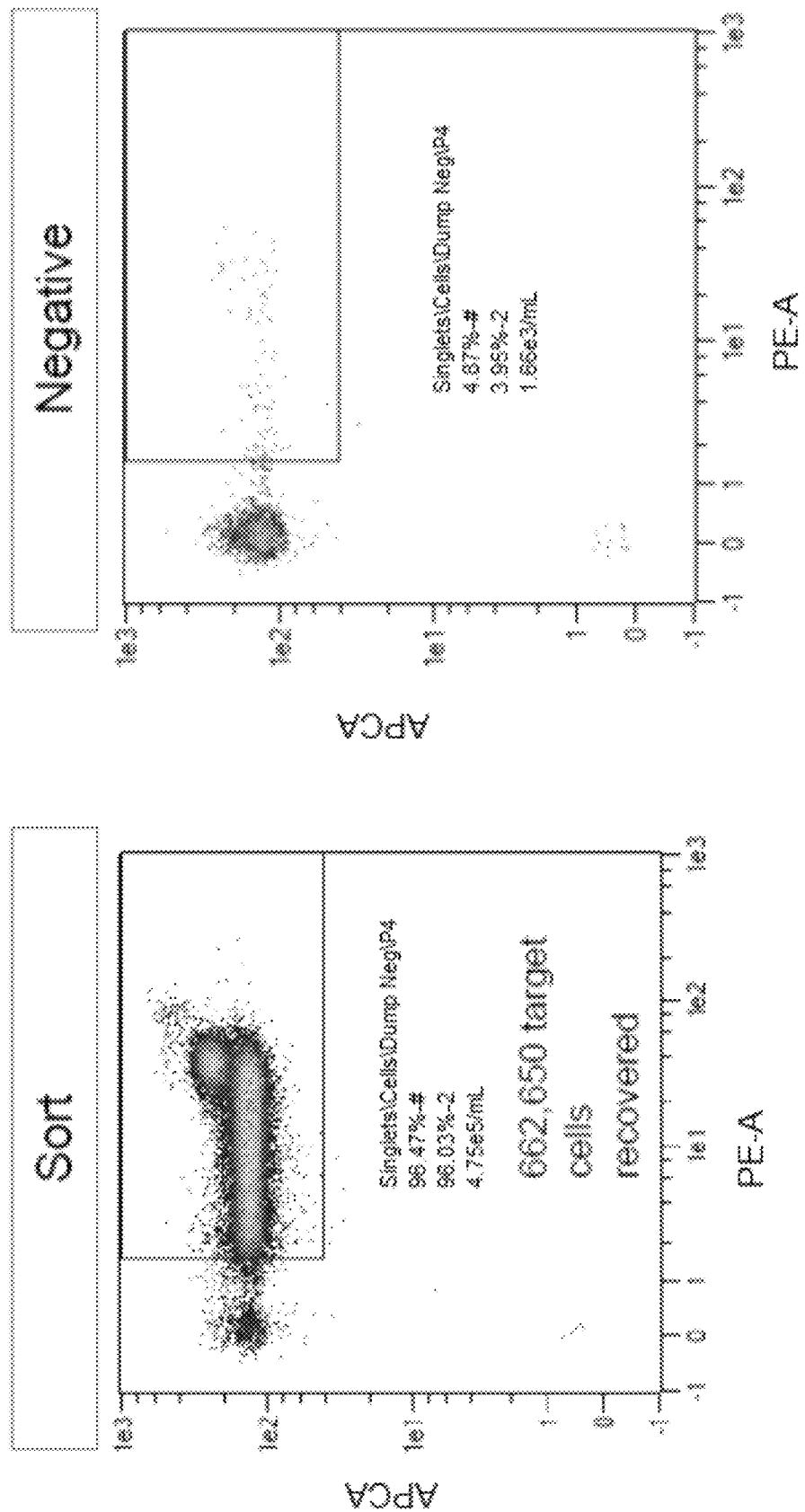
FIG. 5 shows MLA sorting results in accordance with one embodiment of the present disclosure.

MLA Tet-positive and CD45-positive CD8+ T cells obtained from Sort #1 and Sort #2 were combined for subsequent direct sort. FIG. 5 shows, after purity sort, 662,650 MLA Tet-positive and CD45-positive CD8+ T cells were recovered (left panel) as compared with the negative control (right panel).

TABLE 4

Results after Sort #1-Sort #3

| Purity | Depletion Yield | Sort Efficiency | SA Δ Purity | SA Δ Sort Efficiency |
|---|---|---|---|---|
| 96.0% | — | 91.1% | 6.4% | 2.6% |

Memory Phenotype (Post Purity Sort Prior to Expansion)

Figure 6A:
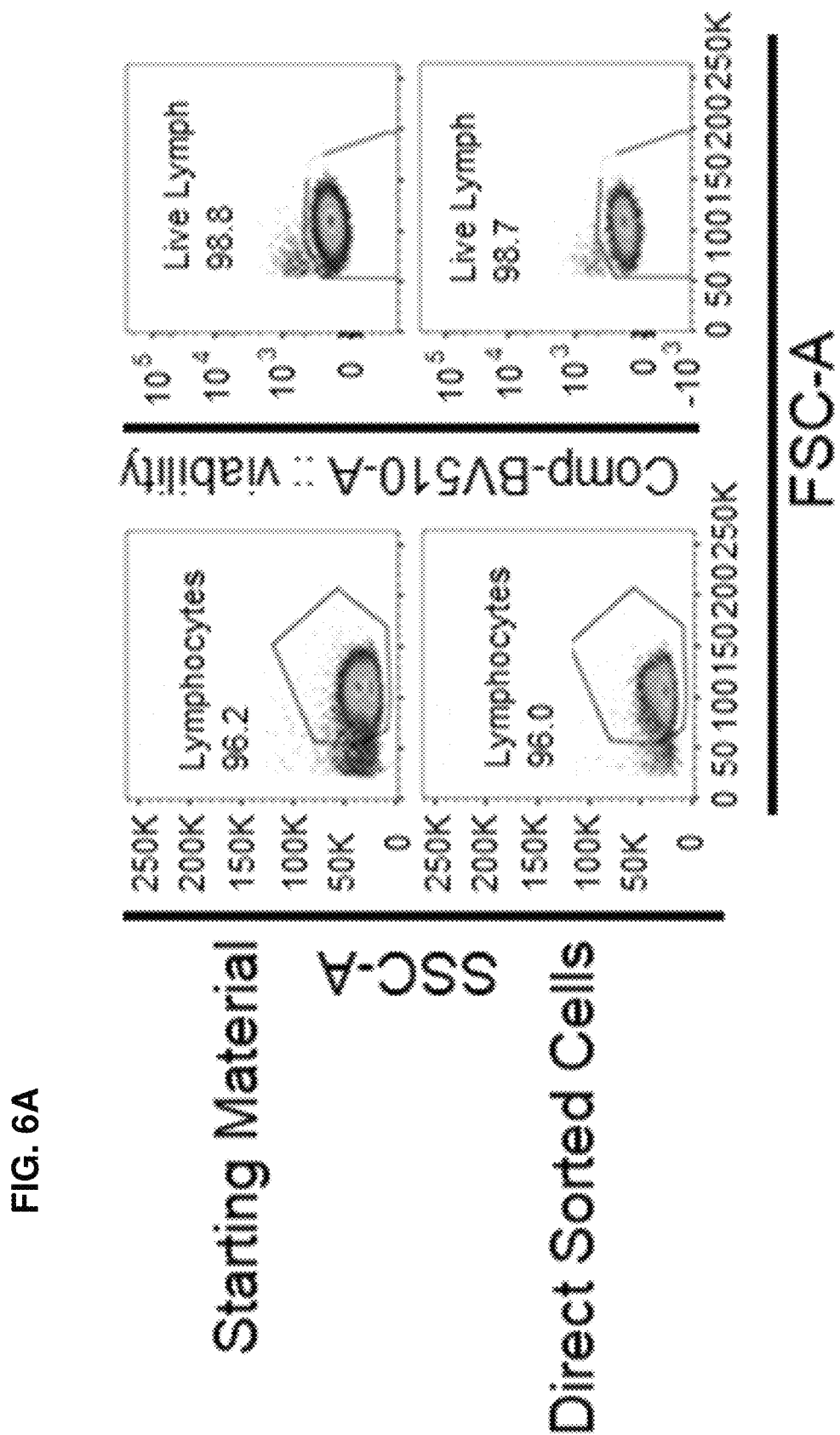
FIG. 6A shows memory phenotype of T cells in the starting materials in accordance with one embodiment of the present disclosure.
Figure 6A:
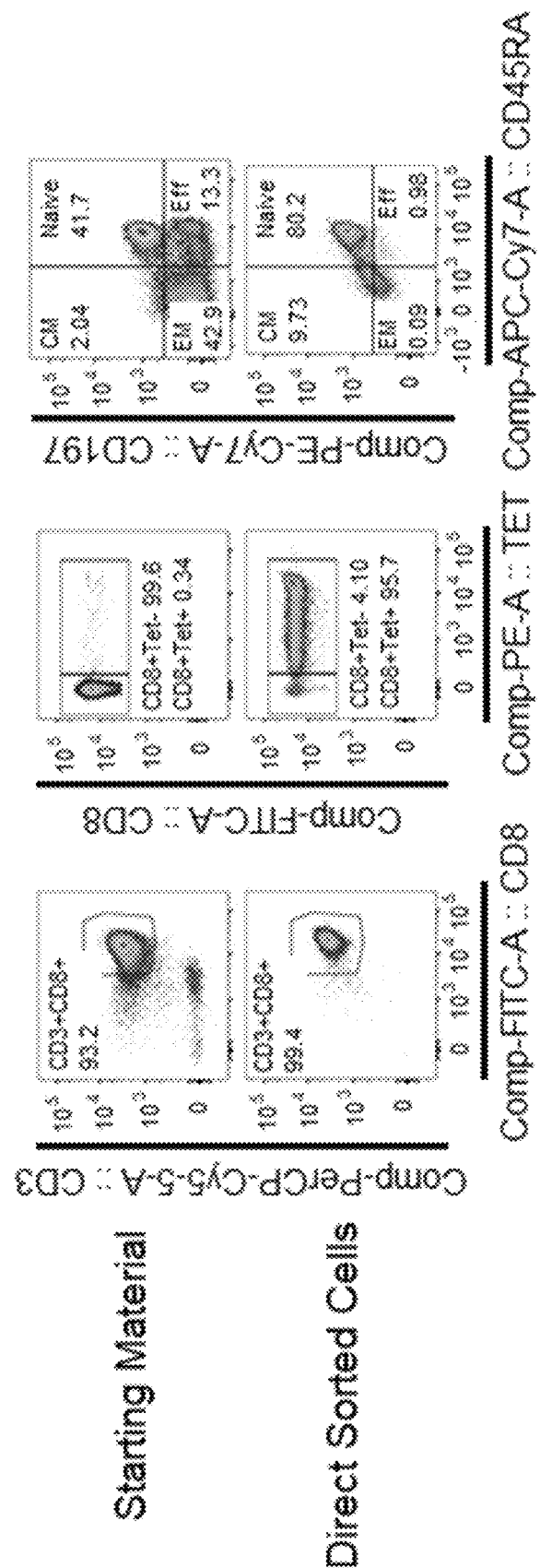

FIG. 6A shows, for example, the enrichment of MLA Tet-positive CD8+ T cells increased from 0.34% in the starting material to 95.75% in the direct sorted cells and that $T_{NAIVE}$ increased from 41.7% in the starting material to 80.2% in the direct sorted cells.

Figure 6B:
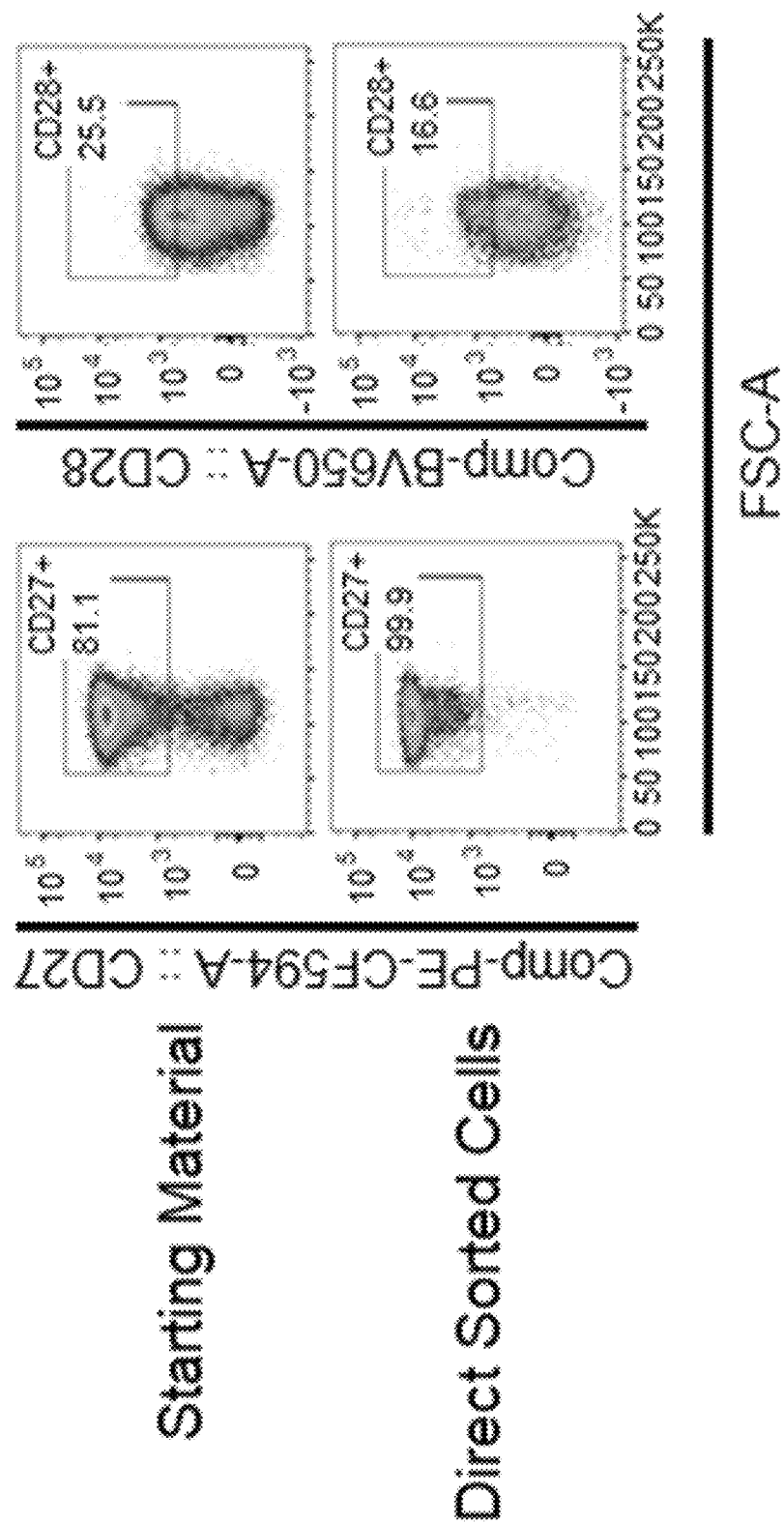
FIG. 6B shows memory phenotype of T cells post MLA direct sort in accordance with another embodiment of the present disclosure.
Figure 6B:
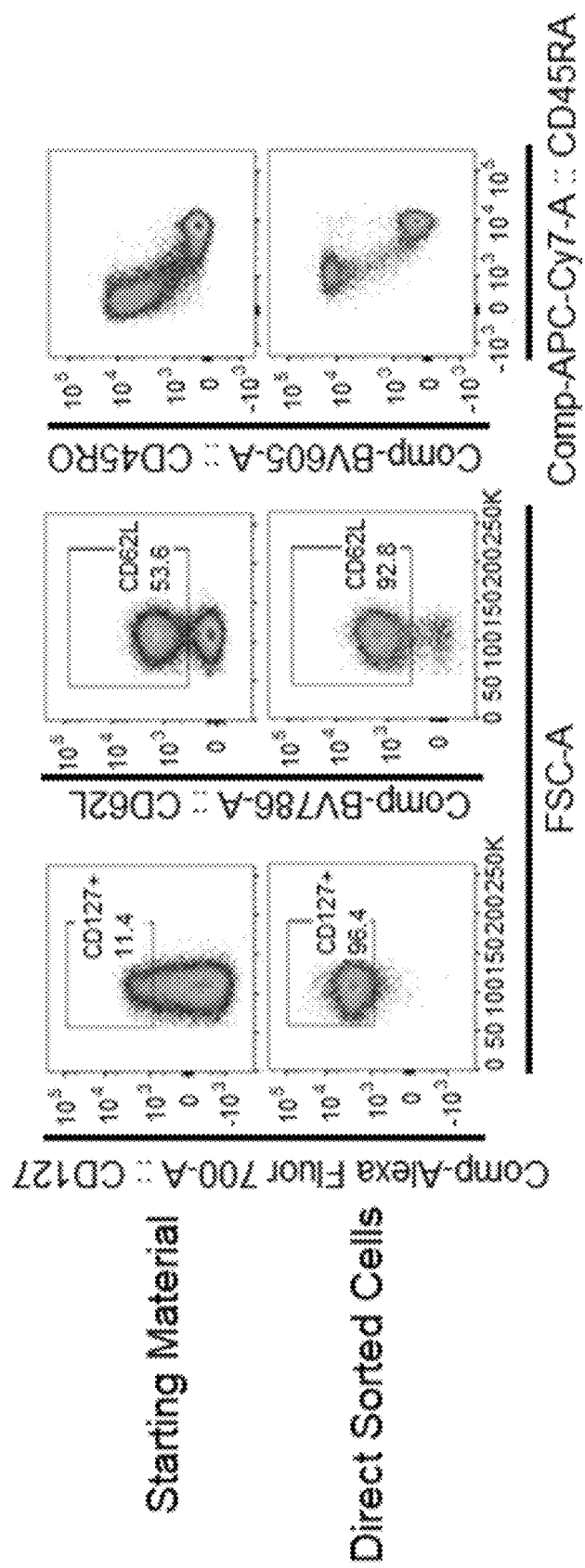

FIG. 6B shows, for example, the enrichment of CD27+ CD8+ T cells increased from 81.1% in the starting material to 99.9% in the direct sorted cells, CD127+CD8+ T cells increased from 11.4% in the starting material to 96.4% in the direct sorted cells, and CD62L+CD8+ T cells increased from 53.6% in the starting material to 92.8% in the direct sorted cells.

Figure 7:
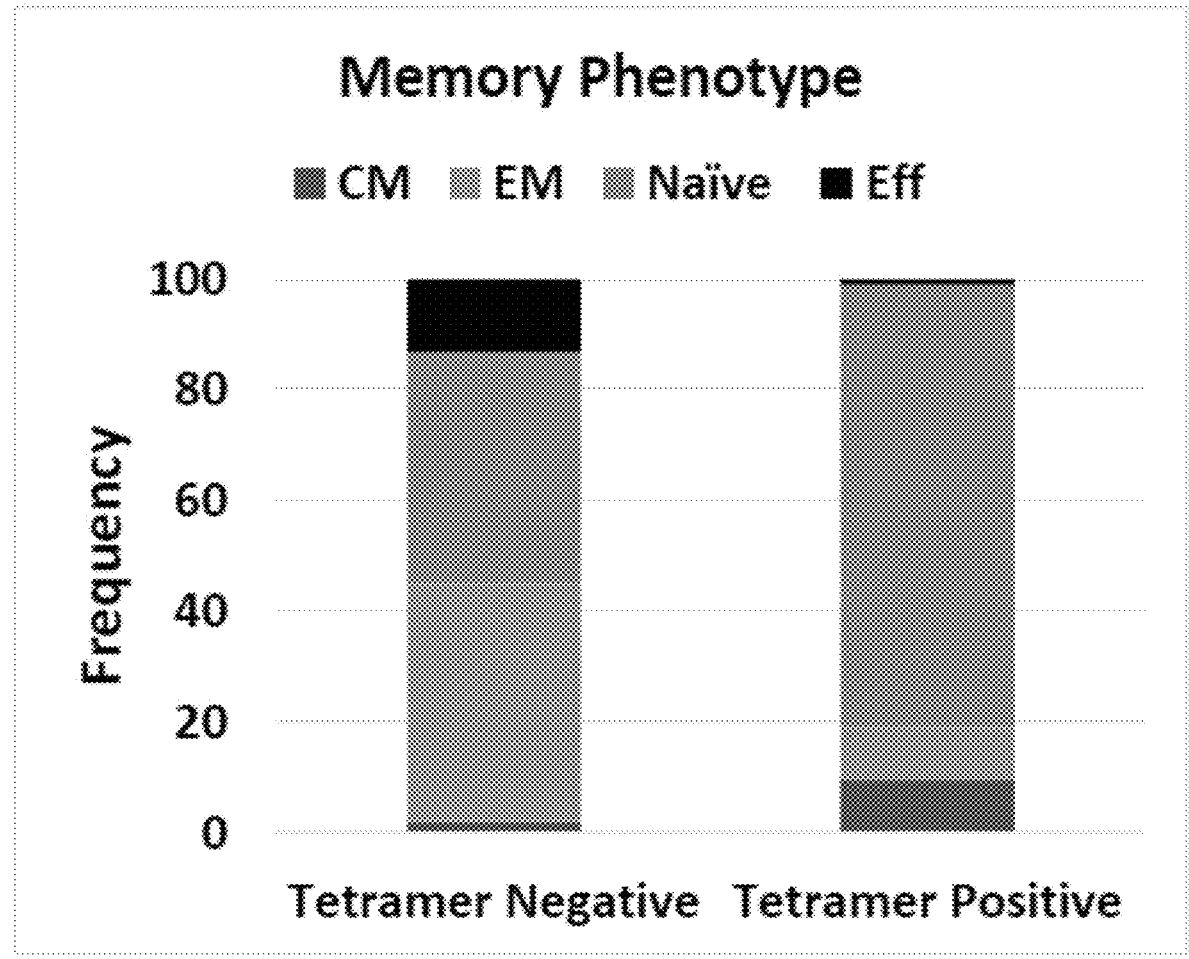
FIG. 7 shows post direct sort memory phenotype, in which a large proportion of tetramer positive precursor are $T_{NAIVE}$ cells.
Figure 8:
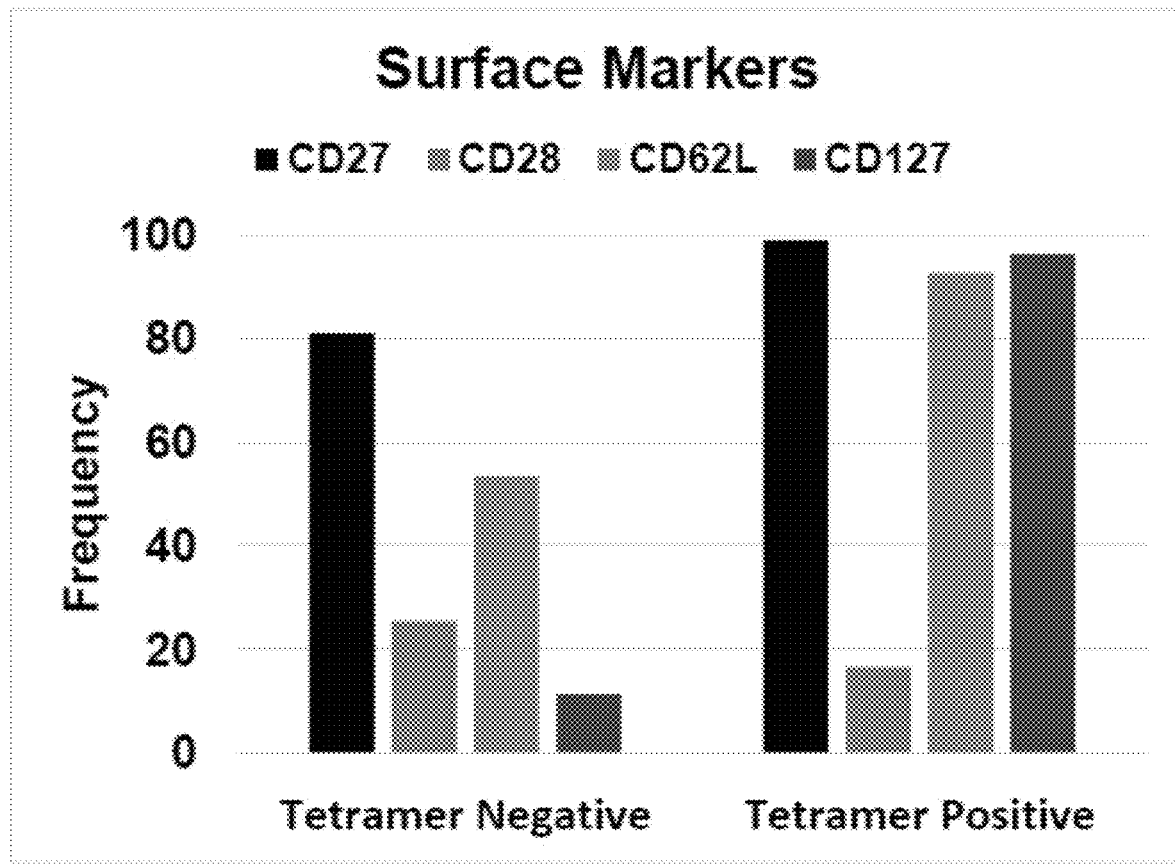
FIG. 8 shows post direct sort memory phenotype, in which a large proportion of tetramer positive precursors are $T_{NAIVE}$ cells expressing CD27 and CD62L.

FIG. 7 shows direct sorted MLA Tet-positive CD8+ T cells contained more $T_{NAIVE}$, more $T_{CM}$, less $T_{EM}$, and less $T_{EFF}$ than MLA Tet-negative CD8+ T cells. Consistently, FIG. 8 shows direct sorted MLA Tet-positive CD8+ T cells expressed more $T_{NAIVE}$ cell markers, e.g., CD27, CD62L, and CD127, than MLA Tet-negative CD8+ T cells.

MA Direct Sort

CD8+ T Cell Selection

Figure 9B:
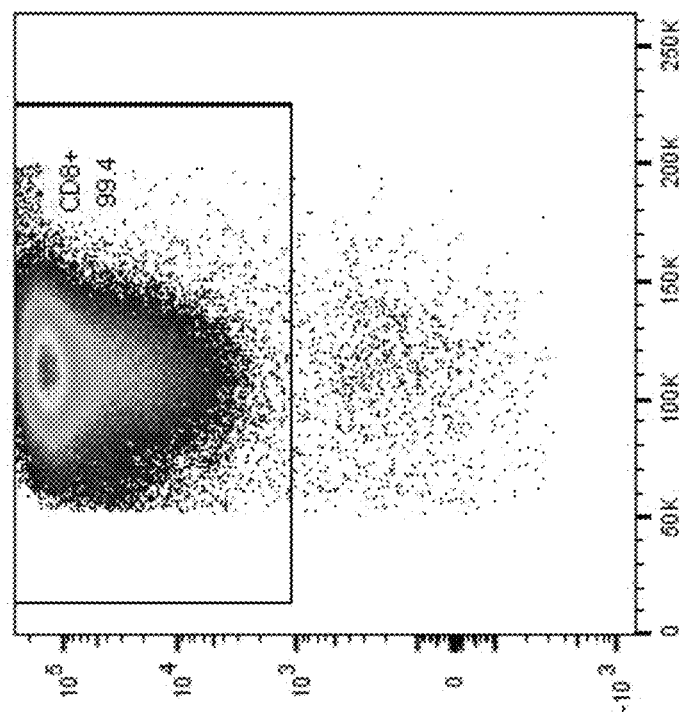
FIGS. 9A-9D show CD8+ cell isolation for MAGEA1 sort.
Figure 9A:
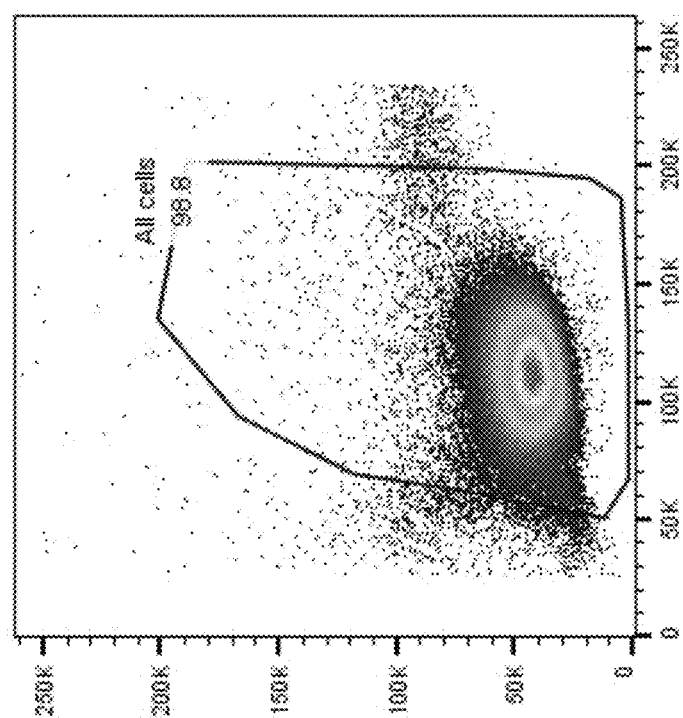
Figure 9D:
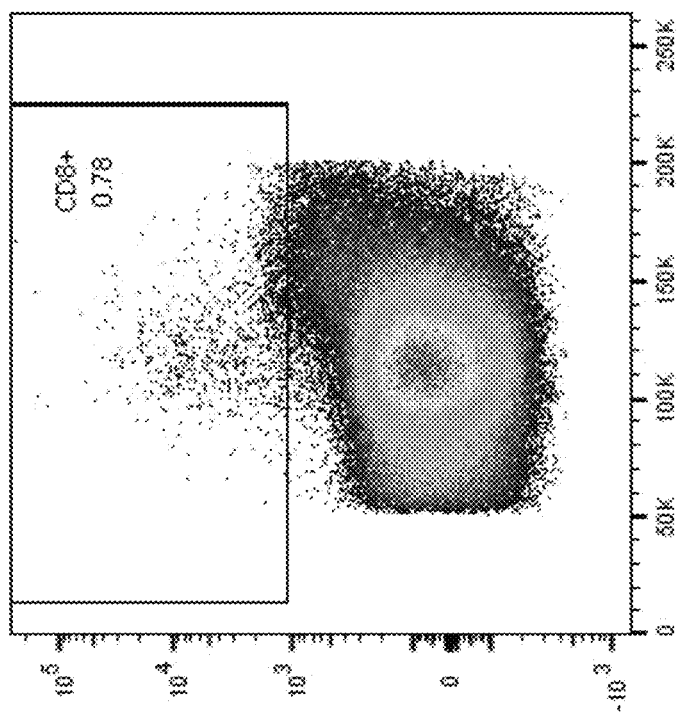
Figure 9C:
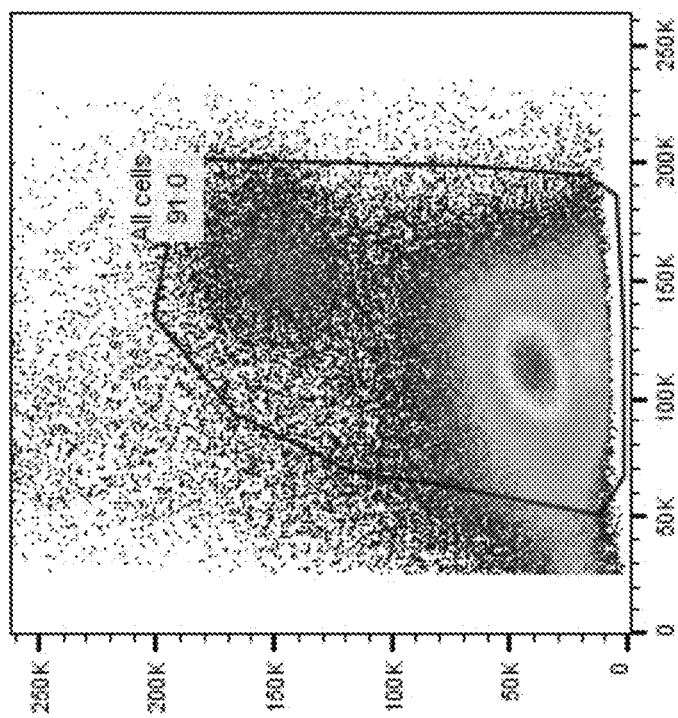

CD8+ T cells were isolated from fresh Leuko Paks obtained from Donor 3 (StemExpress®). FIGS. 9A-9D show the purity of CD8+ T cells used for MAGEA1 direct sorting from Donor 3. FIG. 9A shows 98.8% of lymphocytes present in the isolated CD8+ T cells. FIG. 9B shows 99.4% (1.1×$10^9$ cells) of the lymphocytes were positive for CD8, i.e., the purity is about 99%. In the CD8-negative fractions, FIG. 9C shows 91.0% of cells were lymphocytes and monocytes and FIG. 9D shows 0.78% of these cells were positive for CD8.

Sort #1

Figure 10:
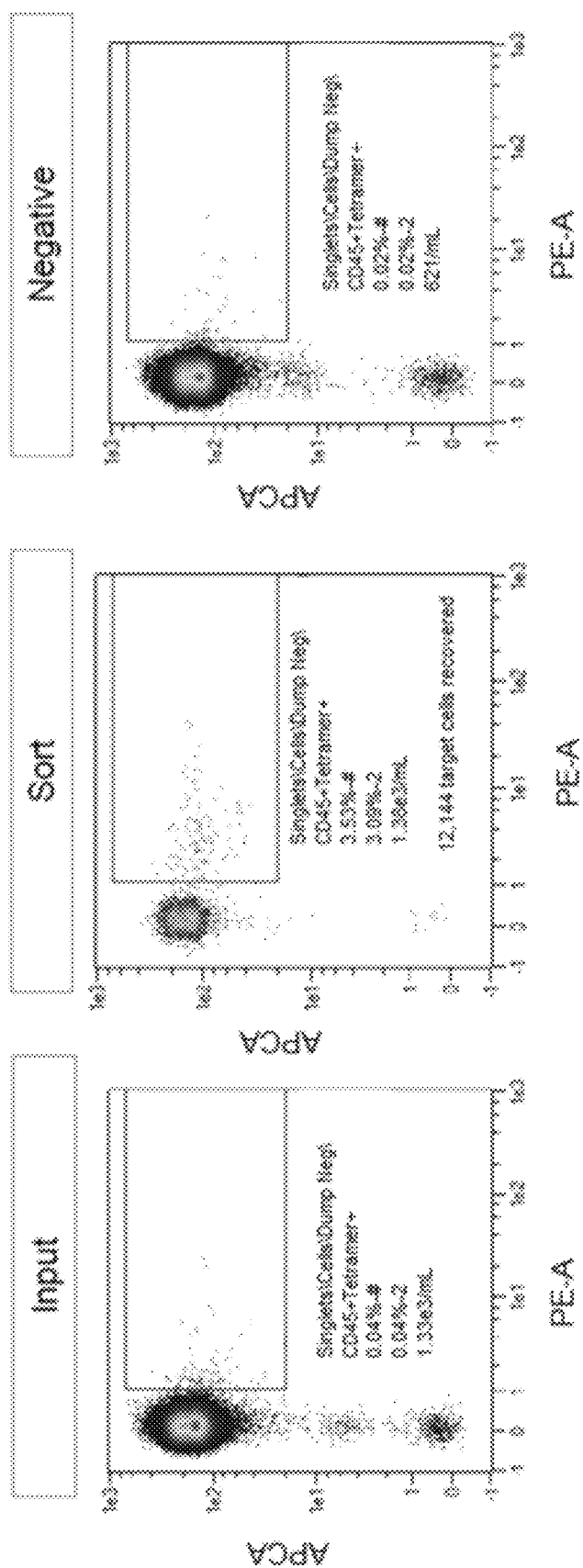
FIG. 10 shows a MAGEA1 sorting in accordance to one embodiment of the present disclosure.

The isolated CD8+ T cells were cultured in the presence of IL-7 overnight, followed by direct sort. In the "dump negative," i.e., CD8+ T cells, which are detected negative for irrelevant peptide-Tet, CD56, CD19, and CD14, were debulked to remove MAGEA1 Tet-negative or CD45-negative CD8+ T cells. FIG. 10 shows, after debulk sort, 12,144 MAGEA1 Tet-positive and CD45-positive CD8+ T cells were recovered (middle panel) as compared with the input (left panel) and the negative control (right panel).

TABLE 5

MAGEA1 following Sort #1

| Purity | Depletion Yield | Sort Efficiency | SA Δ Purity | SA Δ Sort Efficiency |
|---|---|---|---|---|
| 3.1% | 50.0% | 16.9% | 71.7% | 65.3% |

Theoretical purity is 23.7%
Input concentration = 34.0 × $10^6$ cells/ml and 0.04% targets
SA Δ = Self Aware Prediction – Actual Result from Quant
Self Aware Predictions are expected to be accurate due to high background cell concentration and trigger strategy.

Sort #2

Figure 11:
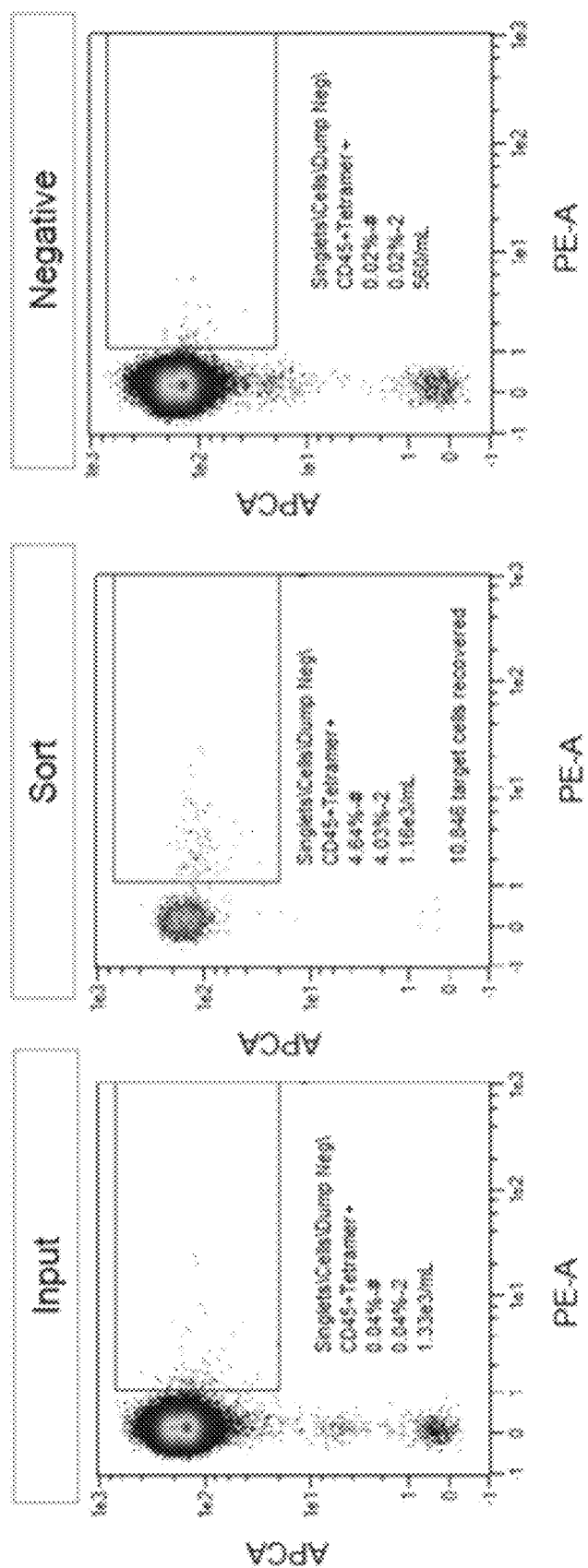
FIG. 11 shows MAGEA1 sorting in accordance to another embodiment of the present disclosure.

Similar to Sort #1, the isolated CD8+ T cells were cultured in the presence of IL-7 overnight, followed by direct sort. In the "dump negative," i.e., CD8+ T cells, which are detected negative for irrelevant peptide-Tet, CD56, CD19, and CD14, were debulked to remove MAGEA1 Tet-negative or CD45-negative CD8+ T cells. FIG. 11 shows, after debulk sort, 10,846 MAGEA1 Tet-positive and CD45-positive CD8+ T cells were recovered (middle panel) as compared with the input (left panel) and the negative control (right panel).

TABLE 6

MAGEA1 following Sort #2

| Purity | Depletion Yield | Sort Efficiency | SA Δ Purity | SA Δ Sort Efficiency |
|---|---|---|---|---|
| 4.0% | 50.0% | 16.7% | 76.9% | 59.2% |

Theoretical purity is 23.7%
Input concentration = about 30 × $10^6$ cells/ml

Sort #3

Figure 12:
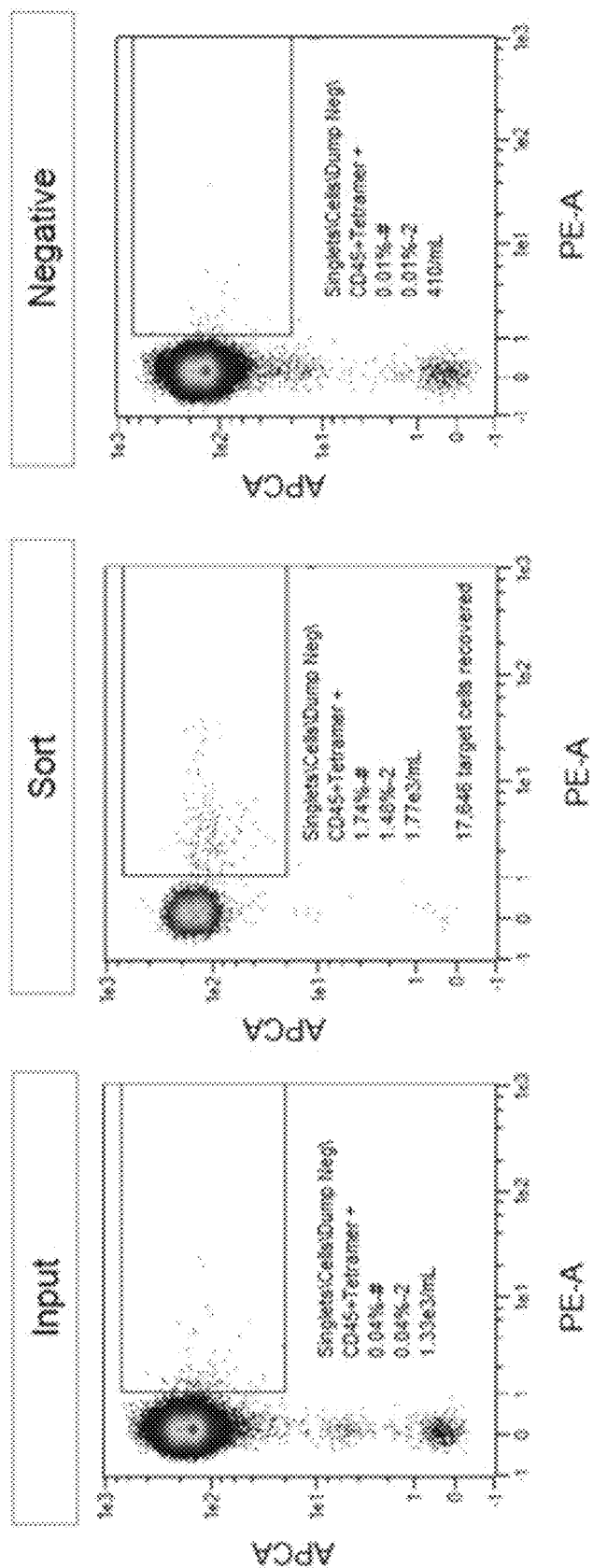
FIG. 12 shows MAGEA1 sorting in accordance to another embodiment of the present disclosure.

The isolated CD8+ T cells were cultured in the presence of IL-7 overnight, followed by direct sort. Without using dump gating, CD8+ T cells were debulked to remove MAGEA1 Tet-negative or CD45-negative CD8+ T cells. FIG. 12 shows, after debulk sort, 17,646 MAGEA1 Tet-positive and CD45-positive CD8+ T cells were recovered (middle panel) as compared with the input (left panel) and the negative control (right panel).

TABLE 7

MAGEA1 after Sort #3

| Purity | Depletion Yield | Sort Efficiency | SA Δ Purity | SA Δ Sort Efficiency |
|---|---|---|---|---|
| 1.5%* | 75.0% | 32.4% | 77.1% | 44.2% |

Theoretical purity is 23.7%
*less purity may be due to the absence of dump gating.
Input concentration = about $30 \times 10^6$ cells/ml Sort #4

Figure 13:
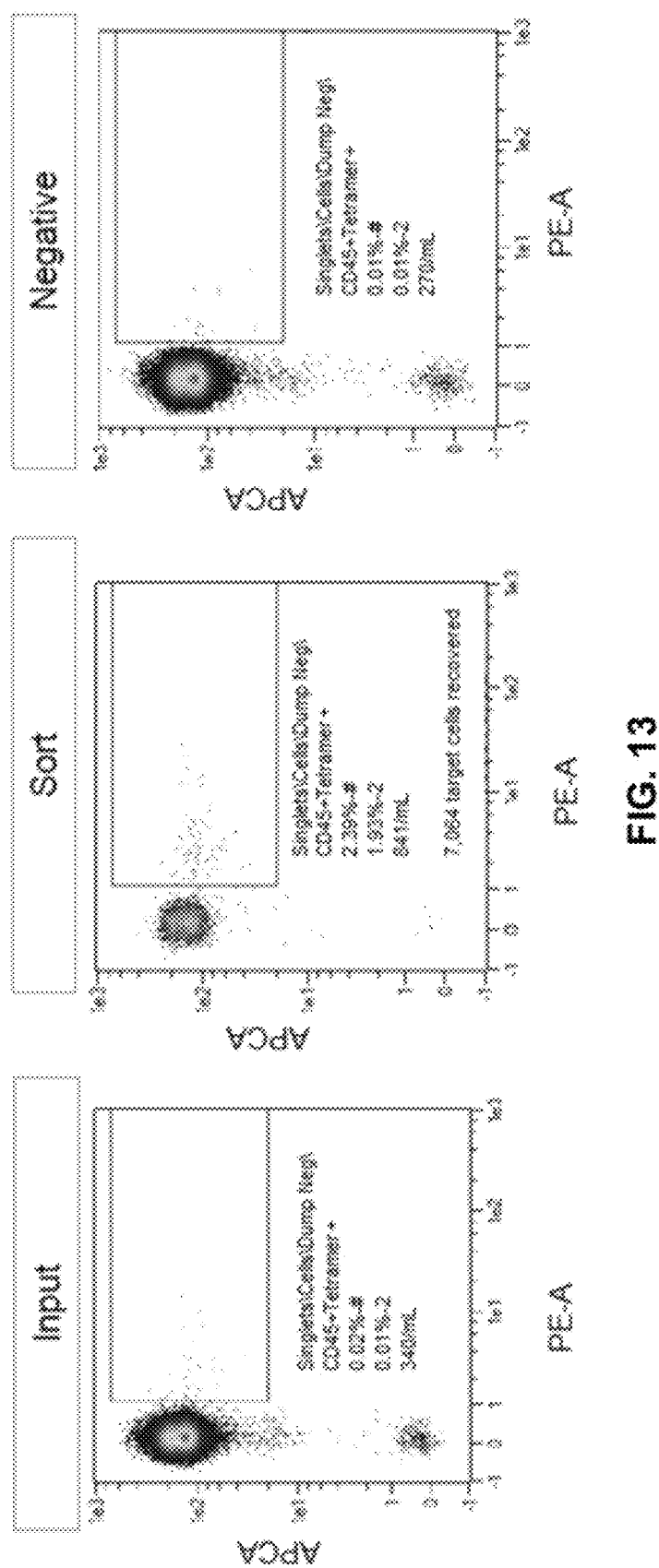
FIG. 13 shows MAGEA1 sorting in accordance to another embodiment of the present disclosure.

Similar to Sort #3, the isolated CD8+ T cells were cultured in the presence of IL-7 overnight, followed by direct sort. Without using dump gating, CD8+ T cells were debulked to remove MAGEA1 Tet-negative or CD45-negative CD8+ T cells. FIG. 13 shows, after debulk sort, 7,064 MAGEA1 Tet-positive and CD45-positive CD8+ T cells were recovered (middle panel) as compared with the input (left panel) and the negative control (right panel).

TABLE 8

MAGEA1 after Sort #4

| Purity | Depletion Yield | Sort Efficiency | SA Δ Purity | SA Δ Sort Efficiency |
|---|---|---|---|---|
| 1.9%* | 0.0% | 21.4% | 78.3% | 67.1% |

Theoretical purity is 23.7%
*less purity may be due to the absence of dump gating.
Input concentration = about $20 \times 10^6$ cells/ml Sort #5

Figure 14:
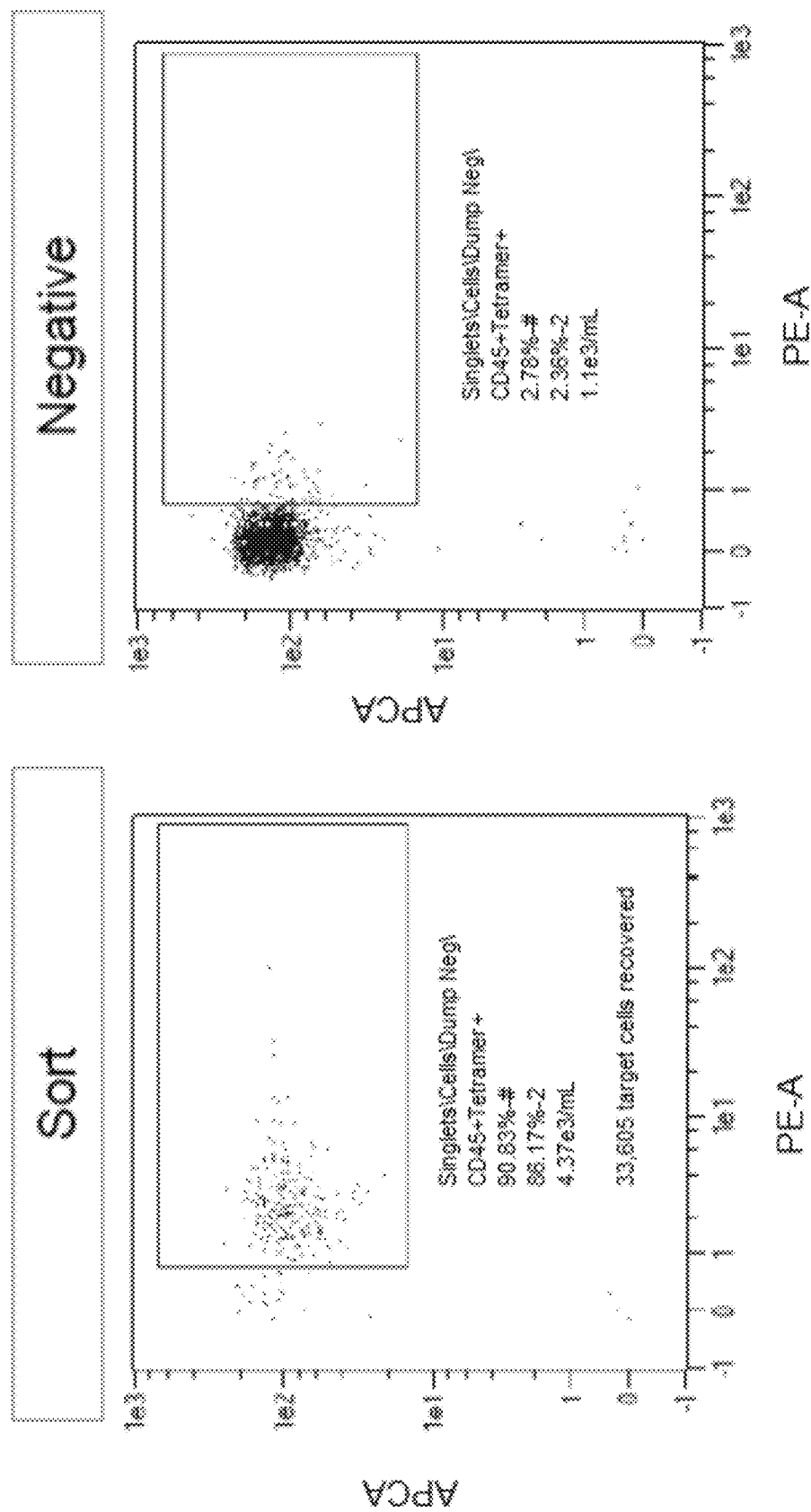
FIG. 14 shows MAGEA1 sorting in accordance to another embodiment of the present disclosure.

MAGEA1 Tet-positive and CD45-positive CD8+ T cells obtained from Sort #1 to Sort #4 were combined for subsequent Sort #5. FIG. 14 shows, after Sort #5, 33,605 MAGEA1 Tet-positive and CD45-positive CD8+ T cells were recovered (left panel) as compared with the negative control (right panel).

TABLE 9

MAGEA1 after direct sort following Sort #1-Sort #4

| Purity | Depletion Yield | Sort Efficiency | SA Δ Purity | SA Δ Sort Efficiency |
|---|---|---|---|---|
| 86.2% | — | 42.7% | 9.9% | 46.6% |

33,605 MAGEA1 Tet-positive and CD45-positive CD8+ T cells obtained from the purity sort were split into two REPs, i.e., 16,802 cells per PEP1 well.

Cell viability and fold expansion of MLA and MAGEA1 sorted cells

To determine cell viability and fold expansion of the purity sorted CD8+ T cells, cells were stained by AOPI, i.e., acridine orange (AO), which can readily diffuse across cell membranes and thus stain the DNA of viable cells, and by propidium iodide (PI), which can enter only cells with compromised membranes and thus stain dead cells.

FIG. 15A shows, post REP1, total number of viable T cells (top panel) and fold expansion (bottom panel) in the MLA Tet sorted- and MAGEA1 Tet sorted-CD8+ T cells.

FIG. 15B shows, post REP2, total number of viable T cells (top panel) and fold expansion (bottom panel) in the MLA Tet sorted- and MAGEA1 Tet sorted-CD8+ T cells.

Figure 16A:
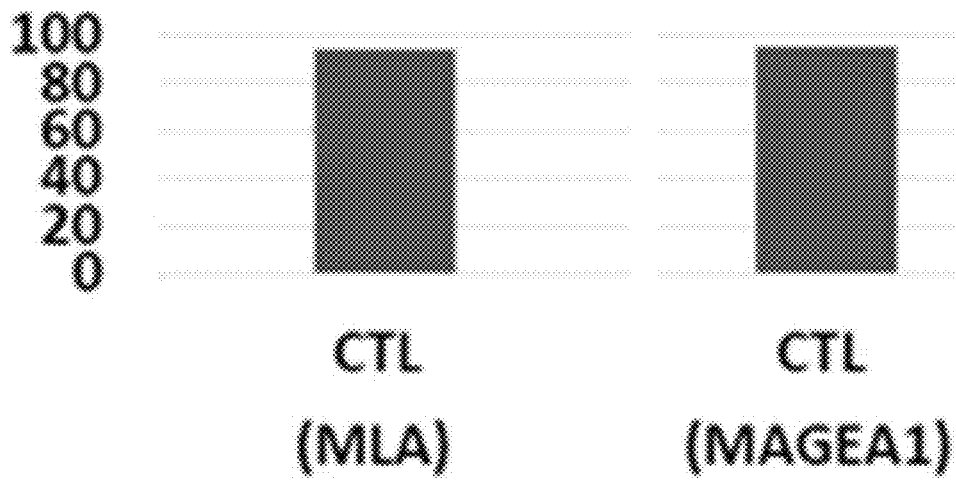
FIGS. 16A and 16B show CD3+CD8+ cells of MLA and MAGEA1 direct sorted T cells post REP1 and post REP2, respectively.

FIG. 16A shows, post REP1, the percentage of CD3+ CD8+ T cells in the MLA Tet sorted- and MAGEA1 sorted-CD8+ T cells.

Figure 16B:
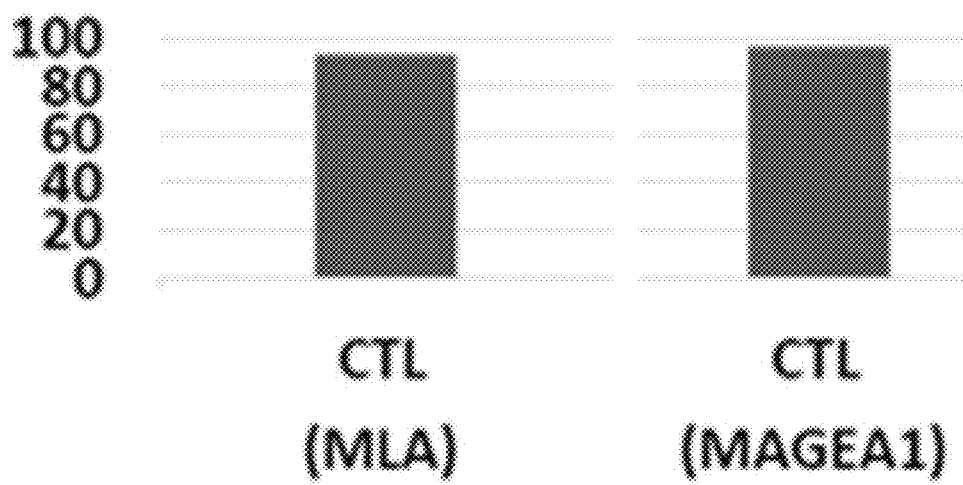

FIG. 16B shows, post REP2, the percentage of CD3+ CD8+ T cells in the MLA Tet sorted- and MAGEA1 sorted-CD8+ T cells.

Figure 17A:
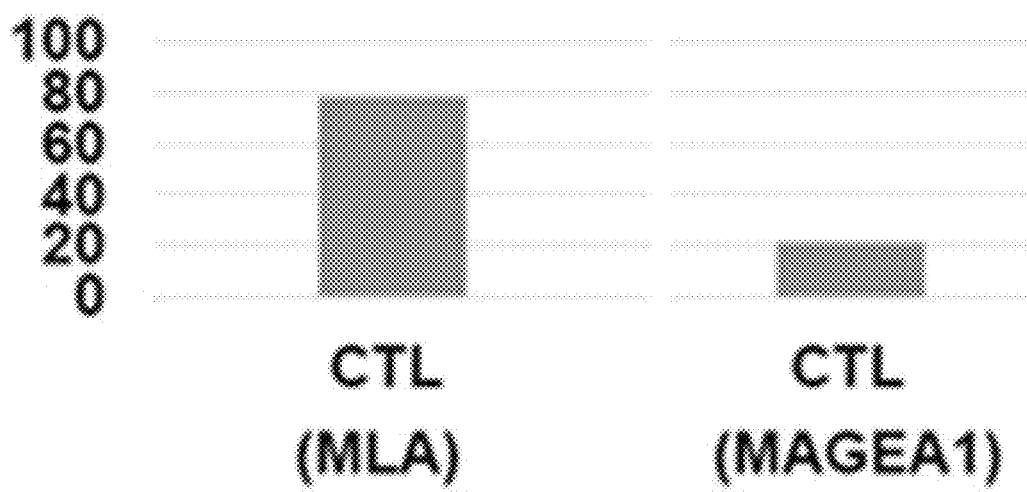
FIGS. 17A and 17B show Tet+CD8+ cells of MLA and MAGEA1 direct sorted T cells post REP1 and post REP2, respectively.

FIG. 17A shows, post REP1, the percentage of MLA Tet+CD8+ T cells in the MLA Tet sorted CD8+ T cells and the percentage of MAGEA1 Tet+CD8+ T cells in the MAGEA1 Tet sorted CD8+ T cells.

Figure 17B:
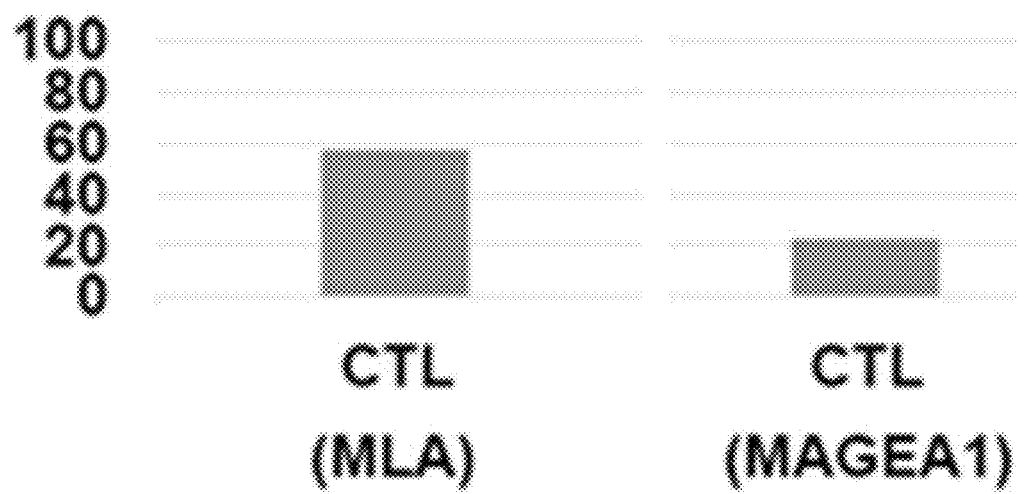

FIG. 17B shows, post REP2, the percentage of MLA Tet+CD8+ T cells in the MLA Tet sorted CD8+ T cells and the percentage of MAGEA1 Tet+CD8+ T cells in the MAGEA1 Tet sorted CD8+ T cells.

Figure 18A:
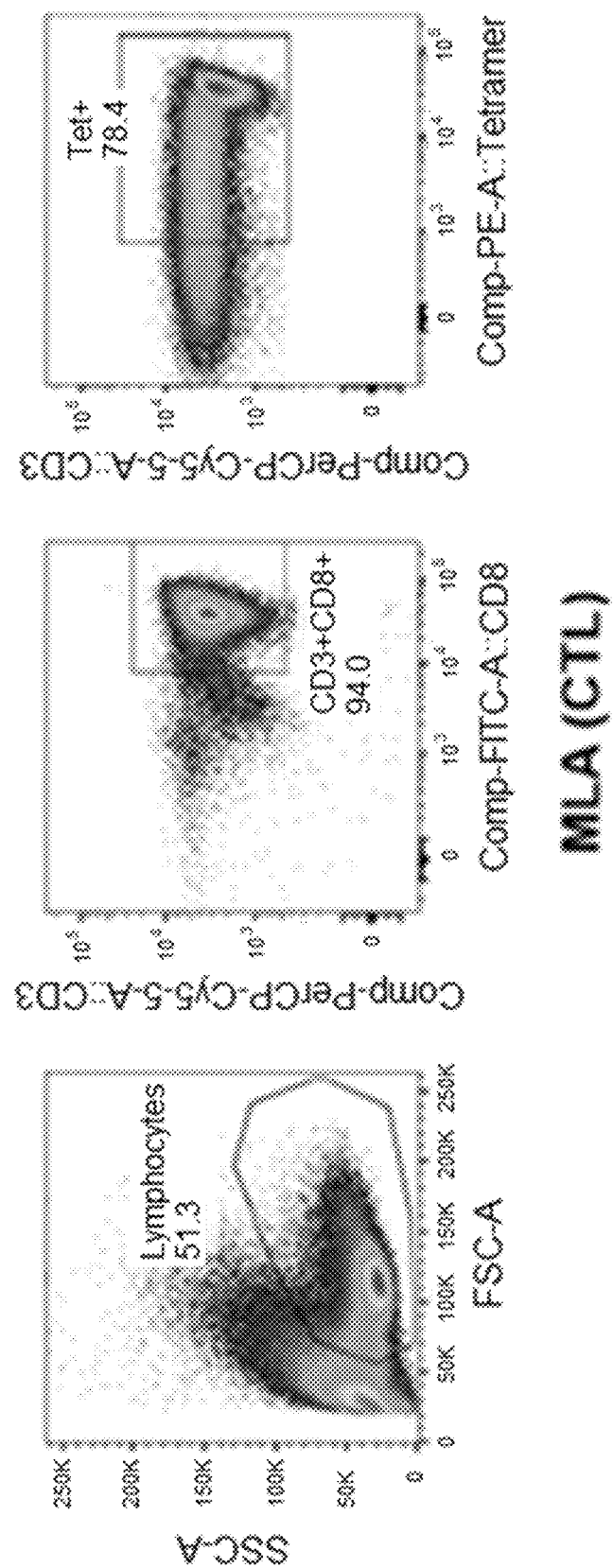
FIG. 18A shows the flow cytometry data of MLA post REP1 in FIGS. 16A and 17A.

FIG. 18A shows the post REP1 flow cytometry data of MLA in FIGS. 16A and 17A.

FIG. 18B shows the post REP2 flow cytometry data of MLA in FIGS. 16B and 17B.

Figure 19A:
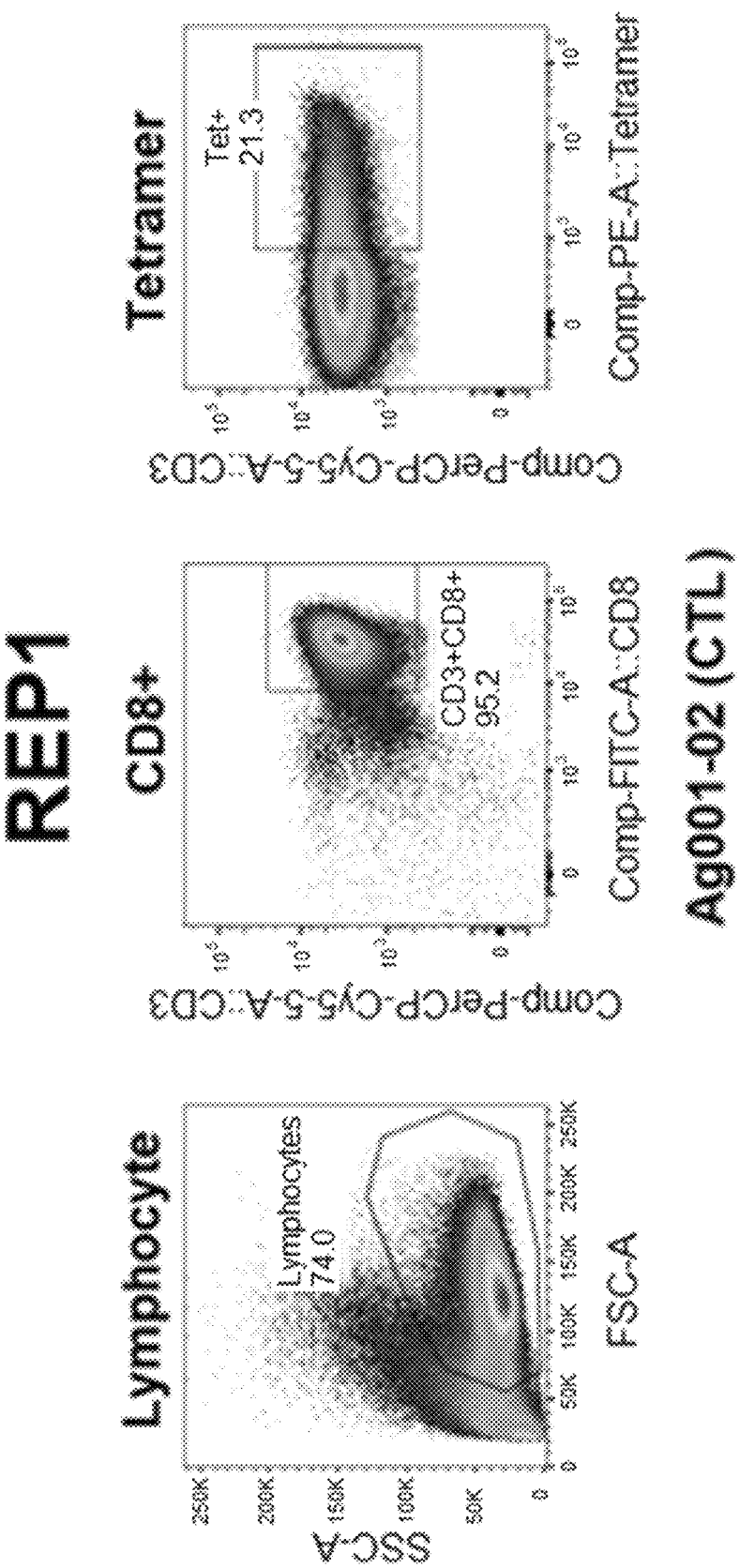
FIG. 19A shows the flow cytometry data of Ag001-002 post REP1.

FIG. 19A shows the post REP1 flow cytometry data of Ag001-02 Tet sorted CD8+ T cells.

FIG. 19B shows the post REP2 flow cytometry data of Ag001-02 Tet sorted CD8+ T cells.

To determine the cytotoxic activity of MLA Tet sorted CD8+ T cells and MAGEA1 Tet sorted CD8+ T cells, T2 killing assays were performed by incubating MLA Tet sorted CD8+ T cells or MAGEA1 Tet sorted CD8+ T cells with T2 cells pulsed with increasing concentrations, e.g., 0 (control), 0.00001, 0.0001, 0.001, 0.01, 0.1, 1, and 10 µg/ml, of MLA peptide or MAGEA1 peptide, respectively.

Figure 20A:
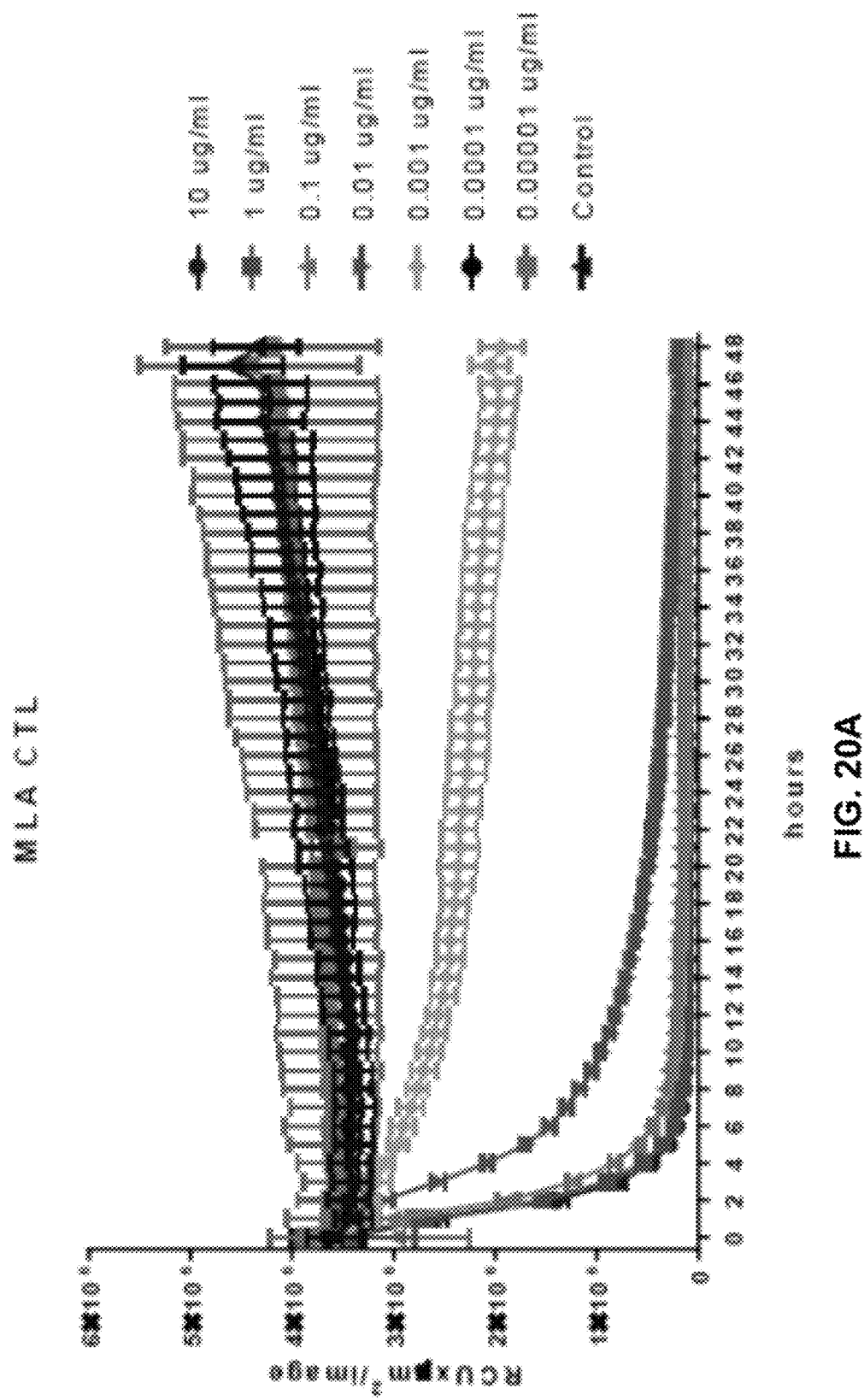
FIG. 20A shows T2 killing assays of MLA direct sorted T cells.
Figure 20B:
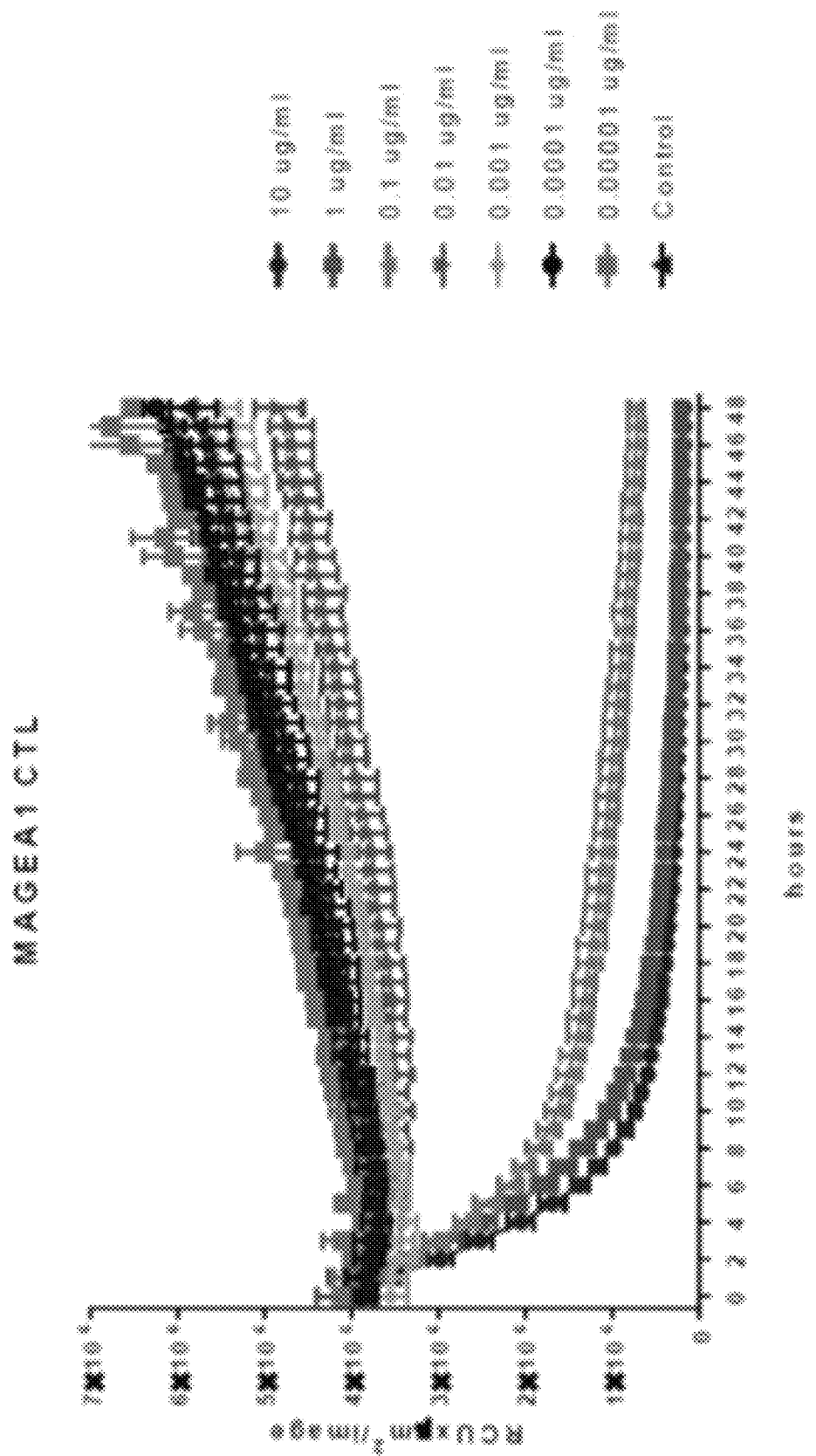
FIG. 20B shows T2 killing assays of MAGEA1 direct sorted T cells.

MLA Tet sorted CTL (FIG. 20A) and MAGEA1 Tet sorted CTL (FIG. 20B), killed T2 cells pulsed with MLA peptide or MAGEA1 peptide in a concentration-dependent manner.

Example 3

Comparison Between Staining Conditions

TCRs are known to trigger and internalize after engaging cognate antigen. pMHC tetramers could fail to stain T cells after these cells have been exposed to cognate antigen. One way to enhance staining intensities may be to inhibit TCR internalization by treating these cells with protein kinase inhibitors (PKI), e.g., dasatinib, before peptide/MHC (pMHC) multimer staining (Lissina et al., *J Immunol Methods* 2009; 340:11-24; the content of which is incorporated by reference by its entirety).

To compare the effects of PKI and temperatures on pMHC multimer staining, healthy donor peripheral blood mononuclear cells (PBMCs) were pretreated with 50 nM Dasatinib (FIG. 21A) or untreated (FIG. 21B) and then stained with two Col6A3-002 peptide (FLLDGSANV (SEQ ID NO: 141)) (Col) tetramers (2Dtet) conjugated to streptavidin BV421 and PE, and five different irrelevant APC tetramers (peptide 1, peptide 2, peptide 3, peptide 4, and peptide 5) at either 37° C. (FIG. 21A) or room-temperature (RT) (FIG. 21B) for 30 minutes. Following tetramer staining, samples were counterstained with tetramer stabilizing antibodies staining against PE and APC at 4° C., followed by staining with anti-CD45 PE-Cy7 antibody at 4° C.

Figure 21A:
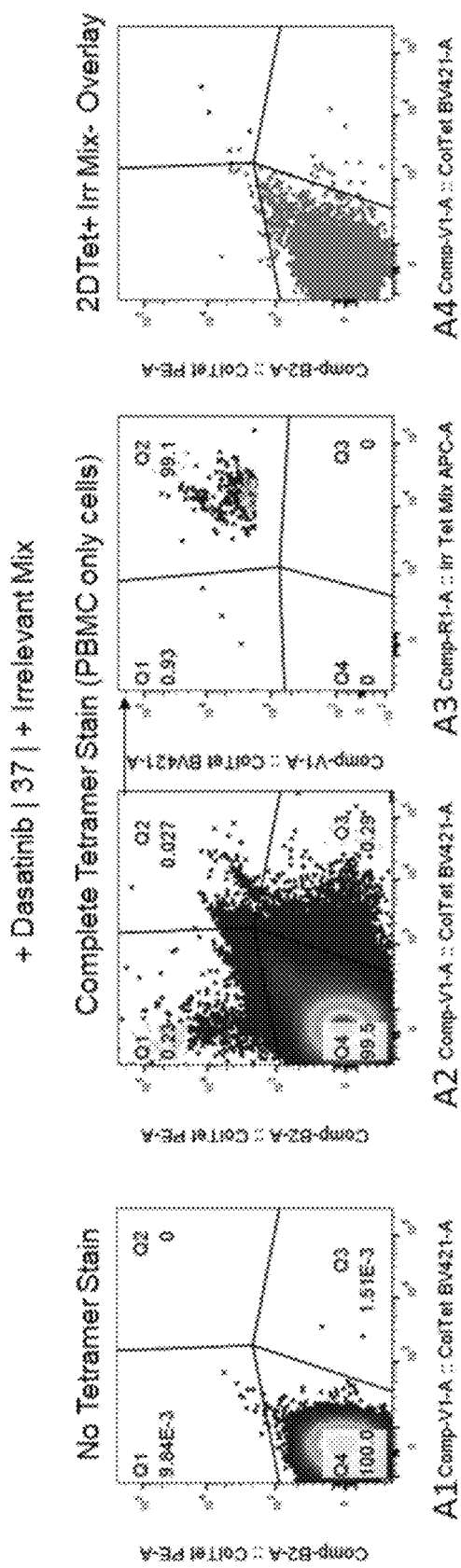
FIG. 21A shows cell sorting in the presence of dasatinib at 37° C.
Figure 21B:
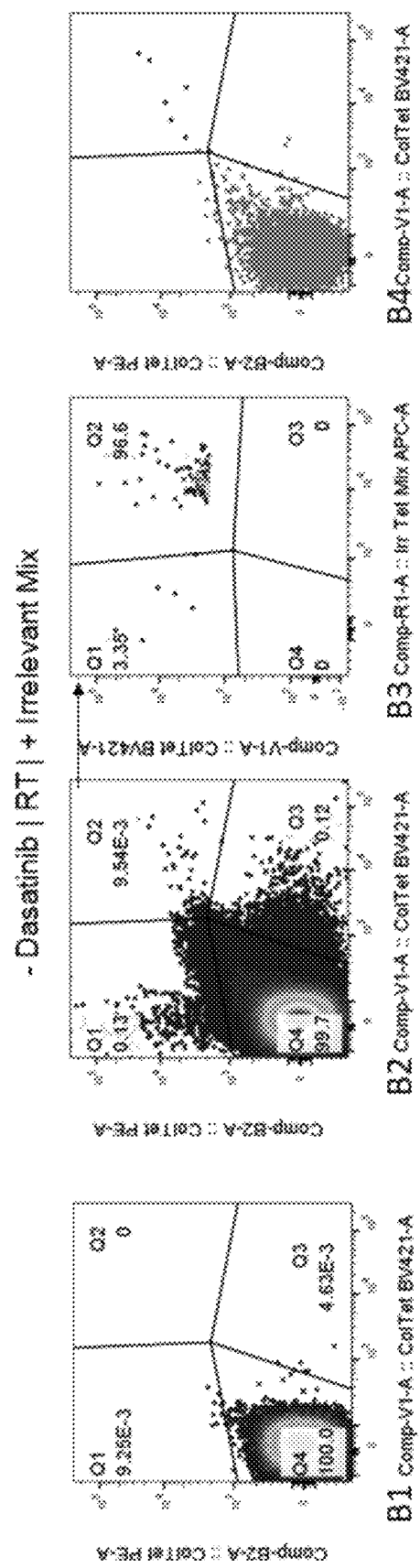
FIG. 21B shows cell sorting in the absence of dasatinib at room temperature.

FIGS. 21A (panel A1) and 21B (panel B1) show the background gating strategy in samples stained with no tetramers.

FIGS. 21A (panel A2) and 21B (panel B2) show the 2Dtet staining with the cells of interest represented in Q2. Dasatinib treatment at 37° C. resulted in 0.027% of Col Tet+ T cells, which is similar to that obtained from without dasatinib treatment at RT, i.e., 0.0095%.

FIGS. 21A (panel A3) and 21B (panel B3) show the Q2 quadrant from FIGS. 21A (panel A2) and 21B (panel B2) against the irrelevant APC tetramers (peptide 1, peptide 2, peptide 3, peptide 4, and peptide 5) with the Q1 quadrant representing the cells of interest. Dasatinib treatment at 37° C. resulted in 0.93% of Col Tet+ T cells, which is similar to that obtained from without dasatinib treatment at RT, i.e., 3.35%.

FIGS. 21A (panel A4) and 21B (panel B4) show the location of the Q1 cells from FIGS. 21A (panel A3) and 21B (panel B3) overlaid on the FIGS. 21A (panel A2) and 21B (panel B2). All cells gated from CD45+single cell lymphocytes. Final frequencies and staining sensitivity show that dasatinib treatment at 37° C. resulted in one Col Tet+ T cells in $4 \times 10^5$ CD45+ cells, which is similar to that obtained from without dasatinib treatment at RT, i.e., one Col Tet+ T cells in $3 \times 10^5$ CD45+ cells.

Example 4

Panel Optimization

To compare the effects of single (1D)- and double (2D)-fluorochrome conjugated pMHC multimers on T cell staining, about $5 \times 10^6$ cells/ml of Col6A3 REP1 (αCol6A3 T cells) cells, which are T cells specifically binding to cells presenting Col6A3-002 peptide/MHC complex on cell surface, and, as a negative control, about $5 \times 10^6$ cells/ml of αMLA T cells, which are T cells specifically binding to cells presenting MLA peptide/MHC complex on cell surface, were stained under the conditions shown in Table 10. All cells were gated from CD45+single cell lymphocytes.

TABLE 10

| Cell concentration | 5e6/mL, single T-cell specificities |
|---|---|
| Tetramer staining | RT, 3 ug/mL*, APC and/or PE COL6A3, 1' at 1000G pre-spin |
| Antibody staining | 4° C., 1:80 dilution, CD45 Pe-Cy7 |

Figure 22A:
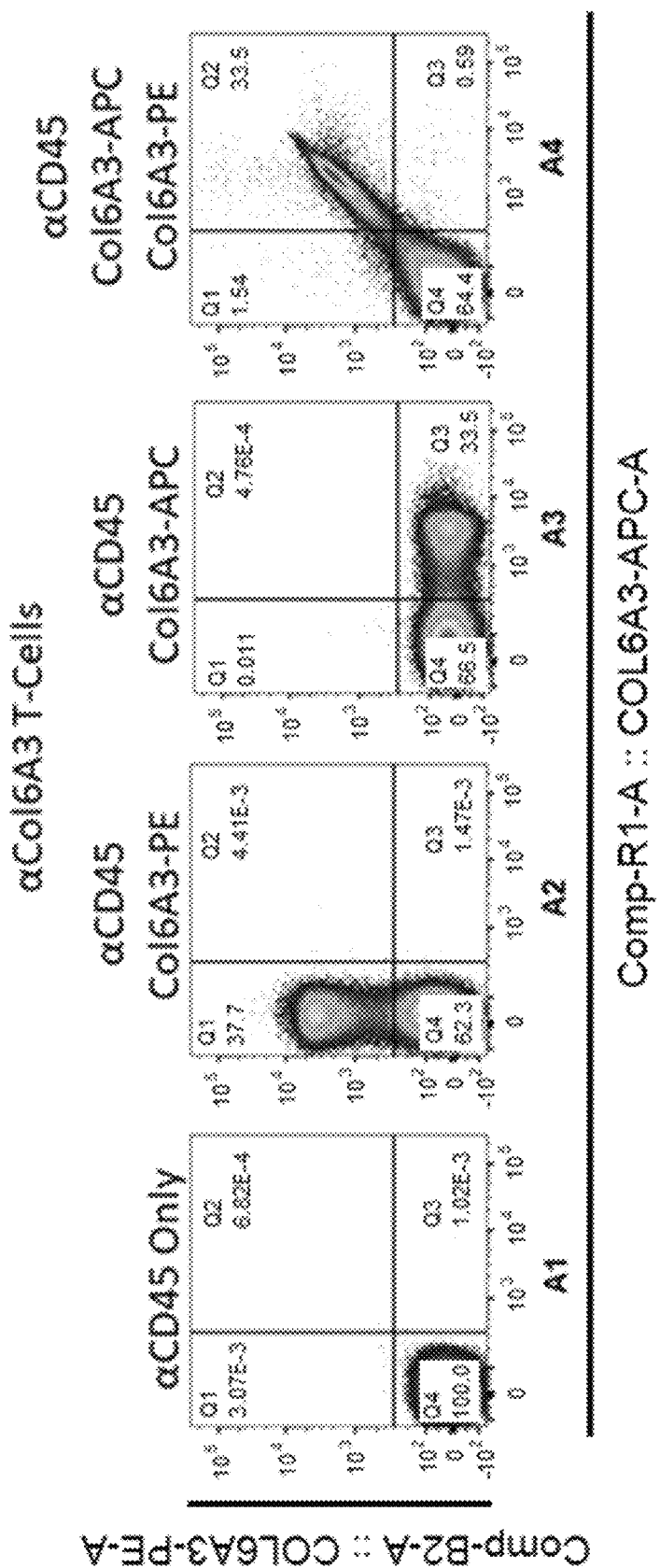
FIG. 22A shows the flow cytometry data of αCol6A3 T cell staining in accordance to one embodiment of the present disclosure.
Figure 22B:
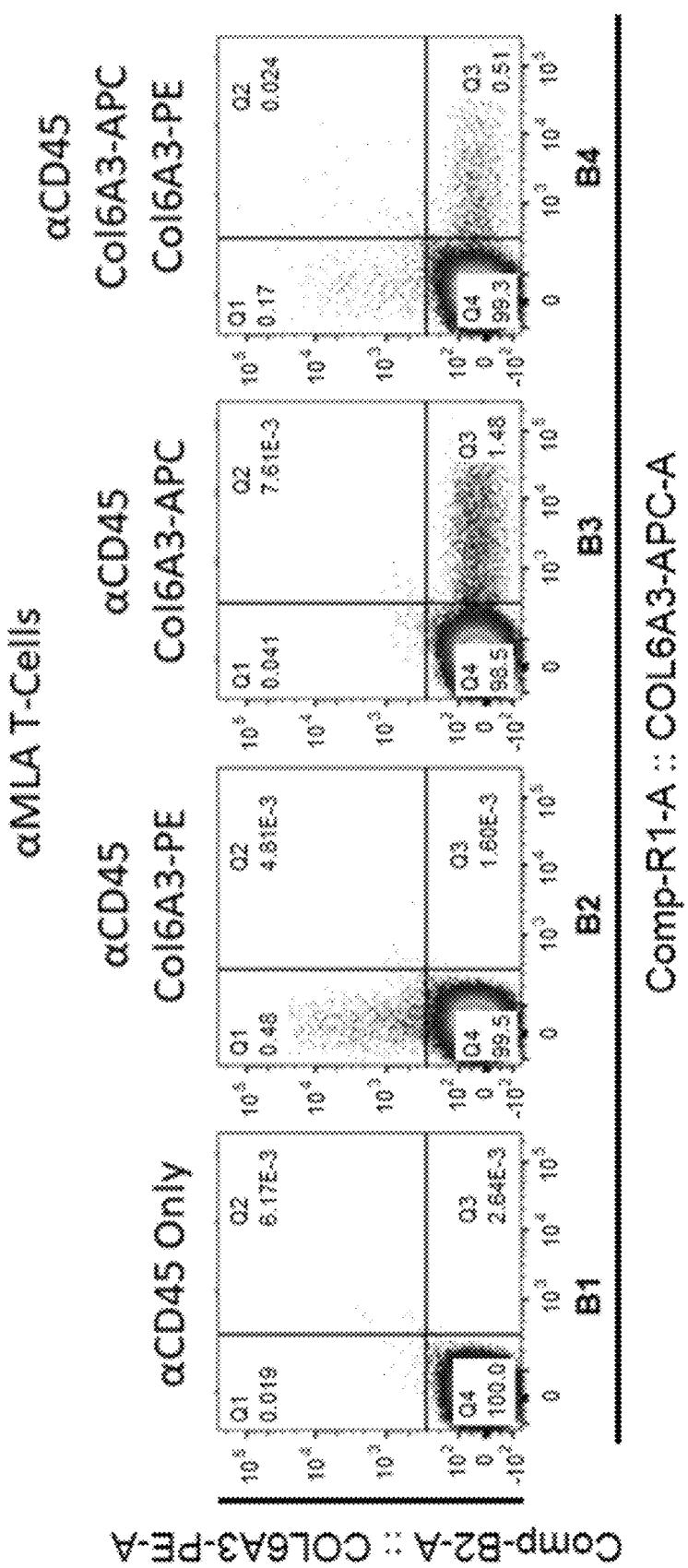
FIG. 22B shows the flow cytometry data of αMLA T cell staining in accordance to one embodiment of the present disclosure.
Figure 22C:
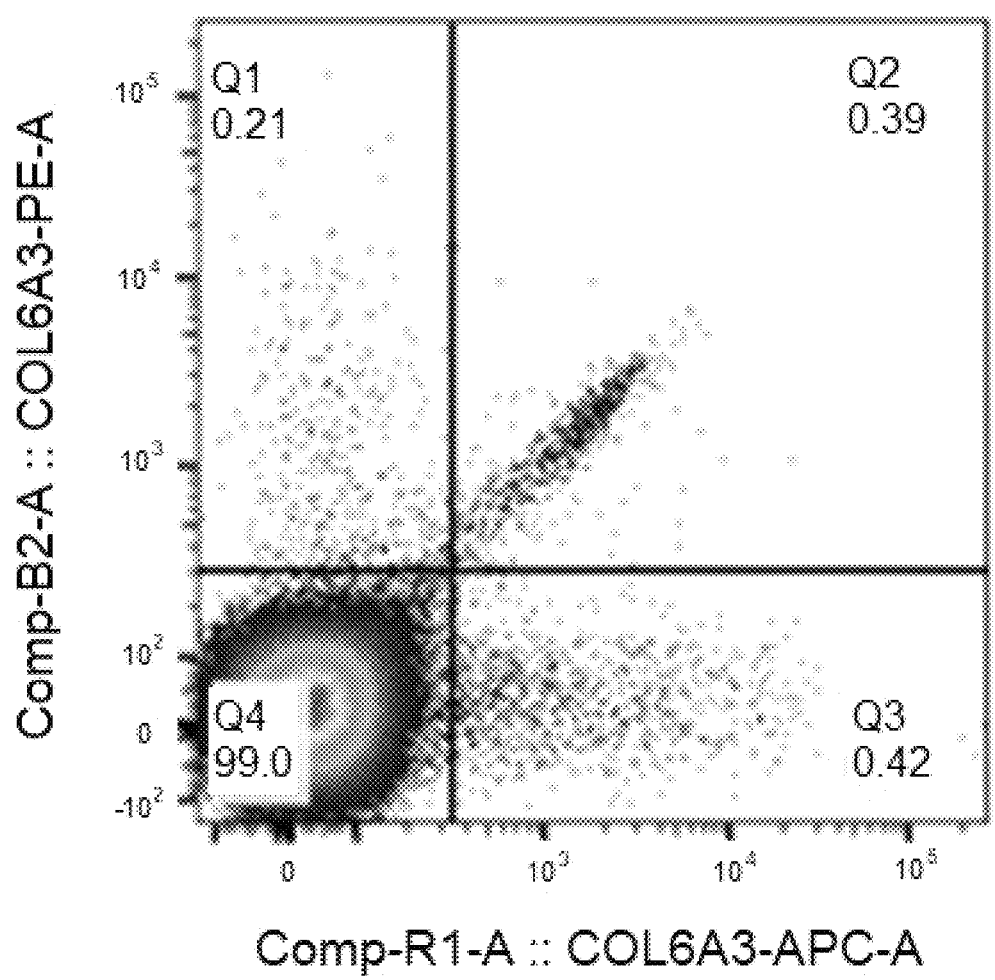
FIG. 22C shows the flow cytometry data of a mixture of stained αCol6A3 T cells and stained αMLA T cells in accordance with one embodiment of the present disclosure.

FIG. 22A (panel A1) shows background APC/PE staining of anti-CD45 antibody (αCD45) stained αCol6A3 T cells. Panel A2 (Q1) shows 37.7% of αCD45+ αCol6A3 T cells were stained positive for Col6A3-PE. Panel A3 (Q3) shows 33.5% of αCD45+ αCol6A3 T cells were stained positive for Col6A3-APC. Panel A4 (Q2) shows 33.5% of αCD45+ αCol6A3 T cells were stained positive for both Col6A3-PE and Col6A3-APC. As a negative control, FIG. 22B shows background APC/PE staining of αCD45 stained αMLA T cells (panel B1), Col6A3-PE stained αMLA T cells (0.48%) (panel B2, Q1), Col6A3-APC stained αMLA T cells (1.48%) (panel B3, Q3), and Col6A3-PE and Col6A3-APC double stained αMLA T cells (0.024%) (panel B4, Q2). FIG. 22C shows mixing stained negative control αMLA T cells with double-stained αCol6A3 T cells at a ratio of 10:1, 0.39% (Q2) of αCol6A3 T cells can also be detected.

To compare the abilities of 1D tetramer and 2D tetramer in detecting low frequency of peptide-specific T cells, double-stained αMLA T cells were mixed or spiked with double-stained (APC/PE) αCol6A3 T cells at a dilution ratio of 3:1, 30:1, and 90:1 followed by flow analysis. The staining conditions are shown in Table 11.

TABLE 11

| Cell concentration | 5e6/mL, titration of mixed T-cell specificities (3 to 100 fold) |
|---|---|

TABLE 11-continued

| Tetramer staining | RT, 3 ug/mL*, APC and/or PE COL6A3, 1' at 1000G pre-spin |
|---|---|
| Antibody staining | 4° C., 1:80 dilution, CD45 Pe-Cy7 |

Figure 23A:
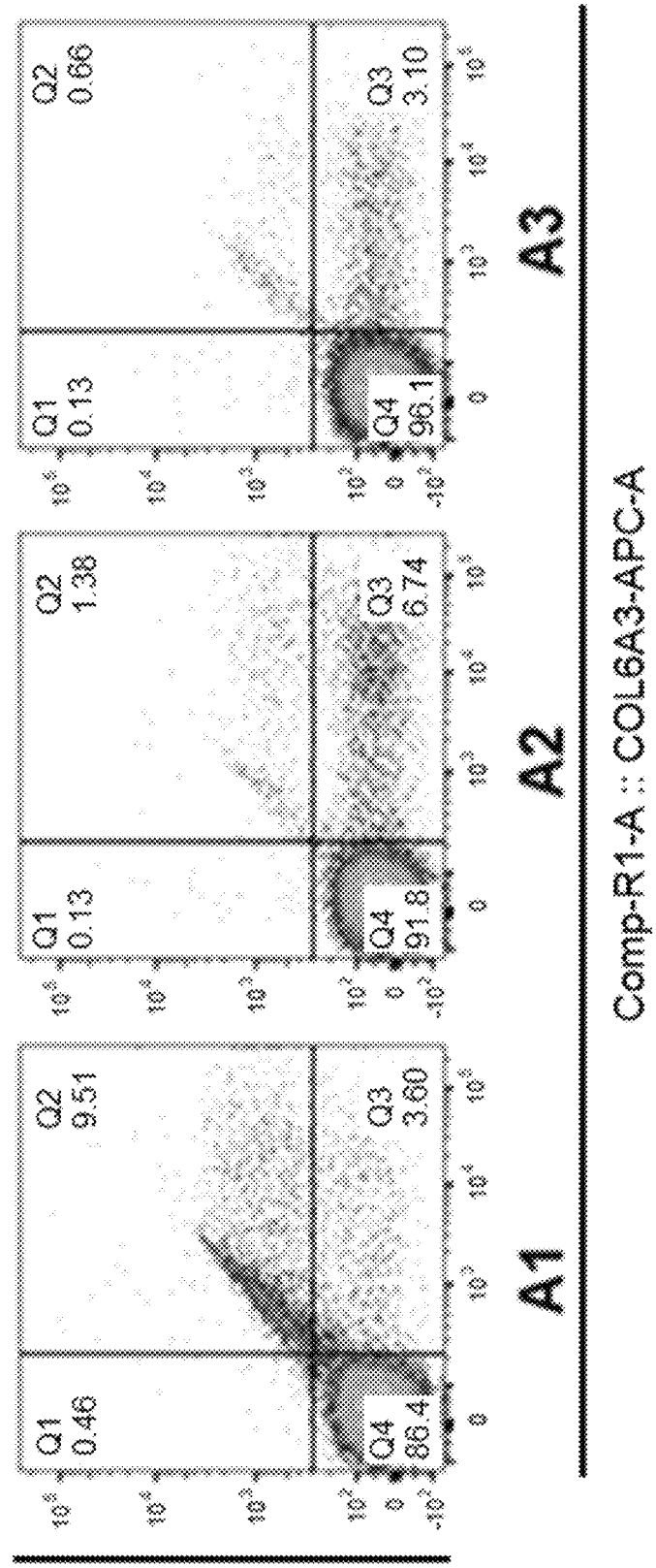
FIG. 23A shows the flow cytometry data using double staining tetramers in accordance with one embodiment of the present disclosure.
Figure 23B:
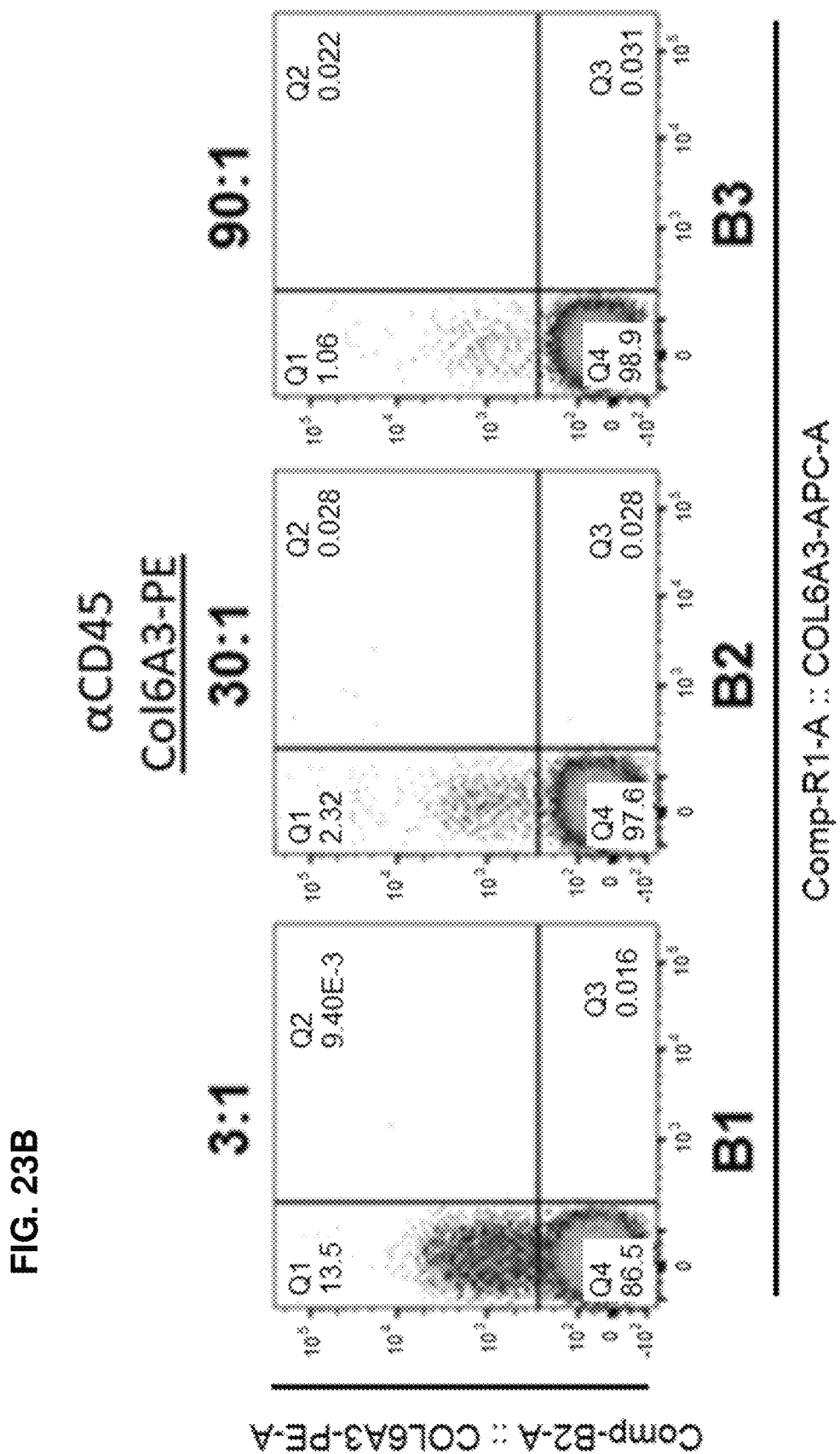
FIG. 23B shows the flow cytometry data using single staining tetramers in accordance with one embodiment of the present disclosure.
Figure 23C:
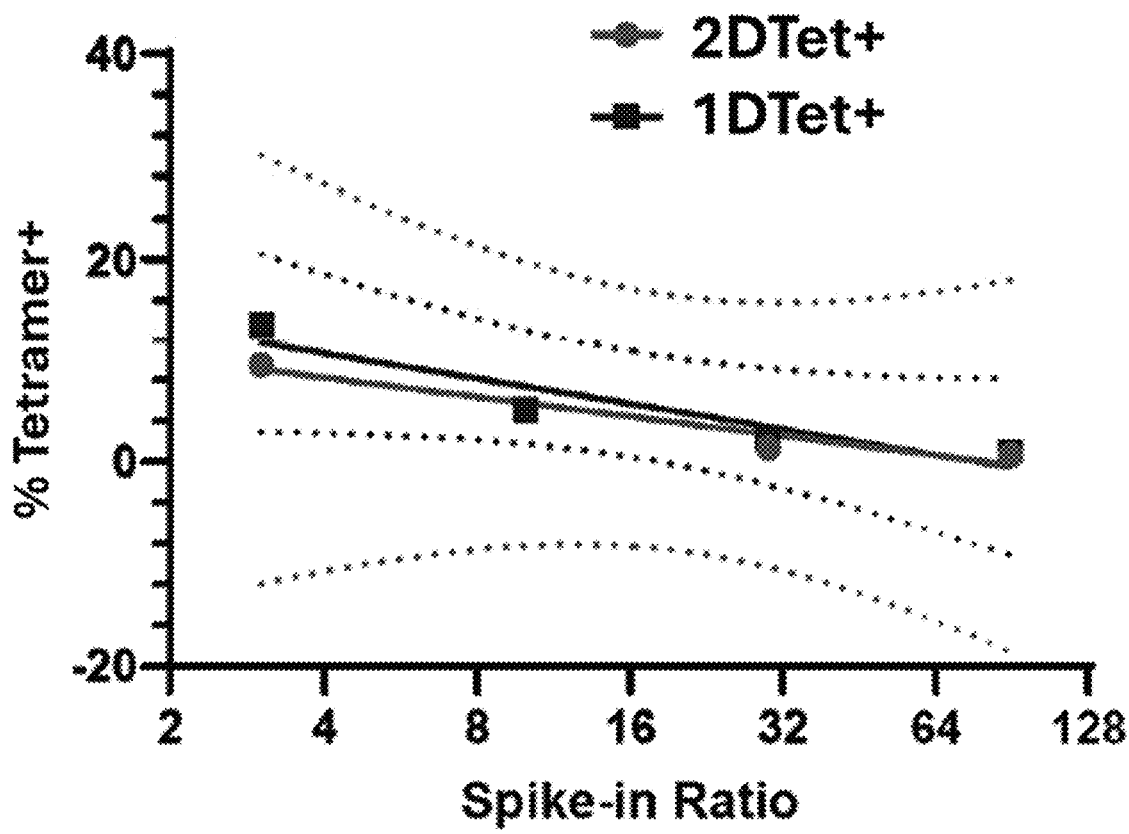
FIG. 23C shows R squared values of double staining tetramers and single staining tetramers in accordance with one embodiment of the present disclosure.

FIG. 23A shows, using double Col6A3-PE/APC staining, αCD45+ αCol6A3 T cells can be detected at a dilution ratio of 3:1 (9.51%) (panel A1, Q2), 30:1 (1.38%) (panel A2, Q2), and 90:1 (0.66%, panel A3, Q2). In contrast, FIG. 23B shows, using single Col6A3-PE staining, αCD45+ αCol6A3 T cells can be detected at a dilution ratio of 3:1 (13.5%) (panel B1, Q1), 30:1 (2.32%) (panel B2, Q1), and 90:1 (1.06%, panel B3, Q1). FIG. 23C shows 2D tetramer staining may have an improved linearity ($R^2$=0.9394) in detecting αCol6A3 T cells over 1D tetramer staining ($R^2$=0.8756) within the tested dilution range.

To further compare the abilities of 1D tetramer and 2D tetramer in detecting low frequency of peptide-specific T cells, double-stained αMLA T cells were mixed or spiked with double-stained (APC/PE) αCol6A3 T cells at a dilution ratio of 3:1, 9:1, 27:1, 81:1, 243:1, and 729:1 followed by flow analysis. The staining conditions are shown in Table 12.

TABLE 12

| Cell concentration | 5e6/mL, titration of mixed T-cell specificities (3 to 100 fold) |
|---|---|
| Tetramer staining | RT, 3 ug/mL*, APC and/or PE COL6A3, 30' at 1000G pre-spin |
| Antibody staining | 4° C., 1:80 dilution, CD45 Pe-Cy7 |

Figure 24A:
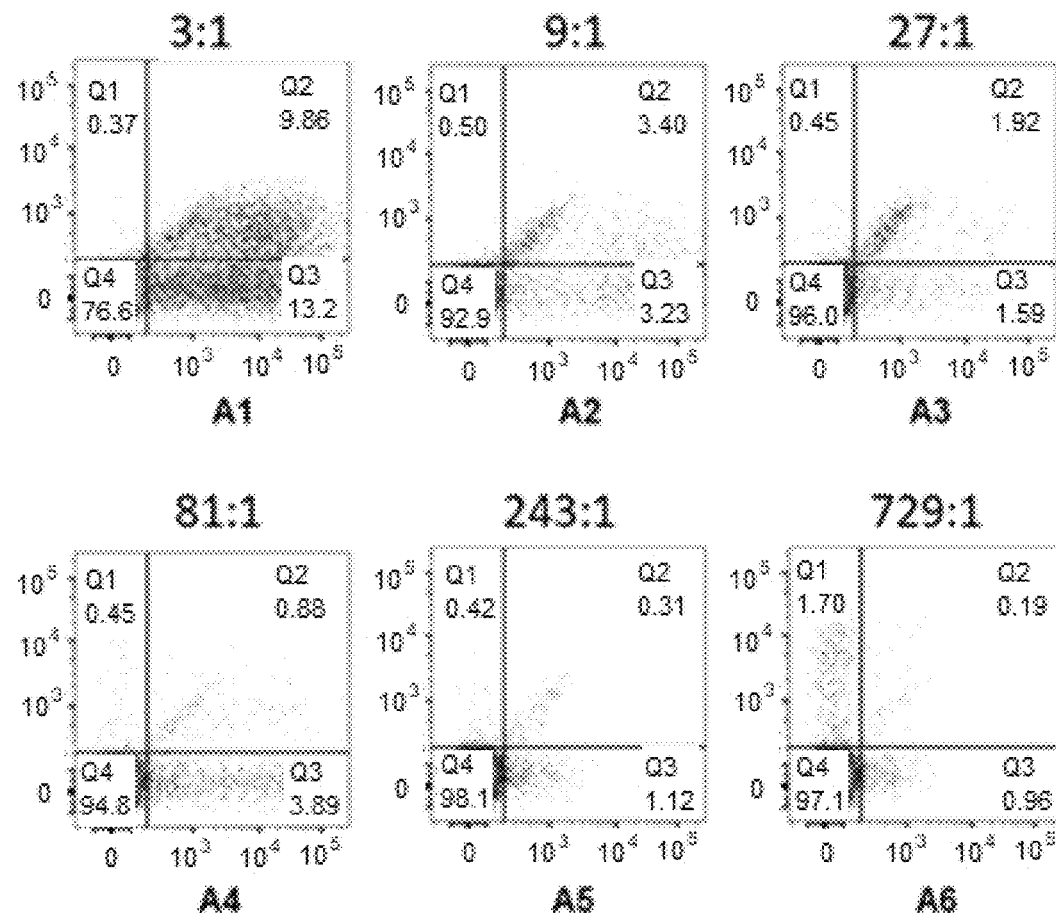
FIG. 24A shows the flow cytometry data using double staining tetramers in accordance with another embodiment of the present disclosure.
Figure 24C:
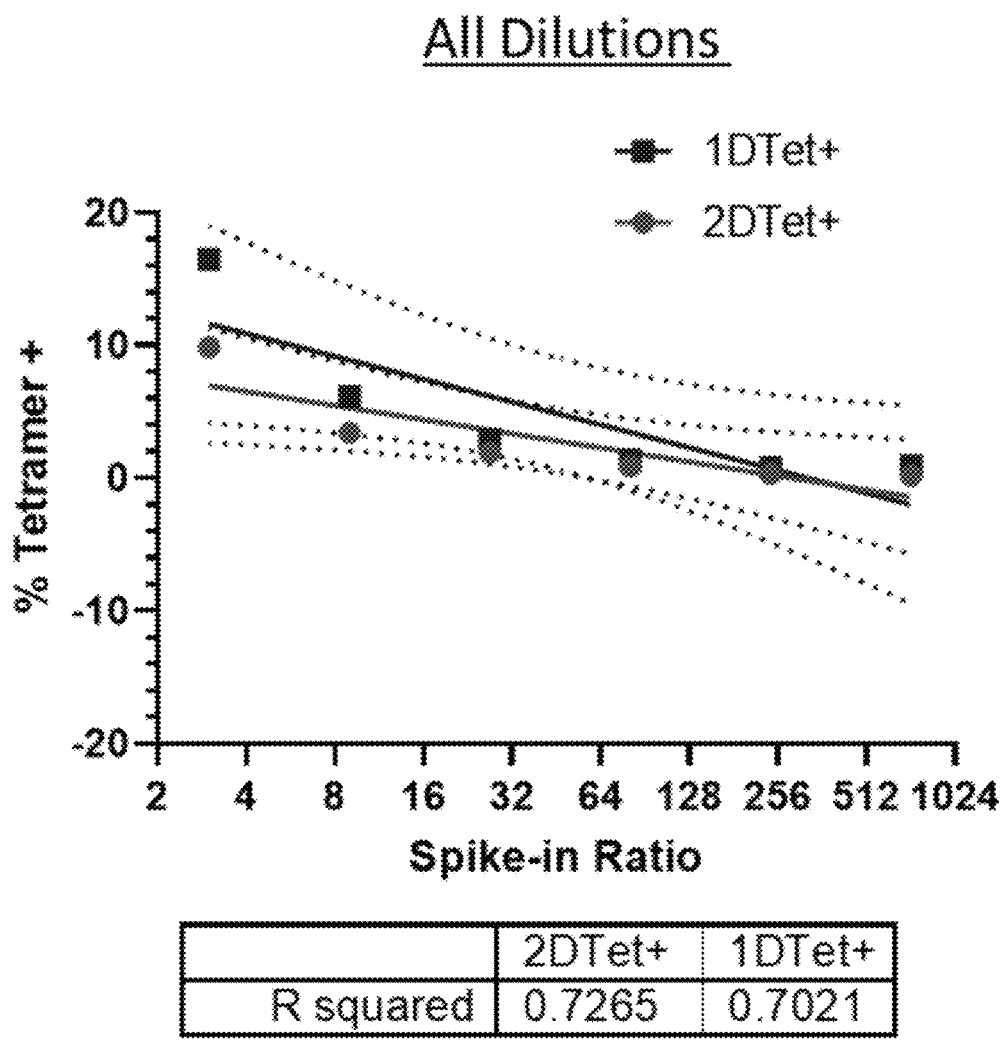
FIG. 24C shows R squared values of double staining tetramers and single staining tetramers in accordance with another embodiment of the present disclosure.
Figure 24D:
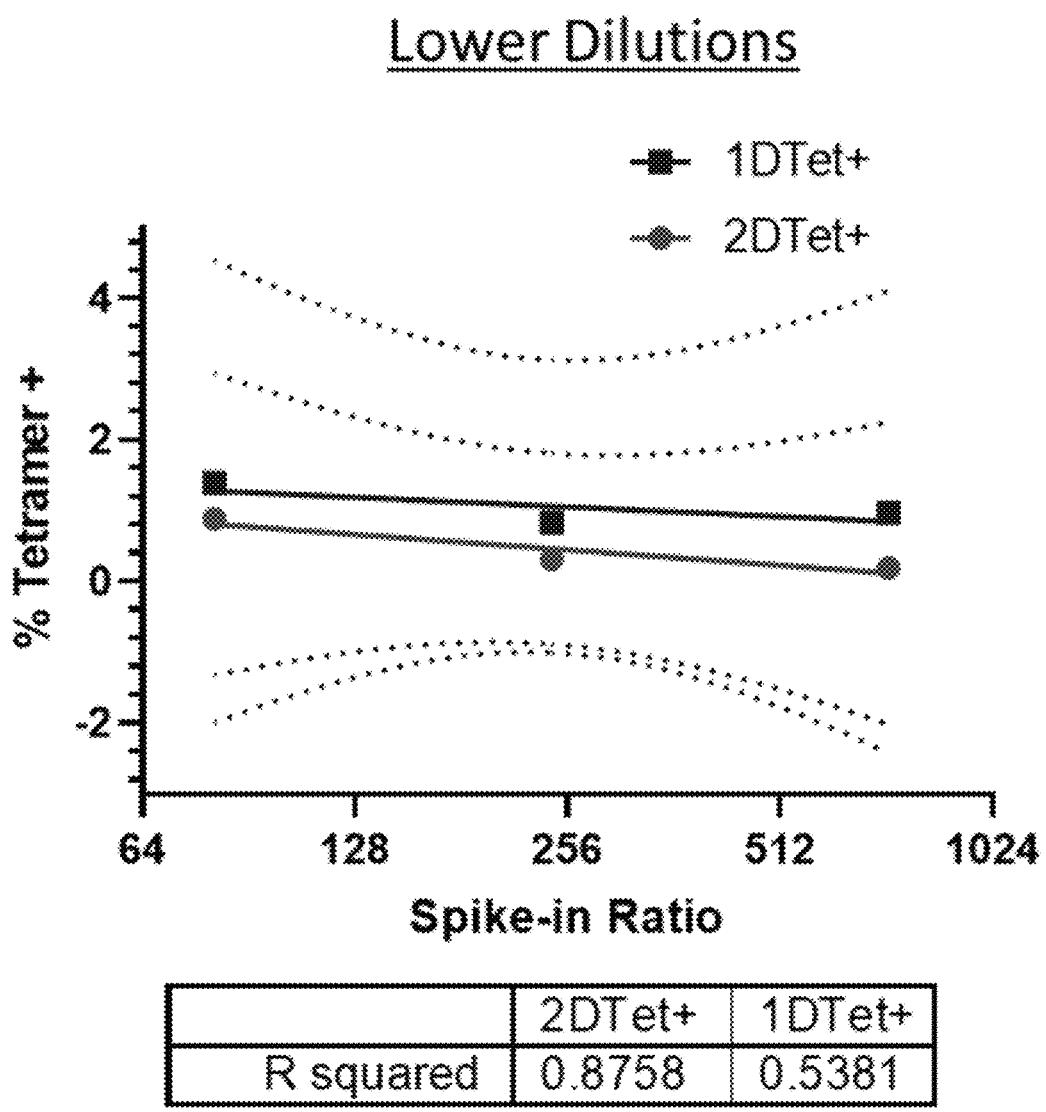
FIG. 24D shows R squared values of double staining tetramers and single staining tetramers in accordance with another embodiment of the present disclosure.

FIG. 24A shows, using double Col6A3-PE/APC staining, αCD45+ αCol6A3 T cells can be detected at a dilution ratio of 3:1 (9.86%) (panel A1, Q2), 9:1 (3.40%) (panel A2, Q2), 27:1 (1.92%) (panel A3, Q2), 81:1 (0.88%) (panel A4, Q2), 243:1 (0.31%) (panel A5, Q2), and 729:1 (0.19%, panel A6, Q2). In contrast, FIG. 24B shows, using single Col6A3-PE staining, αCD45+ αCol6A3 T cells can be detected at a dilution ratio of 3:1 (16.5%) (panel B1, Q1), 9:1 (6.15%) (panel B2, Q1), 27:1 (2.92%) (panel B3, Q1), 81:1 (1.39%) (panel B4, Q1), 243:1 (0.83%) (panel B5, Q1), and 729:1 (0.96%, panel B6, Q1). FIG. 24C shows 2D tetramer staining may have an improved linearity ($R^2$=0.7265) in detecting αCol6A3 T cells over 1D tetramer staining ($R^2$=0.7021) within all the dilution ranges tested. FIG. 24D shows 2D tetramer staining has better linearity (R2=0.8758) in detecting αCol6A3 T cells than 1D tetramer staining (R2=0.5381) within lower dilution ranges, e.g., from 64:1 to 1024:1. These results indicate 2D tetramer staining may be better than 1D tetramer staining in detecting low frequency peptide-specific T cells.

Tungatt et al. (*J Immunol* 2015, 194:463-474) and Dolton et al. (Immunology 2015, 146:11-22) (the contents of which are hereby incorporated by reference by their entireties) disclose that addition of anti-fluorochrome unconjugated antibodies during staining resulted in considerably improved fluorescence intensity with both pMHC tetramers and dextramers and with PE-, APC-, or FITC-based reagents.

To determine the effect of anti-fluorochrome unconjugated antibodies on 1D Tet staining of peptide-specific T cells, αCD45+ αCol6A3 T cells were stained with (i) 1D Tet (APC)±anti-APC primary antibody or (ii) 1D Tet (PE) Tet±anti-PE primary antibody. FIG. 25A (panel A1, Q3) shows addition of anti-APC primary antibody enhances the detection of αCD45+APC-Tet-stained αCol6A3 T cells from 46.3% without anti-APC primary antibody to 63.8% (panel A2, Q3). FIG. 25B shows addition of anti-PE primary antibody enhances the detection of PE-Tet-stained αCD45+ αCol6A3 T cells from 39.1% without anti-APC primary antibody (panel B1, Q1) to 60.6% (panel B2, Q1).

To determine the effect of anti-fluorochrome unconjugated antibodies on 2D Tet staining of peptide-specific T cells, αCD45+ αCol6A3 T cells were stained with (i) 2D Tet (APC+PE)±anti-APC primary antibody and anti-PE primary antibody or (ii) 2D Tet (BV421+PE)±anti-PE primary antibody. FIG. 25C (panel C1, Q2) shows addition of anti-APC primary antibody and anti-PE primary antibody enhances the detection of αCD45+2D Tet (APC+PE)-stained αCol6A3 T cells from 12.0% without anti-APC primary antibody and anti-PE primary antibody to 39.2% (panel C2, Q2). FIG. 25D shows addition of anti-PE primary antibody enhances the detection of 2D Tet (BV421+PE)-stained αCD45+ αCol6A3 T cells from 20.8% without anti-APC primary antibody (panel D1, Q6) to 39.5% (panel D2, Q6). As a negative control, FIG. 25E shows addition of anti-APC primary antibody and anti-PE primary antibody did not detect 2D Tet (APC+PE) stained αMLA T cells (panel E1, Q2), neither did addition of anti-PE primary antibody detect 2D Tet (BV421+PE) stained αMLA T cells (panel E2, Q6). The negative control is shown in FIG. 25C. These results show addition of anti-fluorochrome unconjugated antibodies can enhance the detection of peptide-specific T cells in 1D Tet and 2D Tet staining of peptide-specific T cells.

Figure 26:
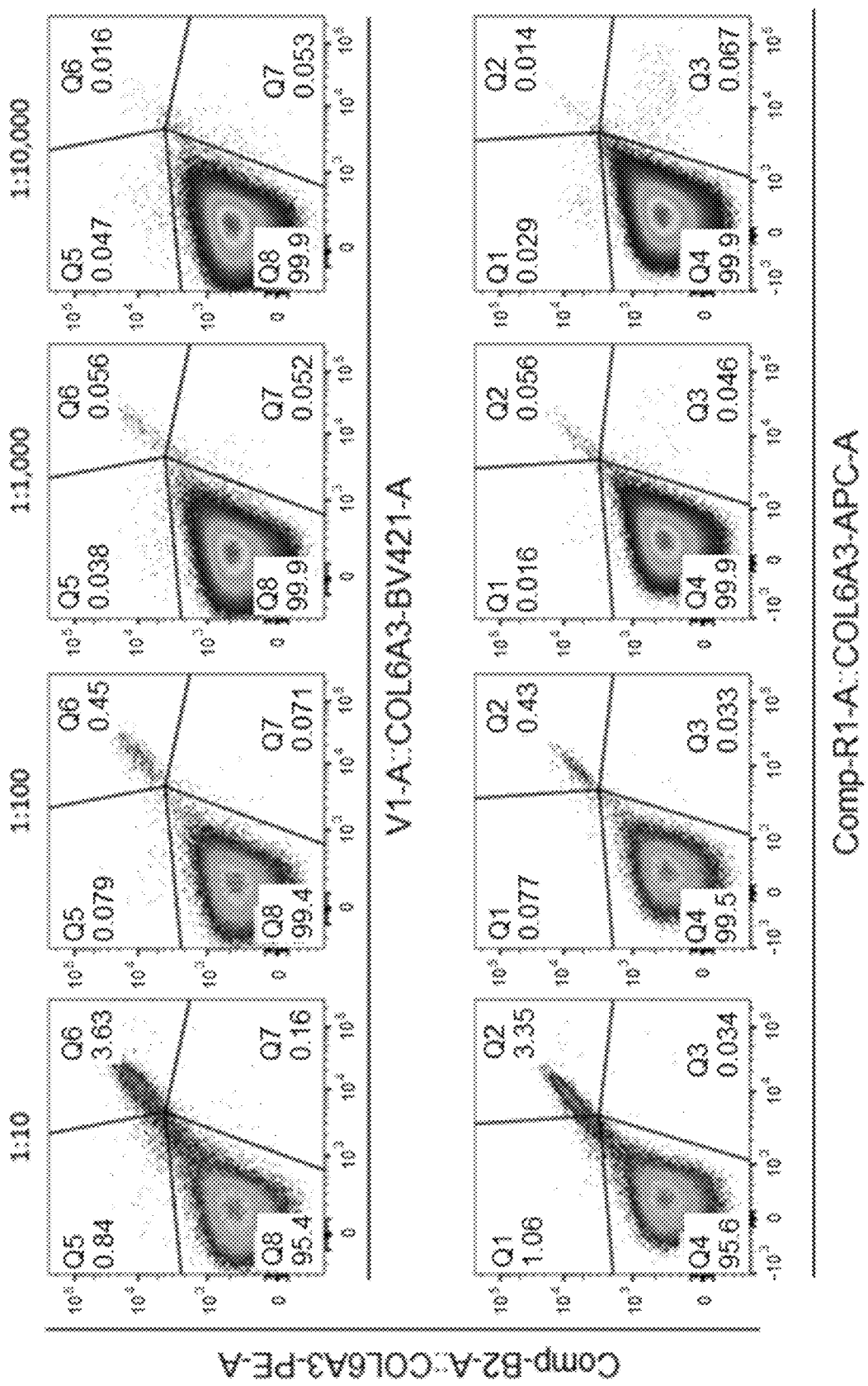
FIG. 26 shows the flow cytometry data of spiked samples in accordance with one embodiment of the present disclosure.

To compare the sensitivity of detection between 2D Tet (PE+BV421) and 2D Tet (APC+PE), 2D Tet (PE+BV421) stained αCol6A3 T cells were spiked into 2D Tet (PE+BV421) stained αMLA T cells at a dilution ratio of 1:10, 1:100, 1:1000, and 1:10000 in the presence of anti-PE primary antibody (FIG. 26, top panels). The negative control for 2D Tet (PE+BV421) staining is shown in FIG. 25E (E2). Similarly, 2D Tet (APC+PE) stained αCD45+αCol6A3 T cells were spiked into 2D Tet (APC+PE) stained αMLA T cells at a dilution ratio of 1:10, 1:100, 1:1000, and 1:10000 in the presence of anti-APC primary antibody and anti-PE primary antibody (FIG. 26, bottom panels). The negative control for 2D Tet (APC+PE) staining is shown in FIG. 25E (E1). These results show, at each dilution ratio, the detection of 2D Tet (APC+PE) stained αCol6A3 T cells (top panels, Q6) and the detection of 2D Tet (PE+BV421) stained αCol6A3 T cells (bottom panels, Q2) are comparable, suggesting equivalent sensitivity of 2D Tet (APC+PE) and 2D Tet (PE+BV421). Use of 2D Tet (PE+BV421), however, may reduce reagent demands, e.g., using a single anti-fluorochrome unconjugated antibody, e.g., anti-PE primary antibody, for 2D Tet (PE+BV421) staining versus two anti-fluorochrome unconjugated antibodies, e.g., anti-APC primary antibody and anti-PE primary antibody, for 2D Tet (APC+PE) staining.

Figure 27:
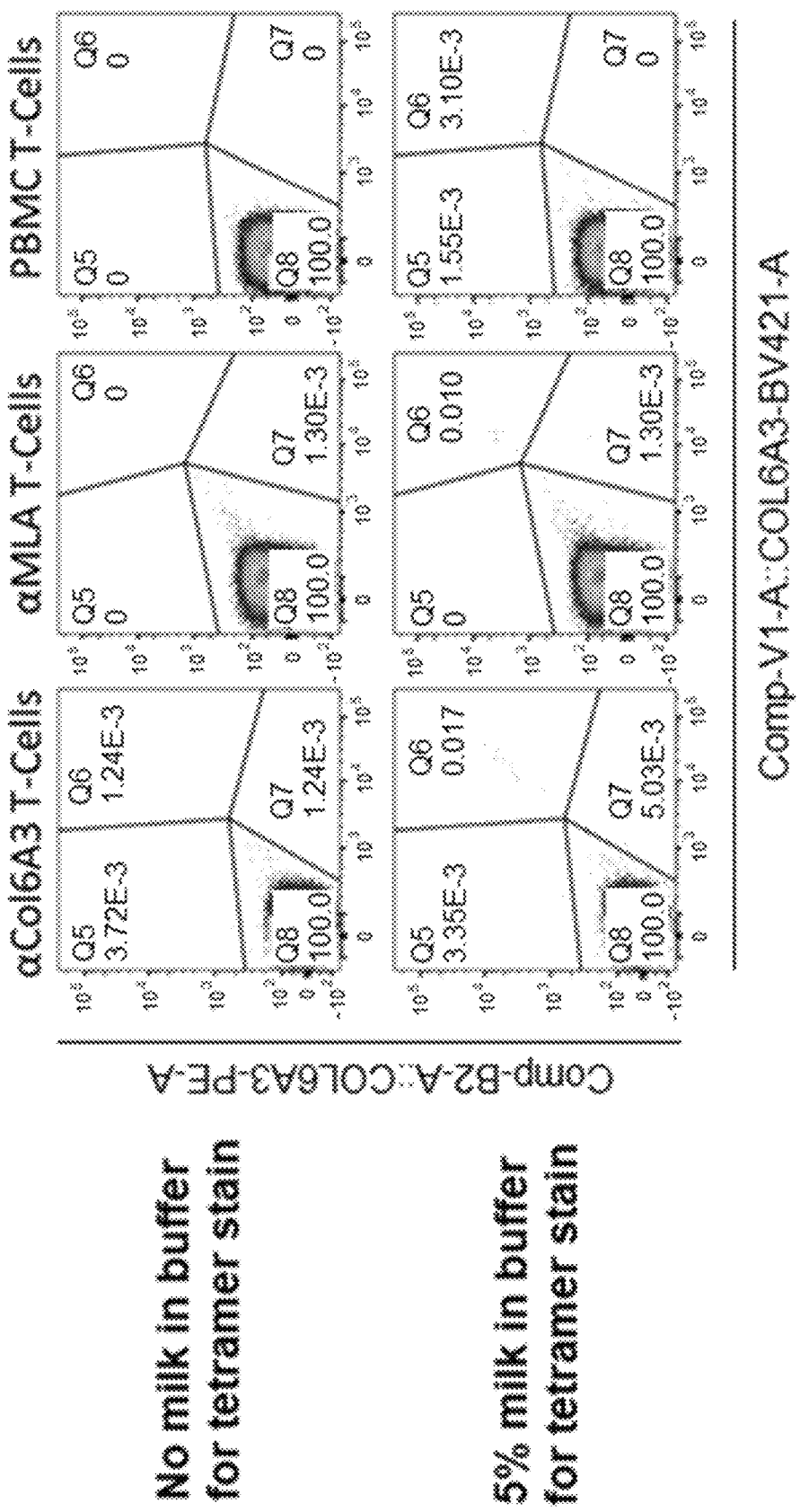
FIG. 27 shows the flow cytometry data using double staining tetramers and blocking agent in accordance with one embodiment of the present disclosure.

To test the ability of background blocking agents, e.g., milk, in detecting unstained T cells, 5% milk buffer was added to wash solutions containing 0.5% Tween 20. For example, unstained αCol6A3 T cells, αMLA T cells, and PBMC T cells were washed with solutions containing 5% milk and 0.5% Tween 20 or washed with solutions containing 0.5% Tween 20 without milk. FIG. 27 shows addition of milk in wash solutions enhances autofluorescence of αCol6A3 T cells (bottom left panel, Q6) and αMLA T cells (bottom middle panel, Q6) as compared with that without milk in wash solutions (top left panel (Q6) and top middle panel (Q6), respectively. Addition of milk in wash solutions may not enhance autofluorescence of PBMC T cells (top and bottom right panels).

The effects of PKI, irrelevant peptide tetramers, temperature on staining

To determine which staining conditions that may provide lowest background and lowest false positive rate, PBMC were stained with or without PKI treatment, e.g., dasatinib (DAS), with or without irrelevant peptide tetramer mix at different tetramer staining temperatures (Hadrup et al., Nat. Methods, 2009, 6:520-526; the content of which is hereby incorporated by reference in its entirety). For example, PBMC cells were stained with 2D Tet (PE+BV421) in the presence or in the absence of irrelevant peptide tetramer mix, e.g., five different irrelevant peptides (e.g., Col6A3-015 (YLMDDFSSL (SEQ ID NO: 16)), MAG-003 (KVLEHVVRV (SEQ ID NO: 118)), MAGEC2-001 (TLDEKVAEL (SEQ ID NO: 161)), MXRA5-003 (LL-WGHPRVALA (SEQ ID NO: 18), and MAGEA1-003 (KV-LEYVIKV (SEQ ID NO: 105)) APC tetramers±DAS treatment, at 37° C. or at room temperature (RT). DAS treatments were performed at 37° C.

For this analysis, at least $0.5 \times 10^6$ events were acquired. With DAS treatment, FIG. 28A, top left panel, shows staining in the presence of irrelevant peptide APC tetramer mix at RT, the detection of 8.04E-3% (Q2) CD45+ Col6A3-specific T cells in PBMC staining with 2D Tet (PE+BV421). These Q2 cells were further analyzed to detect irrelevant peptide positive T cells, i.e., APC/BV421 double-stained cells. Top right panel (Q2), shows the detection of 95.2% irrelevant peptide positive T cells in the BV421/PE double-positive cells detected in Q2 of top left panel. Thus, about 4.76% APC-negative and BV421-positive cells may represent true Col6A3-specific T cells (top right panel, Q1). In the absence of irrelevant peptide APC tetramer mix, Bottom right panel (Q2), shows 0% irrelevant peptide positive T cells in the BV421/PE double-positive cells detected in Q2 (7.17E-3%) of bottom left panel. Thus, 100% of cells in the BV421/PE double-positive cells detected in Q2 of bottom left panel would appear to be true Col6A3-specific T cells (bottom right panel, Q1). These results indicate that addition of irrelevant peptide tetramer mix in tetramer staining at RT can reduce the rate of detecting false positive peptide-specific T cells in PBMC, e.g., from 100% in the absence of irrelevant peptide APC tetramer mix to 4.76% in the presence of irrelevant peptide APC tetramer mix.

Figure 28A:
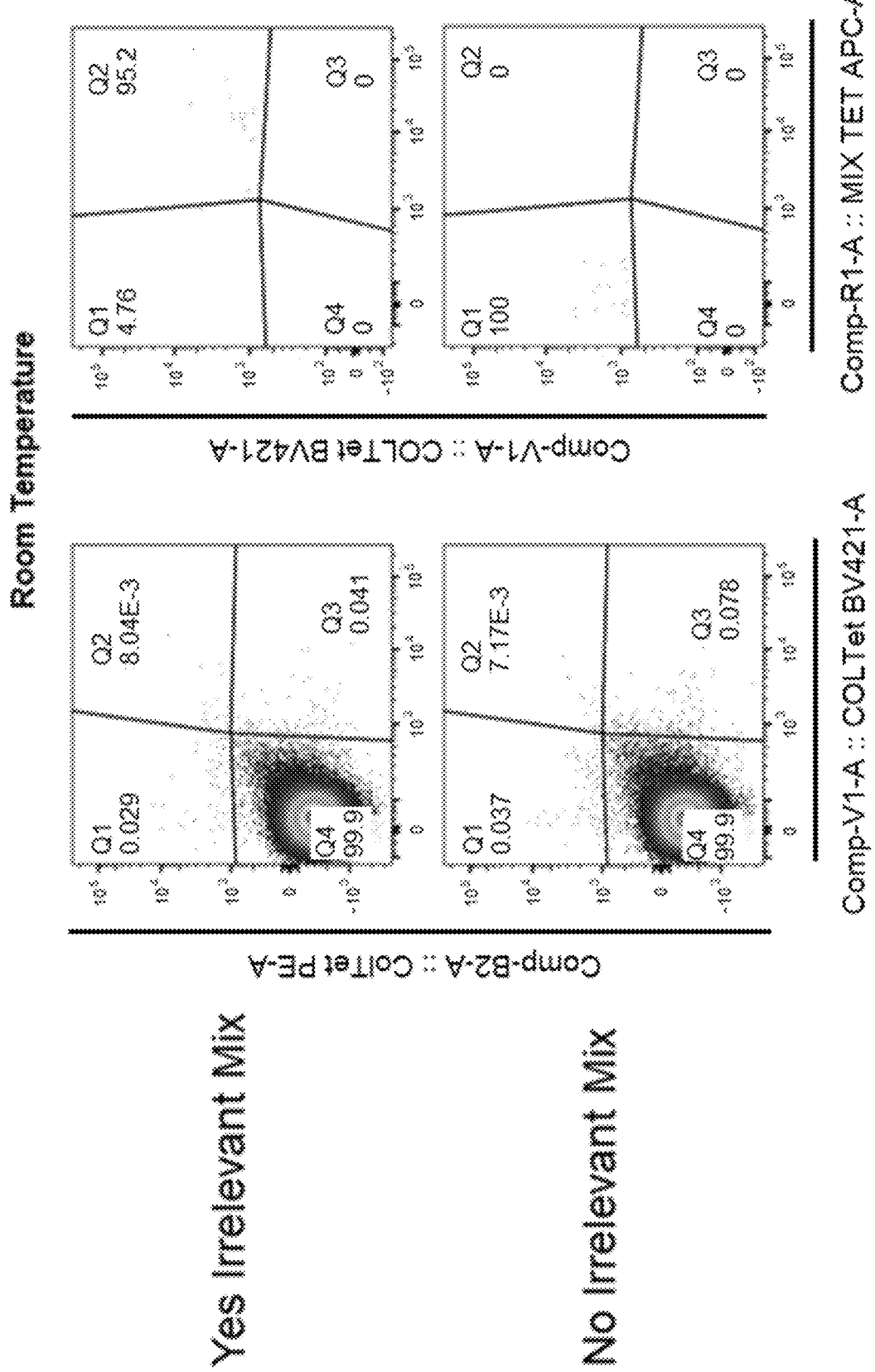
FIG. 28A shows the flow cytometry data using double staining tetramers and irrelevant peptide tetramer at room temperature (RT) in accordance with one embodiment of the present disclosure.
Figure 28B:
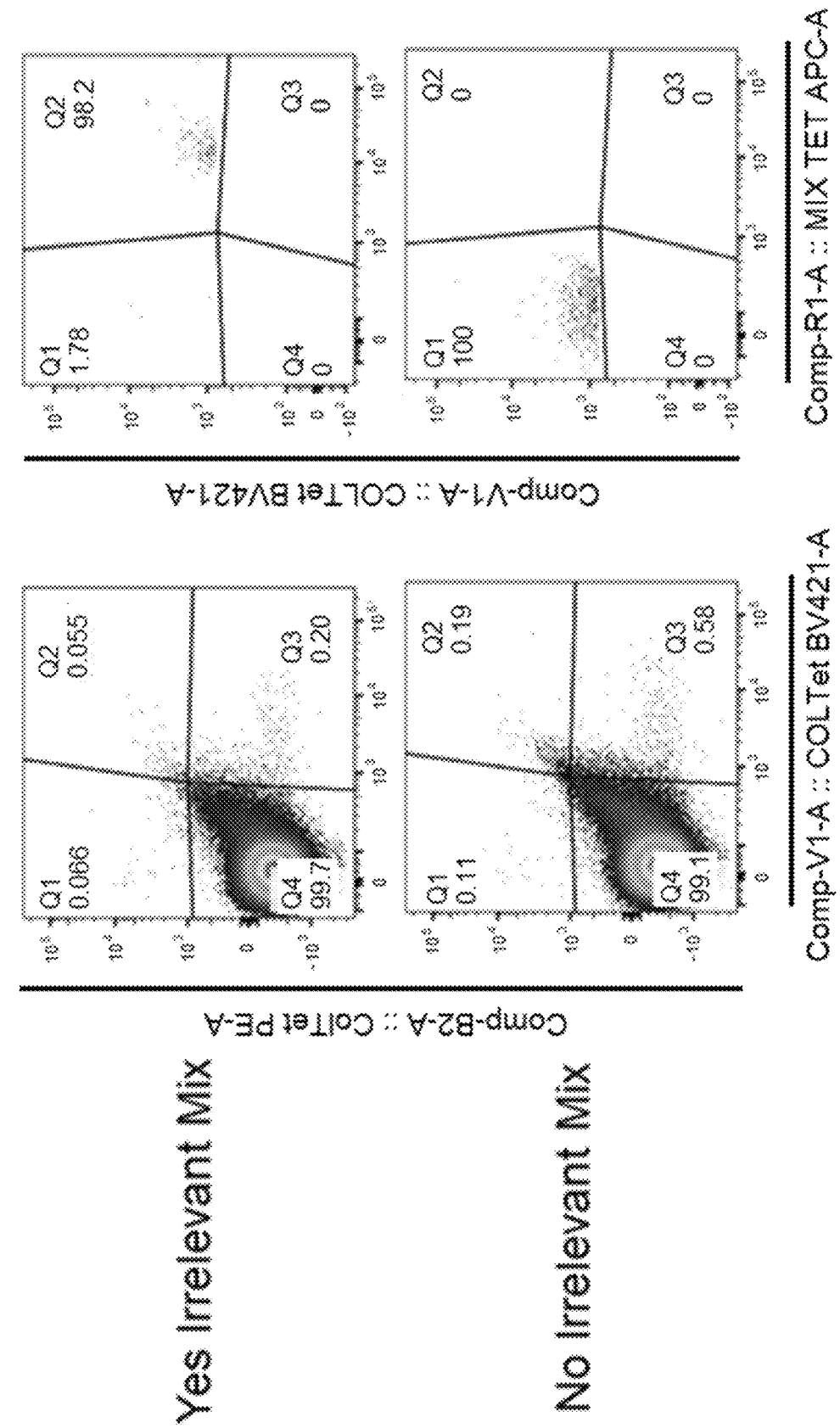
FIG. 28B shows the flow cytometry data using double staining tetramers and irrelevant peptide tetramer at 37° C. in accordance with one embodiment of the present disclosure.

When the experiments shown in FIG. 28A were performed at 37° C., similar results were observed. FIG. 28B, top left panel, shows the detection of 0.055% (Q2) CD45+ Col6A3-specific T cells in PBMC staining with 2D Tet (PE+BV421). These Q2 cells were further analyzed to detect irrelevant peptide positive T cells, i.e., APC/BV421 double-stained cells. Top right panel (Q2), shows the detection of 98.2% irrelevant peptide positive T cells in the BV421/PE double-positive cells detected in Q2 of top left panel. Thus, about 1.78% APC-negative/BV421-positive cells may represent true Col6A3-specific T cells (top right panel, Q1). In contrast, in the absence of irrelevant peptide APC tetramer mix, bottom right panel (Q2), shows 0% irrelevant peptide positive T cells in the BV421/PE double-positive cells detected in Q2 (0.19%) of bottom left panel. Thus, 100% of cells in the BV421/PE double-positive cells detected in Q2 of bottom left panel would appear to be true Col6A3-specific T cells (bottom right panel, Q1). These results indicate that addition of irrelevant peptide tetramer mix in tetramer staining at 37° C. can reduce the rate of detecting false positive peptide-specific T cells in PBMC, e.g., from 100% in the absence of irrelevant peptide APC tetramer mix to 1.78% in the presence of irrelevant peptide APC tetramer mix.

Figure 28C:
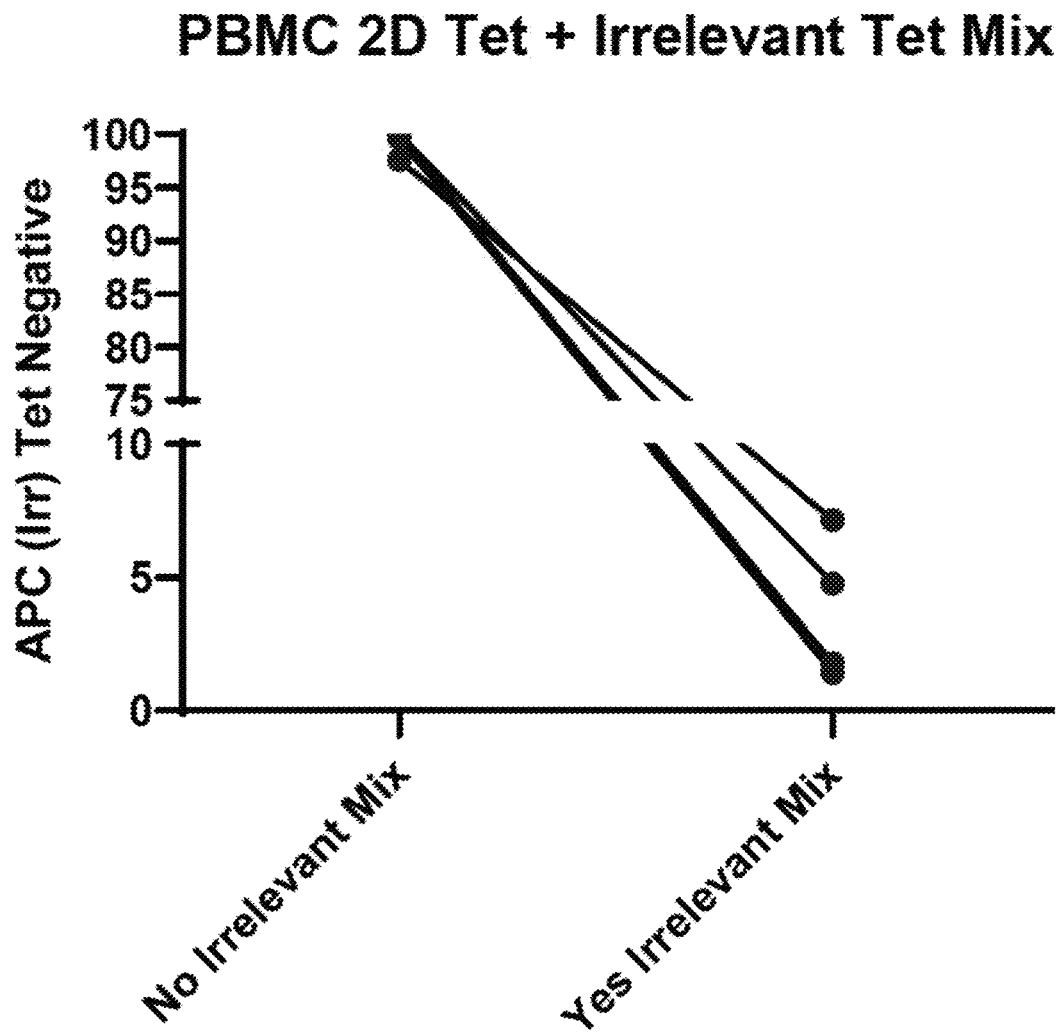
FIG. 28C shows the effect of irrelevant peptide tetramer on staining in accordance with one embodiment of the present disclosure.

FIG. 28C shows addition of irrelevant peptide APC tetramer mix significantly decreases the detection of irrelevant peptide-negative and 2D Tet-positive cells in PBMC, e.g., from an average (n=4) of 99.3±1.14% in the absence of irrelevant peptide APC tetramer mix to 3.77±2.7% in the presence of irrelevant peptide APC tetramer mix. These results indicate that irrelevant peptide tetramer mix can reduce false positive 2D Tet-stained peptide-specific T cells.

Figure 29:
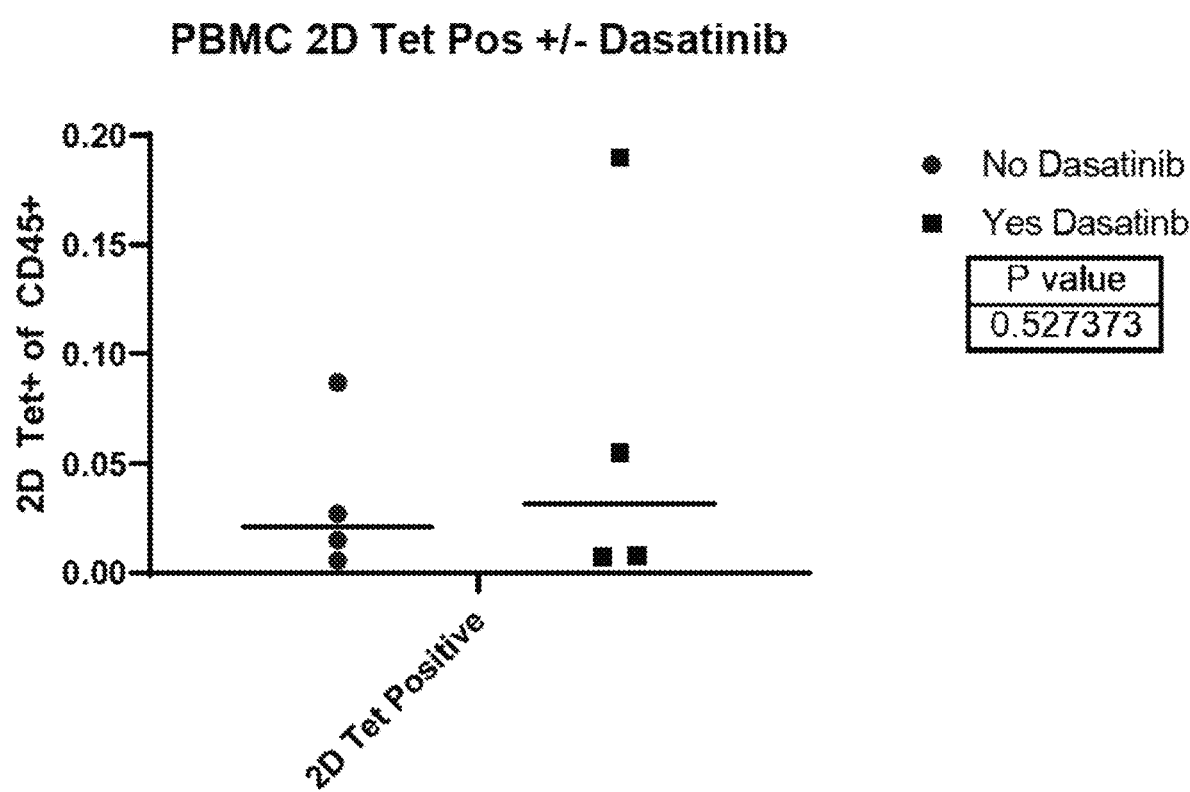
FIG. 29 shows the effect of dasatinib (DAS) on staining in accordance with one embodiment of the present disclosure.

FIG. 29 shows DAS treatment may not significantly increase the detection of background CD45+2D Tet-positive cells in PBMC (n=4, T-test, p=0.527373) as compared with without DAS treatment.

Figure 30:
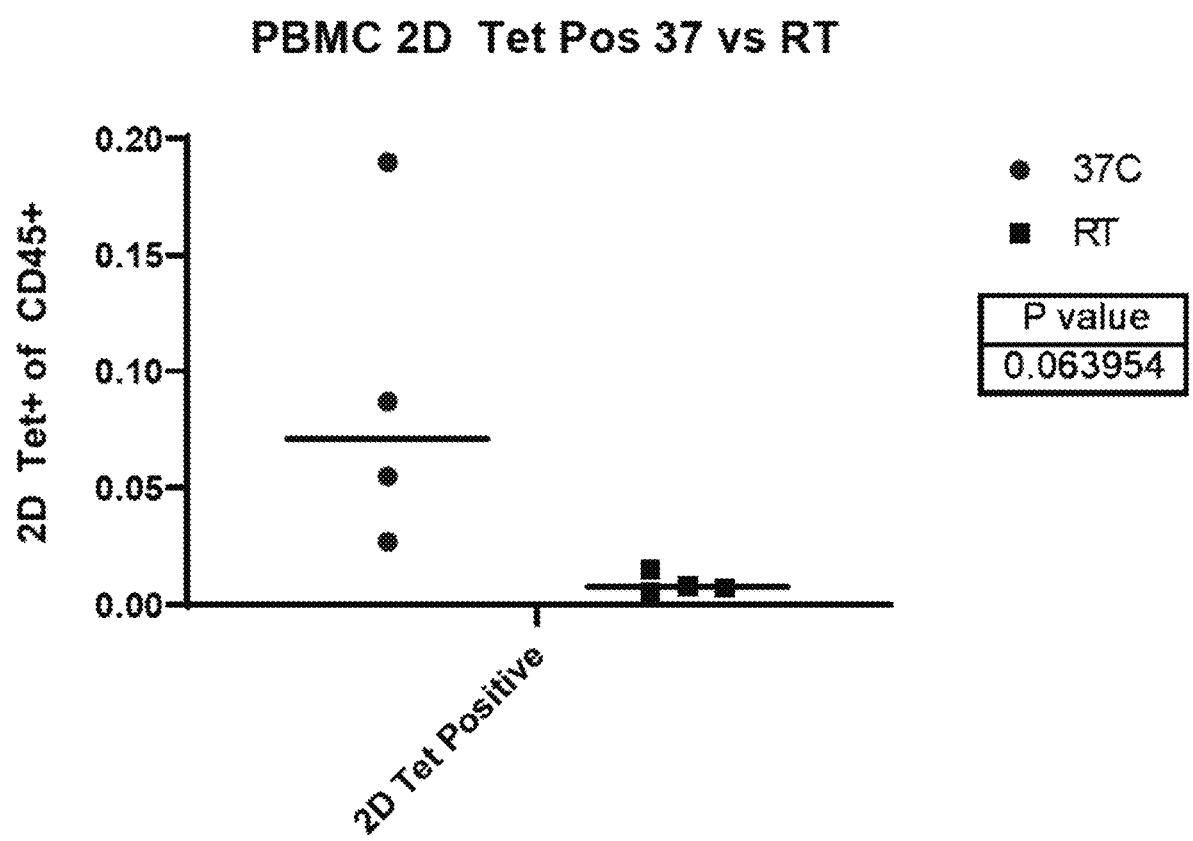
FIG. 30 shows the effect of temperatures on staining in accordance with one embodiment of the present disclosure.

FIG. 30 shows 2D Tet staining at 37° C. tends to increase the detection of background CD45+2D Tet-positive cells in PBMC (n=4, T-test, p=0.063954) as compared with staining at RT.

When staining was performed in the presence of irrelevant peptide APC tetramer mix at RT, with DAS treatment, FIG. 31A, top left panel, shows the detection of 8.04E-3% (Q2) CD45+ Col6A3-specific T cells in PBMC stained with 2D Tet (PE+BV421). These Q2 cells were further analyzed to detect irrelevant peptide positive T cells, i.e., APC/BV421 double-stained cells. Top right panel (Q2), shows the detection of 95.2% of irrelevant peptide positive T cells in the BV421/PE double-positive cells detected in Q2 of top left panel. Thus, about 4.76% of APC-negative/BV421-positive cells may represent true Col6A3-specific T cells (top right panel, Q1). Without DAS treatment, bottom right panel, shows 92.9% (Q2) of irrelevant peptide positive T cells in the BV421/PE double-positive cells detected in Q2 (5.51E-3%) of bottom left panel. Thus, 7.14% of APC-negative/BV421-positive cells in the BV421/PE double-positive cells detected in Q2 of bottom left panel may represent true Col6A3-specific T cells (bottom right panel, Q1).

When staining was performed in the presence of irrelevant peptide APC tetramer mix at 37° C., similar results were observed. With DAS treatment, FIG. 31B, top left panel, shows the detection of 0.055% (Q2) of CD45+ Col6A3-specific T cells in PBMC staining with 2D Tet (PE+BV421). These Q2 cells were further analyzed to detect irrelevant peptide positive T cells, i.e., APC/BV421 double-stained cells. Top right panel (Q2), shows the detection of 98.2% irrelevant peptide positive T cells in the BV421/PE double-positive cells detected in Q2 of top left panel. Thus, about 1.78% APC-negative/BV421-positive cells may represent true Col6A3-specific T cells (top right panel, Q1). Without DAS treatment, bottom right panel, shows 98.6% (Q2) irrelevant peptide positive T cells, i.e., APC/BV421 double-stained cells, in the BV421/PE double-positive cells detected in Q2 (0.027%) of bottom left panel.

To determine which staining conditions that may provide higher staining index (SI), indicating better separation of cells stained positive from cells stained negative, and lower false negative rate, Col6A3 REP1 cells, which were prepared by rapid expansion protocol (REP), were stained±DAS treatment (at 37° C.), ±irrelevant peptide tetramer mix, and staining at RT or 37° C.

Figure 32:
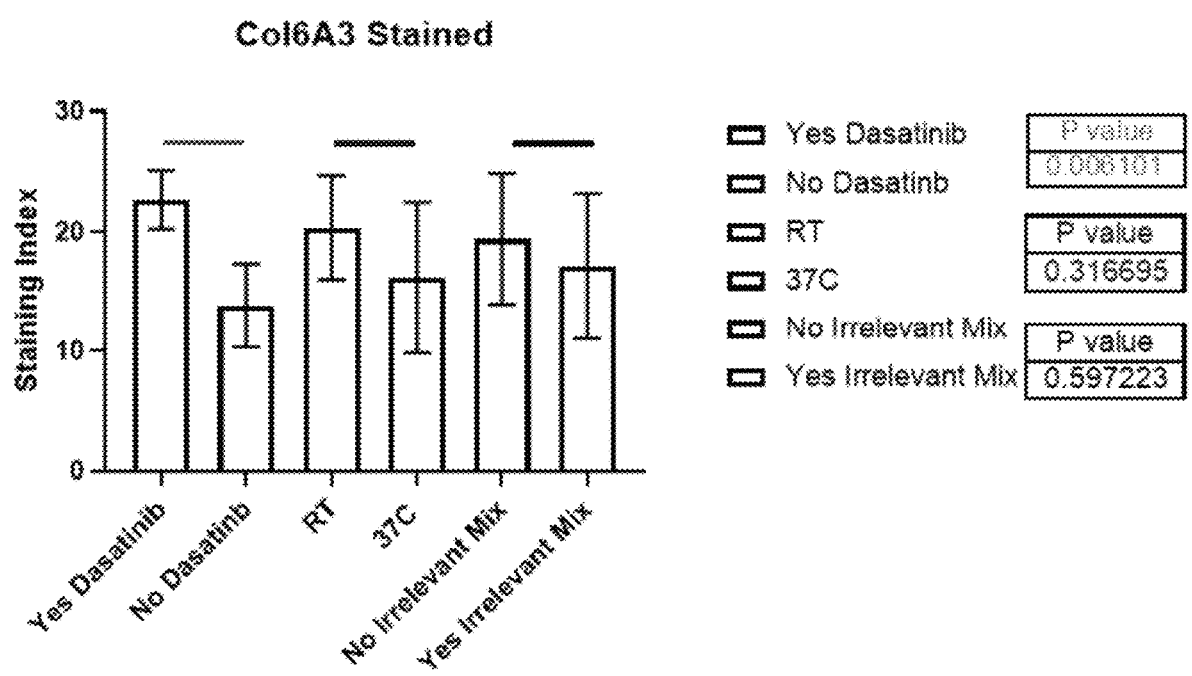
FIG. 32 shows staining indices of staining conditions in accordance with some embodiments of the present disclosure.

Staining index (SI) may be calculated by using formula (I): SI=(mean PE+mean BV421 2Dtet+)−(mean PE+mean BV421 2Dtet−)/2×(SD PE+SD BV421 2Dtet−). FIG. 32 shows DAS treatment significantly increases SI as compared with that without DAS treatment, e.g., P=0.006101. In contrast, staining temperature and irrelevant peptide mix may not significantly affect SI, e.g., RT versus 37° C. (P=0.316695), and ±irrelevant peptide tetramer mix (P=0.597223).

Figure 33A:
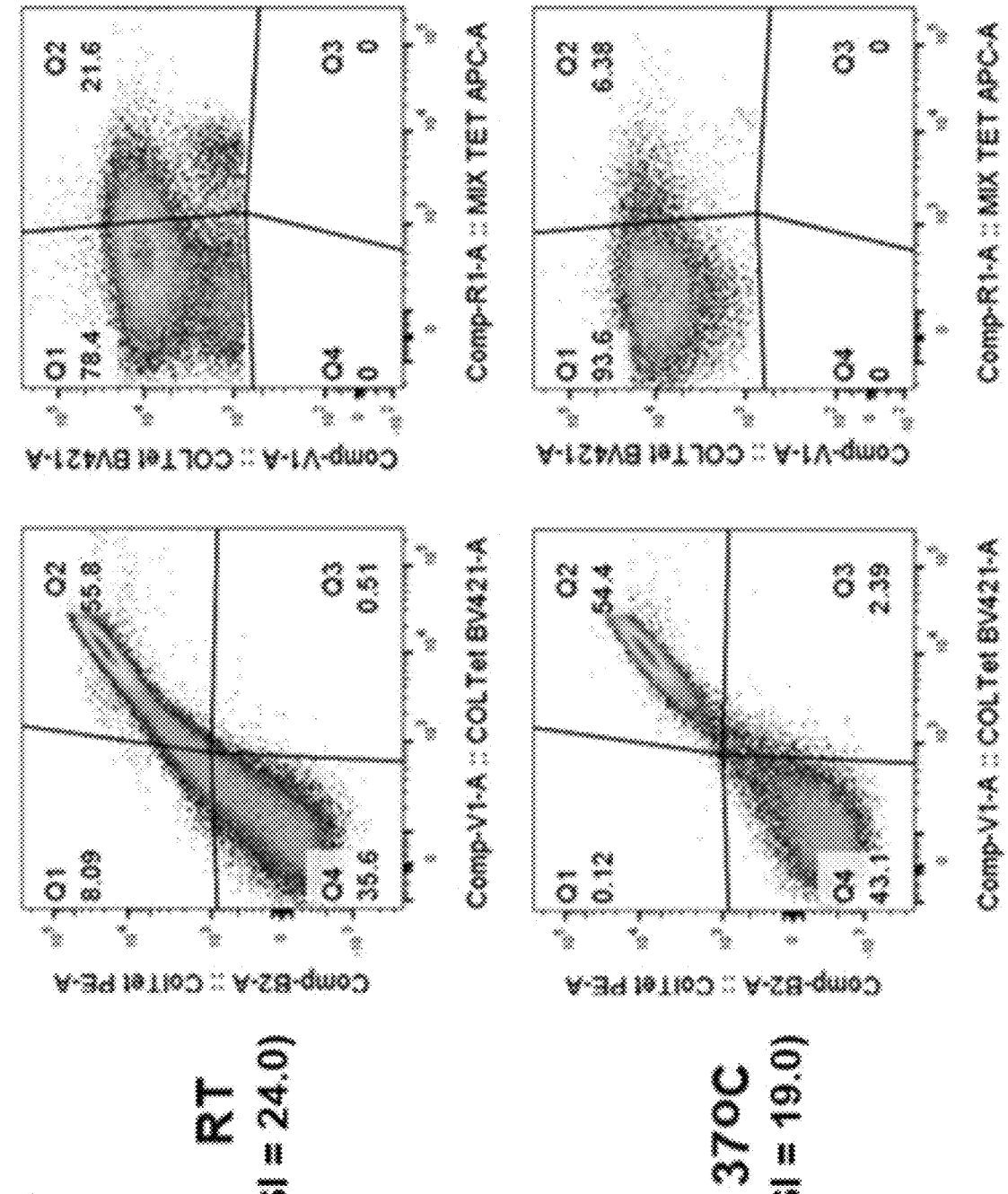
FIG. 33A shows the flow cytometry data obtained from staining conditions in accordance with some embodiments of the present disclosure.

When the staining was performed with DAS treatment and in the presence of irrelevant peptide APC tetramer mix, FIG. 33A, top left panel, shows the detection of 55.8% (Q2) of CD45+ Col6A3 REP1 cells stained with 2D Tet (PE+BV421), when staining was performed at RT. These Q2 cells were further analyzed to detect irrelevant peptide positive T cells, i.e., APC/BV421 double-stained cells. Top right panel (Q2), shows the detection of 21.6% irrelevant peptide positive T cells in the BV421/PE double-positive cells detected in Q2 of top left panel. Thus, about 78.4% APC-negative/BV421-positive cells may represent true Col6A3 REP1 cells (top right panel, Q1) (SI=24.0). When staining was performed at 37° C., bottom right panel (Q2), shows 6.38% irrelevant peptide positive T cells in the BV421/PE double-positive cells detected in Q2 (54.4%) of bottom left panel. Thus, about 93.6% cells may represent true Col6A3 REP1 cells (bottom right panel, Q1) (SI=19.0). These results indicate that tetramer staining temperature at 37° C. with DAS treatment and in the presence of irrelevant peptide tetramer mix may reduce false negative T cells, e.g., from 21.6% at RT to 6.38% at 37° C.

When the staining was performed without DAS treatment and in the presence of irrelevant peptide APC tetramer mix, FIG. 33B, top left panel, shows the detection of 59.2% (Q2) CD45+ Col6A3 REP1 cells stained with 2D Tet (PE+BV421) at RT. These Q2 cells were further analyzed to detect irrelevant peptide positive T cells, i.e., APC/BV421 double-stained cells. Top right panel, shows the detection of 12.4% (Q2) irrelevant peptide positive T cells in the BV421/PE double-positive cells detected in Q2 of top left panel. Thus, about 87.6% APC-negative/BV421-positive cells may represent true Col6A3 REP1 cells (top right panel, Q1) (SI=15.9). When staining was performed at 37° C., FIG. 33B, bottom right panel (Q2), shows 4.12% of irrelevant peptide positive T cells in the BV421/PE double-positive cells detected in Q2 of top left panel. Thus, about 95.9% cells may represent true Col6A3 REP1 cells (bottom right panel, Q1) (SI=9.49). These results indicate that tetramer staining at 37° C. without DAS treatment and in the presence of irrelevant peptide tetramer mix can reduce false negative T cells, e.g., from 12.4% at RT to 4.12% at 37° C.

Comparison between two staining conditions

Condition #1: with DAS treatment+irrelevant peptide tetramer mix, staining at 37° C.

The following Samples #1-#3 were stained under condition #1

Sample #1: αCol6A3 T cells

FIG. 34A, left panel, shows the detection of 25.1% (Q2) CD45+ αCol6A3 T cells stained with 2D Tet (PE+BV421). These Q2 cells were further analyzed to detect irrelevant peptide positive T cells, i.e., APC/BV421 double-stained cells (SI=15.6). Right panel (Q2), shows the detection of 3.18% irrelevant peptide positive T cells in the BV421/PE double-positive cells detected in Q2 of top left panel. Thus, about 96.9% APC-negative/BV421-positive cells may represent true αCol6A3 T cells (right panel, Q1).

Figure 34B:
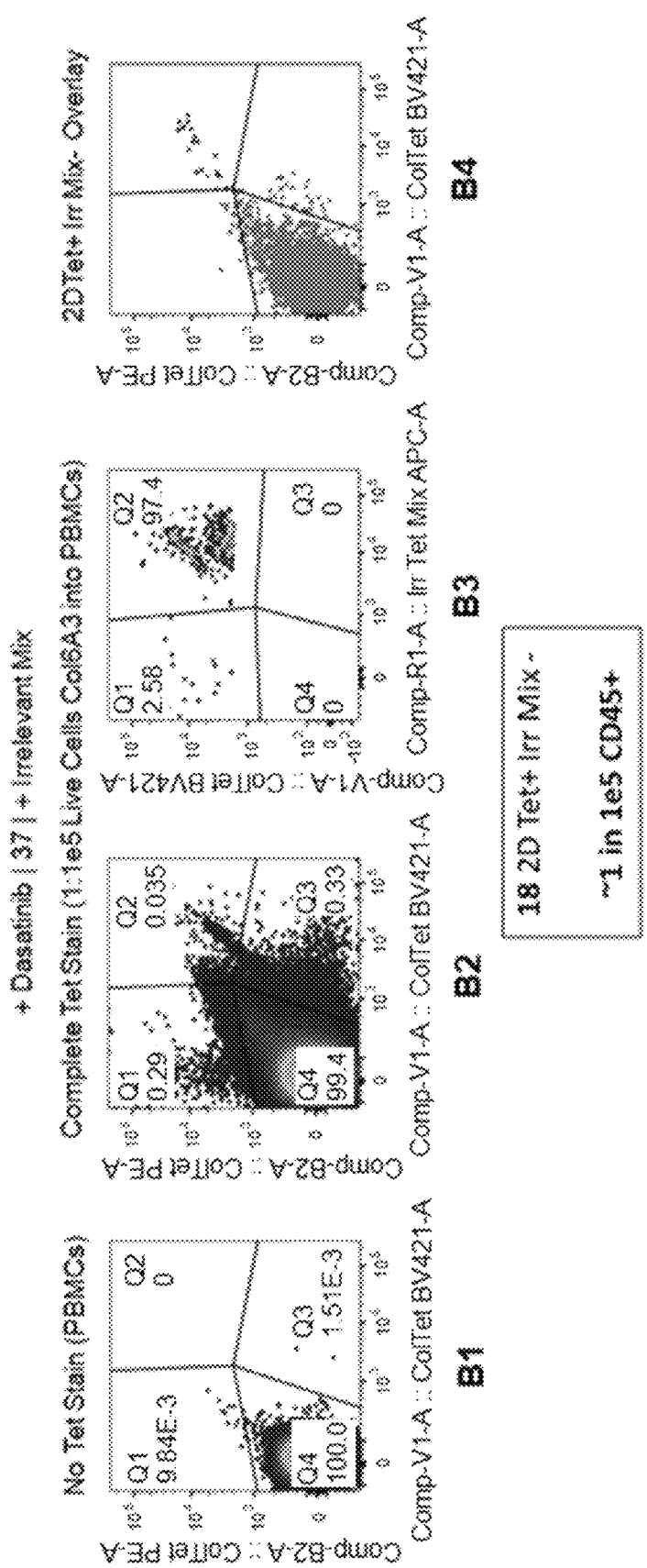
FIG. 34B shows the flow cytometry data obtained from staining condition in accordance with another embodiment of the present disclosure.

Sample #2: αCol6A3 T cells spiked in PBMC (1:1×10$^5$), about 2×10$^6$ CD45+cells acquired FIG. 34B, B2 panel, shows the detection of 0.035% (Q2) CD45+ αCol6A3 T cells spiked in PBMC (1:1×10$^5$) stained with 2D PE/BV421 Tet. These Q2 cells were further analyzed to detect irrelevant peptide positive T cells, i.e., APC/BV421 double-stained cells. FIG. 34B, B3 panel, shows the detection of 97.4% (Q2) of BV421/APC double-positive irrelevant peptide T cells in the BV421/PE double-positive cells detected in Q2 of B2 panel. Thus, about 2.58% APC-negative/BV421-positive cells may represent true αCol6A3 T cells spiked in PBMC (B3 panel, Q1). PBMC without staining (B1 panel) serves as a negative control. B4 panel shows the overlay of Q1 of panel B3 over panel B2.

These results show the detection of 18 2D PE/BV421 Tet-positive and irrelevant peptide APC tetramer-negative events in $2 \times 10^6$ CD45+ cells acquired, i.e., about one αCol6A3 T cell in $1 \times 10^5$ CD45+ cells.

Figure 34C:
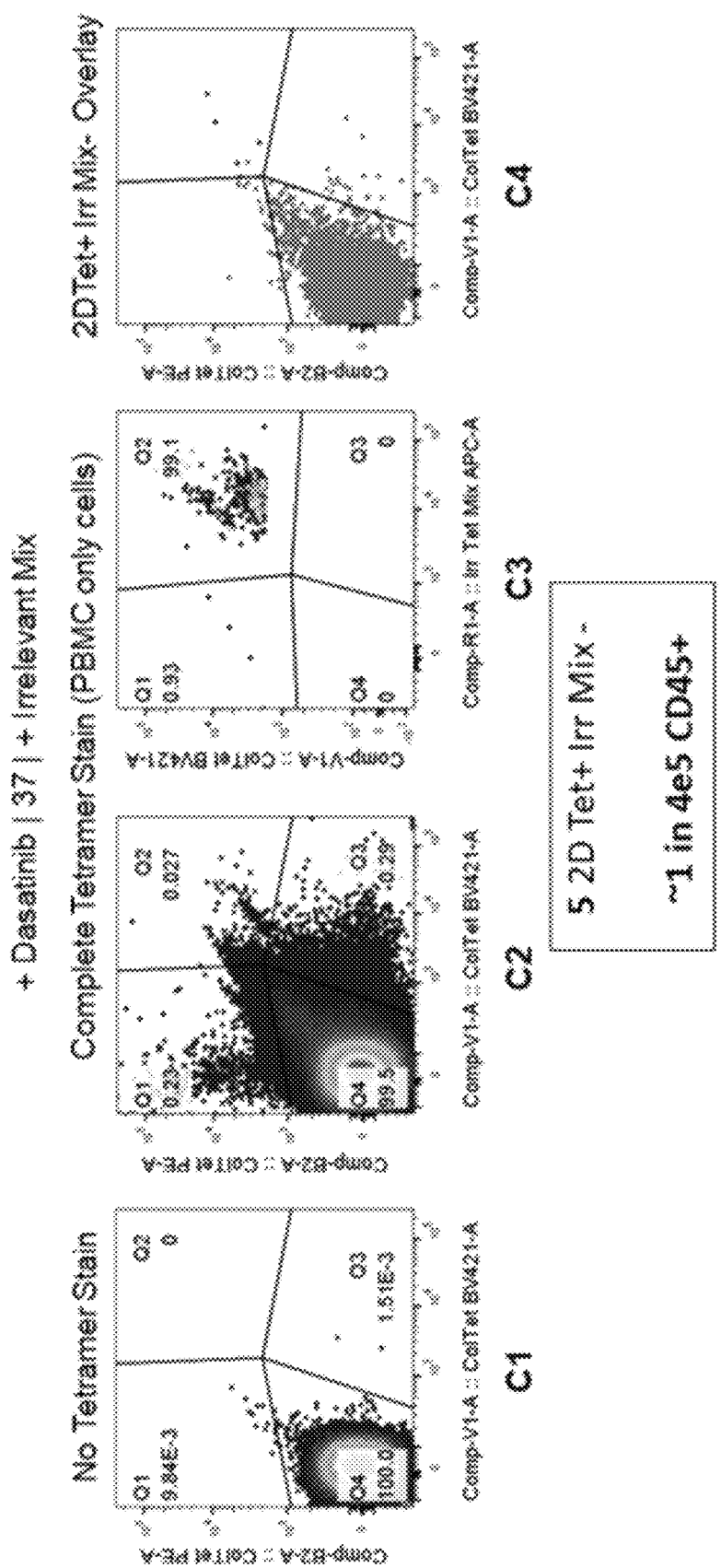
FIG. 34C shows the flow cytometry data obtained from staining condition in accordance with another embodiment of the present disclosure.

Sample #3: only PBMC ($5 \times 10^6$ cells), about $2 \times 10^6$ CD45+ cells acquired FIG. 34C, C2 panel, shows the detection of 0.027% (Q2) CD45+ αCol6A3 T cells in PBMC stained with 2D Tet (PE/BV421). These Q2 cells were further analyzed to detect irrelevant peptide positive T cells, i.e., APC/BV421 double-stained cells. C3 panel shows the detection of 99.1% (Q2) BV421/APC double-positive irrelevant peptide T cells in the BV421/PE double-positive cells detected in Q2 of C2 panel. Thus, about 0.93% APC-negative/BV421-positive cells may represent true αCol6A3 T cells in PBMC (C3 panel, Q1). PBMC without staining (C1 panel) serves as a negative control. C4 panel shows the overlay of Q1 of panel C3 over panel C2. The results show the detection of 5 2D PE/BV421 Tet-positive and irrelevant peptide APC tetramer-negative cells in $2 \times 10^6$ CD45+ cells acquired, i.e., about one αCol6A3 T cell in $4 \times 10^5$ CD45+ cells.

Condition #2: without DAS treatment+irrelevant peptide tetramer mix, staining at RT The following Samples #4-#6 were stained under condition #2

Sample #4: αCol6A3 T cells

Figure 35A:
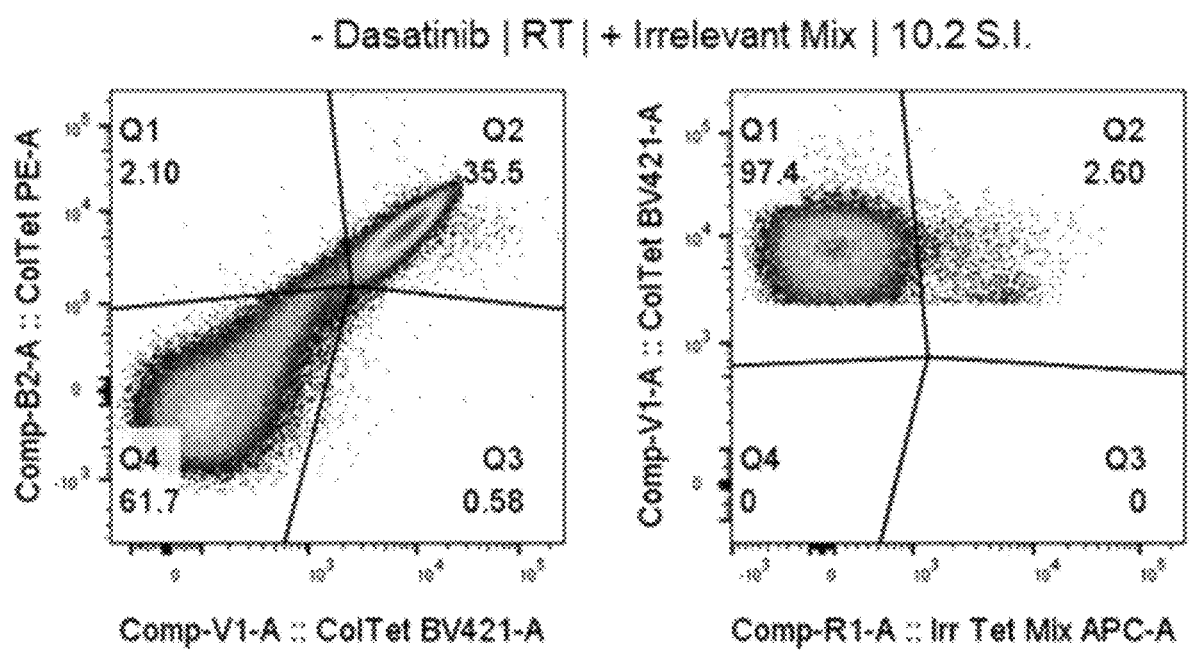
FIG. 35A shows the flow cytometry data obtained from staining condition in accordance with another embodiment of the present disclosure.

FIG. 35A, left panel, shows the detection of 35.5% (Q2) CD45+ αCol6A3 T cells stained with 2D Tet (PE+BV421). These Q2 cells were further analyzed to detect irrelevant peptide positive T cells, i.e., APC/BV421 double-stained cells (SI=10.2). Right panel shows the detection of 2.60% (Q2) irrelevant peptide positive T cells in the BV421/PE double-positive cells detected in Q2 of left panel. Thus, about 97.4% APC-negative/BV421-positive cells may represent true αCol6A3 T cells (right panel, Q1).

Figure 35B:
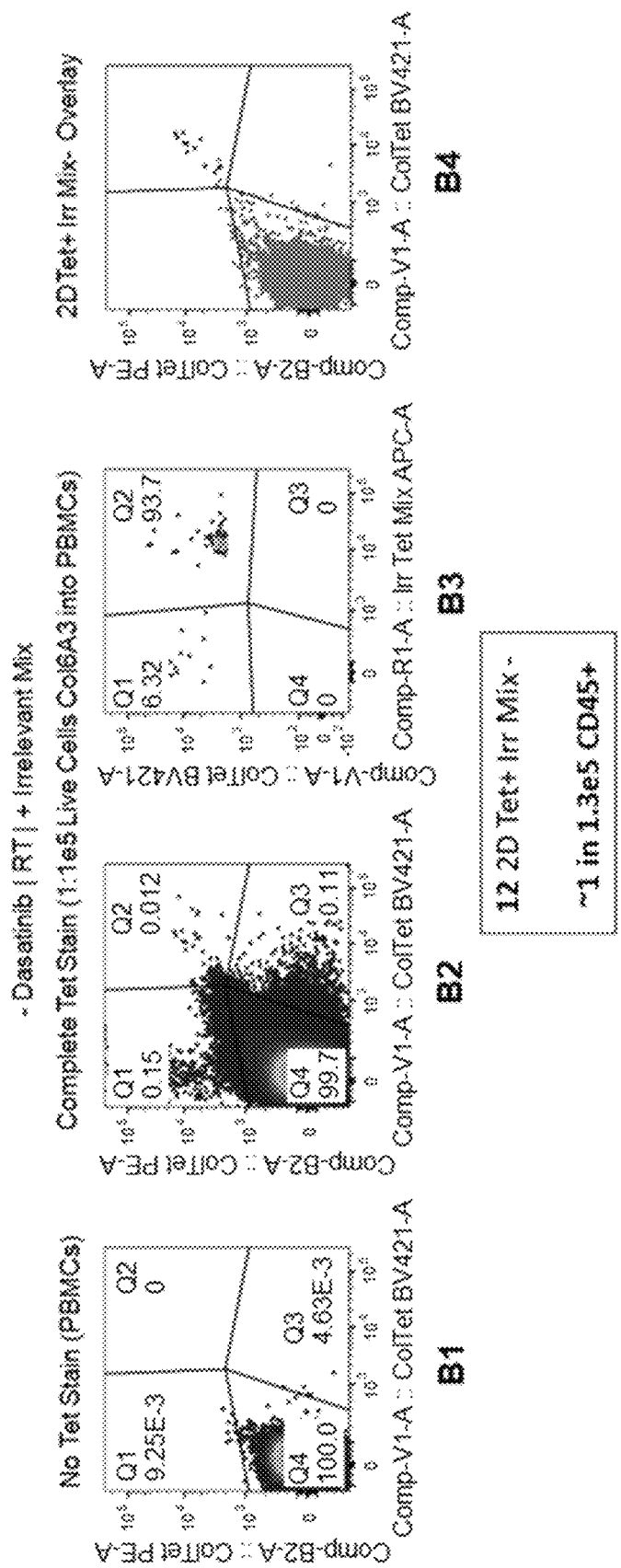
FIG. 35B shows the flow cytometry data obtained from staining condition in accordance with another embodiment of the present disclosure.

Sample #5: αCol6A3 T cells spiked in PBMC ($1:1 \times 10^5$), about $2 \times 10^6$ CD45+cells acquired FIG. 35B, B2 panel, shows the detection of 0.012% (Q2) CD45+ αCol6A3 T cells spiked in PBMC stained with 2D PE/BV421 Tet. These Q2 cells were further analyzed to detect irrelevant peptide positive T cells, i.e., APC/BV421 double-stained cells. FIG. 35B, B3 panel shows the detection of 93.7% (Q2) BV421/APC double-positive irrelevant peptide T cells in the BV421/PE double-positive cells detected in Q2 of B2 panel. Thus, about 6.32% APC-negative/BV421-positive cells may represent true αCol6A3 T cells spiked in PBMC (B3 panel, Q1). PBMC without staining (B1 panel) serves as a negative control. B4 panel shows the overlay of Q1 of panel B3 over panel B2. The results show the detection of 12 2D PE/BV421 Tet-positive and irrelevant peptide APC tetramer-negative cells in $2 \times 10^6$ CD45+ cells acquired, i.e., about one αCol6A3 T cell in $1.7 \times 10^5$ CD45+ cells.

Figure 35C:
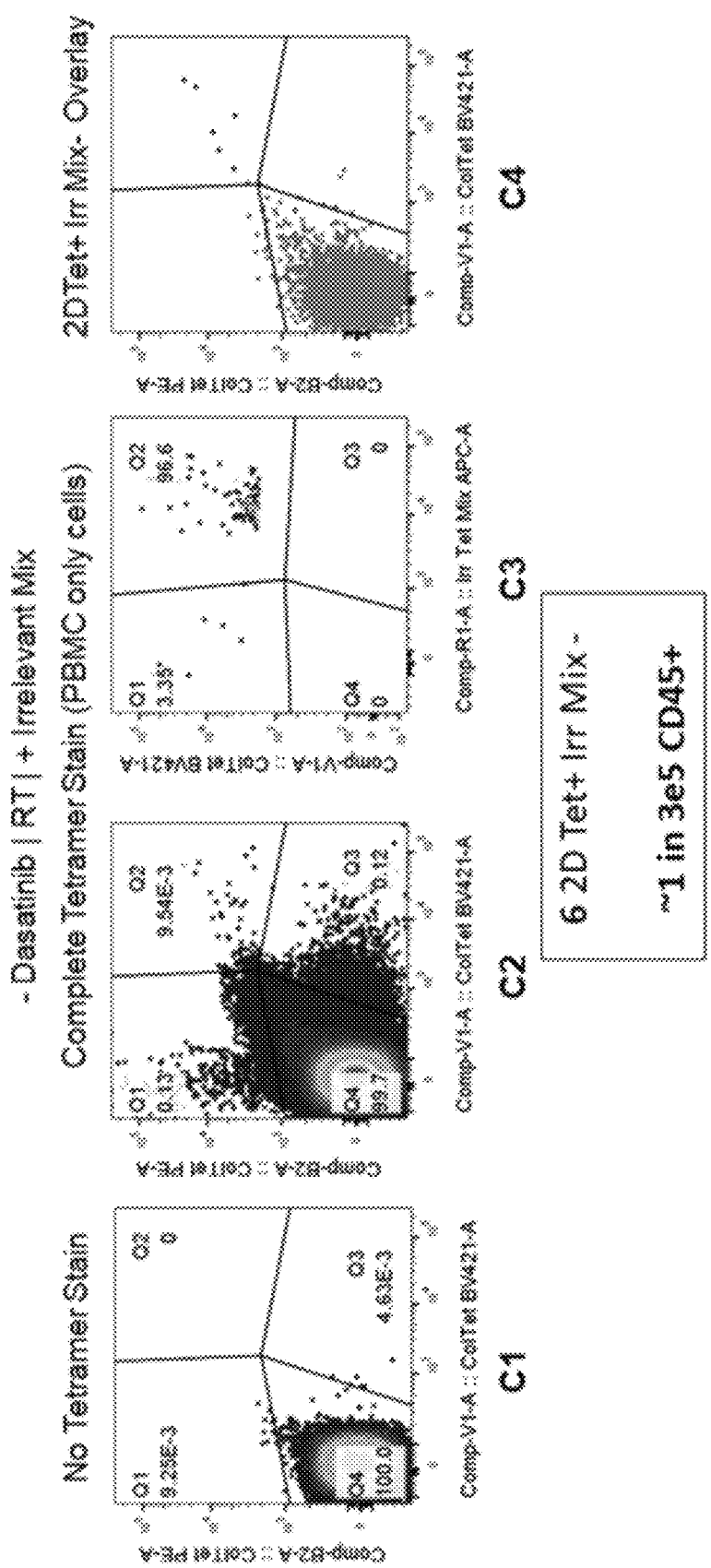
FIG. 35C shows the flow cytometry data obtained from staining condition in accordance with another embodiment of the present disclosure.

Sample #6: only PBMC ($5 \times 10^6$ cells), about $2 \times 10^6$ CD45+ cells acquired FIG. 35C, C2 panel, shows the detection of 9.54E-3% (Q2) CD45+ αCol6A3 T cells in PBMC stained with 2D PE/BV421 Tet. These Q2 cells were further analyzed to detect irrelevant peptide positive T cells, i.e., APC/BV421 double-stained cells. C3 panel shows the detection of 96.6% (Q2) BV421/APC double-positive irrelevant peptide T cells in the BV421/PE double-positive cells detected in Q2 of C2 panel. Thus, about 3.35% APC-negative/BV421-positive cells may represent true αCol6A3 T cells in PBMC (C3 panel, Q1). PBMC without staining (C1 panel) serves as a negative control. C4 panel shows the overlay of Q1 of panel C3 over panel C2. The results show the detection of 6 2D PE/BV421 Tet-positive and irrelevant peptide APC tetramer-negative cells in $2 \times 10^6$ CD45+ cells acquired, i.e., about one αCol6A3 T cell in $3.3 \times 10^5$ CD45+ cells.

As noted above, FIG. 34A, left panel, shows the detection of 25.1% (Q2) CD45+ αCol6A3 T cells stained with 2D Tet (PE+BV421) with DAS treatment and in the presence of irrelevant peptide APC tetramer mix and staining at 37° C. FIG. 35A, left panel, shows the detection of 35.5% (Q2) CD45+ αCol6A3 T cells stained with 2D Tet (PE+BV421) without DAS treatment and in the presence of irrelevant peptide APC tetramer mix and staining at RT. The observation of lower than expected 2D Tet (PE+BV421) staining with DAS treatment (25.1%) than that without DAS treatment (35.5%) was investigated by performing 2D Tet staining under conditions A-G, shown in Table 13.

TABLE 13

| Condition | Dasatinib | Tet Stain Temp | Bench Temp | Centrifuge Temp |
|---|---|---|---|---|
| A | + | 37 | RT | RT |
| B | − | RT | RT | RT |
| C | + | 37 | 4 | 4 |
| D | + | 4 | 4 | 4 |
| E | − | RT | 4 | 4 |
| F | + | RT | 4 | 4 |
| G | − | 4 | 4 | 4 |

Figure 36A:
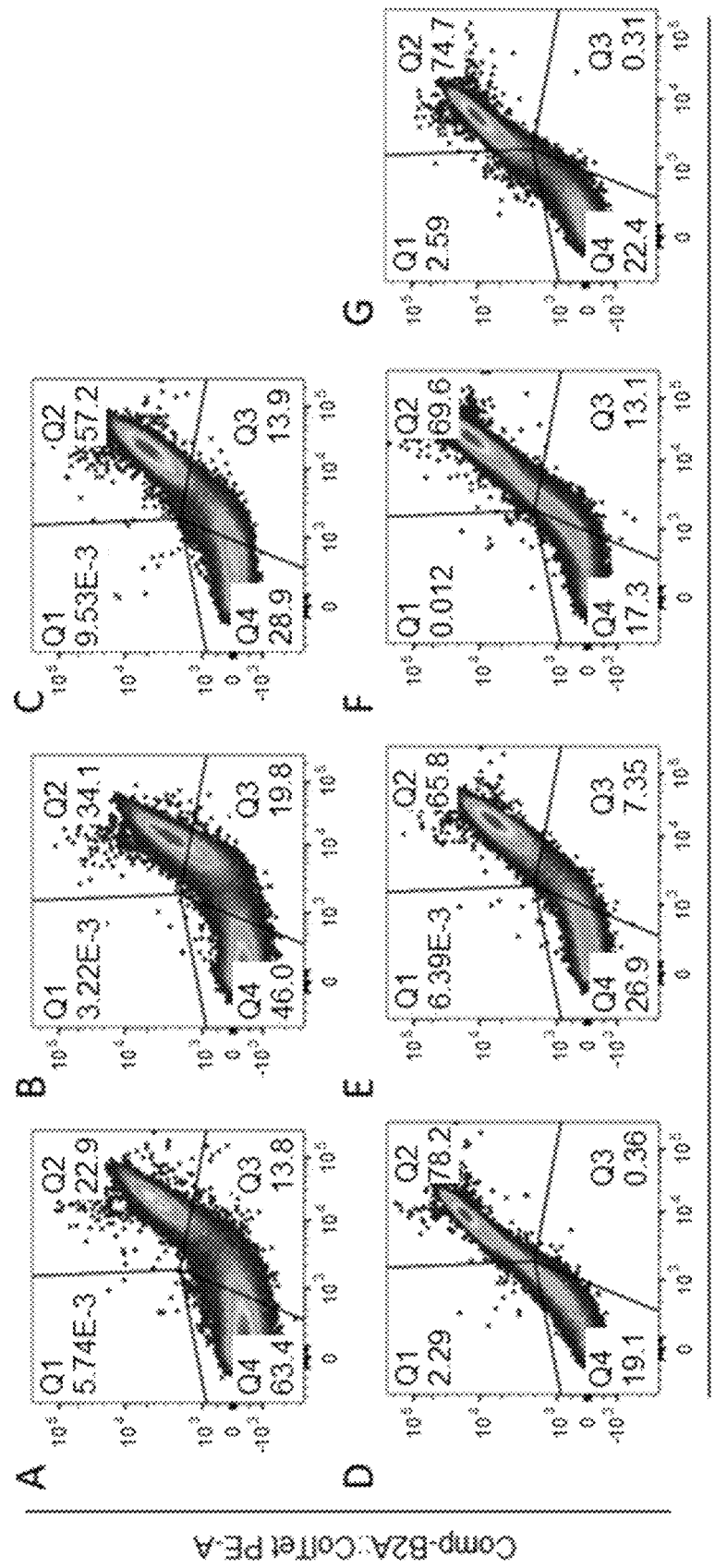
FIG. 36A shows the flow cytometry data obtained from staining conditions in accordance with some embodiments of the present disclosure.

FIG. 36A shows 2D Tet (PE+BV421) staining ±DAS treatment in the presence of irrelevant peptide tetramer mix with bench incubation (e.g., on ice) and centrifugation at 4° C. (Q2s in panels C-G) generally increase the detection of PE/BV421 double-stained CD45+ Col6A3 REP1 cells, as compared with that without any steps performed at 4° C. (Q2s in panels A and B). These Q2 cells were further analyzed to detect irrelevant peptide positive T cells, i.e., APC/BV421 double-stained cells. With DAS treatment, FIG. 36B, panel D (13.7%, Q2) shows performing 2D Tet (PE+BV421) staining, bench incubation, and centrifugation at 4° C. increase the background staining of BV421/APC double-positive irrelevant peptide T cells as compared with that of the 2D Tet (PE+BV421) staining performed at 37° C. (panel C, 2.01%, Q2) or at RT (panel F, 3.07%, Q2). Without DAS treatment, panel G (5.48%, Q2) shows performing 2D Tet (PE+BV421) staining, bench incubation, and centrifugation at 4° C. increases the background staining of BV421/APC double-positive irrelevant peptide T cells as compared with that of the 2D Tet (PE+BV421) staining performed at RT (panel E, 2.80%, Q2).

Figure 36B:
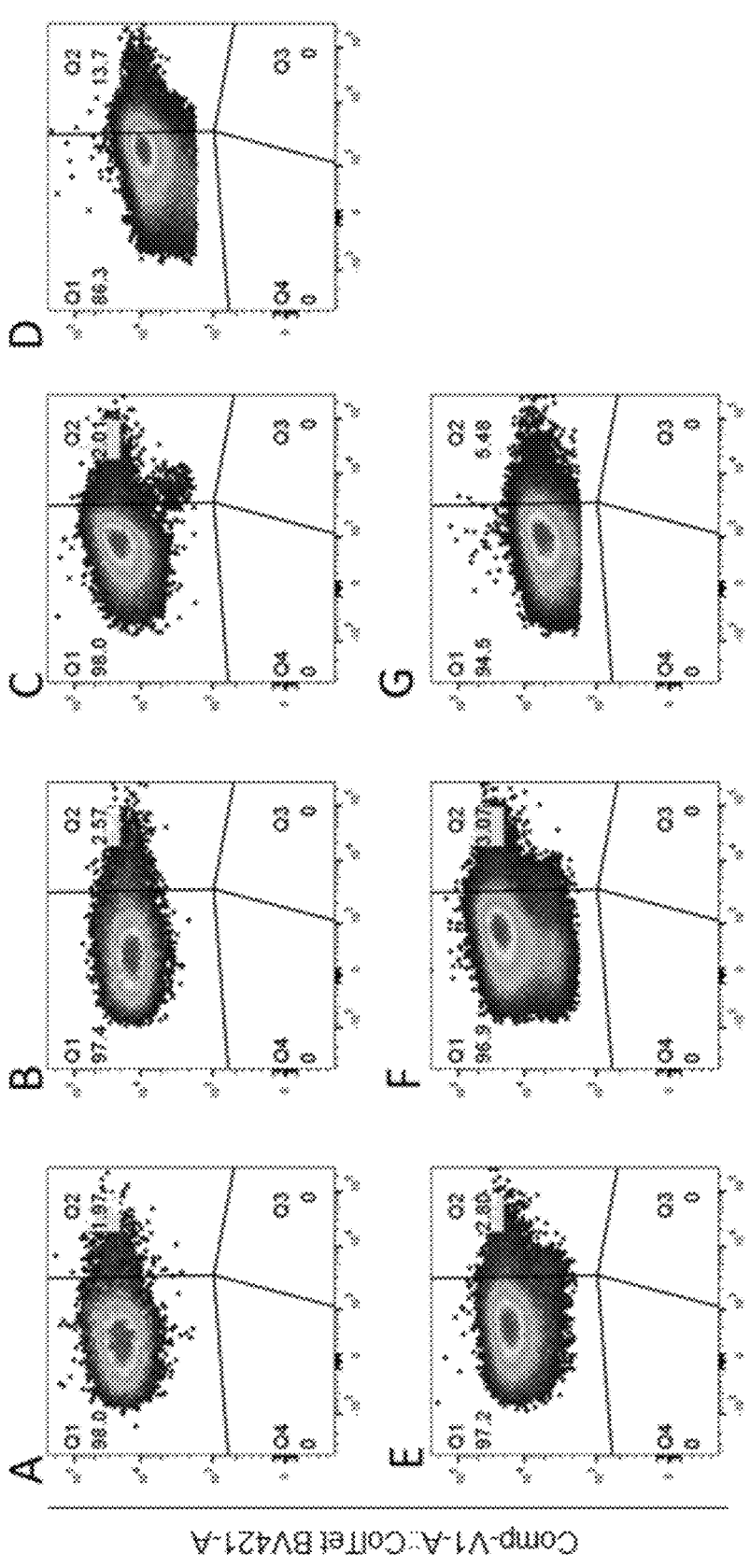
FIG. 36B shows the flow cytometry data obtained from staining conditions in accordance with some embodiments of the present disclosure.
Figure 36C:
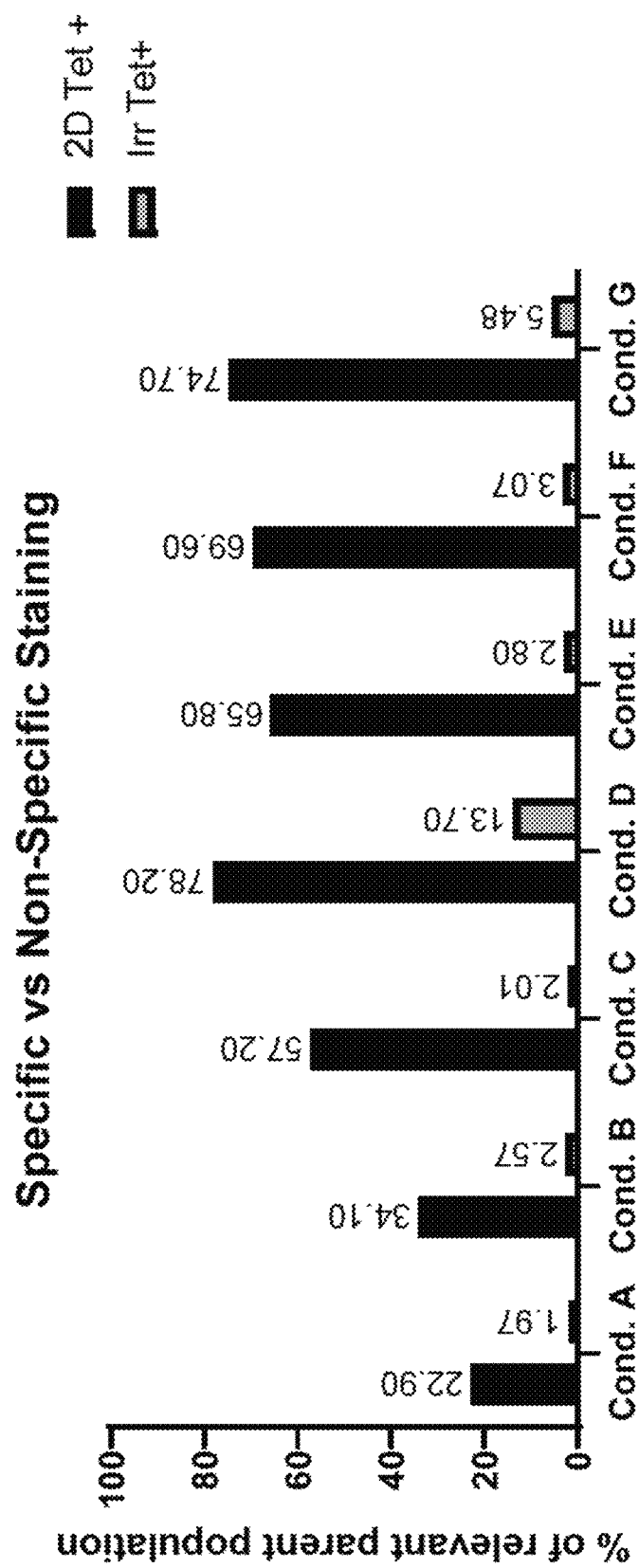
FIG. 36C shows bar diagrams of the data shown in FIGS. 36A and 36B.

FIG. 36C shows bar diagrams for the specific staining (Q2s in FIG. 36A) and the non-specific staining (Q2s in FIG. 36B). The estimation per $1 \times 10^6$ based on flow %, which indicates numbers of peptide-specific T cells per $1 \times 10^6$ of CD45+ cells, may be calculated by the formula: (2Dtet+%× $1 \times 10^6/100$)−((2Dtet+%×$1 \times 10^6/100$)×irrelevant peptide tetramer mix+%/100)). Table 14 summarizes the estimations under the staining conditions A-G. DAS treatment was performed at 37° C. for 30 minutes.

TABLE 14

| Condition | Dasatinib | Tet Stain Temp | Bench Temp | Centrifuge Temp | Estimation per 1e6 based on flow % * |
|---|---|---|---|---|---|
| A | + | 37 | RT | RT | $2.24 \times 10^5$ |
| B | − | RT | RT | RT | $3.32 \times 10^5$ |
| C | + | 37 | 4 | 4 | $5.61 \times 10^5$ |
| D | + | 4 | 4 | 4 | $6.75 \times 10^5$ |
| E | − | RT | 4 | 4 | $6.40 \times 10^5$ |

TABLE 14-continued

| Condition | Dasatinib | Tet Stain Temp | Bench Temp | Centrifuge Temp | Estimation per 1e6 based on flow % * |
|---|---|---|---|---|---|
| F | + | RT | 4 | 4 | $6.75 \times 10^5$ |
| G | − | 4 | 4 | 4 | $7.06 \times 10^5$ |

* (2Dtet + % × 1 × 106/100) − ((2Dtet + % × 1 × 106/100) × irrelevant peptide tetramer mix + %/100)).

These results indicate that performing all staining, spins (centrifugations), and/or washes at 4° C., e.g., staining conditions D and G, may be preferred based on the detection of higher estimated number of peptide-specific T cells per $1 \times 10^6$ CD45+ cells, i.e., $6.75 \times 10^5$ and $7.06 \times 10^5$, respectively, than that of the other conditions, i.e., A, B, C, E, and F.

To investigate PBMC staining under conditions D and G, PBMC ($12.5 \times 10^6$ cells/ml) obtained from 4 donors were stained±DAS treatment (50 nM, at 37° C.), Col6A3-002 BV421 tetramer (3 µg/ml) and Col6A3-002 PE Tetramer (2.5 µg/ml), fluorochrome-labeled anti-CD45 antibody, e.g., PE-Cy7 mouse anti-human CD45 (BD Biosciences), Col6A3-002 BV421 tetramer (3 µg/ml), and APC irrelevant peptides (n=5, e.g., Col6A3-015 (YLMDDFSSL (SEQ ID NO: 16)), MAG-003 (KVLEHWRV (SEQ ID NO: 118)), MAGEC2-001 (TLDEKVAEL (SEQ ID NO: 161)), MXRA5-003 (LLWGHPRVALA (SEQ ID NO: 18), and MAGEA1-003 (KVLEYVIKV (SEQ ID NO: 105)) tetramer mix (3 µg/ml) with all staining, spins, and washes at 4° C.

Figure 37A:
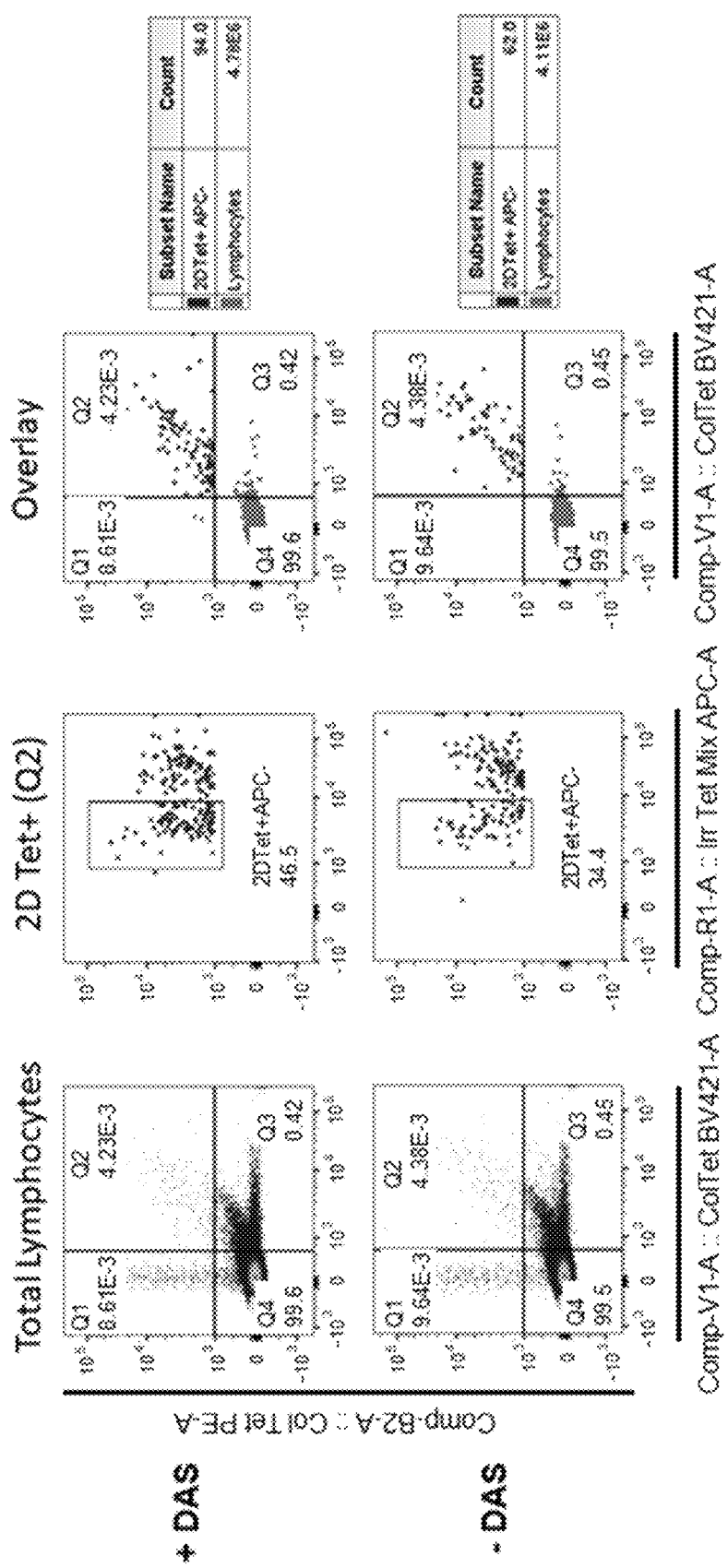
FIG. 37A shows the flow cytometry data obtained from staining conditions in accordance with some embodiments of the present disclosure.

With DAS treatment, FIG. 37A, top left panel, shows the detection of 4.23E-3% (Q2) CD45+ Col6A3 positive T cells in PBMC stained with 2D Tet (PE+BV421). These Q2 cells were further analyzed to detect irrelevant peptide positive T cells, i.e., APC/PE double-stained cells. Top middle panel (boxed), shows the detection of 46.5% 2D Tet (PE+BV421)-positive and irrelevant peptide-negative cells in the BV421/PE double-positive cells detected in Q2 of top left panel. Top right panel shows the overlay of the boxed region of top middle panel over top left panel. These results show the detection of 94 2D PE/BV421 Tet-positive and irrelevant peptide APC tetramer-negative events in $4.78 \times 10^6$ lymphocytes acquired.

Without DAS treatment, FIG. 37A, bottom left panel, shows the detection of 4.38E-3% (Q2) CD45+ Col6A3 positive T cells in PBMC stained with 2D Tet (PE+BV421). These Q2 cells were further analyzed to detect irrelevant peptide positive T cells, i.e., APC/PE double-stained cells. Bottom middle panel (boxed), shows the detection of 34.4% 2D Tet (PE+BV421)-positive and irrelevant peptide-negative cells in the BV421/PE double-positive cells detected in Q2 of bottom left panel. Bottom right panel shows the overlay of the boxed region of bottom middle panel over bottom left panel. These results show the detection of 62 2D PE/BV421 Tet-positive and irrelevant peptide APC tetramer-negative events in $4.11 \times 10^6$ lymphocytes acquired.

Figure 37B:
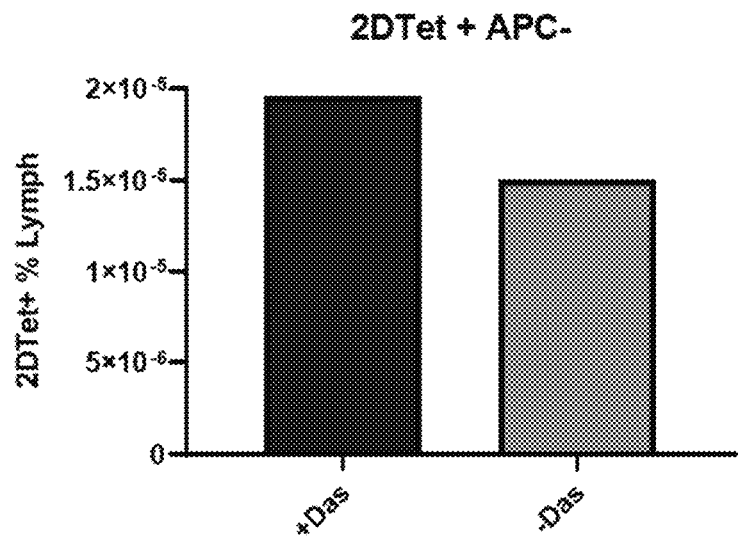
FIG. 37B shows a comparison between with and without DAS treatment in cell staining in accordance with one embodiment of the present disclosure.
Figure 37C:
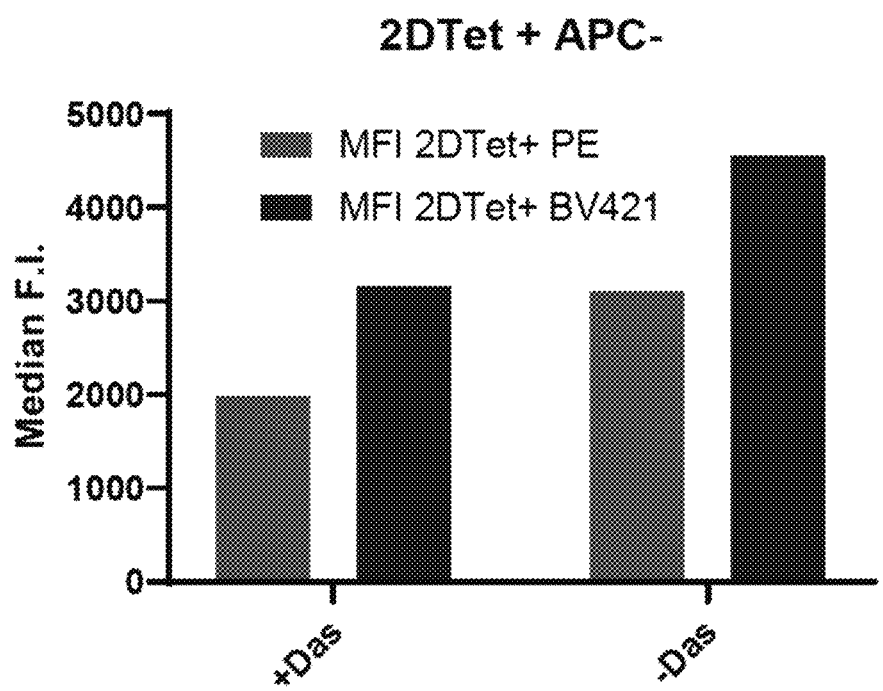
FIG. 37C shows a comparison between with and without DAS treatment in mean fluorescence intensity (MFI) in accordance with one embodiment of the present disclosure.

In sum, FIG. 37B shows DAS treatment increases the detection of 2D Tet (PE+BV421)-positive and irrelevant peptide-negative cells in PBMC, as compared with that without DAS treatment, when all staining, spins (centrifugations), and washes were performed at 4° C. FIG. 37C shows DAS treatment decreases mean fluorescence intensity (MFI) for 2D Tet (PE+BV421)+PE and 2D Tet (PE+BV421)+BV421 as compared with that without DAS treatment, when all staining, spins (centrifugations), and washes were performed at 4° C.

The experiments shown in FIGS. 37A-37D were repeated using a different fluorochrome-labeled anti-CD45 antibody, e.g., PE-Cy™7 mouse anti-human CD45 (BD Biosciences). PBMC ($10 \times 10^6$ cells/nil) obtained from 4 donors were stained with or without DAS treatment (50 nM, at 37° C.), BV421 (3 µg/ml), Col6A3-002 2D Tet (PE+BV421) (2.5 µg/ml), PerCP-Cy™5.5 mouse anti-human CD45 (BD Biosciences), Col6A3-002 BV421 tetramer (3 µg/ml), and APC (n=5) irrelevant tetramer mix (3 µg/ml) with all staining, spins, and washes at 4° C.

Figure 38:
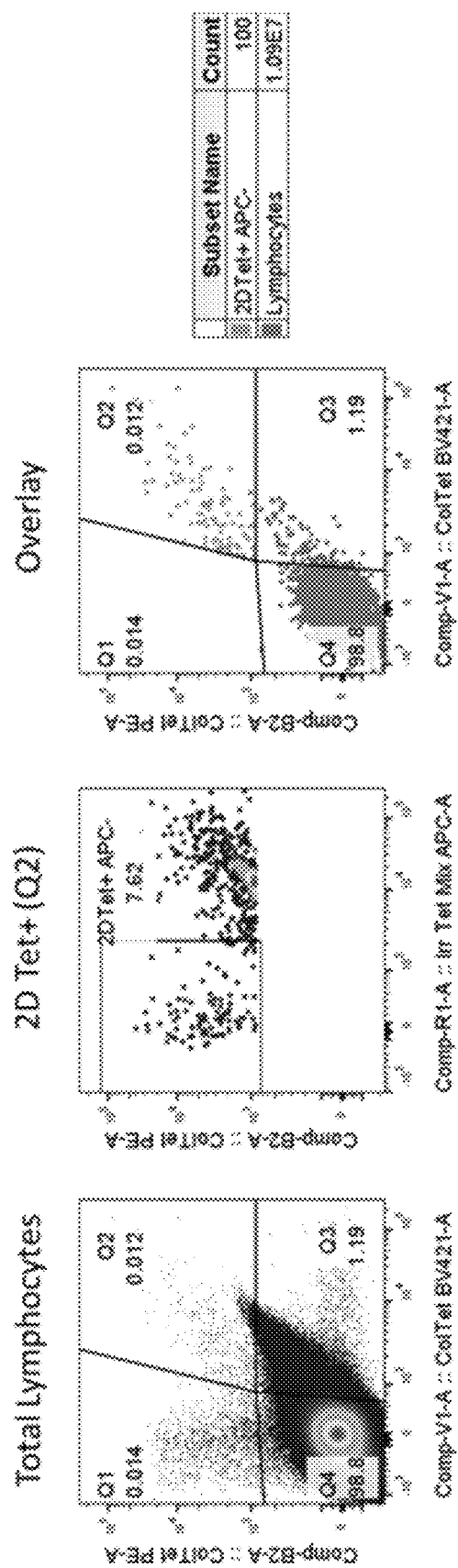
FIG. 38 shows the flow cytometry data obtained from staining condition in accordance with one embodiments of the present disclosure.

Without DAS treatment, FIG. 38, left panel, shows the detection of 0.012% (Q2) CD45+ Col6A3 positive T cells in PBMC stained with 2D Tet (PE+BV421). These Q2 cells were further analyzed to detect irrelevant peptide positive T cells, i.e., APC/PE double-stained cells. Middle panel (boxed) shows the detection of 7.62% 2D Tet (PE+BV421)-positive and irrelevant peptide-negative cells in the BV421/PE double-positive cells detected in Q2 of left panel. Right panel shows the overlay of the boxed region of the middle panel over the left panel. These results show the detection of 100 2D PE/BV421 Tet-positive and irrelevant peptide APC tetramer-negative events in $1.09 \times 10^7$ lymphocytes acquired.

Using Col6A3 PEP1 cells as control, the experiments shown in FIG. 38 was repeated. With DAS treatment, FIG. 39, top left panel, shows the detection of 68.9% (Q2) CD45+ Col6A3 PEP1 cells stained with 2D Tet (PE+BV421). These Q2 cells were further analyzed to detect irrelevant peptide positive T cells, i.e., APC/PE double-stained cells. Top middle panel (boxed) shows the detection of 95.8% 2D Tet (PE+BV421)-positive and irrelevant peptide-negative cells in the BV421/PE double-positive cells detected in Q2 of top left panel. Top right panel shows the overlay of the boxed region of the top middle panel over the top left panel. These results show the detection of 135941 2D PE/BV421 Tet-positive and irrelevant peptide APC tetramer-negative events in 206055 lymphocytes acquired.

Figure 39:
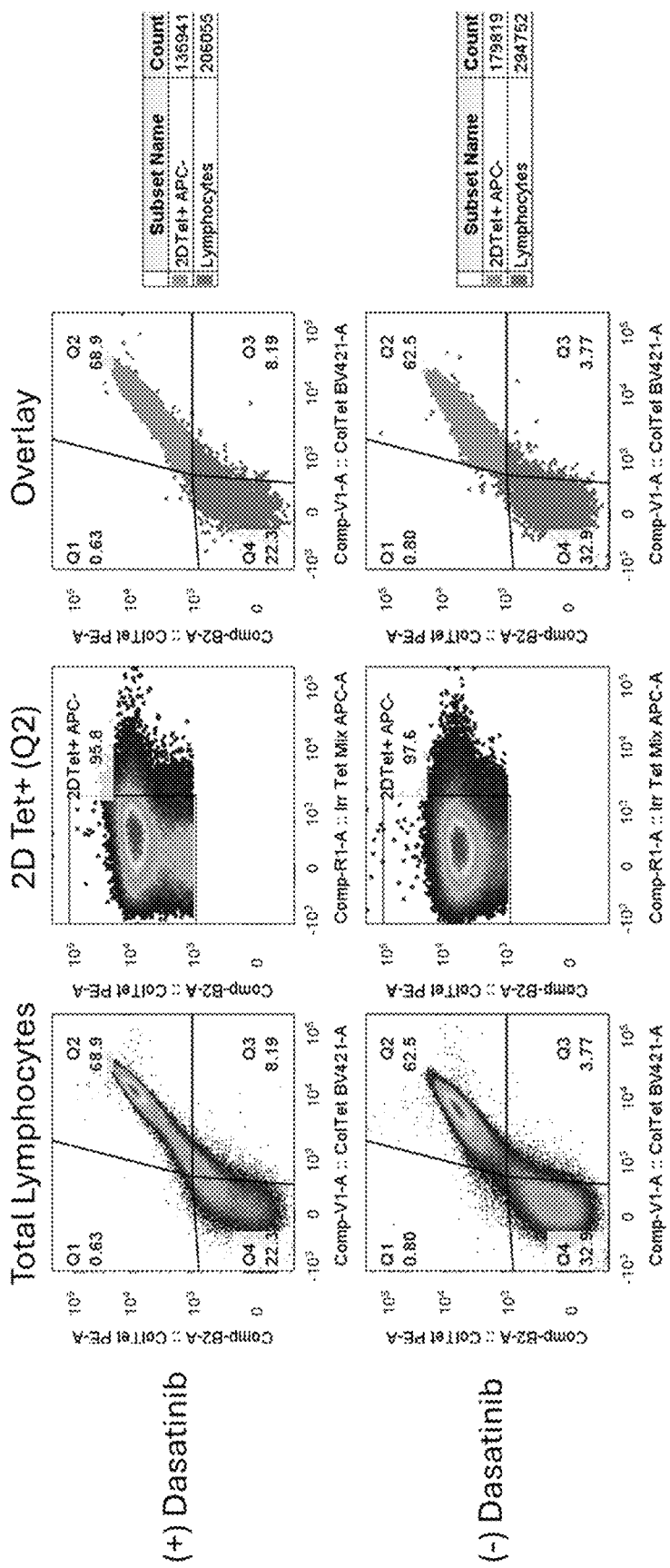
FIG. 39 shows the flow cytometry data obtained from staining conditions in accordance with some embodiments of the present disclosure.

Without DAS treatment, FIG. 39, bottom left panel, shows the detection of 62.5% (Q2) CD45+ Col6A3 PEP1 cells stained with 2D Tet (PE+BV421). These Q2 cells were further analyzed to detect irrelevant peptide positive T cells, i.e., APC/PE double-stained cells. Bottom middle panel (boxed) shows the detection of 97.6% 2D Tet (PE+BV421)-positive and irrelevant peptide-negative cells in the BV421/PE double-positive cells detected in Q2 of bottom left panel. Bottom right panel shows the overlay of the boxed region of the bottom middle panel over the bottom left panel. These results show the detection of 179819 2D PE/BV421 Tet-positive and irrelevant peptide APC tetramer-negative events in 294752 lymphocytes acquired.

Figure 40A:
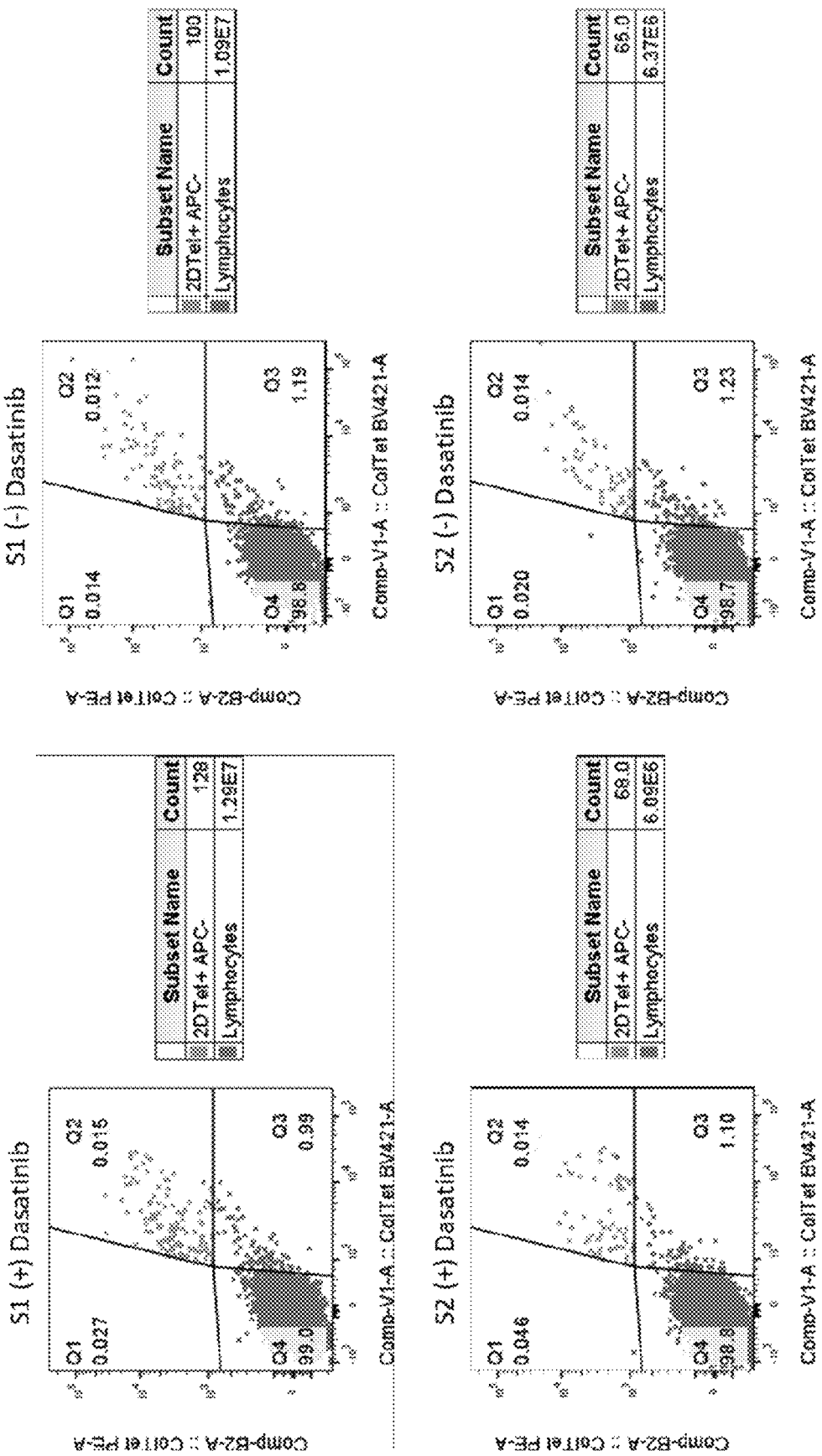
FIG. 40A shows the flow cytometry data obtained from staining conditions in accordance with some embodiments of the present disclosure.

To investigate the effect of high and low numbers of PBMC acquired on 2D Tet detection, four samples, e.g., high numbers (S1 and S2) and low numbers (S3 and S4), were stained. For high numbers of PBMC, FIG. 40A (top left panel) shows, in S1 (with DAS treatment), the detection of 128 2D PE/BV421 Tet-positive and irrelevant peptide APC tetramer-negative events in $1.29 \times 10^7$ lymphocytes acquired. Top right panel shows, in S1 (without DAS treatment), the detection of 100 2D PE/BV421 Tet-positive and irrelevant peptide APC tetramer-negative events in $1.09 \times 10^7$ lymphocytes acquired. Bottom left panel shows, in S2 (with DAS treatment), the detection of 68 2D PE/BV421 Tet-positive and irrelevant peptide APC tetramer-negative events in $6.09 \times 10^6$ lymphocytes acquired. Bottom right panel shows, in S2 (without DAS treatment), the detection of 65 2D PE/BV421 Tet-positive and irrelevant peptide APC tetramer-negative events in $6.37 \times 10^6$ lymphocytes acquired.

Figure 40B:
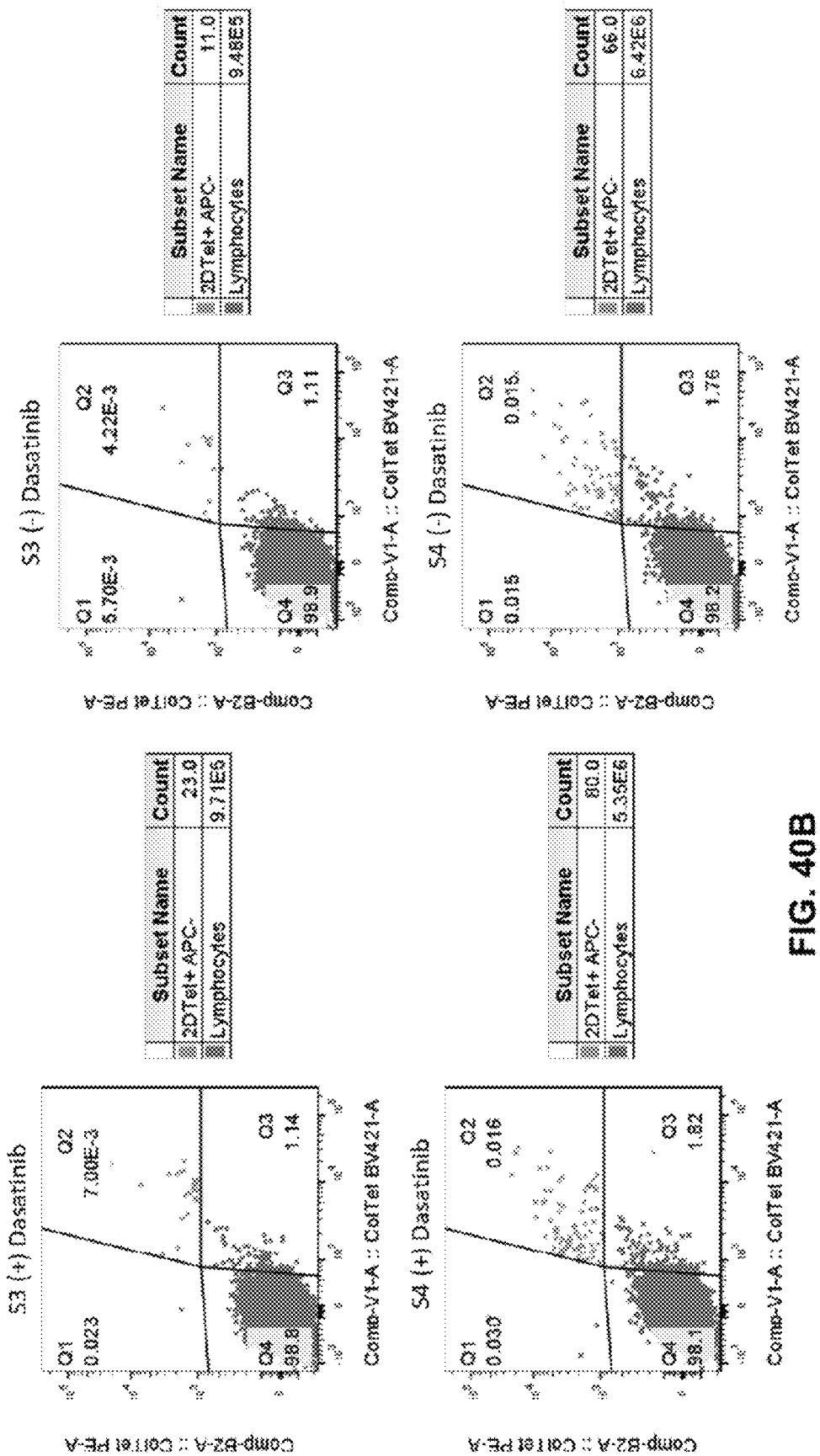
FIG. 40B shows the flow cytometry data obtained from staining conditions in accordance with some embodiments of the present disclosure.

For low numbers of PBMC, FIG. 40B (top left panel) shows, in S3 (with DAS treatment), the detection of 23 2D PE/BV421 Tet-positive and irrelevant peptide APC tetramer-negative events in $9.71 \times 10^5$ lymphocytes acquired. Top right panel shows, in S3 (without DAS treatment), the detection of 11 2D PE/BV421 Tet-positive and irrelevant peptide APC tetramer-negative events in $9.48 \times 10^5$ lymphocytes acquired. Bottom left panel shows, in S4 (with DAS treatment), the detection of 80 2D PE/BV421 Tet-positive and irrelevant peptide APC tetramer-negative events in $5.35 \times 10^6$ lymphocytes acquired. Bottom right panel shows, in S4 (without DAS treatment), the detection of 66 2D PE/BV421 Tet-positive and irrelevant peptide APC tetramer-negative events in $6.42 \times 10^6$ lymphocytes acquired.

Figure 40C:
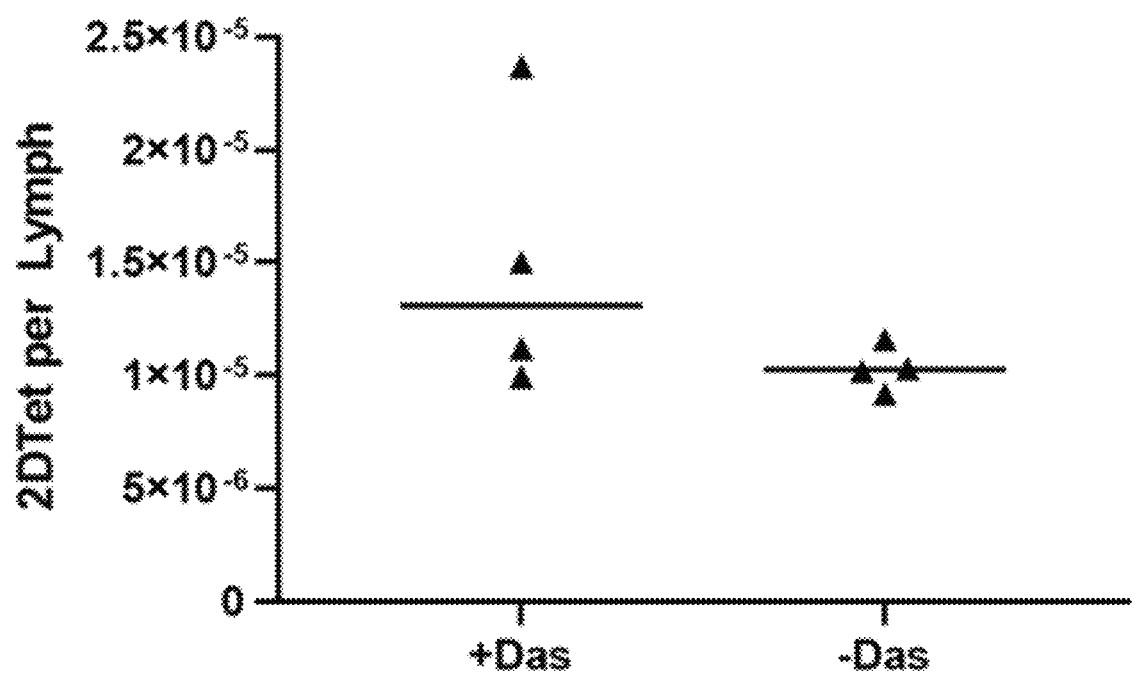
FIG. 40C shows a comparison between with and without DAS treatment in specific T cell frequency in accordance with one embodiment of the present disclosure.

FIG. 40C shows DAS treatment in 2D Tet staining tends to enhance the frequency of detecting 2D Tet-positive cells, as compared with that without DAS treatment.

Figure 40D:
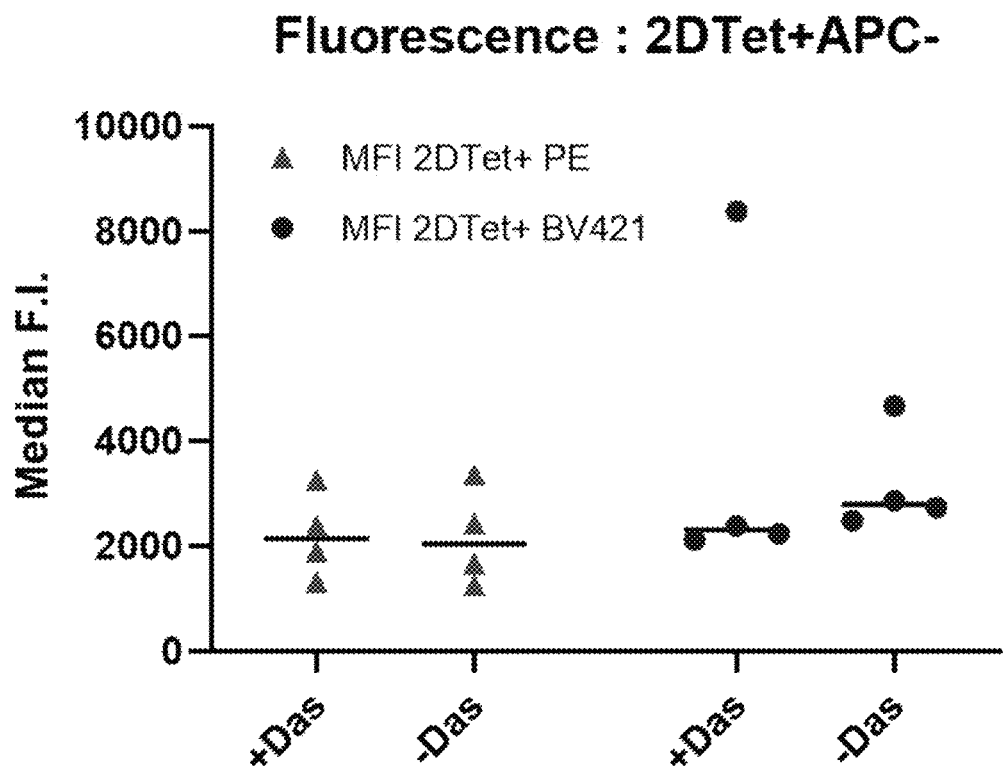
FIG. 40D shows a comparison between with and without DAS treatment in mean fluorescence intensity (MFI) in accordance with another embodiment of the present disclosure.

FIG. 40D shows DAS treatment in 2D Tet staining tends to decrease MFI of 2D Tet+BV421 and may not affect MFI of 2D Tet+PE in the detection of 2D PE/BV421 Tet-positive and irrelevant peptide APC tetramer-negative cells, as compared with that without DAS treatment.

Figure 40E:
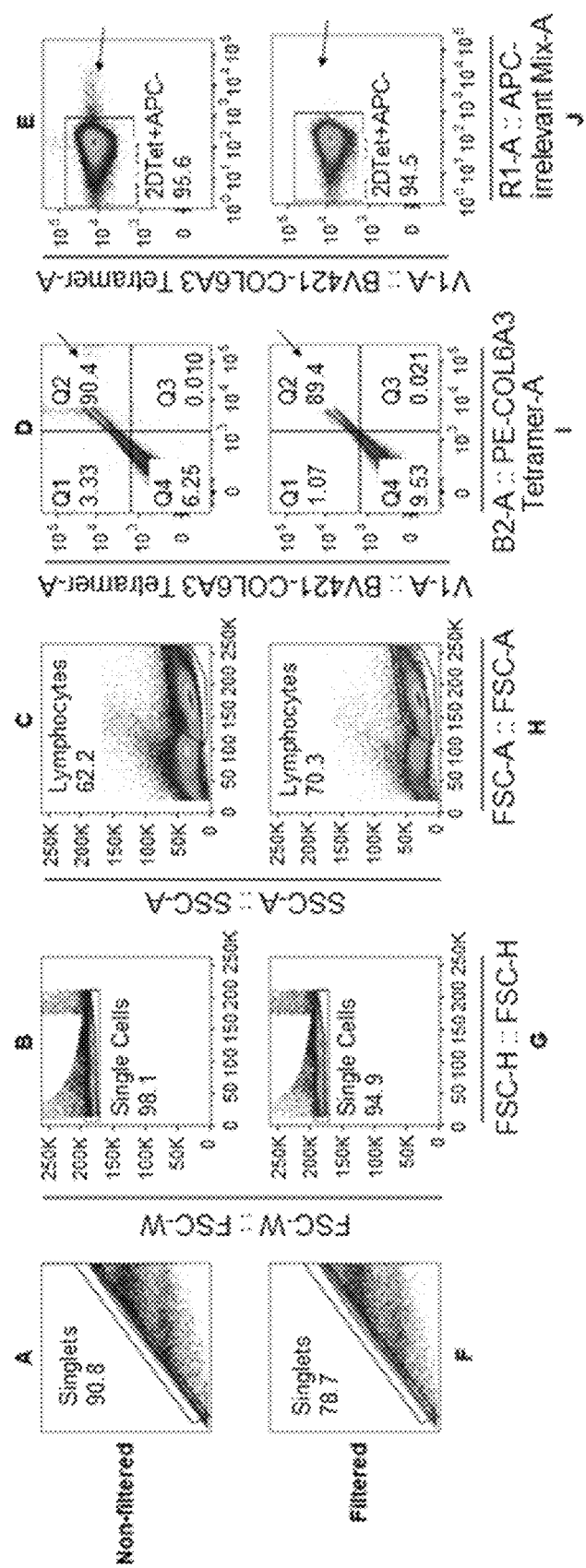
FIG. 40E shows the effect of filtered tetramers on staining in accordance with one embodiment of the present disclosure.

To investigate the effect of filtered and non-filtered 2D Tet on staining, 2D PE/BV421 Tet solution was made to working dilution, and then filtered through 0.2 uM filter. αCol6A3 T cells were stained with filtered or non-filtered 2D PE/BV421 Tet in the presence of irrelevant peptide APC tetramer mix. Using non-filtered 2D PE/BV421 Tet in αCol6A3 T cells staining, FIG. 40E (panels A-E) shows staining aggregates, as indicated by arrows in panels D and E. In contrast, using filtered 2D PE/BV421 Tet in αCol6A3 T cells staining, FIG. 40E (panels F-J) shows reduced staining aggregates, as indicated by arrows in panels I and J. Filtered 2D tetramers show reduced "aggregates" staining in all fluorochromes tested, e.g., APC, BV421, and PE.

In sum, decreasing temperature to 4° C. throughout the staining process may increase staining % and staining intensity. DAS treatment may also increase staining sensitivity since ¼ of DAS-treated samples show about 2× increase of MFI. Thus, one preferred embodiment for the staining conditions may include (1) staining at 4° C., (2) DAS treatment at 37° C., (3) peptide-specific tetramer conjugated with BV421, (4) peptide-specific tetramer conjugated with PE, (5) irrelevant peptides tetramer conjugated with APC, and (6) fluorochrome-labeled anti-CD45 antibody, e.g., PE-Cy™7 mouse anti-human CD45 (BD Biosciences). For example, the optimized panels may include (1) 2D PE (2.5 ug/mL)+BV421 (3 ug/mL) specific tetramers, (2) irrelevant mix (n=5, e.g., Col6A3-015 (YLMDDFSSL (SEQ ID NO: 16)), MAG-003 (KVLEHVVRV (SEQ ID NO: 118)), MAGEC2-001 (TLDEKVAEL (SEQ ID NO: 161)), MXRA5-003 (LLWGHPRVALA (SEQ ID NO: 18), and MAGEA1-003 (KVLEYVIKV (SEQ ID NO: 105)) APC tetramers (3 ug/mL) (sequence similar peptides may be used), (3) anti-APC+anti-PE tetramer stabilizing antibodies (1:50 dilution=10 ug/mL each), (4) DAS (50 nM) treatment at 37° C. for 30 minutes, (5) tubes kept on ice, spun at 4° C., and stained at 4° C. (e.g., in refrigerator) during all stains, which may achieve maximum sensitivity, and (6) filtered tetramers for reducing "aggregate" staining in all fluorochromes.

Example 5

Sorting Optimization

To compare various panels in sorting strategies, PBMC ($4-5 \times 10^6$ cells/ml) were stained±anti-CD45 antibody, e.g., CD45 PE-Cy7, in the presence of 2D PE/BV421 Tet and irrelevant peptide APC tetramer mix. Table 15 summarizes the results.

TABLE 15

| CD45+/− | Trigger | Purity |
|---|---|---|
| + | BV421 | 75.2% |
| + | PE | 77.2% |
| − | BV421 | 73.8% |
| − | PE | 71.9% |

Table 15 shows, with anti-CD45 antibody, BV421 trigger and PE trigger resulted in 75.2% and 77.2% purity, respectively, which are slightly higher than that without anti-CD45 antibody, e.g., 73.8% and 71.9%, respectively. The observed lower purity than the theoretical purity, as calculated based on a Poisson distribution using a model system of known target positive percentage, may be due to generous 2D Tet-positive cell gating. This low purity may be acceptable for sort strategies that contain sequential sorting steps.

To investigate the effect of cell concentrations on purity, four different concentrations of PBMC spiked with about 0.1% of 2D PE/BV421 Tet-positive cells, e.g., $23 \times 10^6$ cells/ml spiked with 0.13% 2D PE/BV421 Tet-positive cells, $44 \times 10^6$ cells/ml spiked with 0.14% 2D PE/BV421 Tet-positive cells, $76 \times 10^6$ cells/ml spiked with 0.09% 2D PE/BV421 Tet-positive cells, and $87 \times 10^6$ cells/ml spiked with 0.12% 2D PE/BV421 Tet-positive cells were analyzed. Table 16 summarizes the results.

TABLE 16

| Concentration ($10^6$ cells/ml) | Purity |
|---|---|
| 23 | 50.60% |
| 44 | 28.40% |
| 76 | 18.90% |
| 87 | 13.90% |

Table 16 shows that the lower the cell concentration the higher the purity. The purity, however, was 13-25% below theoretical purity in all cases. As noted above, the observed lower purity than the theoretical purity may be due to generous 2D Tet-positive cell gating.

To improve purity, two sorting strategies were used. In Strategy #1, only one cartridge was used, i.e., entire cells were loaded unto one cartridge and repeat the sorting process three times using the same cartridge. Assuming that about 0.0004% of 2D Tet-positive cells could be detected by processing $900 \times 10^6$ cells, a total sort efficiency of 95.7% may be obtained by repeat sorting three times using the same cartridge based on sort efficiency of 65% at concentration of $87 \times 10^6$ cells/ml.

In Strategy #2, four cartridges were used, e.g., $900 \times 10^6$ cells were split into three cartridges and each cartridge was used only once. The sort efficiency is assumed to be between 92.8% (similar to that of $25 \times 10^6$ cells/ml) and 79.2% (similar to that of $50 \times 10^6$ cells/ml). For example, if each cartridge holds 10 ml, $1 \times 10^9$ cells, $2 \times 10^9$ cells, or $3 \times 10^9$ cells were processed by Strategy #2, the concentration of $33 \times 10^6$ cells/ml, $66 \times 10^6$ cells/ml, or $100 \times 10^6$ cells/ml would be used in sorting, respectively. The sorting process may take about 5 hours to complete.

Figure 41:
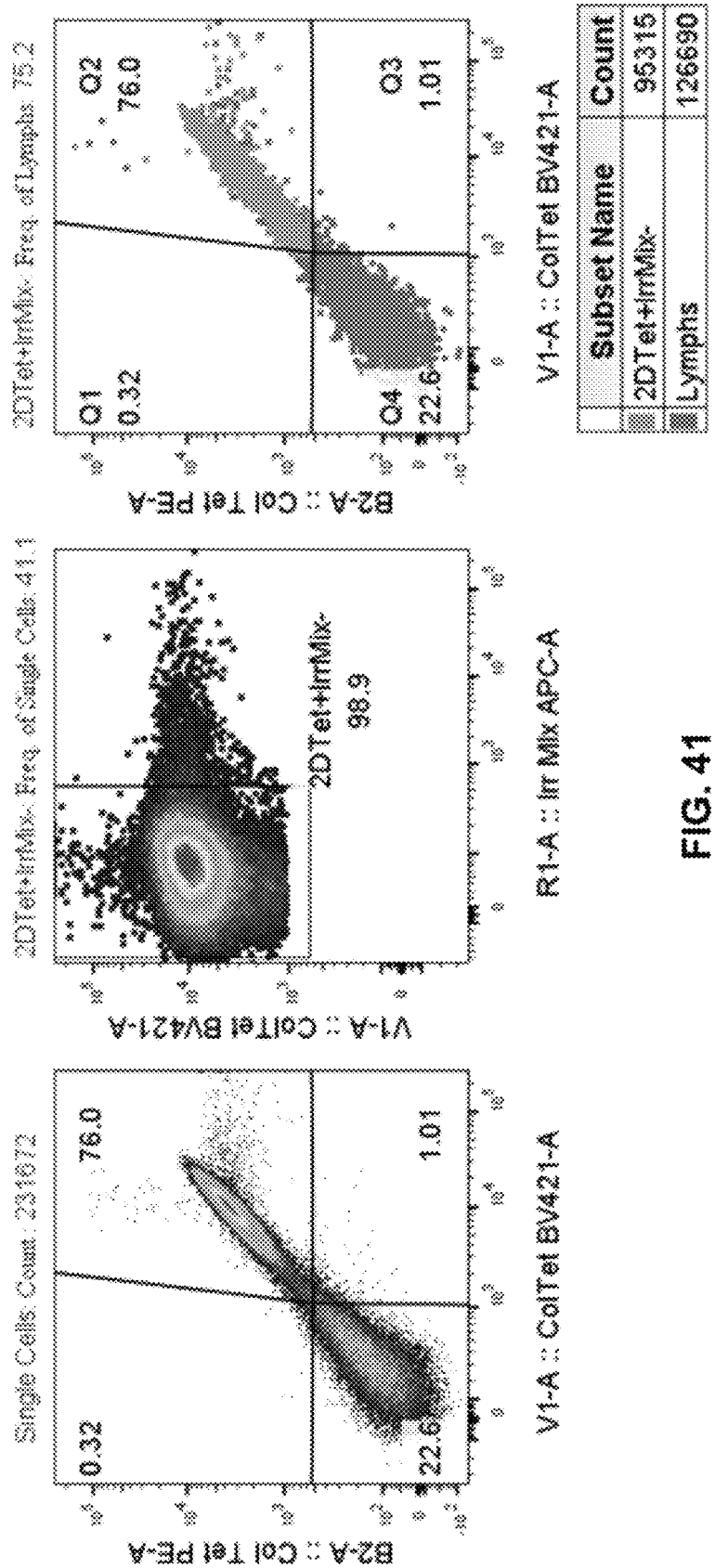
FIG. 41 shows the flow cytometry data obtained from staining condition in accordance with one embodiment of the present disclosure.

To maximize sort efficiency in sorts, the entire sample was processed using a single cartridge at $90-100 \times 10^6$ cells/mL (Strategy #1). As control, FIG. 41, left panel, shows the detection of 76.0% (Q2) Col6A3 PEP1 cells stained with 2D Tet (PE+BV421) in the presence of irrelevant peptide APC tetramer mix. These Q2 cells were further analyzed to detect irrelevant peptide positive T cells, i.e., APC/BV421 double-stained cells. Middle panel (boxed) shows the detection of 98.9% 2D Tet (PE+BV421)-positive and irrelevant peptide-negative cells in the BV421/PE double-positive cells detected in Q2 of left panel. Right panel shows the overlay of the boxed region of middle panel over left panel. These results show the detection of 95315 2D PE/BV421 Tet-positive and irrelevant peptide APC tetramer-negative events in 126690 lymphocytes acquired.

Figure 42:
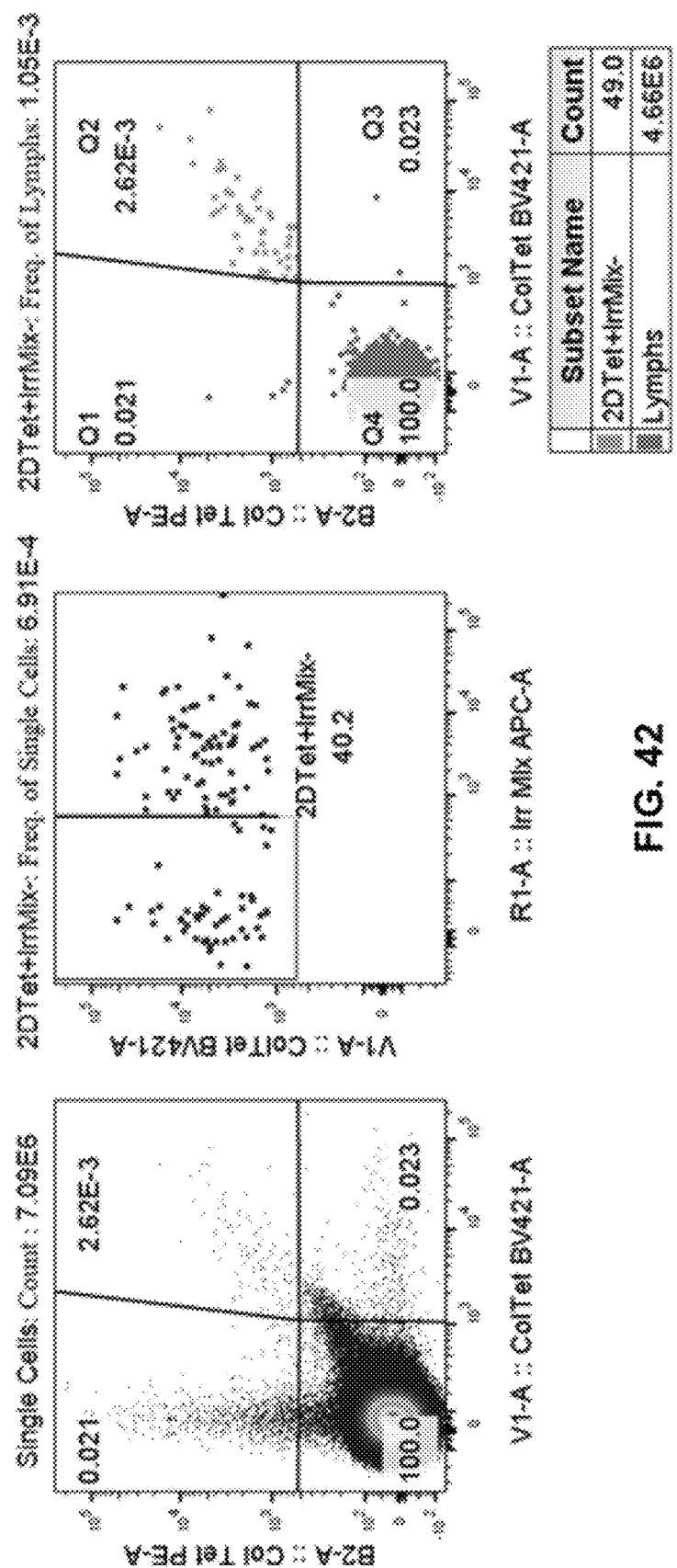
FIG. 42 shows the flow cytometry data obtained from staining condition in accordance with another embodiment of the present disclosure.

FIG. 42 shows an example of gating strategy. FIG. 42, left panel, shows the detection of 2.62E-3% (Q2) BV421/PE double-positive cells in PBMC ($7.09 \times 10^6$ single cells) stained with 2D Tet (PE+BV421) in the presence of irrelevant peptide APC tetramer mix. These Q2 cells were further analyzed to detect irrelevant peptide positive T cells, i.e., APC/BV421 double-stained cells. Middle panel (boxed) shows the detection of 40.2% (frequency of single cells=6.91E-4) 2D Tet (PE+BV421)-positive and irrelevant peptide-negative cells in the BV421/PE double-positive cells detected in Q2 of left panel. The right panel shows the overlay of the boxed region of the middle panel over the left panel. These results show the detection of 49.0 2D PE/BV421 Tet-positive and irrelevant peptide APC tetramer-negative events in $4.66 \times 10^6$ lymphocytes acquired (frequency of lymphocytes=1.05E-3).

Figure 43:
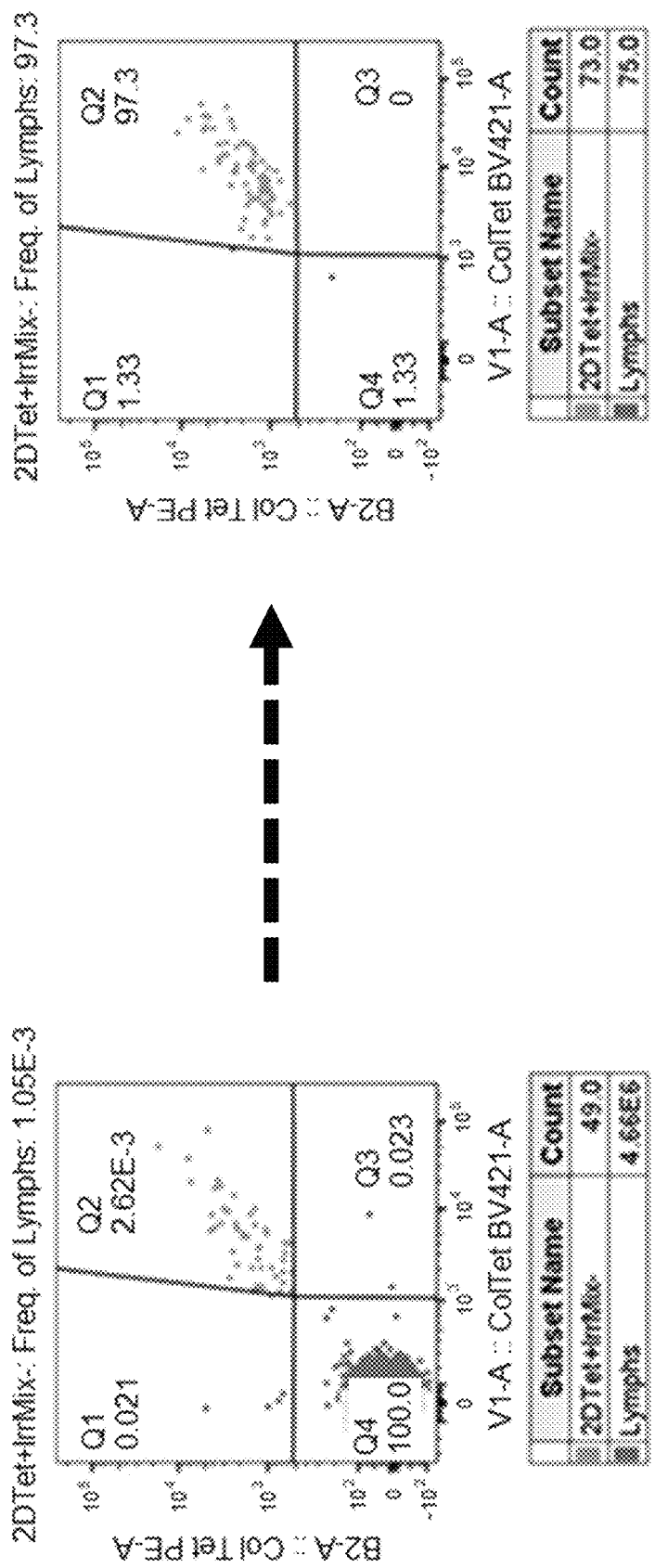
FIG. 43 shows the flow cytometry data obtained from a sorting strategy in accordance with one embodiment of the present disclosure.

FIG. 43 shows an example of sequential depletion of 2DTet+APC− from input sample (left panel, 0.001% (49/$4.66 \times 10^6$)) to final sort (right panel, 97.3% (73/75)). There were 1,877 2D Tet (PE+BV421)-positive and irrelevant peptide-negative events sorted and 536 2D Tet (PE+BV421)-positive and irrelevant peptide-negative cells in waste.

Figure 44:
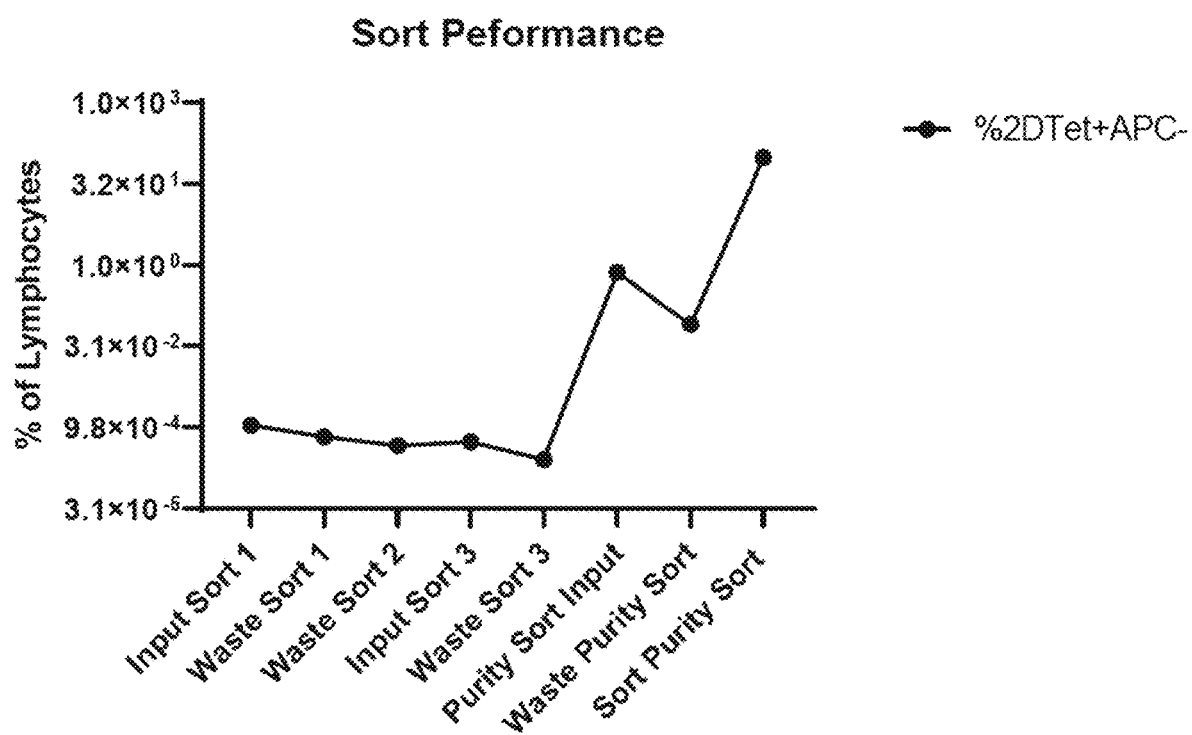
FIG. 44 shows a diagram of sort performance of FIG. 43.

FIG. 44 shows sort performance of about 92,000-fold enrichment (from 0.001% to 97.3%) of 2D Tet (PE+BV421)-positive and irrelevant peptide-negative cells after sequential depletion of 2DTet+APC− from input sample.

Figure 45:
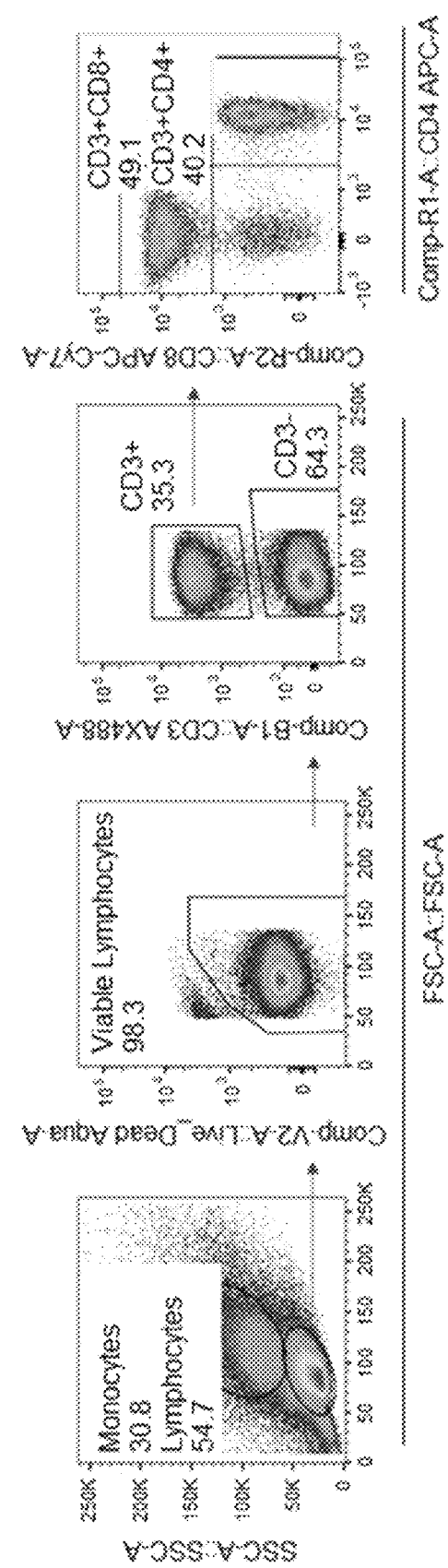
FIG. 45 shows the flow cytometry data obtained from a sorting strategy in accordance with another embodiment of the present disclosure.

To model a full sort of CD8 cells from PBMC panel staining, PBMC ($1 \times 10^9$ cells) were stained and analyzed. FIG. 45 shows 54.7% of lymphocytes (panel A) in PBMC were collected with 98.3% viable cells shown in panel B. Panel C shows 35.3% CD3+ cells in the collected lymphocytes. Panel D shows 49.1% CD3+CD8+ cells in the CD3+ cells.

TABLE 17

| Condition | CD8 of Total Cells | Total Col6A3-002 |
| --- | --- | --- |
| 1e9 PBMC | 9.3% | 1,440 |
| 1e9 CD8 | ~85% (predicted) | 13,161 (predicted) |

Table 20 shows 9.3% of CD8 that were isolated from $1 \times 10^9$ PBMC. The isolated CD8+ cells can be further sorted to yield about 1,440 Col6A3-002-specific CD8+ T cells. Based on these observations, if starting with $1 \times 10^9$ CD8+ cells, one would predict about 85% of which would be CD8+ cells. If so, one would predict about 13,161 Col6A3-002-specific CD8+ T cells to be detected in $1 \times 10^9$ CD8+ cells. Thus, starting with the same number of cells, sorting begins with CD8+ cells may achieve higher yield of peptide-specific T cells than that begins with PBMC.

In sum, in cell sorting, PE trigger may be better than BV421 trigger. To improve sorting using cells at high cell concentrations, e.g., greater than $1 \times 10^8$ cells/ml, high-flow filter cartridges and/or pure CD8 starting population may be used.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

What is claimed is:

1. A method for preparing T cells, comprising
   (a) contacting CD8+ T cells with a first multimer comprising a target peptide in complex with an MHC molecule in the presence of a second multimer comprising an irrelevant peptide in complex with an MHC molecule and a third multimer comprising the target peptide in a complex with an MHC molecule,
   wherein the first multimer is labelled with a first detectable agent, the second multimer is labelled with a second detectable agent, and the third multimer is labelled with a third detectable agent,
   wherein the first, the second, and the third detectable agents are different detectable agents,
   wherein the irrelevant peptide has less than 50% sequence identity to the target peptide,
   wherein the contacting is performed at about 4° C.,
   (b) sorting the contacted CD8+ T cells to collect a first sorted CD8+ T cells that are detected positive for the first and the third detectable agents,
   (c) sorting the first sorted CD8+ T cells to collect a second sorted CD8+ T cells that are detected negative for the second detectable agent,
   wherein the second sorted CD8+ T cells comprise at least 20-fold less false-positive CD8+ T cells that are detected positive for the first and the third detectable agents than that prepared by performing steps (a)-(c) in the absence of the second multimer, and
   (d) expanding the second sorted CD8+ T cells prepared in the presence of the second multimer.

2. The method of claim 1, wherein the contacting is performed in the presence of a first binding agent binding to the first detectable agent and/or a second binding agent binding to the second detectable agent.

3. The method of claim 2, wherein the first binding agent and the second binding agent are antibodies.

4. The method of claim 1, wherein the contacting is performed in the presence of an protein kinase inhibitor (PKI).

5. The method of claim 4, wherein the PKI is at least one selected from the group consisting of afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, and vemurafenib.

6. The method of claim 1, wherein the sorting, the collecting, and the expanding are performed in a closed system.

7. The method of claim 1, wherein the CD8+ T cells are obtained from a blood sample selected from peripheral blood mononuclear cell (PBMC) or a product of leukapheresis.

8. The method of claim 7, wherein the blood sample is obtained from a patient.

9. The method of claim 7, wherein the blood sample is obtained from a donor.

10. The method of claim 1, wherein the multimer is a tetramer.

11. The method of claim 1, wherein the MHC molecule is a class I MHC molecule.

12. The method of claim 1, wherein the first and the second detectable agents each comprise a fluorescent compound.

13. The method of claim 1, wherein the sorting and the collecting are performed by using a microchip-based cell sorter.

14. The method of claim 13, wherein the microchip-based cell sorter is a single-use, disposable, and fully closed microfluidic chip cell sorter.

* * * * *